(12) United States Patent
Paoletti et al.

(10) Patent No.: US 6,780,407 B1
(45) Date of Patent: *Aug. 24, 2004

(54) POX VIRUS COMPRISING DNA SEQUENCES ENCODING CEA AND B7 ANTIGEN

(75) Inventors: Enzo Paoletti, Delmar, NY (US); James Tartaglia, Schenectady, NY (US); William I. Cox, Troy, NY (US)

(73) Assignee: Aventis Pasteur, Swiftwater, PA (US)

( * ) Notice: Subject to any disclaimer, the term of this patent is extended or adjusted under 35 U.S.C. 154(b) by 115 days.

This patent is subject to a terminal disclaimer.

(21) Appl. No.: 09/663,667

(22) Filed: Sep. 15, 2000

Related U.S. Application Data

(60) Division of application No. 08/521,016, filed on Aug. 30, 1995, now abandoned, which is a continuation-in-part of application No. 08/184,009, filed on Jan. 19, 1994, now Pat. No. 5,833,975, which is a continuation-in-part of application No. 08/007,115, filed on Jan. 21, 1993, now abandoned, which is a continuation-in-part of application No. 07/847,977, filed on Mar. 3, 1992, now abandoned, which is a division of application No. 07/478,179, filed on Feb. 14, 1990, now abandoned, which is a continuation-in-part of application No. 07/320,471, filed on Mar. 8, 1989, now Pat. No. 5,155,020, and a continuation-in-part of application No. 07/805,567, filed on Dec. 16, 1991, now Pat. No. 5,378,457, which is a continuation-in-part of application No. 07/638,080, filed on Jan. 7, 1991, now abandoned, and a continuation-in-part of application No. 07/847,951, filed on Mar. 6, 1992, now abandoned, which is a continuation-in-part of application No. 07/713,967, filed on Jun. 11, 1991, now abandoned, which is a continuation-in-part of application No. 07/666,056, filed on Mar. 7, 1991, now abandoned.

(51) Int. Cl.⁷ .................. A01N 63/00; A61K 48/00; A61K 39/100; C12N 15/00

(52) U.S. Cl. .............. 424/93.2; 424/93.6; 424/185.1; 424/199.1; 435/320.1

(58) Field of Search .................. 424/93.2, 93.6, 424/185.1, 199.1; 435/320.1

(56) References Cited

U.S. PATENT DOCUMENTS 5,833,975 A * 11/1998 Paoletti et al. ............. 424/93.2

* cited by examiner

Primary Examiner—Deborah Crouch

(57) ABSTRACT

Attenutated recombinant viruses containing DNA coding for a cytokine and/or a tumor associated antigen, as well as methods and compositions employing the viruses, are disclosed and claimed. The recombinant viruses can be NYVAC or ALVAC recombinant viruses. The DNA can code for at least one of: human tumor necrosis factor; nuclear phosphoprotein p53, wiltype or mutant; human melanoma-associated antigen; IL-2; IFNγ; IL-4; GMCSF; IL-12; B7; erb-B-2 and carcinoembryonic antigen. The recombinant viruses and gene products therefrom are useful for cancer therapy.

12 Claims, 60 Drawing Sheets

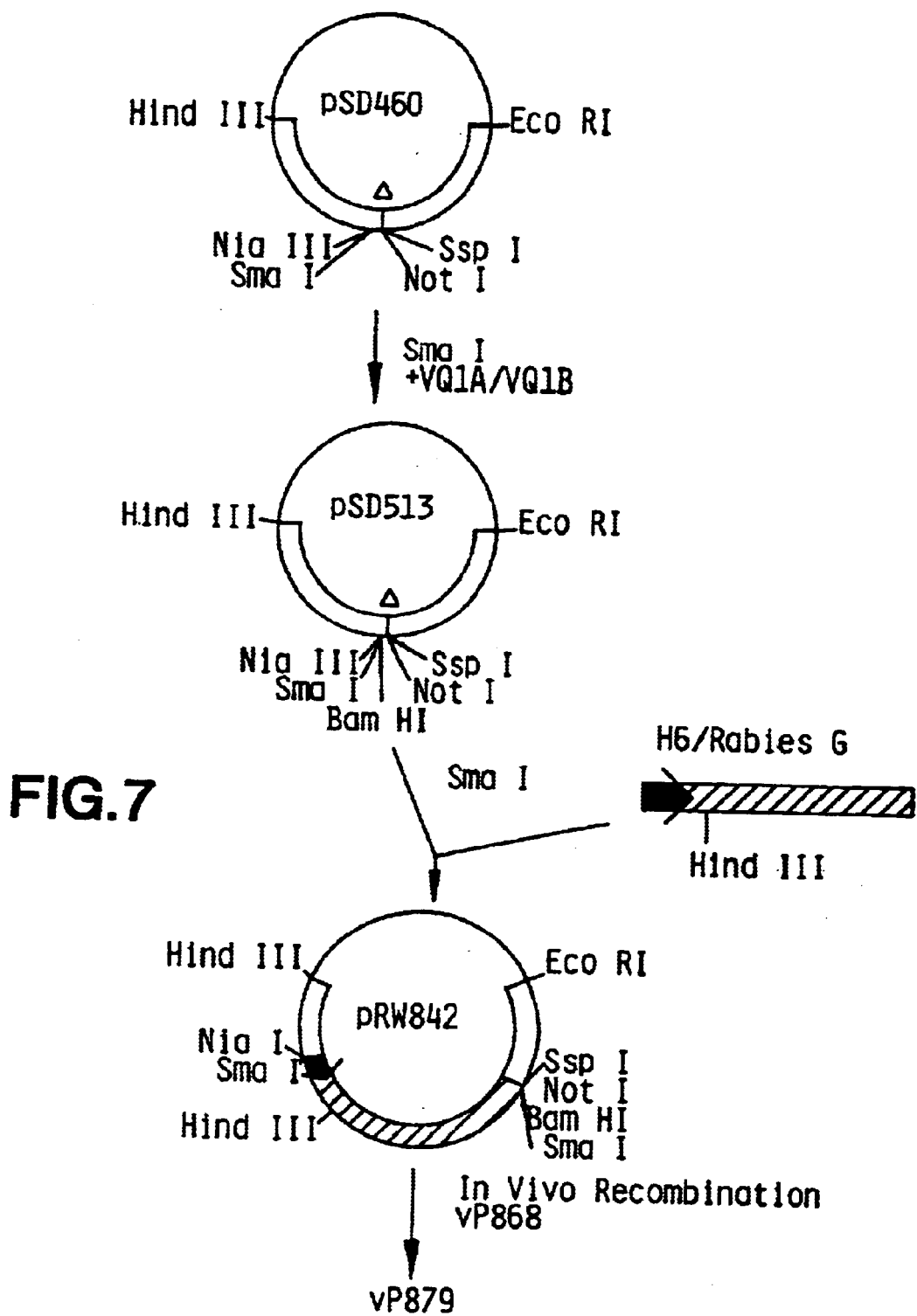

```
   1 TGAATGTTAA ATGTTATACT TTGGATGAAG CTATAAATAT GCATTGGAAA AATAATCCAT
  61 TTAAAGAAAG GATTCAAATA CTACAAAACC TAAGCGATAA TATGTTAACT AAGCTTATTC
 121 TTAACGACGC TTTAAATATA CACAAATAAA CATAATTTTT GTATAACCTA ACAAATAACT
 181 AAAACATAAA AATAATAAAA GGAAATGTAA TATCGTAATT ATTTTACTCA GGAATGGGGT
 241 TAAATATTTA TATCACGTGT ATATCTATAC TGTTATCGTA TACTCTTTAC AATTACTATT
 301 ACGAATATGC AAGAGATAAT AAGATTACGT ATTTAAGAGA ATCTTGTCAT GATAATTGGG
 361 TACGACATAG TGATAAATGC TATTTCGCAT CGTTACATAA AGTCAGTTGG AAAGATGGAT
 421 TTGACAGATG TAACTTAATA GGTGCAAAAA TGTTAAATAA CAGCATTCTA TCGGAAGATA
 481 GGATACCAGT TATATTATAC AAAAATCACT GGTTGGATAA AACAGATTCT GCAATATTCG
 541 TAAAAGATGA AGATTACTGC GAATTTGTAA ACTATGACAA TAAAAAGCCA TTTATCTCAA
 601 CGACATCGTG TAATTCTTCC ATGTTTATG TATGTGTTTC AGATATTATG AGATTACTAT
 661 AAACTTTTTG TATACTTATA TTCCGTAAAC TATATTAATC ATGAAGAAAA TGAAAAAGTA
 721 TAGAAGCTGT TCACGAGCGG TTGTTGAAAA CAACAAAATT ATACATTCAA GATGGCTTAC
 781 ATATACGTCT GTGAGGCTAT CATGGATAAT GACAATGCAT CTCTAAATAG GTTTTTGGAC
 841 AATGGATTCG ACCCTAACAC GGAATATGGT ACTCTACAAT CTCCTCTTGA AATGGCTGTA
 901 ATGTTCAAGA ATACCGAGGC TATAAAAATC TTGATGAGGT ATGGAGCTAA ACCTGTAGTT
 961 ACTCAATGCA CAACTTCTTG TCTGCATGAT GCGGTGTTGA GAGACGACTA CAAAATAGTG
1021 AAAGATCTGT TGAAGAATAA CTATGTAAAC AATGTCTTT ACAGCGGAGG CTTTACTCCT
1081 TTGTGTTTGG CAGCTTACCT TAACAAAGTT AATTTGGTTA AACTTCTATT GGCTCATTCG
1141 GCGGATGTAG ATATTTCAAA CACGGATCGG TTAACTCCTC TACATATAGC CGTATCAAAT
1201 AAAAATTTAA CAATGGTTAA ACTTCTATTG AACAAAGGTG CTGATACTGA CTTGCTGGAT
1261 AACATGGGAC GTACTCCTTT AATGATCGCT GTACAATCTG GAAATATTGA AATATGTAGC
1321 ACACTACTTA AAAAAAATAA AATGTCCAGA ACTGGGAAAA ATTGATCTTG CCAGCTGTAA
1381 TTCATGGTAG AAAAGAAGTG CTCAGGCTAC TTTTCAACAA AGGAGCAGAT GTAAACTACA
1441 TCTTTGAAAG AAATGGAAAA TCATATACTG TTTTGGAATT GATTAAAGAA AGTTACTCTG
1501 AGACACAAAA GAGGTAGCTG AAGTGGTACT CTCAAAATGC AGAACGATGA CTGCGAAGCA
1561 AGAAGTAGAG AAATAACACT TTATGACTTT CTTAGTTGTA GAAAAGATAG AGATATAATG
1621 ATGGTCATAA ATAACTCTGA TATTGCAAGT AAATGCAATA ATAAGTTAGA TTTATTTAAA
1681 AGGATAGTTA AAAAATAGAAA AAAAGAGTTA ATTTGTAGGG TTAAATAAT ACATAAGATC
1741 TTAAAATTTA TAAATACGCA TAATAATAAA AATAGATTAT ACTTATTACC TTCAGAGATA
1801 AAATTTAAGA TATTTACTTA TTTAACTTAT AAAGATCTAA AATGCATAAT TTCTAAATAA
1861 TGAAAAAAAA GTACATCATG AGCAACGCGT TAGTATATTT TACAATGGAG ATTAACGCTC
1921 TATACCGTTC TATGTTTATT GATTCAGATG ATGTTTAGA AAAGAAAGTT ATTGAATATG
1981 AAAACTTTAA TGAAGATGAA GATGACGACG ATGATTATTG TTGTAAATCT GTTTTAGATG
2041 AAGAAGATGA CGCGCTAAAG TATACTATGG TTACAAAGTA TAAGTCTATA CTACTAATGG
2101 CGACTTGTGC AAGAAGGTAT AGTATAGTGA AAATGTTGTT AGATTATGAT TATGAAAAAC
2161 CAAATAAATC AGATCCATAT CTAAAGGTAT CTCCTTTTGCA CATAATTTCA TCTATTCCTA
2221 GTTTAGAATA CTTTTCATTA TATTTGTTTA CAGCTGAAGA CGAAAAAAAT ATATCGATAA
2281 TAGAAGATTA TGTTAACTCT GCTAATAAGA TGAAATTGAA TGAGTCTGTG ATAATAGCTA
2341 TAATCAGAGA AGTTCTAAAA GGAAATAAAA ATCTAACTGA TCAGGATATA AAAACATTGG
2401 CTGATGAAAT CAACAAGGAG GAACTGAATA TAGCTAAACT ATTGTTAGAT AGAGGGGCCA
2461 AAGTAAATTA CAAGGATGTT TACGGTTCTT CAGCTCTCCA TAGAGCTGCT ATTGGTAGGA
2521 AACAGGATAT GATAAAGCTG TTAATCGATC ATGGAGCTGA TGTAAACTCT TTAACTATTG
2581 CTAAAGATAA TCTTATTAAA AAAAATAAT ATCACGTTTA GTAATATTAA AATATATTAA
2641 TAACTCTATT ACTAATAACT CCAGTGGATA TGAACATAAT ACGAAGTTTA TACATTCTCA
2701 TCAAAATCTT ATTGACATCA AGTTAGATTG TGAAAATGAG ATTATGAAAT TAAGGAATAC
2761 AAAAATAGGA TGTAAGAACT TACTAGAATG TTTTATCAAT AATGATATGA ATACAGTATC
2821 TAGGGCTATA AACAATGAAA CGATTAAGAA TTATAAAATAT CATTTCCCTA TATATAATAC
2881 GCTCATAGAA AAATTCATTT CTGAAAGTAT ACTAAGACAC GAATTATTGG ATGGAGTTAT
2941 AAATTCTTTT CAAGGATTCA ATAATAAATT GCCTTACGAG ATTCAGTACA TTATACTGGA
3001 GAATCTTAAT AACCATGAAC TAAAAAAAAT TTTAGATAAT ATACATTAAA AAGGTAAATA
3061 GATCATCTGT TATTATAAGC AAAGATGCTT GTTGCCAATA ATATACAACA GGTATTTGTT
3121 TTTATTTTTA ACTACATATT TGATGTTCAT TCTCTTTATA TAGTATACAC AGAAAATTCA
3181 TAATCCACTT AGAATTTCTA GTTATCTAG
```

FIG.8

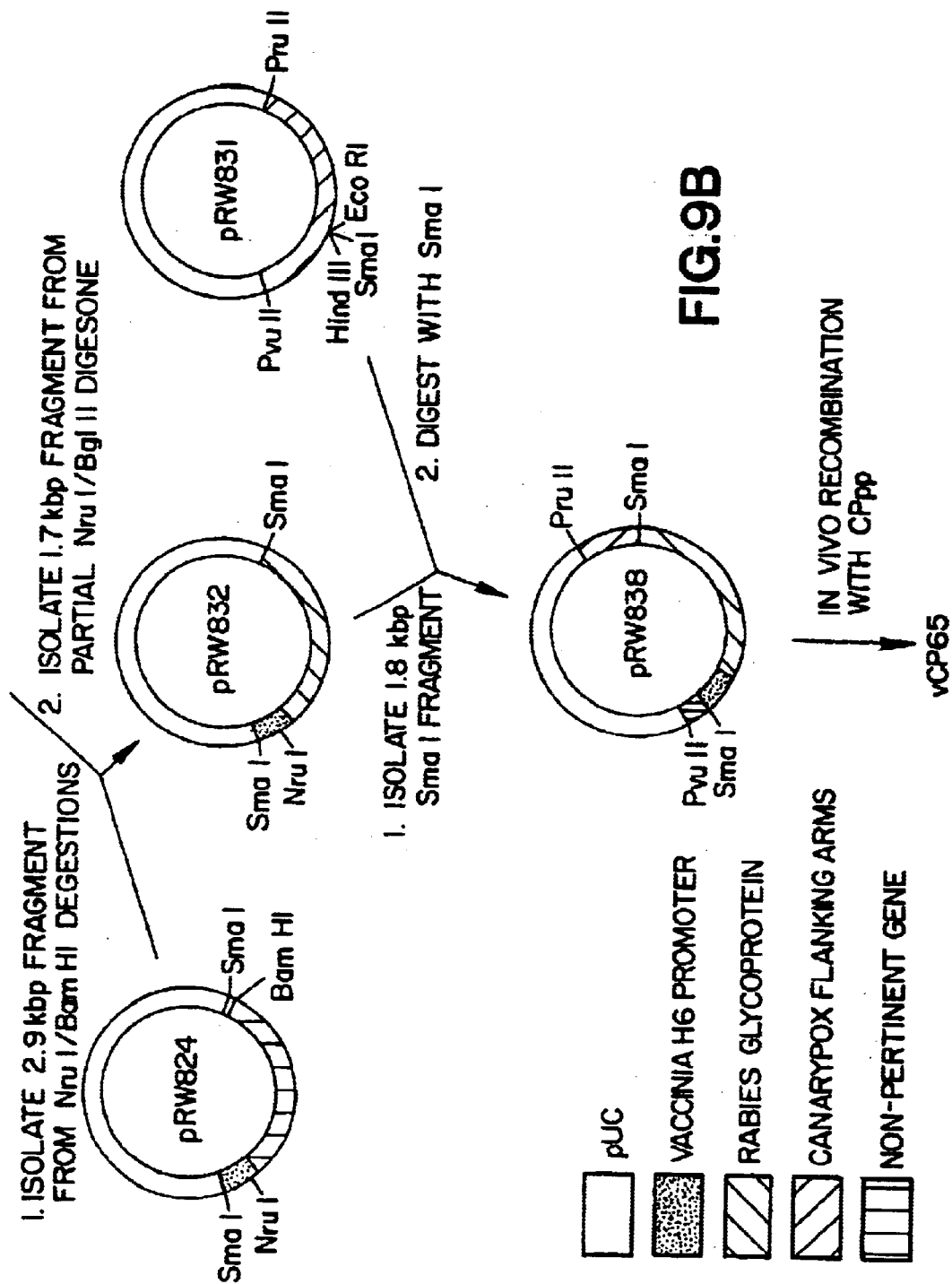

```
   1 GATATCTGTG GTCTATATAT ACTACACCCT ACCGATATTA ACCAACGAGT TTCTCACAAG
  61 AAAACTTGTT TAGTAGATAG AGATTCTTTG ATTGTGTTTA AAAGAAGTAC CAGTAAAAAG
 121 TGTGGCATAT GCATAGAAGA AATAAACAAA AAACATATTT CCGAACAGTA TTTTGGAATT
 181 CTCCCAAGTT GTAAACATAT TTTTTGCCTA TCATGTATAA GACGTTGGGC AGATACTACC
 241 AGAAATACAG ATACTGAAAA TACGTGTCCT GAATGTAGAA TAGTTTTTCC TTTCATAATA
 301 CCCAGTAGGT ATTGGATAGA TAATAAATAT GATAAAAAAA TATTATATAA TAGATATAAG
 361 AAAATGATTT TTACAAAAAT ACCTATAAGA ACAATAAAAA TATAATTACA TTTACGGAAA
 421 ATAGCTGGTT TTAGTTTACC AACTTAGAGT AATTATCATA TTGAATCTAT ATTGTTTTTT
 481 AGTTATATAA AAACATGATT AGCCCCCAAT CGGATGAAAA TATAAAAGAT GTTGAGAATT
 541 TCGAATACAA CAAAAAGAGG AATCGTACGT TGTCCATATC CAAACATATA AATAAAAATT
 601 CAAAAGTAGT ATTATACTGG ATGTTTAGAG ATCAACGTAT ACAAGATAAT TGGGCTTTAA
 661 TTTACGCACA ACGATTACGG TTAAAACTCA AAATACCTCT AAGAATATGC TTTTGTGTCG
 721 TGCCAAAATT TCACACTACT ACTTCTAGAC ACTTTATGTT TTTAATATCC GGTCTTAAAG
 781 AAGTCGCGGA AGAATGTAAA AGACTATGTA TAGGGTTTTC ATTGATATAT GGCGTACCAA
 841 AAGTAATAAT TCCGTGTATA GTAAAAAAAT ACAGAGTCGG AGTAATCATA ACGGATTTCT
 901 TTCCATTACG TGTTCCCGAA AGATTAATGA AACAGACTGT AATATCTCTT CCAGATAACA
 961 TACCTTTTAT ACAAGTAGAC GCTCATAATA TAGTACCTTG TTGGGAAGCT TCTGATAAAG
1021 AAGAATACGG TGCACGAACT TTAAGAAAAA AGATATTTGA TAAATTATAT GAATATATGA
1081 CAGAATTTCC TGTTGTTCGT AAACATCCAT ACGGTCCATT TTCTATATCT ATTGCAAAAC
1141 CCAAAAATAT ATCATTAGAC AAGACGGTAT TACCCGTAAA ATGGGCAACG CCTGGAACAA
1201 AAGCTGGAAT AATTGTTTTA AAAGAATTTA TAAAAAACAG ATTACCGTCA TACGACGCGG
1261 ATCATAACAA TCCTACGTGT GACGCTTTGA GTAACTTATC TCCGTGGCTA CATTTTGGTC
1321 ATGTATCCGC ACAACGTGTT GCCTTAGAAG TATTAAAATG TATACGAGAA AGCAAAAAAA
1381 ACGTTGAAAC GTTTATAGAT GAAATAATTG TAAGAAGAGA ACTATCGGAT AATTTTTGTT
1441 ACTATAACAA ACATTATAT AGTATCCAGT CTACTCATTC ATGGGTTAGA AAAACATTAG
1501 AAGATCACAT TAATGATCCT AGAAAGTATA TATATTCCAT TAAACAACTC GAAAAAGCGG
1561 AAACTCATGA TCCTCTATGG AACGCGTCAC AAATGCAGAT GGTGAGAGAA GGAAAAATGC
1621 ATAGTTTTTT ACGAATGTAT TGGGCTAAGA AGATACTTGA ATGGACTAGA ACACCTGAAG
1681 ACGCTTTGAG TTATAGTATC TATTTGAACA ACAAGTACGA ACTAGACGGC ACGGATCCTA
1741 ACGGATACGT AGGTTGTATG TGGTCTATTT GCGGATTACA CGATAGAGCG TGGAAAGCAA
1801 GACCGATATT TGGAAAGATA AGATATATGA ATTATGAGAG TTCTAAGAAG AAATTTGATG
1861 TTGCTGTATT TATACAGAAA TACAATTAAG ATAAATAATA TACAGCATTG TAACCATCGT
1921 CATCCGTTAT ACGGGGAATA ATATTCCAT ACAGTATTAT TAAATTTTCT TACGAAGAAT
1981 ATAGATCGGT ATTTATCGTT AGTTTATTTT ACATTTATTA ATTAAACATG TCTACTATTA
2041 CCTGTTATGG AAATGACAAA TTTAGTTATA TAATTTATGA TAAAATTAAG ATAATAATAA
2101 TGAAATCAAA TAATTATGTA AATGCTACTA GATTATGTGA ATTACGAGGA AGAAAGTTTA
2161 CGAACTGGAA AAAATTAAGT GAATCTAAAA TATTAGTCGA TAATGTAAAA AAAATAAATG
2221 ATAAAACTAA CCAGTTAAAA ACGGATATGA TTATATACGT TAAGGATATT GATCATAAAG
2281 GAAGAGATAC TTGCGTTAC TATGTACACC AAGATCTGGT ATCTTCTATA TCAAATTGGA
2341 TATCTCCGTT ATTCGCCGTT AAGGTAAATA AAATTATTAA CTATTATATA TGTAATGAAT
2401 ATGATATACG ACTTAGCGAA ATGGAATCTG ATATGACAGA AGTAATAGAT GTAGTTGATA
2461 AATTAGTAGG AGGATACAAT GATGAAATAG CAGAAATAAT ATATTTGTTT AATAAATTTA
2521 TAGAAAAATA TATTGCTAAC ATATCGTTAT CAACTGAATT ATCTAGTATA TTAAATAATT
2581 TTATAAATTT TATAAATTTT AATAAAAAAT ACAATAACGA CATAAAGATA TTTAATCTTT
2641 AATTCTTGAT CTGAAAAACA CATCTATAAA ACTAGATAAA AAGTTATTCG ATAAAGATAA
2701 TAATGAATCG AACGATGAAA AATTGGAAAC AGAAGTTGAT AAGCTAATTT TTTTCATCTA
2761 AATAGTATTA TTTTATTGAA GTACGAAGTT TACGTTAGA TAAATAATAA AGGTCGATTT
2821 TTACTTTGTT AAATATCAAA TATGTCATTA TCTGATAAAG ATACAAAAAC ACACGGTGAT
2881 TATCAACCAT CTAACGAACA GATATTACAA AAAATACGTC GGACTATGGA AAACGAAGCT
2941 GATAGCCTCA ATAGAAGAAG CATTAAAGAA ATTGTTGTAG ATGTTATGAA GAATTGGGAT
3001 CATCCTCAAC GAAGAAATAG ATAAAGTTCT AAACTGGAAA AATGATACAT TAAACGATTT
3061 AGATCATCTA AATACAGATG ATAATATTAA GGAAATCATA CAATGTCTGA TTAGAGAATT
3121 TGCGTTTAAA AAGATCAATT CTATTATGTA TAGTTATGCT ATGGTAAAAC TCAATTCAGA
3181 TAACGAACAT TGAAAGATAA AATTAAGGAT TATTTTATAG AAACTATTCT TAAAGACAAA
3241 CGTGGTTATA AACAAAGCC ATTACCCGGA TTGGAAACTA AAATACTAGA TAGTATTATA
3301 AGATTTTAAA AACATAAAAT TAATAGGTTT TTATAGATTG ACTTATTATA TACAATATGG
3361 ATAAAAGATA TATATCAACT AGAAAGTTGA ATGACGGATT CTTAATTTTA TATTATGATT
3421 CAATAGAAAT TATTGTCATG TCGTGTAATC ATTTTATAAA TATATCAGCG TTACTAGCTA
3481 AGAAAAACAA GGACTTTAAT GAATGGCTAA AGATAGAATC ATTTAGAGAA ATAATAGATA
3541 CTTTAGATAA AATTAATTAC GATCTAGGAC AACGATATTG TGAAGAACTT ACGGCGCATC
3601 ACATTCCAGT GTAATTATTG AGGTCAAAGC TAGTAACTTA ATAGATGACA GGACAGCTG
```

FIG.11

```
   1 TGTCTGGACT AACTGATTTC ATGGAACAAT TTTCATCAAA AATATCAGTT ATACCTAGTT
  61 CTACAAAGAC AGAACTTTGA TGTTATGTTT GTGTTTGTAT AGAAAATTTT GGGATACTAA
 121 CTGATATTTC TGAATATTTC TGAATATTTC ATGTTACTTA CTTACTCCTA TCTTAGACGA
 181 TAATAAAATT CGAGGCGTAA TATGTTTTTC CAAATATTTG AAATTCTTAT ACGTATCGGC
 241 GAAGAAAAGT AACATACTAT AAGTGTTATG CAAGTAAGGT ATGTTAATGA TATTGGATTT
 301 AATTTCATTG ACAATACATA TGTCCAAACA TTCCACTCGT AATTATGTAC GGAACGACTT
 361 TAGTTAAATA CTTAGTCACA AAAAACTTAT GACTGTCATT ATCTGAAAAC GGTGATTCCC
 421 ATAAATCAGA ATACTTAATA TTAAATAGAA TGCTCGCTTC TGGAGGTTTC CGGATACTAG
 481 ATAACATATC TTCTGTATTA TAGTTTAATT CACTCATTTT ATTACATAAT ACAGTAACAT
 541 CTCCCGAAAC CAATGATGTT ATATTAGATT TACTTACATA CTTCTTGTAA CTATCATGAA
 601 TACGTTTGTT GATGTCTATA AAGAAGATGG ATGTATATTC TGTTCTAGAT AGCAAGTTCT
 661 TTAAGTTATT CTTTGTCTGT ATTACTATCA TCGTCTTCAT CATCGTCTAA AGGTAGCATT
 721 ATATAATAAA TCTAATAGTT GATTTCTCGA TCTATCAGTA CTCGCTTTCA ATAACATTTT
 781 TACTATAAGC ATAATAGAAG GCGGTGATAT CACTATATTT TTATCGGGTA TTCTTTTAGT
 841 AATTAGTTAG TTCGTAGAAT TTCGTAGAGA TAAAAGCCAA TTTGTTGTTG ATACTGCTTA
 901 CGTTACTCAT GTTTCTTGTT TCTGTTAATT AACAGGTATA CCCTTACAAT AAGTTTAATT
 961 AACTTTTAGG TTTTTGTGAA GAACTTTTAG CTTCTAGTTC CCTTATCCAT AATTGGGTCT
1021 TAGATCTAGA TTCTTCCCAT GTATAAAGGG GGACATACCC AAAATCTTTA AATGCTTTGT
1081 CCGTTTCTAT AGTAAATGTC GTACATTCCT TAATCAAAGT ATAAGGATTT AGTAAAGGCG
1141 TGTAAGAACA AATAGGTGAA GTAATACTC TTAAACCTTT ATTAATATTA GCGATAAACC
1201 TTAAACACCA TAAAGGAAGA CATGTATTCC GTAGATCCAT CCCTAATTGA TTAAAGAAAT
1261 GCATGTTAAA ATCATGATAA TGTTCAGTAG GAGAGGTATC GTAACAGTAA TACACGTTAT
1321 TGCAGAGAGG ACTATGTTGA CCATTTTCTA TCATATTTCT TGCTGCTAAA ATATGCATCC
1381 AAGCTACGTT TCCTGCATAG ACTCTGCTAT GAAATACTTT ATCATCCGCA TATTTATACA
1441 TTTTCCTGCT TTTATACGAT CTTCTGTATA AAGTTTCTAG TACTGGACAG TATTCTCCGA
1501 AAACACGTAA TGGGCGTAGC GACAAGTGCA TAATCTAAGT CCTATATTAG ACATAGTACC
1561 GTTAGCTTCT AGTATATATT TCTCAGATAA CTTGTTTACT AAGAGGATAA GCCTCTTTAT
1621 GGTTAGATTG ATAATACGTA TTCTCGTTTC CTCTTATCAT CGCATCTCCG GAGAAAGTTA
1681 GGACCTACCG CAGAATAACT ACTCGTATAT ACTAAGACTT TTACGCCGTT ATACAGACAA
1741 GAATCTACTA CGTTCTTCGT TCCGTTGATA TTAACGTCCA TTATAGAGTC GTTAGTAAAC
1801 TTACCCGCTA CATCATTTAT CGAAGCAATA TGAATGACCA CATCTGCTGA TCTAAGCGCT
1861 TCGTCCAAAG TACTTTTATT TCTAACATCT CCAATCACGG GAACTATCTT TATTATATTA
1921 CATTTTTCTA CAAGATCTAG TAACCATTGG TCGATTCTAA TATCGTAAAC ACGAACTTCT
1981 TTTTAAAGAG GATTCGAACA AGATAAGATT ATTTATAATG TGTCTACCTA AAAATCCACA
2041 CCCTCCGGTT ACCACGTATA CTAGTGTACG CATTTTGAGT ATTAACTATA TAAGACCAAA
2101 ATTATATTTT CATTTTCTGT TATATTATAC TATATAATAA AAACAAATAA ATATACGAAT
2161 ATTATAAGAA ATTTAGAACA CGTTATTAAA GTATTGCCTT TTTTATTAAC GGCGTGTTCT
2221 TGTAATTGCC GTTTAGAATA GTCTTTATTT ACTTTAGATA ACTCTTCTAT CATAACCGTC
2281 TCCTTATTCC AATCTTCTTC AGAAGTACAT GAGTACTTAC CGAAGTTTAT CATCATAGAG
2341 ATTATATATG AAGAAA
```

FIG.12

```
   1 AGATATTTGT TAGCTTCTGC CGGAGATACC GTGAAAATCT ATTTTCTGGA AGGAAAGGGA
  61 GGTCTTATCT ATTCTGTCAG CAGAGTAGGT TCCTCTAATG ACGAAGACAA TAGTGAATAC
 121 TTGCATGAAG GTCACTGTGT AGAGTTCAAA ACTGATCATC AGTGTTTGAT AACTCTAGCG
 181 TGTACGAGTC CTTCTAACAC TGTGGTTTAT TGGCTGGAAT AAAAGGATAA AGACACCTAT
 241 ACTGATTCAT TTCATCTGT CAACGTTTCT CTAAGAGATT CATAGGTATT ATTATTACAT
 301 CGATCTAGAA GTCTAATAAC TGCTAAGTAT ATTATTGGAT TTAACGCGCT ATAAACGCAT
 361 CCAAAACCTA CAAATATAGG AGAAGCTTCT CTTATGAAAC TTCTTAAAGC TTTACTCTTA
 421 CTATTACTAC TCAAAAGAGA TATTACATTA ATTATGTGAT GAGGCATCCA ACATATAAAG
 481 AAGACTAAAG CTGTAGAAGC TGTTATGAAG AATATCTTAT CAGATATATT AGATGCATTG
 541 TTAGTTCTGT AGATCAGTAA CGTATAGCAT ACGAGTATAA TTATCGTAGG TAGTAGGTAT
 601 CCTAAAATAA ATCTGATACA GATAATAACT TTGTAAATCA ATTCAGCAAT TTCTCTATTA
 661 TCATGATAAT GATTAATACA CAGCGTGTCG TTATTTTTTG TTACGATAGT ATTTCTAAAG
 721 TAAAGAGCAG GAATCCCTAG TATAATAGAA ATAATCCATA TGAAAAATAT AGTAATGTAC
 781 ATATTTCTAA TGTTAACATA TTTATAGGTA AATCCAGGAA GGGTAATTTT TACATATCTA
 841 TATACGCTTA TTACAGTTAT TAAAAATATA CTTGCAAACA TGTTAGAAGT AAAAAAGAAA
 901 GAACTAATTT TACAAAGTGC TTTACCAAAA TGCCAATGGA AATTACTTAG TATGTATATA
 961 ATGTATAAAG GTATGAATAT CACAAACAGC AAATCGGCTA TTCCCAAGTT GAGAAACGGT
1021 ATAATAGATA TATTTCTAGA TACCATTAAT AACCTTATAA GCTTGACGTT TCCTATAATG
1081 CCTACTAAGA AAACTAGAAG ATACATACAT ACTAACGCCA TACGAGAGTA ACTACTCATC
1141 GTATAACTAC TGTTGCTAAC AGTGACACTG ATGTTATAAC TCATCTTTGA TGTGGTATAA
1201 ATGTATAATA ACTATATTAC ACTGGTATTT TATTTCAGTT ATATACTATA TAGTATTAAA
1261 AATTATATTT GTATAATTAT ATTATTATAT TCAGTGTAGA AAGTAAAATA CTATAAATAT
1321 GTATCTCTTA TTTATAACTT ATTAGTAAAG TATGTACTAT TCAGTTATAT TGTTTTATAA
1381 AAGCTAAATG CTACTAGATT GATATAAATG AATATGTAAT AAATTAGTAA TGTAGTATAC
1441 TAATATTAAC TCACATTATG AATACTACTA ATCACGAAGA ATGCAGTAAA ACATATGATA
1501 CAAACATGTT AACAGTTTTA AAAGCCATTA GTAATAAACA GTACAATATA ATTAAGTCTT
1561 TACTTAAAAA AGATATTAAT GTTAATAGAT TATTAACTAG TTATTCTAAC GAAATATATA
1621 AACATTTAGA CATTACATTA TGTAATATAC TTATAGAACG TGCAGCAGAC ATAAACATTA
1681 TAGATAAGAA CAATCGTACA CCGTTGTTTT ATGCGGTAAA GAATAGTGAT TATGATATGG
1741 TTAAACTCCT ATTAAAAAAT GGCGCGAATG TAAATTTACA AGATAGTATA GGATATTCAT
1801 GTCTTCACAT CGCAGGTATA CATAATAGTA ACATAGAAAT AGTAGATGCA TTGATATCAT
1861 ACAAACCAGA TTTAAACTCC CGCGATTGGG TAGGTAGAAC ACCGCTACAT ATCTTCGTGA
1921 TAGAATCTAA CTTTGAAGCT GTGAAATTAT TATTAAAGTC AGGTGCATAT GTAGGTTTGA
1981 AAGACAAATG TAAGCATTTT CCTATACACC ATTCTGTAAT GAAATTAGAT CACTTAATAT
2041 CAGGATTGTT ATTAAAATAT GGAGCAAATC CAAATACAAT TAACGGCAAT GGAAAAACAT
2101 TATTAAGCAT TGCTGTAACA TCTAATAATA CACTACTGGT AGAACAGCTG CTGTTATATG
2161 GAGCAGAAGT TAATAATGGT GGTTATGATG TTCCAGCTCC TATTATATCC GCTGTCAGTG
2221 TTAACAATTA TGATATTGTT AAGATACTGA TACATAATGG TGCGAATATA AATGTATCCA
2281 CGGAAGATGG TAGAACGTCT TTACATACAG CTATGTTTTG GAATAACGCT AAAATAATAG
2341 ATGAGTTGCT TAACTATGGA AGTGACATAA ACAGCGTAGA TACTTATGGT AGAACTCCGT
2401 TATCTTGTTA TCGTAGCTTA AGTTATGATA TCGCTACTAA ACTAATATCA CGTATCATTA
2461 TAACAGATGT CTATCGTGAA GCACCAGTAA ATATCAGCGG ATTTATAATT AATTTAAAAA
2521 CTATAGAAAA TAATGATATA TTCAAATTAA TTAAAGATGA TTGTATTAAA GAGATAAACA
2581 TACTTAAAAG TATAACCCTT AATAAATTTC ATTCATCTGA CATATTTATA CGATATAATA
2641 CTGATATATG TTTATTAACG AGATTTATTC AACATCCAAA GATAATAGAA CTAGACAAAA
2701 AACTCTACGC TTATAAATCT ATAGTCAACG AGAGAAAAAT CAAAGCTACT TACAGGTATT
2761 ATCAAATAAA AAAAGTATTA ACTGTACTAC CTTTTTCAGG ATATTTCTCT ATATTGCCGT
2821 TTGATGTGTT AGTATATATA CTTGAATTCA TCTATGATAA TAATATGTTG GTACTTATGA
```

FIG.14A

```
2941 AATGGCAGGA ATTTTGTGTA AACTAAGCCA CATACTTGCC AATGAAAAAA ATAGTAGAAA
3001 GGATACTATT TTAATGGGAT TAGATGTTAA GGTTCCTTGG GATTATAGTA ACTGGGCATC
3061 TGTTAACTTT TACGACGTTA GGTTAGATAC TGATGTTACA GATTATAATA ATGTTACAAT
3121 AAAATACATG ACAGGATGTG ATATTTTTCC TCATATAACT CTTGGAATAG CAAATATGGA
3181 TCAATGTGAT AGATTTGAAA ATTTCAAAAA GCAAATAACT GATCAAGATT TACAGACTAT
3241 TTCTATAGTC TGTAAAGAAG AGATGTGTTT TCCTCAGAGT AACGCCTCTA AACAGTTGGG
3301 AGCGAAAGGA TGCGCTGTAG TTATGAAACT GGAGGTATCT GATGAACTTA GAGCCCTAAG
3361 AAATGTTCTG CTGAATGCGG TACCCTGTTC GAAGGACGTG TTTGGTGATA TCACAGTAGA
3421 TAATCCGTGG AATCCTCACA TAACAGTAGG ATATGTTAAG GAGGACGATG TCGAAAACAA
3481 GAAACGCCTA ATGGAGTGCA TGTCCAAGTT TAGGGGGCAA GAAATACAAG TTCTAGGATG
3541 GTATTAATAA GTATCTAAGT ATTTGGTATA ATTTATTAAA TAGTATAATT ATAACAAATA
3601 ATAAATAACA TGATAACGGT TTTTATTAGA ATAAAATAGA GATAATATCA TAATGATATA
3661 TAATACTTCA TTACCAGAAA TGAGTAATGG AAGACTTATA AATGAACTGC ATAAAGCTAT
3721 AAGGTATAGA GATATAAATT TAGTAAGGTA TATACTTAAA AAATGCAAAT ACAATAACGT
3781 AAATATACTA TCAACGTCTT TGTATTTAGC CGTAAGTATT TCTGATATAG AAATGGTAAA
3841 ATTATTACTA GAACACGGTG CCGATATTTT AAAATGTAAA AATCCTCCTC TTCATAAAGC
3901 TGCTAGTTTA GATAATACAG AAATTGCTAA ACTACTAATA GATTCTGGCG CTGACATAGA
3961 ACAGATACAT TCTGGAAATA GTCCGTTATA TATTTCTGTA TATAGAAACA ATAAGTCATT
4021 AACTAGATAT TTATTAAAAA AAGGTGTTAA TTGTAATAGA TTCTTTCTAA ATTATTACGA
4081 TGTACTGTAT GATAAGATAT CTGATGATAT GTATAAAATA TTTATAGATT TTAATATTGA
4141 TCTTAATATA CAAACTAGAA ATTTTGAAAC TCCGTTACAT TACGCTATAA AGTATAAGAA
4201 TATAGATTTA ATTAGGATAT TGTTAGATAA TAGTATTAAA ATAGATAAAA GTTTATTTTT
4261 GCATAAACAG TATCTCATAA AGGCACTTAA AAATAATTGT AGTTACGATA TAATAGCGTT
4321 ACTTATAAAT CACGGAGTGC CTATAAACGA ACAAGATGAT TTAGGTAAAA CCCCATTACA
4381 TCATTCGGTA ATTAATAGAA GAAAAGATGT AACAGCACTT CTGTTAAATC TAGGAGCTGA
4441 TATAAACGTA ATAGATGACT GTATGGGCAG TCCCTTACAT TACGCTGTTT CACGTAACGA
4501 TATCGAAACA ACAAAGACAC TTTTAGAAAG AGGATCTAAT GTTAATGTGG TTAATAATCA
4561 TATAGATACC GTTCTAAATA TAGCTGTTGC ATCTAAAAAC AAAACTATAG TAAACTTATT
4621 ACTGAAGTAC GGTACTGATA CAAAGTTGGT AGGATTAGAT AAACATGTTA TTCACATAGC
4681 TATAGAAATG AAAGATATTA ATATACTGAA TGCGATCTTA TTATATGGTT GCTATGTAAA
4741 CGTCTATAAT CATAAAGGTT TCACTCCTCT ATACATGGCA GTTAGTTCTA TGAAAACAGA
4801 ATTTGTTAAA CTCTTACTTG ACCACGGTGC TTACGTAAAT GCTAAAGCTA AGTTATCTGG
4861 AAATACTCCT TTACATAAAG CTATGTTATC TAATAGTTTT AATAATATAA AATTACTTTT
4921 ATCTTATAAC GCCGACTATA ATTCTAAA TAATCACGGT AATACGCCTC TAACTTGTGT
4981 TAGCTTTTTA GATGACAAGA TAGCTATTAT GATAATATCT AAAATGATGT TAGAAATATC
5041 TAAAAATCCT GAAATAGCTA ATTCAGAAGG TTTTATAGTA AACATGGAAC ATATAAACAG
5101 TAATAAAAGA CTACTATCTA TAAAAGAATC ATGCGAAAAA GAACTAGATG TTATAACACA
5161 TATAAAGTTA AATTCTATAT ATTCTTTTAA TATCTTTCTT GACAATAACA TAGATCTTAT
5221 GGTAAAGTTC GTAACTAATC CTAGAGTTAA TAAGATACCT GCATGTATAC GTATATATAG
5281 GGAATTAATA CGGAAAAATA AATCATTAGC TTTTCATAGA CATCAGCTAA TAGTTAAAGC
5341 TGTAAAAGAG AGTAAGAATC TAGGAATAAT AGGTAGGTTA CCTATAGATA TCAAACATAT
5401 AATAATGGAA CTATTAAGTA ATAATGATTT ACATTCTGTT ATCACCAGCT GTTGTAACCC
5461 AGTAGTATAA AGTGATTTTA TTCAATTACG AAGATAAACA TTAAATTTGT TAACAGATAT
5521 GAGTTATGAG TATTTAACTA AAGTTACTTT AGGTACAAAT AAAATATTAT GTAATATAAT
5581 AGAAAATTAT CTTGAGTCTT CATTTCCATC ACCGTCTAAA TTTATTATTA AAACCTTATT
5641 ATATAAGGCT GTTGAGTTTA GAAATGTAAA TGCTGTAAAA AAAATATTAC AGAATGATAT
5701 TGAATATGTT AAAGTAGATA GTCATGGTGT CTCGCCTTTA CATATTATAG CTATGCCTTC
5761 AAATTTTTCT CTCATAGACG CTGACATGTA TTCAGAATTT AATGAAATTA GTAATAGACT
```

FIG. 14B

```
5821 TCAAAAATCT AAAGATAGTA ACGAATTTCA ACGAGTTAGT CTACTAAGGA CAATTATAGA
5881 ATATGGTAAT GATAGTGATA TTAATAAGTG TCTAACATTA GTAAAAACGG ATATACAGAG
5941 TAACGAAGAG ATAGATATTA TAGATCTTTT GATAAATAAA GGAATAGATA TAAATATTAA
6001 AGACGATTTA GGAAACACAG CTTTGCATTA CTCGTGTGAT TATGCTAAGG GATCAAAGAT
6061 AGCTAAAAAG TTACTAGATT GTGGAGCAGA TCCTAACATA GTTAATGATT TAGGTGTTAC
6121 ACCACTAGCG TGTGCCGTTA ATACTTGCAA CGAGATACTA GTAGATATTC TGTTAAATAA
6181 TGATGCGAAT CCTGATTCAT CTTCCTCATA TTTTTTAGGT ACTAATGTGT TACATACAGC
6241 CGTAGGTACC GGTAATATAG ATATTGTAAG ATCTTTACTT ACGGCTGGTG CCAATCCTAA
6301 TGTAGGAGAT AAATCTGGAG TTACTCCTTT GCACGTTGCT GCAGCTGATA AAGACAGTTA
6361 TCTGTTAATG GAGATGCTAC TAGATAGCGG GGCAGATCCA AATATAAAAT GCGCAAACGG
6421 TTTTACTCCT TTGTTTAATG CAGTATATGA TCATAACCGT ATAAAGTTAT TATTTCTTTA
6481 CGGGGCTGAT ATCAATATTA CTGACTCTTA CGGAAATACT CCTCTTACTT ATATGACTAA
6541 TTTTGATAAT AAATATGTAA ATTCAATAAT TATCTTACAA ATATATCTAC TTAAAAAAGA
6601 ATATAACGAT GAAAGATTGT TTCCACCTGG TATGATAAAA AATTTAAACT TTATAGAATC
6661 AAACGATAGT CTTAAAGTTA TAGCTAAAAA GTGTAATTCG TTAATACGCT ATAAGAAAAA
6721 TAAAGACATA GATGCAGATA ACGTATTATT GGAGCTTTTA GAGGAAGAGG AAGAAGATGA
6781 AATAGACAGA TGGCATACTA CATGTAAAAT ATCTTAAATA GTAATTAAAT CATTGAAATA
6841 TTAACTTACA AGATGATCGA GGTCACTTAT TATACTCTTT AATAATGGGT ACAAAGAGTA
6901 TTCATACGTT AGTTAAATCT AACGATGTAA TACGTGTTCG TGAATTAATA AAGGATGATA
6961 GATGTTTGAT AAATAAAAGA AATAGAAGAA ATCAGTCACC TGTATATATA GCTATATACA
7021 AAGGACTTTA TGAAATGACT GAAATGTTAT TGCTAAATAA TGCAAGTCTA GATACTAAAA
7081 TACCTTCTTT AATTATAGCA GCTAAAAATA ATGACTTACC TATGATAAAA TTATTGATAC
7141 AATACGGGGC AAAATTAAAT GATATTTATT TAAGGGACAC AGCATTAATG ATAGCTCTCA
7201 GAAATGGTTA CCTAGATATA GCTGAATATT TACTTTCATT AGGAGCAGAA TTTGTTAAAT
7261 ACAGACATAA GGTAATATAT AAATATCTAT CAAAAGATGC GTATGAATTA CTTTTTAGAT
7321 TTAATTATGA CGTTAATATA ATAGATTGAG A
```

FIG.14C

```
  1 AAAAAGGATCCGGGTTAATTAATTAGTCATCAGGCAGGGCGAGAACGAGACTATCTGCTC
 61 GTTAATTAATTAGAGCTTCTTTATTCTATACTTAAAAAGTGAAAATAAATACAAAGGTTC
121 TTGAGGGTTGTGTTAAATTGAAAGCGAGAAATAATCATAAATTATTTCATTATCGCGATA
181 TCCGTTAAGTTTGTATCGTAATGAGCACTGAAAGCATGATCCGGGACGTGGAGCTGGCCG
241 AGGAGGCGCTCCCCAAGAAGACAGGGGGGCCCCAGGGCTCCAGGCGGTGCTTGTTCCTCA
301 GCCTCTTCTCCTTCCTGATCGTGGCAGGCGCCACCACGCTCTTCTGCCTGCTGCACTTTG
361 GAGTGATCGGCCCCCAGAGGGAAGAGTCCCCCAGGGACCTCTCTCTAATCAGCCCTCTGG
421 CCCAGGCAGTCAGATCATCTTCTCGAACCCCGAGTGACAAGCCTGTAGCCCATGTTGTAG
481 CAAACCCTCAAGCTGAGGGGCAGCTCCAGTGGCTGAACCGCCGGGCCAATGCCCTCCTGG
541 CCAATGGCGTGGAGCTGAGAGATAACCAGCTGGTGGTGCCATCAGAGGGCCTGTACCTCA
601 TCTACTCCCAGGTCCTCTTCAAGGGCCAAGGCTGCCCCTCCACCCATGTGCTCCTCACCC
661 ACACCATCAGCCGCATCGCCGTCTCCTACCAGACCAAGGTCAACCTCCTCTCTGCCATCA
721 AGAGCCCCTGCCAGAGGGAGACCCCAGAGGGGGCTGAGGCCAAGCCCTGGTATGAGCCCA
781 TCTATCTGGGAGGGGTCTTCCAGCTGGAGAAGGGTGACCGACTCAGCGCTGAGATCAATC
841 GGCCCGACTATCTCGACTTTGCCGAGTCTGGGCAGGTCTACTTTGGGATCATTGCCCTGT
901 GATTTTTATTCTAGAATCGATCCCGGGTTTTTATGACTAGTTAATCACGGCCGCTTATAA
961 AGATC
```

FIG. 15

```
  1 GATCTCAAGCCGTCTTTTCTGGTGTAATAAAAATTAATTAATTACTCGAGCCCAGCTTGA
 61 TTCTTTATTCTATACTTAAAAAGTGAAAATAAATACAAAGGTTCTTGAGGGTTGTGTTAA
121 ATTGAAAGCGAGAAATAATCATAAATTATTTCATTATCGCGATATCCGTTAAGTTTGTAT
181 CGTAATGAGCACTGAAAGCATGATCCGGGACGTGGAGCTGGCCGAGGAGGCGCTCCCCAA
241 GAAGACAGGGGGGCCCCAGGGCTCCAGGCGGTGCTTGTTCCTCAGCCTCTTCTCCTTCCT
301 GATCGTGGCAGGCGCCACCACGCTCTTCTGCCTGCTGCACTTTGGAGTGATCGGCCCCCA
361 GAGGGAAGAGTCCCCCAGGGACCTCTCTCTAATCAGCCCTCTGGCCCAGGCAGTCAGATC
421 ATCTTCTCGAACCCCGAGTGACAAGCCTGTAGCCCATGTTGTAGCAAACCCTCAAGCTGA
481 GGGGCAGCTCCAGTGGCTGAACCGCCGGGCCAATGCCCTCCTGGCCAATGGCGTGGAGCT
541 GAGAGATAACCAGCTGGTGGTGCCATCAGAGGGCCTGTACCTCATCTACTCCCAGGTCCT
601 CTTCAAGGGCCAAGGCTGCCCCTCCACCCATGTGCTCCTCACCCACACCATCAGCCGCAT
661 CGCCGTCTCCTACCAGACCAAGGTCAACCTCCTCTCTGCCATCAAGAGCCCCTGCCAGAG
721 GGAGACCCCAGAGGGGGCTGAGGCCAAGCCCTGGTATGAGCCCATCTATCTGGGAGGGGT
781 CTTCCAGCTGGAGAAGGGTGACCGACTCAGCGCTGAGATCAATCGGCCCGACTATCTCGA
841 CTTTGCCGAGTCTGGGCAGGTCTACTTTGGGATCATTGCCCTGTGATTTTTATTGGGAGA
901 TCTAATTTAATTTAATTTATATAACTTATTTTTTGAATATACTTTTA
```

FIG. 16

```
   1 GATTAAAGAAAGTTACTCTGAGACACAAAAGAGGTAGCTGAAGTGGTACTCTCAAAGGTA
  61 CCCCCGGGTTAATTAATTAGTCATCAGGCAGGGCGAGAACGAGACTATCTGCTCGTTAAT
 121 TAATTAGGTCGACGGATCCCCGGGTTCTTTATTCTATACTTAAAAAGTGAAAATAAATAC
 181 AAAGGTTCTTGAGGGTTGTGTTAAATTGAAAGCGAGAAATAATCATAAATTATTTCATTA
 241 TCGCGATATCCGTTAAGTTTGTATCGTAATGGAGGAGCCGCAGTCAGATCCTAGCGTCGA
 301 GCCCCTCTGAGTCAGGAAACATTTTCAGACCTATGGAAACTACTTCCTGAAAACAACGT
 361 TCTGTCCCCTTGCCGTCCCAAGCAATGGATGATTTGATGCTGTCCCCGGACGATATTGA
 421 ACAATGGTTCACTGAAGACCCAGGTCCAGATGAAGCTCCCAGAATGCCAGAGGCTGCTCC
 481 CCGCGTGGCCCCTGGACCAGCAGCTCCTACACCGGCGGCCCCTGCACCAGCCCCCTCCTG
 541 GCCCCTGTCATCTTCTGTCCCTTCCCAGAAAACCTACCAGGGCAGCTACGGTTTCCGTCT
 601 GGGCTTCTTGCATTCTGGGACAGCCAAGTCTGTGACTTGCACGTACTCCCCTGCCCTCAA
 661 CAAGATGTTTTGCCAACTGGCCAAGACCTGCCCTGTGCAGCTGTGGGTTGATTCCACACC
 721 CCCGCCCGGCACCCGCGTCCGCGCCATGGCGCATCTACAAGCAGTCACAGCACATGACGGA
 781 GGTTGTGAGGCGCTGCCCCCACCATGAGCGCTGCTCAGATAGCGATGGTCTGGCCCCTCC
 841 TCAGCATCTTATCCGAGTGGAAGGAAATTTGCGTGTGGAGTATTTGGATGACAGAAACAC
 901 TTTTCGACATAGTGTGGTGGTGCCCTATGAGCCGCCTGAGGTTGGCTCTGACTGTACCAC
 961 CATCCACTACAACTACATGTGTAACAGTTCCTGCATGGGCGGCATGAACCGGAGGCCCAT
1021 CCTCACCATCATCACACTGGAAGACTCCAGTGGTAATCTACTGGGACGGAACAGCTTTGA
1081 GGTGCGTGTTTGTGCCTGTCCTGGGAGAGACCGGCGCACAGAGGAAGAGAATCTCCGCAA
1141 GAAAGGGGAGCCTCACCACGAGCTGCCCCCAGGGAGCACTAAGCGAGCACTGCCCAACAA
1201 CACCAGCTCCTCTCCCCAGCCAAAGAAGAAACCACTGGATGGAGAATATTTCACCCTTCA
1261 GATCCGTGGGCGTGAGCGCTTCGAGATGTTCCGAGAGCTGAATGAGGCCTTGGAACTCAA
1321 GGATGCCCAGGCTGGGAAGGAGCCAGGGGGGAGCAGGGCTCACTCCAGCCACCTGAAGTC
1381 CAAAAAGGGTCAGTCTACCTCCCGCCATAAAAAACTCATGTTCAAGACAGAAGGGCCTGA
1441 CTCAGACTGAACGCGTTTTTATCCCGGGCTCGAGTCTAGAATCGATCCCGGGTTTTTATG
1501 ACTAGTTAATCA
```

FIG.17

```
   1 GGTACGTGACTAATTAGCTATAAAAAGGATCTTAATTAATTAGTCATCAGGCAGGGCGAG
  61 AACGAGACTATCTGCTCGTTAATTAATTAGGTCGACGGATCCCCGGGTTCTTTATTCTA
 121 TACTTAAAAAGTGAAAATAAATACAAAGGTTCTTGAGGGTTGTGTTAAATTGAAAGCGAG
 181 AAATAATCATAAATTATTTCATTATCGCGATATCCGTTAAGTTTGTATCGTAATGGAGGA
 241 GCCGCAGTCAGATCCTAGCGTCGAGCCCCTCTGAGTCAGGAAACATTTTCAGACCTATG
 301 GAAACTACTTCCTGAAAACAACGTTCTGTCCCCTTGCCGTCCCAAGCAATGGATGATTT
 361 GATGCTGTCCCCGGACGATATTGAACAATGGTTCACTGAAGACCCAGGTCCAGATGAAGC
 421 TCCCAGAATGCCAGAGGCTGCTCCCCGCGTGGCCCCTGGACCAGCAGCTCCTACACCGGC
 481 GGCCCCTGCACCAGCCCCCTCCTGGCCCCTGTCATCTTCTGTCCCTTCCCAGAAAACCTA
 541 CCAGGGCAGCTACGGTTTCCGTCTGGGCTTCTTGCATTCTGGGACAGCCAAGTCTGTGAC
 601 TTGCACGTACTCCCCTGCCCTCAACAAGATGTTTTGCCAACTGGCCAAGACCTGCCCTGT
 661 GCAGCTGTGGGTTGATTCCACACCCCCGCCCGGCACCCGCGTCCGCGCCATGGCCATCTA
 721 CAAGCAGTCACAGCACATGACGGAGGTTGTGAGGCGCTGCCCCCACCATGAGCGCTGCTC
 781 AGATAGCGATGGTCTGGCCCCTCCTCAGCATCTTATCCGAGTGGAAGGAAATTTGCGTGT
 841 GGAGTATTTGGATGACAGAAACACTTTTCGACATAGTGTGGTGGTGCCCTATGAGCCGCC
 901 TGAGGTTGGCTCTGACTGTACCACCATCCACTACAACTACATGTGTAACAGTTCCTGCAT
 961 GGGCGGCATGAACCGGAGGCCCATCCTCACCATCATCACACTGGAAGACTCCAGTGGTAA
1021 TCTACTGGGACGGAACAGCTTTGAGGTGCGTGTTTGTGCCTGTCCTGGGAGAGACCGGCG
1081 CACAGAGGAAGAGAATCTCCGCAAGAAAGGGGAGCCTCACCACGAGCTGCCCCCAGGGAG
1141 CACTAAGCGAGCACTGCCCAACAACACCAGCTCCTCTCCCCAGCCAAAGAAGAAACCACT
1201 GGATGGAGAATATTTCACCCTTCAGATCCGTGGGCGTGAGCGCTTCGAGATGTTCCGAGA
1261 GCTGAATGAGGCCTTGGAACTCAAGGATGCCCAGGCTGGGAAGGAGCCAGGGGGGAGCAG
1321 GGCTCACTCCAGCCACCTGAAGTCCAAAAAGGGTCAGTCTACCTCCCGCCATAAAAAACT
1381 CATGTTCAAGACAGAAGGGCCTGACTCAGACTGAACGCGTTTTTATCCCGGGCTCGAGTC
1441 TAGAATCGATCCCGGGTTTTTATGACTAGTTAATCACGGCCGC
```

FIG.18

```
   1 AAAAAGGATCCGGGTTAATTAATTAGTCATCAGGCAGGGCGAGAACGAGACTATCTGCTC
  61 GTTAATTAATTAGAGCTTCTTTTATTCTATACTTAAAAAGTGAAAATAAATACAAAGGTTC
 121 TTGAGGGTTGTGTTAAATTGAAAGCGAGAAATAATCATAAATTATTTCATTATCGCGATA
 181 TCCGTTAAGTTTGTATCGTAATGTCTCTTGAGCAGAGGAGTCTGCACTGCAAGCCTGAGG
 241 AAGCCCTTGAGGCCCAACAAGAGGCCCTGGGCCTGGTGTGTGTGCAGGCTGCCACCTCCT
 301 CCTCCTCTCCTCTGGTCCTGGGCACCCTGGAGGAGGTGCCCACTGCTGGGTCAACAGATC
 361 CTCCCCAGAGTCCTCAGGGAGCCTCCGCCTTTCCCACTACCATCAACTTCACTCGACAGA
 421 GGCAACCCAGTGAGGGTTCCAGCAGCCGTGAAGAGGAGGGGCCAAGCACCTCTTGTATCC
 481 TGGAGTCCTTGTTCCGAGCAGTAATCACTAAGAAGGTGGCTGATTTGGTTGGTTTTCTGC
 541 TCCTCAAATATCGAGCCAGGGAGCCAGTCACAAAGGCAGAAATGCTGGAGAGTGTCATCA
 601 AAAATTACAAGCACTGTTTTCCTGAGATCTTCGGCAAAGCCTCTGAGTCCTTGCAGCTGG
 661 TCTTTGGCATTGACGTGAAGGAAGCAGACCCCACCGGCCACTCCTATGTCCTTGTCACCT
 721 GCCTAGGTCTCTCCTATGATGGCCTGCTGGGTGATAATCAGATCATGCCCAAGACAGGCT
 781 TCCTGATAATTGTCCTGGTCATGATTGCAATGGAGGGCGGCCATGCTCCTGAGGAGGAAA
 841 TCTGGGAGGAGCTGAGTGTGATGGAGGTGTATGATGGGAGGGAGCACAGTGCCTATGGGG
 901 AGCCCAGGAAGCTGCTCACCCAAGATTTGGTGCAGGAAAAGTACCTGGAGTACGGCAGGT
 961 GCCGGACAGTGATCCCGCACGCTATGAGTTCCTGTGGGGTCCAAGGGCCCTCGCTGAAAC
1021 CAGCTATGTGATTTTTATTCTAGAATCGATCCCGGGTTTTTATGACTAGTTAATCACGGC
1081 CGCTTATAAGATC
```

FIG. 19

```
   1 ATAAATCACTTTTTTATACTAATATTTAATTAATTAAGCTTGGTACCCTCGAAGCTTCTTT
  61 ATTCTATACTTAAAAAGTGAAAATAAATACAAAGGTTCTTGAGGGTTGTGTTAAATTGAA
 121 AGCGAGAAATAATCATAAATTATTTCATTATCGCGATATCCGTTAAGTTTGTATCGTAAT
 181 GTCTCTTGAGCAGAGGAGTCTGCACTGCAAGCCTGAGGAAGCCCTTGAGGCCCAACAAGA
 241 GGCCCTGGGCCTGGTGTGTGTGCAGGCTGCCACCTCCTCCTCCTCTCCTCTGGTCCTGGG
 301 CACCCTGGAGGAGGTGCCCACTGCTGGGTCAACAGATCCTCCCCAGAGTCCTCAGGGAGC
 361 CTCCGCCTTTCCCACTACCATCAACTTCACTCGACAGAGGCAACCCAGTGAGGGTTCCAG
 421 CAGCCGTGAAGAGGAGGGGCCAAGCACCTCTTGTATCCTGGAGTCCTTGTTCCGAGCAGT
 481 AATCACTAAGAAGGTGGCTGATTTGGTTGGTTTTCTGCTCCTCAAATATCGAGCCAGGGA
 541 GCCAGTCACAAAGGCAGAAATGCTGGAGAGTGTCATCAAAAATTACAAGCACTGTTTTCC
 601 TGAGATCTTCGGCAAAGCCTCTGAGTCCTTGCAGCTGGTCTTTGGCATTGACGTGAAGGA
 661 AGCAGACCCCACCGGCCACTCCTATGTCCTTGTCACCTGCCTAGGTCTCTCCTATGATGG
 721 CCTGCTGGGTGATAATCAGATCATGCCCAAGACAGGCTTCCTGATAATTGTCCTGGTCAT
 781 GATTGCAATGGAGGGCGGCCATGCTCCTGAGGAGGAAATCTGGGAGGAGCTGAGTGTGAT
 841 GGAGGTGTATGATGGGAGGGAGCACAGTGCCTATGGGGAGCCCAGGAAGCTGCTCACCCA
 901 AGATTTGGTGCAGGAAAAGTACCTGGAGTACGGCAGGTGCCGGACAGTGATCCCGCACGC
 961 TATGAGTTCCTGTGGGGTCCAAGGGCCCTCGCTGAAACCAGCTATGTGATTTTTATTCTA
1021 GAACTAGTGGATCCCCCGGGTAGCTAGCTAATTTTTCTTTTACGTATTATATATGTAATA
1081 AACG
```

```
   1 GAAGCAATAG CTTGTATGCT TTTTATTTGA TTAACTAGTC ATAAAAATCG GGATCCTTCT
  61 TTATTCTATA CTTAAAAAGT GAAAATAAAT ACAAAGGTTC TTGAGGGTTG TGTTAAATTG
 121 AAAGCGAGAA ATAATCATAA ATTATTTCAT TATCGCGATA TCCGTTAAGT TTGTATCGTA
 181 ATGGAGTCTC CCTCGGCCCC TCCCCACAGA TGGTGCATCC CCTGGCAGAG GCTCCTGCTC
 241 ACAGCCTCAC TTCTAACCTT CTGGAACCCG CCCACCACTG CCAAGCTCAC TATTGAATCC
 301 ACGCCGTTCA ATGTCGCAGA GGGGAAGGAG GTGCTTCTAC TTGTCCACAA TCTGCCCCAG
 361 CATCTTTTTG GCTACAGCTG GTACAAAGGT GAAAGAGTGG ATGGCAACCG TCAAATTATA
 421 GGATATGTAA TAGGAACTCA ACAAGCTACC CCAGGGCCCG CATACAGTGG TCGAGAGATA
 481 ATATACCCCA ATGCATCCCT GCTGATCCAG AACATCATCC AGAATGACAC AGGATTCTAC
 541 ACCCTACACG TCATAAAGTC AGATCTTGTG AATGAAGAAG CAACTGGCCA GTTCCGGGTA
 601 TACCCGGAGC TGCCCAAGCC CTCCATCTCC AGCAACAACT CCAAACCCGT GGAGGACAAG
 661 GATGCTGTGG CCTTCACCTG TGAACCTGAG ACTCAGGACG CAACCTACCT GTGGTGGGTA
 721 AACAATCAGA GCCTCCCGGT CAGTCCAGG CTGCAGCTGT CCAATGGCAA CAGGACCCTC
 781 ACTCTATTCA ATGTCACAAG AAATGACACA GCAAGCTACA AATGTGAAAC CCAGAACCCA
 841 GTGAGTGCCA GGCGCAGTGA TTCAGTCATC CTGAATGTCC TCTATGGCCC GGATGCCCCC
 901 ACCATTTCCC CTCTAAACAC ATCTTACAGA TCAGGGGAAA ATCTGAACCT CTCCTGCCAC
 961 GCAGCCTCTA ACCCACCTGC ACAGTACTCT TGGTTTGTCA ATGGGACTTT CCAGCAATCC
1021 ACCCAAGAGC TCTTTATCCC CAACATCACT GTGAATAATA GTGGATCCTA TACGTGCCAA
1081 GCCCATAACT CAGACACTGG CCTCAATAGG ACCACAGTCA CGACGATCAC AGTCTATGCA
1141 GAGCCACCCA AACCCTTCAT CACCAGCAAC AACTCCAACC CCGTGGAGGA TGAGGATGCT
1201 GTAGCCTTAA CCTGTGAACC TGAGATTCAG AACACAACCT ACCTGTGGTG GGTAAATAAT
1261 CAGAGCCTCC CGGTCAGTCC CAGGCTGCAG CTGTCCAATG ACAACAGGAC CCTCACTCTA
1321 CTCAGTGTCA CAAGGAATGA TGTAGGACCC TATGAGTGTG GAATCCAGAA CGAATTAAGT
1381 GTTGACCACA GCGACCCAGT CATCCTGAAT GTCCTCTATG GCCCAGACGA CCCCACCATT
1441 TCCCCCTCAT ACACCTATTA CCGTCCAGGG GTGAACCTCA GCCTCTCCTG CCATGCAGCC
1501 TCTAACCCAC CTGCACAGTA TTCTTGGCTG ATTGATGGGA ACATCCAGCA ACACACACAA
1561 GAGCTCTTTA TCTCCAACAT CACTGAGAAG AACAGCGGAC TCTATACCTG CCAGGCCAAT
1621 AACTCAGCCA GTGGCCACAG CAGGACTACA GTCAAGACAA TCACAGTCTC TGCGGAGCTG
1681 CCCAAGCCCT CCATCTCCAG CAACAACTCC AAACCCGTGG AGGACAAGGA TGCTGTGGCC
1741 TTCACCTGTG AACCTGAGGC TCAGAACACA ACCTACCTGT GGTGGGTAAA TGGTCAGAGC
1801 CTCCCAGTCA GTCCCAGGCT GCAGCTGTCC AATGGCAACA GGACCCTCAC TCTATTCAAT
1861 GTCACAAGAA ATGACGCAAG AGCCTATGTA TGTGGAATCC AGAACTCAGT GAGTGCAAAC
1921 CGCAGTGACC CAGTCACCCT GGATGTCCTC TATGGCCCGG ACACCCCCAT CATTTCCCCC
1981 CCAGACTCGT CTTACCTTTC GGGAGCGAAC CTCAACCTCT CCTGCCACTC GGCCTCTAAC
2041 CCATCCCCGC AGTATTCTTG GCGTATCAAT GGGATACCGC AGCAACACAC ACAAGTTCTC
2101 TTTATCGCCA AAATCACGCC AAATAATAAC GGGACCTATG CCTGTTTTGT CTCTAACTTG
2161 GCTACTGGCC GCAATAATTC CATAGTCAAG AGCATCACAG TCTCTGCATC TGGAACTTCT
2221 CCTGGTCTCT CAGCTGGGGC CACTGTCGGC ATCATGATTG GAGTGCTGGT TGGGGTTGCT
2281 CTGATATAGT TTTTATCTCG AGGAATTCCT GCAGCCCGGG GTGACCTAAT TAATTAAGCT
2341 ACAAATAGTT TCGTTTTCAC CTTGTCTAAT AACTAATTAA TTAACCGGGT TTTTATAGCT
2401 AATTAGTCAA ATGTGAGTTA ATATTAGTAT ACTA
```

FIG.22

```
   1 TAAAAATAAA TCACTTTTTA TACTAATATT TAATTAATTA AGCTTGGTAC CCTCGAAGCT
  61 TCTTTATTCT ATACTTAAAA AGTGAAAATA AATACAAAGG TTCTTGAGGG TTGTGTTAAA
 121 TTGAAAGCGA GAAATAATCA TAAATTATTT CATTATCGCG ATATCCGTTA AGTTTGTATC
 181 GTAATGGAGT CTCCCTCGGC CCCTCCCCAC AGATGGTGCA TCCCCTGGCA GAGGCTCCTG
 241 CTCACAGCCT CACTTCTAAC CTTCTGGAAC CCGCCCACCA CTGCCAAGCT CACTATTGAA
 301 TCCACGCCGT TCAATGTCGC AGAGGGGAAG GAGGTGCTTC TACTTGTCCA CAATCTGCCC
 361 CAGCATCTTT TTGGCTACAG CTGGTACAAA GGTGAAAGAG TGGATGGCAA CCGTCAAATT
 421 ATAGGATATG TAATAGGAAC TCAACAAGCT ACCCCAGGGC CGCATACAG TGGTCGAGAG
 481 ATAATATACC CCAATGCATC CCTGCTGATC CAGAACATCA TCCAGAATGA CACAGGATTC
 541 TACACCCTAC ACGTCATAAA GTCAGATCTT GTGAATGAAG AAGCAACTGG CCAGTTCCGG
 601 GTATACCCGG AGCTGCCCAA GCCCTCCATC TCCAGCAACA ACTCCAAACC CGTGGAGGAC
 661 AAGGATGCTG TGGCCTTCAC CTGTGAACCT GAGACTCAGG ACGCAACCTA CCTGTGGTGG
 721 GTAAACAATC AGAGCCTCCC GGTCAGTCCC AGGCTGCAGC TGTCCAATGG CAACAGGACC
 781 CTCACTCTAT TCAATGTCAC AAGAAATGAC ACAGCAAGCT ACAAATGTGA AACCCAGAAC
 841 CCAGTGAGTG CCAGGCGCAG TGATTCAGTC ATCCTGAATG TCCTCTATGG CCCGGATGCC
 901 CCCACCATTT CCCCTCTAAA CACATCTTAC AGATCAGGGG AAAATCTGAA CCTCTCCTGC
 961 CACGCAGCCT CTAACCCACC TGCACAGTAC TCTTGGTTTG TCAATGGGAC TTTCCAGCAA
1021 TCCACCCAAG AGCTCTTTAT CCCCAACATC ACTGTGAATA ATAGTGGATC CTATACGTGC
1081 CAAGCCCATA ACTCAGACAC TGGCCTCAAT AGGACCACAG TCACGACGAT CACAGTCTAT
1141 GCAGAGCCAC CCAAACCCTT CATCACCAGC AACAACTCCA ACCCCGTGGA GGATGAGGAT
1201 GCTGTAGCCT TAACCTGTGA ACCTGAGATT CAGAACACAA CCTACCTGTG GTGGGTAAAT
1261 AATCAGAGCC TCCCGGTCAG TCCCAGGCTG CAGCTGTCCA ATGACAACAG GACCCTCACT
1321 CTACTCAGTG TCACAAGGAA TGATGTAGGA CCCTATGAGT GTGGAATCCA GAACGAATTA
1381 AGTGTTGACC ACAGCGACCC AGTCATCCTG AATGTCCTCT ATGGCCCAGA CGACCCCACC
1441 ATTTCCCCCT CATACACCTA TTACCGTCCA GGGGTGAACC TCAGCCTCTC CTGCCATGCA
1501 GCCTCTAACC CACCTGCACA GTATTCTTGG CTGATTGATG GAACATCCA GCAACACACA
1561 CAAGAGCTCT TTATCTCCAA CATCACTGAG AAGAACAGCG GACTCTATAC CTGCCAGGCC
1621 AATAACTCAG CCAGTGGCCA CAGCAGGACT ACAGTCAAGA CAATCACAGT CTCTGCGGAG
1681 CTGCCCAAGC CCTCCATCTC CAGCAACAAC TCCAAACCCG TGGAGGACAA GGATGCTGTG
1741 GCCTTCACCT GTGAACCTGA GGCTCAGAAC ACAACCTACC TGTGGTGGGT AAATGGTCAG
1801 AGCCTCCCAG TCAGTCCCAG GCTGCAGCTG TCCAATGGCA ACAGGACCCT CACTCTATTC
1861 AATGTCACAA GAAATGACGC AAGAGCCTAT GTATGTGGAA TCCAGAACTC AGTGAGTGCA
1921 AACCGCAGTG ACCCAGTCAC CCTGGATGTC CTCTATGGGC CGGACACCCC CATCATTTCC
1981 CCCCAGACT CGTCTTACCT TTCGGGAGCG AACCTCAACC TCTCCTGCCA CTCGGCCTCT
2041 AACCCATCCC CGCAGTATTC TTGGCGTATC AATGGGATAC CGCAGCAACA CACACAAGTT
2101 CTCTTTATCG CCAAAATCAC GCCAAATAAT AACGGGACCT ATGCCTGTTT TGTCTCTAAC
2161 TTGGCTACTG GCCGCAATAA TTCCATAGTC AAGAGCATCA CAGTCTCTGC ATCTGGAACT
2221 TCTCCTGGTC TCTCAGCTGG GGCCACTGTC GGCATCATGA TTGGAGTGCT GGTTGGGGTT
2281 GCTCTGATAT AGTTTTTATC TCGAGGGATC CCCCGGGTAG CTAGCTAATT TTTCTTTTAC
2341 GTATTATAT
```

FIG.23

```
  1  ATGTACAGCATGCAGCTCGCATCCTGTGTCACATTGACACTTGTGCTCCTTGTCAACAGC
 61  GCACCCACTTCAAGCTCCACTTCAAGCTCTACAGCGGAAGCACAGCAGCAGCAGCAGCAG
121  CAGCAGCAGCAGCAGCAGCACCTGGAGCAGCTGTTGATGGACCTACAGGAGCTCCTGAGC
181  AGGATGGAGAATTACAGGAACCTGAAACTCCCCAGGATGCTCACCTTCAAATTTTACTTG
241  CCCAAGCAGGCCACAGAATTGAAAGATCTTCAGTGCCTAGAAGATGAACTTGGACCTCTG
301  CGGCATGTTCTGGATTTGACTCAAAGCAAAAGCTTTCAATTGGAAGATGCTGAGAATTTC
361  ATCAGCAATATCAGAGTAACTGTTGTAAAACTAAAGGGCTCTGACAACACATTTGAGTGC
421  CAATTCGATGATGAGTCAGCAACTGTGGTGGACTTTCTGAGGAGATGGATAGCCTTCTGT
481  CAAAGCATCATCTCAACAAGCCCTCAATAA
```

FIG.24

```
  1  ATGTACAGGATGCAACTCCTGTCTTGCATTGCACTAAGTCTTGCACTTGTCACAAACAGT
 61  GCACCTACTTCAAGTTCTACAAAGAAAACACAGCTACAACTGGAGCATTTACTTCTGGAT
121  TTACAGATGATTTTGAATGGAATTAATAATTACAAGAATCCCAAACTCACCAGGATGCTC
181  ACATTTAAGTTTTACATGCCCAAGAAGGCCACAGAACTGAAACATCTTCAGTGTCTAGAA
241  GAAGAACTCAAACCTCTGGAGGAAGTGCTAAATTTAGCTCAAAGCAAAAACTTTCACTTA
301  AGACCCAGGGACTTAATCAGCAATATCAACGTAATAGTTCTGGAACTAAAGGGATCTGAA
361  ACAACATTCATGTGTGAATATGCTGATGAGACAGCAACCATTGTAGAATTTCTGAACAGA
421  TGGATTACCTTTTGTCAAAGCATCATCTCAACACTGACTTGA
```

FIG.25

```
  1  ACATCATGCAGTGGTTAAACAAAAACATTTTTATTCTCAAATGAGATAAAGTGAAAATAT
 61  ATATCATTATATTACAAAGTACAATTATTTAGGTTTAATCATGAACGCTACACACTGCAT
121  CTTGGCTTTGCAGCTCTTCCTCATGGCTGTTTCTGGCTGTTACTGCCACGGCACAGTCAT
181  TGAAAGCCTAGAAAGTCTGAATAACTATTTTAACTCAAGTGGCATAGATGTGGAAGAAAA
241  GAGTCTCTTCTTGGATATCTGGAGGAACTGGCAAAAGGATGGTGACATGAAAATCCTGCA
301  GAGCCAGATTATCTCTTTCTACCTCAGACTCTTTGAAGTCTTGAAAGACAATCAGGCCAT
361  CAGCAACAACATAAGCGTCATTGAATCACACCTGATTACTACCTTCTTCAGCAACAGCAA
421  GGCGAAAAAGGATGCATTCATGAGTATTGCCAAGTTTGAGGTCAACAACCCACAGGTCCA
481  GCGCCAAGCATTCAATGAGCTCATCCGAGTGGTCCACCAGCTGTTGCCGGAATCCAGCCT
541  CAGGAAGCGGAAAAGGAGTCGCTGCTGATTCGGGTGGGGAAGAGATTGTCCCAATAA
```

FIG.26

```
  1  ACATCATGCAGTGGTTAAACAAAAACATTTTTATTCTCAAATGAGATAAAGTGAAAATAT
 61  ATATCATTATATTACAAAGTACAATTATTTAGGTTTAATCATGAAATATACAAGTTATAT
121  CTTGGCTTTTCAGCTCTGCATCGTTTGGGTTCTCTTGGCTGTTACTGCCAGGACCCATA
181  TGTAAAAGAAGCAGAAAACCTTAAGAAATATTTTAATGCAGGTCATTCAGATGTAGCGGA
241  TAATGGAACTCTTTTCTTAGGCATTTGAAGAATTGGAAAGAGGAGAGTGACAGAAAAT
301  AATGCAGAGCCAAATTGTCTCCTTTTACTTCAAACTTTTAAAAACTTTAAAGATGACCA
361  GAGCATCCAAAAGAGTGTGGAGACCATCAAGGAAGACATGAATGTCAAGTTTTTCAATAG
421  CAACAAAAGAAACGAGATGACTTCGAAAAGCTGACTAATTATTCGGTAACTGACTTGAA
481  TGTCCAACGCAAAGCAATACATGAACTCATCCAAGTGATGGCTGAACTGTCGCCAGCAGC
541  TAAAACAGGGAAGCGAAAAAGGAGTCAGATGCTGTTTCAAGGTCGAAGAGCATCCCAGTA
601  A
```

FIG.27

```
1     AAGCTTCTATCAAAAGTCTTAATGAGTTAGGTGTAGATAGTATAGATATTACTACAAAGG
61    TATTCATATTTCCTATCAATTCTAAAGTAGATGATATTAATAACTCAAAGATGATGATAG
121   TAGATAATAGATACGCTCATATAATGACTGCAAATTTGGACGGTTCACATTTTAATCATC
181   ACGCGTTCATAAGTTTCAACTGCATAGATCAAAATCTCACTAAAAAGATAGCCGATGTAT
241   TTGAGAGAGATTGGACATCTAACTACGCTAAAGAAATTACAGTTATAAATAATACATAAT
301   GGATTTGTTATCATCAGTTATATTTAACATAAGTACAATAAAAAGTATTAAATAAAAAT
361   ACTTACTTACGAAAAAATGTCATTATTACAAAAACTATATTTTACAGAACAATCTATAGT
421   AGAGTCCTTTAAGAGTTATAATTTAAAAGATAACCATAATGTAATATTTACCACATCAGA
481   TGATGATACTGTTGTAGTAATAAATGAAGATAATGTACTGTTATCTACAAGATTATTATC
541   ATTTGATAAAATTCTGTTTTTTAACTCCTTTAATAACGGTTTATCAAAATACGAAACTAT
601   TAGTGATACAATATTAGATATAGATACTCATAATTATTATATACCTAGTTCTTCTTCTTT
661   GTTAGATATTCTAAAAAAAAGAGCGTGTGATTTAGAATTAGAAGATCTAAATTATGCGTT
721   AATAGGAGACAATAGTAACTTATATTATAAAGATATGACTTACATGAATAATTGGTTATT
781   TACTAAAGGATTATTAGATTACAAGTTTGTATTATTGCGCGATGTAGATAAATGTTACAA
841   ACAGTATAATAAAAAGAATACTATAATAGATATAATACATCGCGATAACAGACAGTATAA
901   CATATGGGTTAAAAATGTTATAGAATACTGTTCTCCTGGCTATATATTATGGTTACATGA
961   TCTAAAAGCCGCTGCTGAAGATGATTGGTTAAGATACGATAACCGTATAAACGAATTATC
1021  TGCGGATAAAATTATACACTTTCGAGTTCATAGTTATATTAGAAAATAATATAAAACATTT
1081  ACGAGTAGGTACAATAATTGTACATCCAAACAAGATAATAGCTAATGGTACATCTAATAA
1141  TATACTTACTGATTTTCTATCTTACGTAGAAGAACTAATATATCATCATAATTCATCTAT
1201  AATATTGGCCGGATATTTTTTAGAATTCTTTGAGACCACTATTTTATCAGAATTTATTTC
1261  TTCATCTTCTGAATGGGTAATGAATAGTAACTGTTTAGTACACCTGAAAACAGGGTATGA
1321  AGCTATACTCTTTGATGCTAGTTTATTTTCCAACTCTCTACTAAAAGCAATTATGTAAA
1381  ATATTGGACAAAGAAAACTTTGCAGTATAAGAACTTTTTTAAAGACGGTAAACAGTTAGC
1441  AAAATATATAATTAAGAAAGATAGTCAGGTGATAGATAGAGTATGTTATTTACACGCAGC
1501  TGTATATAATCACGTAACTTACTTAATGGATACGTTTAAAATTCCTGGTTTTGATTTTAA
1561  ATTCTCCGGAATGATAGATATACTACTGTTTGGAATATTGCATAAGGATAATGAGAATAT
1621  ATTTTATCCGAAACGTGTTTCTGTAACTAATATAATATCAGAATCTATCTATGCAGATTT
1681  TTACTTTATATCAGATGTTAATAAATTCAGTAAAAAGATAGAATATAAAACTATGTTTCC
1741  TATACTCGCAGAAAACTACTATCCAAAAGGAAGGCCCTATTTTACACATACATCTAACGA
1801  AGATCTTCTGTCTATCTGTTTATGCGAAGTAACAGTTTGTAAAGATATAAAAAATCCATT
1861  ATTATATTCTAAAAAGGATATATCAGCAAAACGATTCATAGGTTTATTTACATCTGTCGA
1921  TATAAATACGGCTGTTGAGTTAAGAGGATATAAAATAAGAGTAATAGGATGTTTAGAATG
1981  GCCTGAAAAGATAAAAATATTTAATTCTAATCCTACATACATTAGATTATTACTAACAGA
2041  AAGACGTTTAGATATTCTACATTCCTATCTGCTTAAATTTAATATAACAGAGGATATAGC
2101  TACCAGAGATGGAGTCAGAAATAATTTACCTATAATTTCTTTTATCGTCAGTTATTGTAG
2161  ATCGTATACTTATAAATTACTAAATTGCCATATGTACAATTCGTGTAAGATAACAAAGTG
2221  TAAATATAATCAGGTAATATATAATCCTATATAGGAGTATATATAATTGAAAAGTAAAA
2281  TATAAATCATATAATAATGAAACGAAATATCAGTAATAGACAGGAACTGGCAGATTCTTC
2341  TTCTAATGAAGTAAGTACTGCTAAATCTCCAAAATTAGATAAAAATGATACAGCAAATAC
2401  AGCTTCATTCAACGAATTACCTTTTAATTTTTCAGACACACCTTATTACAAACTAACTA
2461  AGTCAGATGATGAGAAAGTAAATATAAATTTAACTTATGGGTATAATATAATAAAGATTC
2521  ATGATATTAATAATTTACTTAACGATGTTAATAGACTTATTCCATCAACCCCTTCAAACC
2581  TTTCTGGATATTATAAAATACCAGTTAATGATATTAAAATAGATTGTTTAAGAGATGTAA
2641  ATAATTATTTGGAGGTAAAGGATATAAAATTAGTCTATCTTTCACATGGAAATGAATTAC
2701  CTAATATTAATAATTATGATAGGAATTTTTAGGATTTACAGCTGTTATATGTATCAACA
2761  ATACAGGCAGATCTATGGTTATGGTAAAACACTGTAACGGGAAGCAGCATTCTATGGTAA
2821  CTGGCCTATGTTTAATAGCCAGATCATTTTACTCTATAAACATTTTACCACAAATAATAG
2881  GATCCTCTAGATATTTAATATTATATCTAACAACAACAAAAAAATTTAACGATGTATGGC
2941  CAGAAGTATTTTCTACTAATAAAGATAAAGATAGTCTATCTTATCTACAAGATATGAAAG
3001  AAGATAATCATTTAGTAGTAGCTACTAATATGGAAAGAAATGTATACAAAAACGTGGAAG
3061  CTT
```

FIG.28

```
1    GAGCTCGCGGCCGCCTATCAAAAGTCTTAATGAGTTAGGTGTAGATAGTATAGATATTAC
61   TACAAAGGTATTCATATTTCCTATCAATTCTAAAGTAGATGATATTAATAACTCAAAGAT
121  GATGATAGTAGATAATAGATACGCTCATATAATGACTGCAAATTTGGACGGTTCACATTT
181  TAATCATCACGCGTTCATAAGTTTCAACTGCATAGATCAAAATCTCACTAAAAAGATAGC
241  CGATGTATTTGAGAGAGATTGGACATCTAACTACGCTAAAGAAATTACAGTTATAAATAA
301  TACATAATGGATTTTGTTATCATCAGTTATATTTAACATAAGTACAATAAAAAGTATTAA
361  ATAAAAATACTTACTTACGAAAAATGACTAATTAGCTATAAAAACCCGGGCTGCAGCTCG
421  AGGAATTCTTTTTATTGATTAACTAGTCAAATGAGTATATATAATTGAAAAGTAAAATA
481  TAAATCATATAATAATGAAACGAAATATCAGTAATAGACAGGAACTGGCAGATTCTTCTT
541  CTAATGAAGTAAGTACTGCTAAATCTCCAAAATTAGATAAAAATGATACAGCAAATACAG
601  CTTCATTCAACGAATTACCTTTTAATTTTTTCAGACACACCTTATTACAAACTAACTAAG
661  TCAGATGATGAGAAAGTAAATATAAATTTAACTTATGGGTATAATATAATAAAGATTCAT
721  GATATTAATAATTTACTTAACGATGTTAATAGACTTATTCCATCAACCCCTTCAAACCTT
781  TCTGGATATTATAAAATACCAGTTAATGATATTAAAATAGATTGTTTAAGAGATGTAAAT
841  AATTATTTGGAGGTAAAGGATATAAAATTAGTCTATCTTTCACATGGAAATGAATTACCT
901  AATATTAATAATTATGATAGGAATTTTTTAGGATTTACAGCTGTTATATGTATCAACAAT
961  ACAGGCAGATCTATGGTTATGGTAAAACACTGTAACGGGAAGCAGCATTCTATGGTAACT
1021 GGCCTATGTTTAATAGCCAGATCATTTTACTCTATAAACATTTTACCACAAATAATAGGA
1081 TCCTCTAGATATTTAATATTATATCTAACAACAACAAAAAAATTTAACGATGTATGGCCA
1141 GAAGTATTTCTACTAATAAAGATAAAGATAGTCTATCTTATCTACAAGATATGAAAGAA
1201 GATAATCATTTAGTAGTAGCTACTAATATGGAAAGAAATGTATACAAAAACGTGGAAGCT
1261 TTTATATTAAATAGCATATTACTAGAAGATTTAAAATCTAGACTTAGTATAACAAAACAG
1321 TTAAATGCCAATATCGATTCTATATTTCATCATAACAGTAGTACATTAATCAGTGATATA
1381 CTGAAACGATCTACAGACTCAACTATGCAAGGAATAAGCAATATGCCAATTATGTCTAAT
1441 ATTTTAACTTTAGAACTAAAACGTTCTACCAATACTAAAAATAGGATACGTGATAGGCTG
1501 TTAAAAGCTGCAATAAATAGTAAGGATGTAGAAGAAATACTTTGTTCTATACCTTCGGAG
1561 GAAAGAACTTTAGAACAACTTAAGTTTAATCAAACTTGTATTTATGAAGGTACC
```

FIG.29

```
1    GAATTCGAATAAAAAAATGATAAAGTAGGTTCAGTTTTATTGCTGGTTGTGTTAGTTCTC
61   TCTAAAAATGGGTCTCAACCCCCAGCTAGTTGTCATCCTGCTCTTCTTTCTCGAATGTAC
121  CAGGAGCCATATCCACGGATGCGACAAAAATCACTTGAGAGAGATCATCGGCATTTTGAA
181  CGAGGTCACAGGAGAAGGGACGCCATGCACGGAGATGGATGTGCCAAACGTCCTCACAGC
241  AACGAAGAACACCACAGAGAGTGAGCTCGTCTGTAGGGCTTCCAAGGTGCTTCGTATATT
301  TTATTTAAAACATGGGAAAACTCCATGCTTGAAGAAGAACTCTAGTGTTCTCATGGAGCT
361  GCAGAGACTCTTTCGGGCTTTTCGATGCCTGGATTCATCGATAAGCTGCACCATGAATGA
421  GTCCAAGTCCACATCACTGAAAGACTTCCTGGAAAGCCTAAAGAGCATCATGCAAATGCA
481  TTACTCGTAG
```

FIG.30

```
1    GAATAAAAAAATGATAAAGTAGGTTCAGTTTTATTGCTGGTTGTGTTAGTTCTCTCTAAA
61   AATGGGTCTCACCTCCCAACTGCTTCCCCTCTGTTCTTCCTGCTAGCATGTGCCGGCAA
121  CTTTGTCCACGGACACAAGTGCGATATCACCTTACAGGAGATCATCAAAACTTTGAACAG
181  CCTCACAGAGCAGAAGACTCTGTGCACCGAGTTGACCGTAACAGACATCTTTGCTGCCTC
241  CAAGAACACAACTGAGAAGGAAACCTTCTGCAGGGCTGCGACTGTGCTCCGGCAGTTCTA
301  CAGCCACCATGAGAAGGACACTGGCTGCCTGGGTGCGACTGCACAGCAGTTCCACAGGCA
361  CAAGCAGCTGATCCGATTCCTGAAAGGGCTCGACAGGAACCTCTGGGCCTGGCGGGCTT
421  GAATTCCTGTCCTGTGAAGGAAGCCAACCAGAGTACGTTGGAAAACTTCTTGGAAAGGCT
481  AAAGACGATCATGAGAGAGAAATATTCAAAGTGTTCGAGCTGA
```

FIG.31

```
1    GAATAAAAAAATGATAAAGTAGGTTCAGTTTTATTGCTGGTTGTGTTAGTTCTCTCTAAA
61   AATGTGGCTGCAGAGCCTGCTGCTCTTGGGCACTGTGGCCTGCAGCATCTCTGCACCCGC
121  CCGCTCGCCCAGCCCCAGCACGCAGCCCTGGGAGCATGTGAATGCCATCCAGGAGGCCCG
181  GCGTCTCCTGAACCTGAGTAGAGACACTGCTGCTGAGATGAATGAAACAGTAGAAGTCAT
241  CTCAGAAATGTTTGACCTCCAGGAGCCGACCTGCCTACAGACCCGCCTGGAGCTGTACAA
301  GCAGGGCCTGCGGGGCAGCCTCACCAAGCTCAAGGGCCCCTTGACCATGATGGCCAGCCA
361  CTACAAGCAGCACTGCCCTCCAACCCCGGAAACTTCCTGTGCAACCCAGACTATCACCTT
421  TGAAAGTTTCAAAGAGAACCTGAAGGACTTTCTGCTTGTCATCCCCTTTGACTGCTGGGA
481  GCCAGTCCAGGAGTGA
```

FIG.32

```
1    CAAAATTGAAAATATATAATTACAATATAAAATGTGTCACCAGCAGTTGGTCATCTCTTG
61   GTTTTCCCTGGTTTTTCTGGCATCTCCCCTCGTGGCCATATGGGAACTGAAGAAAGATGT
121  TTATGTCGTAGAATTGGATTGGTATCCGGATGCCCCTGGAGAAATGGTGGTCCTCACCTG
181  TGACACCCCTGAAGAAGATGGTATCACCTGGACCTTGGACCAGAGCAGTGAGGTCTTAGG
241  CTCTGGCAAAACCCTGACCATCCAAGTCAAAGAGTTTGGAGATGCTGGCCAGTACACCTG
301  TCACAAAGGAGGCGAGGTTCTAAGCCATTCGCTCCTGCTGCTTCACAAAAAGGAAGATGG
361  AATTTGGTCCACTGATATTTTAAAGGACCAGAAAGAACCCAAAAATAAGACCTTTCTAAG
421  ATGCGAGGCCAAGAATTATTCTGGACGTTTCACCTGCTGGTGGCTGACGACAATCAGTAC
481  TGATTTGACATTCAGTGTCAAAAGCAGCAGAGGCTCTTCTGACCCCCCAAGGGGTGACGTG
541  CGGAGCTGCTACACTCTCTGCAGAGAGAGTCAGAGGGGACAACAAGGAGTATGAGTACTC
601  AGTGGAGTGCCAGGAGGACAGTGCCTGCCCAGCTGCTGAGGAGAGTCTGCCCATTGAGGT
661  CATGGTGGATGCCGTTCACAAGCTCAAGTATGAAAACTACACCAGCAGCTTCTTCATCAG
721  GGACATCATCAAACCTGACCCACCCAAGAACTTGCAGCTGAAGCCATTAAAGAATTCTCG
781  GCAGGTGGAGGTCAGCTGGGAGTACCCTGACACCTGGAGTACTCCACATTCCTACTTCTC
841  CCTGACATTCTGCGTTCAGGTCCAGGGCAAGAGCAAGAGAGAAAGAAAGATAGAGTCTT
901  CACGGACAAGACCTCAGCCACGGTCATCTGCCGCAAAAATGCCAGCATTAGCGTGCGGGC
961  CCAGGACCGCTACTATAGCTCATCTTGGAGCGAATGGGCATCTGTGCCCTGCAGTTAG
```

FIG.33

```
1    GAATAAAAAAATGATAAAGTAGGTTCAGTTTTATTGCTGGTTGTGTTAGTTCTCTCTAAA
61   AATGTGTCCAGCGCGCAGCCTCCTCCTTGTGGCTACCCTGGTCCTCCTGGACCACCTCAG
121  TTTGGCCAGAAACCTCCCCGTGGCCACTCCAGACCCAGGAATGTTCCCATGCCTTCACCA
181  CTCCCAAAACCTGCTGAGGGCCGTCAGCAACATGCTCCAGAAGGCCAGACAAACTCTAGA
241  ATTTTACCCTTGCACTTCTGAAGAGATTGATCATGAAGATATCACAAAAGATAAACCAG
301  CACAGTGGAGGCCTGTTTACCATTGGAATTAACCAAGAATGAGAGTTGCCTAAATTCCAG
361  AGAGACCTCTTTCATAACTAATGGGAGTTGCCTGGCCTCCAGAAAGACCTCTTTTATGAT
421  GGCCCTGTGCCTTAGTAGTATTTATGAAGACTTGAAGATGTACCAGGTGGAGTTCAAGAC
481  CATGAATGCAAAGCTTCTGATGGATCCTAAGAGGCAGATCTTTCTAGATCAAAACATGCT
541  GGCAGTTATTGATGAGCTGATGCAGGCCCTGAATTTCAACAGTGAGACTGTGCCACAAAA
601  ATCCTCCCTTGAAGAACCGGATTTTTATAAAACTAAAATCAAGCTCTGCATACTTCTTCA
661  TGCTTTCAGAATTCGGGCAGTGACTATTGACAGAGTGACGAGCTATCTGAATGCTTCCTA
721  A
```

FIG.34

```
  1 ATGGCTTGCAATTGTCAGTTGATGCAGGATACACCACTCCTCAAGTTTCCATGTCCAAGG
 61 CTCATTCTTCTCTTTGTGCTGCTGATTCGTCTTTCACAAGTGTCTTCAGATGTTGATGAA
121 CAACTGTCCAAGTCAGTGAAAGATAAGGTATTGCTGCCTTGCCGTTACAACTCTCCTCAT
181 GAAGATGAGTCTGAAGACCGAATCTACTGGCAAAAACATGACAAAGTGGTGCTGTCTGTC
241 ATTGCTGGGAAACTAAAAGTGTGGCCCGAGTATAAGAACCGGACTTTATATGACAACACT
301 ACCTACTCTCTTATCATCCTGGGCCTGGTCCTTTCAGACCGGGGCACATACAGCTGTGTC
361 GTTCAAAAGAAGGAAAGAGGAACGTATGAAGTTAAACACTTGGCTTTAGTAAAGTTGTCC
421 ATCAAAGCTGACTTCTCTACCCCCAACATAACTGAGTCTGGAAACCCATCTGCAGACACT
481 AAAAGGATTACCTGCTTTGCTTCCGGGGGTTTCCCAAAGCCTCGCTTCTCTTGGTTGGAA
541 AATGGAAGAGAATTACCTGGCATCAATACGACAATTTCCCAGGATCCTGAATCTGAATTG
601 TACACCATTAGTAGCCAACTAGATTTCAATACGACTCGCAACCACACCATTAAGTGTCTC
661 ATTAAATATGGAGATGCTCACGTGTCAGAGGACTTCACCTGGGAAAAACCCCCAGAAGAC
721 CCTCCTGATAGCAAGAACACACTTGTGCTCTTTGGGGCAGGATTCGGCGCAGTAATAACA
801 GTCGTCGTCATCGTTGTCATCATCAAATGCTTCTGTAAGCACAGAAGCTGTTTCAGAAGA
861 AATGAGGCAAGCAGAGAAACAAACAACAGCCTTACCTTCGGGCCTGAAGAAGCATTAGCT
901 GAACAGACCGTCTTCCTTTAG
```

FIG.35

```
1   ATGGGCCACACACGGAGGCAGGGAACATCACCATCCAAGTGTCCATACCTCAATTTCTTT
61  CAGCTCTTGGTGCTGGCTGGTCTTTCTCACTTCTGTTCAGGTGTTATCCACGTGACCAAG
121 GAAGTGAAAGAAGTGGCAACGCTGTCCTGTGGTCACAATGTTTCTGTTGAAGAGCTGGCA
181 CAAACTCGCATCTACTGGCAAAAGGAGAAGAAAATGGTGCTGACTATGATGTCTGGGGAC
241 ATGAATATATGGCCCGAGTACAAGAACCGGACCATCTTTGATATCACTAATAACCTCTCC
301 ATTGTGATCCTGGCTCTGCGCCCATCTGACGAGGGCACATACGAGTGTGTTGTTCTGAAG
361 TATGAAAAAGACGCTTTCAAGCGGGAACACCTGGCTGAAGTGACGTTATCAGTCAAAGCT
421 GACTTCCCTACACCTAGTATATCTGACTTTGAAATTCCAACTTCTAATATTAGAAGGATA
481 ATTTGCTCAACCTCTGGAGGTTTTCCAGAGCCTCACCTCTCCTGGTTGGAAAATGGAGAA
541 GAATTAAATGCCATCAACACAACAGTTTCCCAAGATCCTGAAACTGAGCTCTATGCTGTT
601 AGCAGCAAACTGGATTTCAATATGACAACCAACCACAGCTTCATGTGTCTCATCAAGTAT
661 GGACATTTAAGAGTGAATCAGACCTTCAACTGGAATACAACCAAGCAAGAGCATTTTCCT
721 GATAACCTGCTCCCATCCTGGGCCATTACCTTAATCTCAGTAAATGGAATTTTTGTGATA
781 TGCTGCCTGACCTACTGCTTTGCCCCAAGATGCAGAGAGAGAAGGAGGAATGAGAGATTG
841 AGAAGGGAAAGTGTACGCCCTGTATAA
```

FIG.37

```
1    ATGACTGCCATGGAGGAGTCACAGTCGGATATCAGCCTCGAGCTCCCTCTGAGCCAGGAG
61   ACATTTTCAGGCTTATGGAAACTACTTCCTCCAGAAGATATCCTGCCATCACCTCACTGC
121  ATGGACGATCTGTTGCTGCCCCAGGATGTTGAGGAGTTTTTTGAAGGCCCAAGTGAAGCC
181  CTCCGAGTGTCAGGAGCTCCTGCAGCACAGGACCCTGTCACCGAGACCCCTGGGCCAGTG
241  GCCCCTGCCCCAGCCCACTCCATGGCCCCTGTCATCTTTTGTCCCTTCTCAAAAAACTTAC
301  CAGGGCAACTATGGCTTCCACCTGGGCTTCCTGCAGTCTGGGACAGCCAAGTCTGTTATG
361  TGCACGTACTCTCCTCCCCTCAATAAGCTATTCTGCCAGCTGGCGAAGACGTGCCCTGTG
421  CAGTTGTGGGTCAGCGCCACACCTCCAGCTGGGAGCCGTGTCCGCGCCATGGCCATCTAC
481  AAGAAGTCACAGCACATGACGGAGGTCGTGAGACGCTGCCCCCACCATGAGCGCTGCTCC
541  GATGGTGATGGCCTGGCTCCTCCCCAGCATCTTATCCGGGTGGAAGGAAATTTGTATCCG
601  GAGTATCTGGAAGACAGGCAGACTTTTCGCCACAGCGTGGTGGTACCTTATGAGCCACCC
661  GAGGCCGGCTCTGAGTATACCACCATCCACTACAAGTACATGTGTAATAGCTCCTGCATG
721  GGGGGCATGAACCGCCGACCTATCCTTACCATCATCACACTGGAAGACTCCAGTGGGAAC
781  CTTCTGGGACGGGACAGCTTTGAGGTTCGTGTTTGTGCCTGCCCTGGGAGAGACCGCCGT
841  ACAGAAGAAGAAAATTTCCGCAAAAAGGAAGTCCTTTGCCCTGAACTGCCCCCAGGGAGC
901  GCAAAGAGAGCGCTGCCCACCTGCACAAGCGCCTCTCCCCCGCAAAAGAAAAAACCACTT
961  GATGGAGAGTATTTCACCCTCAAGATCCGCGGGCGTAAACGCTTCGAGATGTTCCGGGAG
1021 CTGAATGAGGCCTTAGAGTTAAAGGATGCCCATGCTACAGAGGAGTCTGGAGACAGCAGG
1081 GCTCACTCCAGCTACCTGAAGACCAAGAAGGGCCAGTCTACTTCCCGCCATAAAAAAACA
1141 ATGGTCAAGAAAGTGGGGCCTGACTCAGACTGA
```

FIG.38

```
1    ATGGAGGAGCCGCAGTCAGATCCTAGCGTCGAGCCCCCTCTGAGTCAGGAAACATTTTCA
61   GACCTATGGAAACTACTTCCTGAAAACAACGTTCTGTCCCCCTTGCCGTCCCAAGCAATG
121  GATGATTTGATGCTGTCCCCGGACGATATTGAACAATGGTTCACTGAAGACCCAGGTCCA
181  GATGAAGCTCCCAGAATGCCAGAGGCTGCTCCCCGCGTGGCCCTGCACCAGCAGCTCCT
241  ACACCGGCGGCCCCTGCACCAGCCCCTCCTGGCCCTGTCATCTTCTGTCCCTTCCCAG
301  AAAACCTACCAGGGCAGCTACGGTTTCCGTCTGGGCTTCTTGCATTCTGGGACAGCCAAG
361  TCTGTGACTTGCACGTACTCCCCTGCCCTCAACAAGATGTTTTGCCAACTGGCCAAGACC
421  TGCCCTGTGCAGCTGTGGGTTGATTCCACACCCCGCCCGGCACCCGCGTCCGCGCCATG
481  GCCATCTACAAGCAGTCACAGCACATGACGGAGGTTGTGAGGCGCTGCCCCCACCATGAG
541  CGCTGCTCAGATAGCGATGGTCTGGCCCCTCCTCAGCATCTTATCCGAGTGGAAGGAAAT
601  TTGCGTGTGGAGTATTTGGATGACAGAAACACTTTTCGACATAGTGTGGTGGTGCCCTAT
661  GAGCCGCCTGAGGTTGGCTCTGACTGTACCACCATCCACTACAACTACATGTGTAACAGT
721  TCCTGCATGGGCGGCATGAACCGGAGGCCCATCCTCACCATCATCACACTGGAAGACTCC
781  AGTGGTAATCTACTGGGACGGAACAGCTTTGAGGTGCGTGTTTGTGCCTGTCCTGGGAGA
841  GACCGGCGCACAGAGGAAGAGAATCTCCGCAAGAAAGGGGAGCCTCACCACGAGCTGCCC
901  CCAGGGAGCACTAAGCGAGCACTGCCCAACAACACCAGCTCCTCTCCCCAGCCAAAGAAG
961  AAACCACTGGATGGAGAATATTTCACCCTTCAGATCCGTGGGCGTGAGCGCTTCGAGATG
1021 TTCCGAGAGCTGAATGAGGCCTTGGAACTCAAGGATGCCCAGGCTGGGAAGGAGCCAGGG
1081 GGGAGCAGGGCTCACTCCAGCCACCTGAAGTCCAAAAAGGGTCAGTCTACCTCCCGCCAT
1141 AAAAAACTCATGTTCAAGACAGAAGGGCCTGACTCAGACTGA
```

MATERIALS

TUMOR MODEL; RM1 (DR. T. THOMPSON, BAYLOR COLLEGE OF MEDICINE)

MICE; MALE C57BL/6 MICE, 5 MICE PER GROUP

VIRAL VECTORS; ALVAC (Virogenetics Corporation)
        Parental
        Hu-TNFα ──→ TNF assay
        Mu-IL2 ──→ IL-2 assay
        Mu-IFNγ
        Mu-B7 ──→ Flow cytometry
        Mu-IL12
        Mu-GMCSF B7 Expression on Infected RM1 cells (24 hr. incubation)

FIG. 45 Tumor Outgrowth — Tumor Inhibition Study

Tumor Outgrowth
Virus Combination Study

Tumor Outgrowth
Individual Mice
Virus Combination Study

Survival
Virus Combination Study

Effect of TNFα on Cell Growth

Tumor Size

Parental vs TNFα + IL2 (D24) p<0.05    Parental vs TNFα + GMCSF (D24) p<0.05

Parental vs IL12; p<0.05, Parental vs TNFα + IL2; p<0.005,
Parental vs TNFα + IL12; p<0.005, Parental vs TNFα + GMCSF; p<0.005, Tumor Size Primary CTL Assay Primary CTL Assay Primary CTL Assay

SEQUENCE LISTING (1) GENERAL INFORMATION:

(iii) NUMBER OF SEQUENCES: 217

(2) INFORMATION FOR SEQ ID NO: 1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 1:

TAATTAACTA GCTACCCGGG                                                   20

(2) INFORMATION FOR SEQ ID NO: 2:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

GTACATTAAT TGATCGATGG GCCCTTAA                                              28

(2) INFORMATION FOR SEQ ID NO: 3:

(i) SEQUENCE CHARACTERISTICS:
         (A) LENGTH: 73 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 3:

AGCTTCCCGG GTAAGTAATA CGTCAAGGAG AAAACGAAAC GATCTGTAGT TAGCGGCCGC           60

CTAATTAACT AAT                                                              73

(2) INFORMATION FOR SEQ ID NO: 4:

(i) SEQUENCE CHARACTERISTICS:
         (A) LENGTH: 69 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 4:

AGGGCCCATT CATTATGCAG TTCCTCTTTT GCTTTGCTAG ACATCAATCG CCGGCGGATT           60

AATTGATTA                                                                   69

(2) INFORMATION FOR SEQ ID NO: 5:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 5:

TTAGTTAATT AGGCGGCCGC                                                       20

(2) INFORMATION FOR SEQ ID NO: 6:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 6:

CGATTACTAT GAAGGATCCG TT                                                    22

(2) INFORMATION FOR SEQ ID NO: 7:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 7:

TAATGATACT TCCTAGGCAA                                                       20

(2) INFORMATION FOR SEQ ID NO: 8:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

CGATTACTAG ATCTGAGCTC CCCGGGCTCG AGGGATCCGT T                                41

(2) INFORMATION FOR SEQ ID NO: 9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

TAATGATCTA GACTCGAGGG GCCCGAGCTC CCTAGGCAA                                   39

(2) INFORMATION FOR SEQ ID NO: 10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

GATCCGAATT CTAGCT                                                           16

(2) INFORMATION FOR SEQ ID NO: 11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

GCTTAAGATC GA                                                               12

(2) INFORMATION FOR SEQ ID NO: 12:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

TATGAGTAAC TTAACTCTTT TGTTAATTAA AAGTATATTC AAAAAATAAG TTATATAAAT            60

```
AGATCTGAAT TCGTT                                                   75

(2) INFORMATION FOR SEQ ID NO: 13:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

ACTCATTGAA TTGAGAAAAC AATTAATTTT CATATAAGTT TTTTATTCAA TATATTTATC   60

TAGACTTAAG CAA                                                     73

(2) INFORMATION FOR SEQ ID NO: 14:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

AAAATGGGCG TGGATTGTTA ACTTTATATA ACTTATTTTT TGAATATAC               49

(2) INFORMATION FOR SEQ ID NO: 15:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

ACACGAATGA TTTTCTAAAG TATTTGGAAA GTTTTATAGG TAGTTGATAG AACAAAATAC   60

ATAATTT                                                            67

(2) INFORMATION FOR SEQ ID NO: 16:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

TGTGCTTACT AAAAGATTTC ATAAACCTTT CAAAATATCC ATCAACTATC T            51

(2) INFORMATION FOR SEQ ID NO: 17:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:
```

TGTAAAAATA AATCACTTTT TATACTAAGA TCTCCCGGGC TGCAGC            46

(2) INFORMATION FOR SEQ ID NO: 18:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

TGTTTTATGT ATTAAAACAT TTTTATTTAG TGAAAAATAT GATTCTAGAG GGCCCGACGT    60

CGCCGG                                                              66

(2) INFORMATION FOR SEQ ID NO: 19:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

TTTCTGTATA TTTGCACCAA TTTAGATCTT ACTCAAAATA TGTAACAATA              50

(2) INFORMATION FOR SEQ ID NO: 20:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

TGTCATTTAA CACTATACTC ATATTAATAA AAATAATATT TATT                    44

(2) INFORMATION FOR SEQ ID NO: 21:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

GATCCTGAGT ACTTTGTAAT ATAATGATAT ATATTTTCAC TTTATCTCAT TTGAGAATAA    60

AAAGATCTTA GG                                                       72

(2) INFORMATION FOR SEQ ID NO: 22:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

```
GACTCATGAA ACATTATATT ACTATATATA AAAGTGAAAT AGAGTAAACT CTTATTTTTC        60

TAGAATCCTT AA                                                            72
```

(2) INFORMATION FOR SEQ ID NO: 23:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

```
GATCCAGATC TCCCGGGAAA AAAATTATTT AACTTTTCAT TAATAGGGAT TTGACGTATG        60

TAGCGTACTA GG                                                            72
```

(2) INFORMATION FOR SEQ ID NO: 24:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

```
GTCTAGAGGG CCCTTTTTTT AATAAATTGA AAAGTAATTA TCCCTAAACT GCATACTACG        60

CATGATCCTT AA                                                            72
```

(2) INFORMATION FOR SEQ ID NO: 25:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

```
GGGAGATCTC TCGAGCTGCA GGGCGCCGGA TCCTTTTTCT                              40
```

(2) INFORMATION FOR SEQ ID NO: 26:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 26:

```
CCCTCTAGAG AGCTCGACGT CCCGCGGCCT AGGAAAAAGA                              40
```

(2) INFORMATION FOR SEQ ID NO: 27:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 27:

CGATATCCGT TAAGTTTGTA TCGTAATGGG CTCCAGATCT TCTACCAGGA TCCCGGTAC            59

(2) INFORMATION FOR SEQ ID NO: 28:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 28:

CGGGATCCTG GTAGAAGATC TGGAGCCCAT TACGATACAA ACTTAACGGA TATCG               55

(2) INFORMATION FOR SEQ ID NO: 29:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 29:

AATTCGAGCT CCCCGGG                                                         17

(2) INFORMATION FOR SEQ ID NO: 30:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 30:

CCCGGGGAGC TCG                                                             13

(2) INFORMATION FOR SEQ ID NO: 31:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 31:

CTTTTTATAA AAAGTTAACT ACGTAG                                               26

(2) INFORMATION FOR SEQ ID NO: 32:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 32:

GATCCTACGT AGTTAACTTT TTATAAAAAG AGCT                                      34

(2) INFORMATION FOR SEQ ID NO: 33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 33:

```
CTTAACTCAG CTGACTATCC                                              20
```

(2) INFORMATION FOR SEQ ID NO: 34:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 34:

```
TACGTAGTTA ACTTTTTATA AAAATCATAT TTTTGTAGTG GCTC                   44
```

(2) INFORMATION FOR SEQ ID NO: 35:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 35:

```
AATTCAGGAT CGTTCCTTTA CTAGTTGAGA TTCTCAAGGA TGATGGGATT TAATTTTTAT   60

AAGCTTG                                                            67
```

(2) INFORMATION FOR SEQ ID NO: 36:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 36:

```
AATTCAAGCT TATAAAAATT AAATCCCATC ATCCTTGAGA ATCTCAACTA GTAAAGGAAC   60

GATCCTG                                                            67
```

(2) INFORMATION FOR SEQ ID NO: 37:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 37:

```
CTAGACACTT TATGTTTTTT AATATCCGGT CTTAAAAGCT TCCCGGGGAT CCTTATACGG   60
```

```
GGAATAAT                                                                   68

(2) INFORMATION FOR SEQ ID NO: 38:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 38:

ATTATTCCCC GTATAAGGAT CCCCCGGGAA GCTTTTAAGA CCGGATATTA AAAAACATAA          60

AGTGT                                                                      65

(2) INFORMATION FOR SEQ ID NO: 39:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 39:

GCTTCCCGGG AATTCTAGCT AGCTAGTTT                                            29

(2) INFORMATION FOR SEQ ID NO: 40:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 40:

ACTCTCAAAA GCTTCCCGGG AATTCTAGCT AGCTAGTTTT TATAAA                         46

(2) INFORMATION FOR SEQ ID NO: 41:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 41:

GATCTTTATA AAAACTAGCT AGCTAGAATT CCCGGGAAGC TTTTGAGAGT                     50

(2) INFORMATION FOR SEQ ID NO: 42:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 42:

CTGAAATTAT TTCATTATCG CGATATCCGT TAAGTTTGTA TCGTAATGGT TCCTCAGGCT          60
```

```
CTCCTGTTTG T                                                          71

(2) INFORMATION FOR SEQ ID NO: 43:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 43:

CATTACGATA CAAACTTAAC GGATATCGCG ATAATGAAAT AATTTCAG                   48

(2) INFORMATION FOR SEQ ID NO: 44:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 44:

ACCCCTTCTG GTTTTTCCGT TGTGTTTTGG GAAATTCCCT ATTTACACGA TCCCAGACAA      60

GCTTAGATCT CAG                                                        73

(2) INFORMATION FOR SEQ ID NO: 45:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 45:

CTGAGATCTA AGCTTGTCTG GGATCGTGTA AATAGGGAAT TTCCCAAAAC A               51

(2) INFORMATION FOR SEQ ID NO: 46:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 46:

CAACGGAAAA ACCAGAAGGG GTACAAACAG GAGAGCCTGA GGAAC                      45

(2) INFORMATION FOR SEQ ID NO: 47:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 47:

GGATCCCCGG G                                                          11
```

(2) INFORMATION FOR SEQ ID NO: 48:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 48:

```
TCATTATCGC GATATCCGTG TTAACTAGCT AGCTAATTTT TATTCCCGGG ATCCTTATCA    60
```

(2) INFORMATION FOR SEQ ID NO: 49:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 49:

```
GTATAAGGAT CCCGGGAATA AAAATTAGCT AGCTAGTTAA CACGGATATC GCGATAATGA    60
```

(2) INFORMATION FOR SEQ ID NO: 50:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 50:

```
GACAATCTAA GTCCTATATT AGAC                                          24
```

(2) INFORMATION FOR SEQ ID NO: 51:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 51:

```
GGATTTTTAG GTAGACAC                                                 18
```

(2) INFORMATION FOR SEQ ID NO: 52:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 52:

```
TCATCGTCTT CATCATCG                                                 18
```

(2) INFORMATION FOR SEQ ID NO: 53:

(i) SEQUENCE CHARACTERISTICS:

(A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 53:

GTCTTAAACT TATTGTAAGG GTATACCTG                                          29

(2) INFORMATION FOR SEQ ID NO: 54:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 54:

AACGATTAGT TAGTTACTAA AAGCTTGCTG CAGCCCGGGT TTTTTATTAG TTTAGTTAGT        60

C                                                                        61

(2) INFORMATION FOR SEQ ID NO: 55:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 55:

GACTAACTAA CTAATAAAAA ACCCGGGCTG CAGCAAGCTT TTTGTAACTA ACTAATCGTT        60

(2) INFORMATION FOR SEQ ID NO: 56:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 56:

GCACGGAACA AAGCTTATCG CGATATCCGT TAAGTTTGTA TCGTAATGCT ATCAATCACG        60

ATTCTGTTCC TGCTCATAGC AGAGGGCTCA TCTCAGAAT                               99

(2) INFORMATION FOR SEQ ID NO: 57:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 57:

ATTCTGAGAT GAGCCCTCTG CTATGAGCAG GAACAGAATC GTGATTGATA GCATTACGAT        60

ACAAACTTAA CGGATATCGC GATAAGCTTT GTTCCGTGC                               99

(2) INFORMATION FOR SEQ ID NO: 58:

```
        (i) SEQUENCE CHARACTERISTICS:
            (A) LENGTH: 66 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 58:

GAAAAATTTA AAGTCGACCT GTTTTGTTGA GTTGTTTGCG TGGTAACCAA TGCAAATCTG      60

GTCACT                                                                66

(2) INFORMATION FOR SEQ ID NO: 59:

(i) SEQUENCE CHARACTERISTICS:
            (A) LENGTH: 66 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 59:

TCTAGCAAGA CTGACTATTG CAAAAAGAAG CACTATTTCC TCCATTACGA TACAAACTTA      60

ACGGAT                                                                66

(2) INFORMATION FOR SEQ ID NO: 60:

(i) SEQUENCE CHARACTERISTICS:
            (A) LENGTH: 87 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 60:

ATCCGTTAAG TTTGTATCGT AATGGAGGAA ATAGTGCTTC TTTTTGCAAT AGTCAGTCTT      60

GCTAGAAGTG ACCAGATTTG CATTGGT                                         87

(2) INFORMATION FOR SEQ ID NO: 61:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 61:

TACCACGCAA ACAACTCAAC AAAACAGGTC GACTTTAAAT TTTTCTGCA                  49

(2) INFORMATION FOR SEQ ID NO: 62:

(i) SEQUENCE CHARACTERISTICS:
            (A) LENGTH: 132 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 62:

GTACAGGTCG ACAAGCTTCC CGGGTATCGC GATATCCGTT AAGTTTGTAT CGTAATGAAT      60
```

```
ACTCAAATTC TAATACTCAC TCTTGTGGCA GCCATTCACA CAAATGCAGA CAAAATCTGC      120

CTTGGACATC AT                                                         132
```

(2) INFORMATION FOR SEQ ID NO: 63:

(i) SEQUENCE CHARACTERISTICS:
        (A) LENGTH: 132 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 63:

```
ATGATGTCCA AGGCAGATTT TGTCTGCATT TGTGTGAATG GCTGCCACAA GAGTGAGTAT       60

TAGAATTTGA GTATTCATTA CGATACAAAC TTAACGGATA TCGCGATACC CGGGAAGCTT      120

GTCGACCTGT AC                                                         132
```

(2) INFORMATION FOR SEQ ID NO: 64:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 64:

```
ATAACATGCG GTGCACCATT TGTATATAAG TTAACGAATT CCAAGTCAAG C                51
```

(2) INFORMATION FOR SEQ ID NO: 65:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 65:

```
GCTTGACTTG GAATTCGTTA ACTTATATAC AAATGGTGCA CCGCATGTTA T                51
```

(2) INFORMATION FOR SEQ ID NO: 66:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 66:

```
ATCATCTCGC GATATCCGTT AAGTTTGTAT CGTAATGAGC ACTGAAAGCA TGATC            55
```

(2) INFORMATION FOR SEQ ID NO: 67:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 67:

ATCATCTCTA GAATAAAAAT CACAGGGCAA TGATCCC                                37

(2) INFORMATION FOR SEQ ID NO: 68:

(i) SEQUENCE CHARACTERISTICS:
      (A) LENGTH: 3209 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 68:

| | | | | | |
|---|---|---|---|---|---|
| TGAATGTTAA | ATGTTATACT | TTGGATGAAG | CTATAAATAT | GCATTGGAAA | AATAATCCAT | 60 |
| TTAAAGAAAG | GATTCAAATA | CTACAAAACC | TAAGCGATAA | TATGTTAACT | AAGCTTATTC | 120 |
| TTAACGACGC | TTTAAATATA | CACAAATAAA | CATAATTTTT | GTATAACCTA | ACAAATAACT | 180 |
| AAAACATAAA | AATAATAAAA | GGAAATGTAA | TATCGTAATT | ATTTTACTCA | GGAATGGGGT | 240 |
| TAAATATTTA | TATCACGTGT | ATATCTATAC | TGTTATCGTA | TACTCTTTAC | AATTACTATT | 300 |
| ACGAATATGC | AAGAGATAAT | AAGATTACGT | ATTTAAGAGA | ATCTTGTCAT | GATAATTGGG | 360 |
| TACGACATAG | TGATAAATGC | TATTTCGCAT | CGTTACATAA | AGTCAGTTGG | AAAGATGGAT | 420 |
| TTGACAGATG | TAACTTAATA | GGTGCAAAAA | TGTTAAATAA | CAGCATTCTA | TCGGAAGATA | 480 |
| GGATACCAGT | TATATTATAC | AAAAATCACT | GGTTGGATAA | AACAGATTCT | GCAATATTCG | 540 |
| TAAAAGATGA | AGATTACTGC | GAATTTGTAA | ACTATGACAA | TAAAAAGCCA | TTTATCTCAA | 600 |
| CGACATCGTG | TAATTCTTCC | ATGTTTTATG | TATGTGTTTC | AGATATTATG | AGATTACTAT | 660 |
| AAACTTTTTG | TATACTTATA | TTCCGTAAAC | TATATTAATC | ATGAAGAAAA | TGAAAAAGTA | 720 |
| TAGAAGCTGT | TCACGAGCGG | TTGTTGAAAA | CAACAAAATT | ATACATTCAA | GATGGCTTAC | 780 |
| ATATACGTCT | GTGAGGCTAT | CATGGATAAT | GACAATGCAT | CTCTAAATAG | GTTTTTGGAC | 840 |
| AATGGATTCG | ACCCTAACAC | GGAATATGGT | ACTCTACAAT | CTCCTCTTGA | AATGGCTGTA | 900 |
| ATGTTCAAGA | ATACCGAGGC | TATAAAAATC | TTGATGAGGT | ATGGAGCTAA | ACCTGTAGTT | 960 |
| ACTGAATGCA | CAACTTCTTG | TCTGCATGAT | GCGGTGTTGA | GAGACGACTA | CAAAATAGTG | 1020 |
| AAAGATCTGT | TGAAGAATAA | CTATGTAAAC | AATGTTCTTT | ACAGCGGAGG | CTTTACTCCT | 1080 |
| TTGTGTTTGG | CAGCTTACCT | TAACAAAGTT | AATTTGGTTA | AACTTCTATT | GGCTCATTCG | 1140 |
| GCGGATGTAG | ATATTTCAAA | CACGGATCGG | TTAACTCCTC | TACATATAGC | CGTATCAAAT | 1200 |
| AAAAATTTAA | CAATGGTTAA | ACTTCTATTG | AACAAAGGTG | CTGATACTGA | CTTGCTGGAT | 1260 |
| AACATGGGAC | GTACTCCTTT | AATGATCGCT | GTACAATCTG | GAAATATTGA | AATATGTAGC | 1320 |
| ACACTACTTA | AAAAAAATAA | AATGTCCAGA | ACTGGGAAAA | ATTGATCTTG | CCAGCTGTAA | 1380 |
| TTCATGGTAG | AAAAGAAGTG | CTCAGGCTAC | TTTTCAACAA | AGGAGCAGAT | GTAAACTACA | 1440 |
| TCTTTGAAAG | AAATGGAAAA | TCATATACTG | TTTTGGAATT | GATTAAAGAA | AGTTACTCTG | 1500 |
| AGACACAAAA | GAGGTAGCTG | AAGTGGTACT | CTCAAAATGC | AGAACGATGA | CTGCGAAGCA | 1560 |
| AGAAGTAGAG | AAATAACACT | TTATGACTTT | CTTAGTTGTA | GAAAGATAG | AGATATAATG | 1620 |
| ATGGTCATAA | ATAACTCTGA | TATTGCAAGT | AAATGCAATA | ATAAGTTAGA | TTTATTTAAA | 1680 |
| AGGATAGTTA | AAAATAGAAA | AAAAGAGTTA | ATTTGTAGGG | TTAAAATAAT | ACATAAGATC | 1740 |
| TTAAAATTTA | TAAATACGCA | TAATAATAAA | AATAGATTAT | ACTTATTACC | TTCAGAGATA | 1800 |
| AAATTTAAGA | TATTTACTTA | TTTAACTTAT | AAAGATCTAA | AATGCATAAT | TTCTAAATAA | 1860 |

-continued

```
TGAAAAAAAA GTACATCATG AGCAACGCGT TAGTATATTT TACAATGGAG ATTAACGCTC    1920

TATACCGTTC TATGTTTATT GATTCAGATG ATGTTTTAGA AAAGAAAGTT ATTGAATATG    1980

AAAACTTTAA TGAAGATGAA GATGACGACG ATGATTATTG TTGTAAATCT GTTTTAGATG    2040

AAGAAGATGA CGCGCTAAAG TATACTATGG TTACAAAGTA TAAGTCTATA CTACTAATGG    2100

CGACTTGTGC AAGAAGGTAT AGTATAGTGA AAATGTTGTT AGATTATGAT TATGAAAAAC    2160

CAAATAAATC AGATCCATAT CTAAAGGTAT CTCCTTTGCA CATAATTTCA TCTATTCCTA    2220

GTTTAGAATA CTTTTCATTA TATTTGTTTA CAGCTGAAGA CGAAAAAAAT ATATCGATAA    2280

TAGAAGATTA TGTTAACTCT GCTAATAAGA TGAAATTGAA TGAGTCTGTG ATAATAGCTA    2340

TAATCAGAGA AGTTCTAAAA GGAAATAAAA ATCTAACTGA TCAGGATATA AAAACATTGG    2400

CTGATGAAAT CAACAAGGAG GAACTGAATA TAGCTAAACT ATTGTTAGAT AGAGGGCCA    2460

AAGTAAATTA CAAGGATGTT TACGGTTCTT CAGCTCTCCA TAGAGCTGCT ATTGGTAGGA    2520

AACAGGATAT GATAAAGCTG TTAATCGATC ATGGAGCTGA TGTAAACTCT TTAACTATTG    2580

CTAAAGATAA TCTTATTAAA AAAAAATAAT ATCACGTTTA GTAATATTAA AATATATTAA    2640

TAACTCTATT ACTAATAACT CCAGTGGATA TGAACATAAT ACGAAGTTTA TACATTCTCA    2700

TCAAATCTT ATTGACATCA AGTTAGATTG TGAAAATGAG ATTATGAAAT TAAGGAATAC    2760

AAAAATAGGA TGTAAGAACT TACTAGAATG TTTTATCAAT AATGATATGA ATACAGTATC    2820

TAGGGCTATA AACAATGAAA CGATTAAAAA TTATAAAAAT CATTTCCCTA TATATAATAC    2880

GCTCATAGAA AAATTCATTT CTGAAAGTAT ACTAAGACAC GAATTATTGG ATGGAGTTAT    2940

AAATTCTTTT CAAGGATTCA ATAATAAATT GCCTTACGAG ATTCAGTACA TTATACTGGA    3000

GAATCTTAAT AACCATGAAC TAAAAAAAAT TTTAGATAAT ATACATTAAA AAGGTAAATA    3060

GATCATCTGT TATTATAAGC AAAGATGCTT GTTGCCAATA ATATACAACA GGTATTTGTT    3120

TTTATTTTTA ACTACATATT TGATGTTCAT TCTCTTTATA TAGTATACAC AGAAAATTCA    3180

TAATCCACTT AGAATTTCTA GTTATCTAG                                       3209
```

(2) INFORMATION FOR SEQ ID NO: 69:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 69:

```
ATCATCGAAT TCTGAATGTT AAATGTTATA CTTG                                   34
```

(2) INFORMATION FOR SEQ ID NO: 70:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 70:

```
GGGGGTACCT TTGAGAGTAC CACTTCAG                                          28
```

(2) INFORMATION FOR SEQ ID NO: 71:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 71:

GGGTCTAGAG CGGCCGCTTA TAAAGATCTA AAATGCATAA TTTC                          44

(2) INFORMATION FOR SEQ ID NO: 72:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 72:

ATCATCCTGC AGGTATTCTA AACTAGGAAT AGATG                                    35

(2) INFORMATION FOR SEQ ID NO: 73:

(i) SEQUENCE CHARACTERISTICS:
            (A) LENGTH: 82 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 73:

GTACGTGACT AATTAGCTAT AAAAAGGATC CGGTACCCTC GAGTCTAGAA TCGATCCCGG          60

GTTTTTATGA CTAGTTAATC AC                                                  82

(2) INFORMATION FOR SEQ ID NO: 74:

(i) SEQUENCE CHARACTERISTICS:
            (A) LENGTH: 82 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 74:

GGCCGTGATT AACTAGTCAT AAAAACCCGG GATCGATTCT AGACTCGAGG GTACCGGATC          60

CTTTTTATAG CTAATTAGTC AC                                                  82

(2) INFORMATION FOR SEQ ID NO: 75:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 75:

TCGGGATCCG GGTTAATTAA TTAGTCATCA GGCAGGGCG                                39

(2) INFORMATION FOR SEQ ID NO: 76:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 76:

TAGCTCGAGG GTACCTACGA TACAAACTTA ACGGATATCG                     40

(2) INFORMATION FOR SEQ ID NO: 77:

(i) SEQUENCE CHARACTERISTICS:
        (A) LENGTH: 3659 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 77:

GATATCTGTG GTCTATATAT ACTACACCCT ACCGATATTA ACCAACGAGT TTCTCACAAG      60

AAAACTTGTT TAGTAGATAG AGATTCTTTG ATTGTGTTTA AAAGAAGTAC CAGTAAAAAG     120

TGTGGCATAT GCATAGAAGA AATAAACAAA AAACATATTT CCGAACAGTA TTTTGGAATT     180

CTCCCAAGTT GTAAACATAT TTTTTGCCTA TCATGTATAA GACGTTGGGC AGATACTACC     240

AGAAATACAG ATACTGAAAA TACGTGTCCT GAATGTAGAA TAGTTTTTCC TTTCATAATA     300

CCCAGTAGGT ATTGGATAGA TAATAAATAT GATAAAAAAA TATTATATAA TAGATATAAG     360

AAAATGATTT TTACAAAAAT ACCTATAAGA ACAATAAAAA TATAATTACA TTTACGAAAA     420

ATAGCTGGTT TTAGTTTACC AACTTAGAGT AATTATCATA TTGAATCTAT ATTGTTTTTT     480

AGTTATATAA AAACATGATT AGCCCCCAAT CGGATGAAAA TATAAAGAT GTTGAGAATT      540

TCGAATACAA CAAAAGAGG AATCGTACGT TGTCCATATC CAAACATATA AATAAAAATT     600

CAAAAGTAGT ATTATACTGG ATGTTTAGAG ATCAACGTGT ACAAGATAAT TGGGCTTTAA     660

TTTACGCACA ACGATTAGCG TTAAAACTCA AAATACCTCT AAGAATATGC TTTTGTGTCG     720

TGCCAAAATT TCACACTACT ACTTCTAGAC ACTTTATGTT TTTAATATCC GGTCTTAAAG     780

AAGTCGCGGA AGAATGTAAA AGACTATGTA TAGGGTTTTC ATTGATATAT GGCGTACCAA     840

AAGTAATAAT TCCGTGTATA GTAAAAAAAT ACAGAGTCGG AGTAATCATA ACGGATTTCT     900

TTCCATTACG TGTTCCCGAA AGATTAATGA AACAGACTGT AATATCTCTT CCAGATAACA     960

TACCTTTTAT ACAAGTAGAC GCTCATAATA TAGTACCTTG TTGGGAAGCT TCTGATAAAG    1020

AAGAATACGG TGCACGAACT TTAAGAAAAA AGATATTTGA TAAATTATAT GAATATATGA    1080

CAGAATTTCC TGTTGTTCGT AAACATCCAT ACGGTCCATT TTCTATATCT ATTGCAAAAC    1140

CCAAAAATAT ATCATTAGAC AAGACGGTAT TACCCGTAAA ATGGGCAACG CCTGAACAA     1200

AAGCTGGAAT AATTGTTTTA AAAGAATTTA TAAAAAACAG ATTACCGTCA TACGACGCGG    1260

ATCATAACAA TCCTACGTGT GACGCTTTGA GTAACTTATC TCCGTGGCTA CATTTTGGTC    1320

ATGTATCCGC ACAACGTGTT GCCTTAGAAG TATTAAAATG TATACGAGAA AGCAAAAAAA    1380

ACGTTGAAAC GTTTATAGAT GAAATAATTG TAAGAAGAGA ACTATCGGAT AATTTTTGTT    1440

ACTATAACAA ACATTATGAT AGTATCCAGT CTACTCATTC ATGGGTTAGA AAAACATTAG    1500

AAGATCACAT TAATGATCCT AGAAAGTATA TATATTCCAT TAAACAACTC GAAAAGCGG    1560

AAACTCATGA TCCTCTATGG AACGCGTCAC AAATGCAGAT GGTGAGAGAA GGAAAAATGC    1620

```
ATAGTTTTTT ACGAATGTAT TGGGCTAAGA AGATACTTGA ATGGACTAGA ACACCTGAAG     1680

ACGCTTTGAG TTATAGTATC TATTTGAACA ACAAGTACGA ACTAGACGGC ACGGATCCTA     1740

ACGGATACGT AGGTTGTATG TGGTCTATTT GCGGATTACA CGATAGAGCG TGGAAAGCAA     1800

GACCGATATT TGGAAAGATA AGATATATGA ATTATGAGAG TTCTAAGAAG AAATTTGATG     1860

TTGCTGTATT TATACAGAAA TACAATTAAG ATAAATAATA TACAGCATTG TAACCATCGT     1920

CATCCGTTAT ACGGGAATA ATATTACCAT ACAGTATTAT TAAATTTTCT TACGAAGAAT      1980

ATAGATCGGT ATTTATCGTT AGTTATTTT ACATTTATTA ATTAAACATG TCTACTATTA      2040

CCTGTTATGG AAATGACAAA TTTAGTTATA TAATTTATGA TAAAATTAAG ATAATAATAA     2100

TGAAATCAAA TAATTATGTA AATGCTACTA GATTATGTGA ATTACGAGGA AGAAAGTTTA     2160

CGAACTGGAA AAAATTAAGT GAATCTAAAA TATTAGTCGA TAATGTAAAA AAAATAAATG     2220

ATAAAACTAA CCAGTTAAAA ACGGATATGA TTATATACGT TAAGGATATT GATCATAAAG     2280

GAAGAGATAC TTGCGGTTAC TATGTACACC AAGATCTGGT ATCTTCTATA TCAAATTGGA     2340

TATCTCCGTT ATTCGCCGTT AAGGTAAATA AAATTATTAA CTATTATATA TGTAATGAAT     2400

ATGATATACG ACTTAGCGAA ATGGAATCTG ATATGACAGA AGTAATAGAT GTAGTTGATA     2460

AATTAGTAGG AGGATACAAT GATGAAATAG CAGAAATAAT ATATTTGTTT AATAAATTTA     2520

TAGAAAAATA TATTGCTAAC ATATCGTTAT CAACTGAATT ATCTAGTATA TTAAATAATT     2580

TTATAAATTT TATAAATTTT AATAAAAAAT ACAATAACGA CATAAAGATA TTTAATCTTT     2640

AATTCTTGAT CTGAAAAACA CATCTATAAA ACTAGATAAA AAGTTATTCG ATAAAGATAA     2700

TAATGAATCG AACGATGAAA AATTGGAAAC AGAAGTTGAT AAGCTAATTT TTTTCATCTA     2760

AATAGTATTA TTTTATTGAA GTACGAAGTT TTACGTTAGA TAAATAATAA AGGTCGATTT     2820

TTACTTTGTT AAATATCAAA TATGTCATTA TCTGATAAAG ATACAAAAAC ACACGGTGAT     2880

TATCAACCAT CTAACGAACA GATATTACAA AAAATACGTC GGACTATGGA AAACGAAGCT     2940

GATAGCCTCA ATAGAAGAAG CATTAAAGAA ATTGTTGTAG ATGTTATGAA GAATTGGGAT     3000

CATCCTCAAC GAAGAAATAG ATAAAGTTCT AAACTGGAAA AATGATACAT TAAACGATTT     3060

AGATCATCTA AATACAGATG ATAATATTAA GGAAATCATA CAATGTCTGA TTAGAGAATT     3120

TGCGTTTAAA AAGATCAATT CTATTATGTA TAGTTATGCT ATGGTAAAAC TCAATTCAGA     3180

TAACGAACAT TGAAAGATAA AATTAAGGAT TATTTTATAG AAACTATTCT TAAAGACAAA     3240

CGTGGTTATA AACAAAAGCC ATTACCCGGA TTGGAAACTA AAATACTAGA TAGTATTATA     3300

AGATTTAAA AACATAAAAT TAATAGGTTT TTATAGATTG ACTTATTATA TACAATATGG      3360

ATAAAGATA TATATCAACT AGAAAGTTGA ATGACGGATT CTTAATTTTA TATTATGATT      3420

CAATAGAAAT TATTGTCATG TCGTGTAATC ATTTTATAAA TATATCAGCG TTACTAGCTA     3480

AGAAAAACAA GGACTTTAAT GAATGGCTAA AGATAGAATC ATTTAGAGAA ATAATAGATA     3540

CTTTAGATAA AATTAATTAC GATCTAGGAC AACGATATTG TGAAGAACTT ACGGCGCATC     3600

ACATTCCAGT GTAATTATTG AGGTCAAAGC TAGTAACTTA ATAGATGACA GGACAGCTG     3659
```

(2) INFORMATION FOR SEQ ID NO: 78:

(i) SEQUENCE CHARACTERISTICS:
        (A) LENGTH: 2356 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 78:

```
TGTCTGGACT AACTGATTTC ATGGAACAAT TTTCATCAAA AATATCAGTT ATACCTAGTT     60

CTACAAAGAC AGAACTTTGA TGTTATGTTT GTGTTTGTAT AGAAAATTTT GGGATACTAA    120

CTGATATTTC TGAATATTTC TGAATATTTC ATGTTACTTA CTTACTCCTA TCTTAGACGA    180

TAATAAAATT CGAGGCGTAA TATGTTTTTC CAAATATTTG AAATTCTTAT ACGTATCGGC    240

GAAGAAAAGT AACATACTAT AAGTGTTATG CAAGTAAGGT ATGTTAATGA TATTGGATTT    300

AATTTCATTG ACAATACATA TGTCCAAACA TTCCACTCGT AATTATGTAC GGAACGACTT    360

TAGTTAAATA CTTAGTCACA AAAAACTTAT GACTGTCATT ATCTGAAAAC GGTGATTCCC    420

ATAAATCAGA ATACTTAATA TTAAATAGAA TGCTCGCTTC TGGAGGTTTC CGGATACTAG    480

ATAACATATC TTCTGTATTA TAGTTTAATT CACTCATTTT ATTACATAAT ACAGTAACAT    540

CTCCCGAAAC CAATGATGTT ATATTAGATT TACTTACATA CTTCTTGTAA CTATCATGAA    600

TACGTTTGTT ATGATCTATA AAGAAGATGG ATGTATATTC TGTTCTAGAT AGCAAGTTCT    660

TTAAGTTATT CTTTGTCTGT ATTACTATCA TCGTCTTCAT CATCGTCTAA AGGTAGCATT    720

ATATAATAAA TCTAATAGTT GATTTCTCGA TCTATCAGTA CTCGCTTTCA ATAACATTTT    780

TACTATAAGC ATAATAGAAG GCGGTGATAT CACTATATTT TTATCGGGTA TTCTTTTAGT    840

AATTAGTTAG TTCGTAGAAT TTCGTAGAGA TAAAAGCCAA TTTGTTGTTG ATACTGCTTA    900

CGTTACTCAT GTTTCTTGTT TCTGTTAATT AACAGGTATA CCCTTACAAT AAGTTTAATT    960

AACTTTTAGG TTTTTGTGAA GAACTTTTAG CTTCTAGTTC CCTTATCCAT AATTGGGTCT   1020

TAGATCTAGA TTCTTCCCAT GTATAAAGGG GGACATACCC AAAATCTTTA AATGCTTTGT   1080

CCGTTTCTAT AGTAAATGTC GTACATTCCT TAATCAAAGT ATAAGGATTT AGTAAAGGCG   1140

TGTAAGAACA AATAGGTGAT AGTAATACTC TTAAACCTTT ATTAATATTA GCGATAAACC   1200

TTAAACACCA TAAAGGAAGA CATGTATTCC GTAGATCCAT CCCTAATTGA TTAAAGAAAT   1260

GCATGTTAAA ATCATGATAA TGTTCAGTAG GAGAGGTATC GTAACAGTAA TACACGTTAT   1320

TGCAGAGAGG ACTATGTTGA CCATTTTCTA TCATATTTCT TGCTGCTAAA ATATGCATCC   1380

AAGCTACGTT TCCTGCATAG ACTCTGCTAT GAAATACTTT ATCATCCGCA TATTTATACA   1440

TTTTCCTGCT TTTATACGAT CTTCTGTATA AAGTTTCTAG TACTGGACAG TATTCTCCGA   1500

AAACACCTAA TGGGCGTAGC GACAAGTGCA TAATCTAAGT CCTATATTAG ACATAGTACC   1560

GTTAGCTTCT AGTATATATT TCTCAGATAA CTTGTTTACT AAGAGGATAA GCCTCTTTAT   1620

GGTTAGATTG ATAATACGTA TTCTCGTTTC CTCTTATCAT CGCATCTCCG GAGAAAGTTA   1680

GGACCTACCG CAGAATAACT ACTCGTATAT ACTAAGACTC TTACGCCGTT ATACAGACAA   1740

GAATCTACTA CGTTCTTCGT TCCGTTGATA TTAACGTCCA TTATAGAGTC GTTAGTAAAC   1800

TTACCCGCTA CATCATTTAT CGAAGCAATA TGAATGACCA CATCTGCTGA TCTAAGCGCT   1860

TCGTCCAAAG TACTTTTATT TCTAACATCT CCAATCACGG GAACTATCTT TATTATATTA   1920

CATTTTTCTA CAAGATCTAG TAACCATTGG TCGATTCTAA TATCGTAAAC ACGAACTTCT   1980

TTTTAAAGAG GATTCGAACA AGATAAGATT ATTTATAATG TGTCTACCTA AAAATCCACA   2040

CCCTCCGGTT ACCACGTATA CTAGTGTACG CATTTTGAGT ATTAACTATA TAAGACCAAA   2100

ATTATATTTT CATTTTCTGT TATATTATAC TATATAATAA AAACAAATAA ATATACGAAT   2160

ATTATAAGAA ATTTAGAACA CGTTATTAAA GTATTGCCTT TTTTATTAAC GGCGTGTTCT   2220

TGTAATTGCC GTTAGAATA GTCTTTATTT ACTTTAGATA ACTCTTCTAT CATAACCGTC   2280

TCCTTATTCC AATCTTCTTC AGAAGTACAT GAGTACTTAC CGAAGTTTAT CATCATAGAG   2340
```

```
ATTATATATG AAGAAA                                                        2356

(2) INFORMATION FOR SEQ ID NO: 79:

(i) SEQUENCE CHARACTERISTICS:
         (A) LENGTH: 965 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 79:

AAAAAGGATC CGGGTTAATT AATTAGTCAT CAGGCAGGGC GAGAACGAGA CTATCTGCTC          60

GTTAATTAAT TAGAGCTTCT TTATTCTATA CTTAAAAAGT GAAATAAAT ACAAAGGTTC         120

TTGAGGGTTG TGTTAAATTG AAAGCGAGAA ATAATCATAA ATTATTTCAT TATCGCGATA        180

TCCGTTAAGT TTGTATCGTA ATGAGCACTG AAAGCATGAT CCGGGACGTG GAGCTGGCCG        240

AGGAGGCGCT CCCCAAGAAG ACAGGGGGGC CCCAGGGCTC CAGGCGGTGC TTGTTCCTCA        300

GCCTCTTCTC CTTCCTGATC GTGGCAGGCG CCACCACGCT CTTCTGCCTG CTGCACTTTG        360

GAGTGATCGG CCCCCAGAGG GAAGAGTCCC CCAGGGACCT CTCTCTAATC AGCCCTCTGG        420

CCCAGGCAGT CAGATCATCT TCTCGAACCC CGAGTGACAA GCCTGTAGCC CATGTTGTAG        480

CAAACCCTCA AGCTGAGGGG CAGCTCCAGT GGCTGAACCG CCGGGCCAAT GCCCTCCTGG        540

CCAATGGCGT GGAGCTGAGA GATAACCAGC TGGTGGTGCC ATCAGAGGGC CTGTACCTCA        600

TCTACTCCCA GGTCCTCTTC AAGGGCCAAG GCTGCCCCTC CACCCATGTG CTCCTCACCC        660

ACACCATCAG CCGCATCGCC GTCTCCTACC AGACCAAGGT CAACCTCCTC TCTGCCATCA        720

AGAGCCCCTG CCAGAGGGAG ACCCCAGAGG GGGCTGAGGC CAAGCCCTGG TATGAGCCCA        780

TCTATCTGGG AGGGGTCTTC CAGCTGGAGA AGGGTGACCG ACTCAGCGCT GAGATCAATC        840

GGCCCGACTA TCTCGACTTT GCCGAGTCTG GGCAGGTCTA CTTTGGGATC ATTGCCCTGT        900

GATTTTTATT CTAGAATCGA TCCCGGGTTT TTATGACTAG TTAATCACGG CCGCTTATAA        960

AGATC                                                                   965

(2) INFORMATION FOR SEQ ID NO: 80:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 80:

ATCATCAAGC TTGATTCTTT ATTCTATAC                                           29

(2) INFORMATION FOR SEQ ID NO: 81:

(i) SEQUENCE CHARACTERISTICS:
         (A) LENGTH: 37 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 81:

CATGCTTTCA GTGCTCATTA CGATACAAAC TTAACGG                                  37
```

(2) INFORMATION FOR SEQ ID NO: 82:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 82:

TTAACGGATA TCGCGATAAT G                                                21

(2) INFORMATION FOR SEQ ID NO: 83:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 83:

ACTACTAAGC TTCTTTATTC TATACTTAAA AAGTG                        35

(2) INFORMATION FOR SEQ ID NO: 84:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 84:

ATGAGCACTG AAAGCATG                                                      18

(2) INFORMATION FOR SEQ ID NO: 85:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 85:

GGGCTCAAGC TTGCGGCCGC TCATTAGACA AGCGAATGAG GGAC             44

(2) INFORMATION FOR SEQ ID NO: 86:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 86:

AGATCTCCCG GGCTCGAGTA ATTAATTAAT TTTTATTACA CCAGAAAAGA CGGCTTGAGA     60

TC                                                                                                62

-continued (2) INFORMATION FOR SEQ ID NO: 87:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 87:

```
TAATTACTCG AGCCCGGGAG ATCTAATTTA ATTTAATTTA TATAACTCAT TTTTTGAATA        60

TACT                                                                    64
```

(2) INFORMATION FOR SEQ ID NO: 88:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 88:

```
TATCTCGAAT TCCCGCGGCT TTAAATGGAC GGAACTCTTT TCCCC                        45
```

(2) INFORMATION FOR SEQ ID NO: 89:

(i) SEQUENCE CHARACTERISTICS:
        (A) LENGTH: 947 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 89:

```
GATCTCAAGC CGTCTTTTCT GGTGTAATAA AAATTAATTA ATTACTCGAG CCCAGCTTGA        60

TTCTTTATTC TATACTTAAA AAGTGAAAAT AAATACAAAG GTTCTTGAGG GTTGTGTTAA       120

ATTGAAAGCG AGAAATAATC ATAAATTATT TCATTATCGC GATATCCGTT AAGTTTGTAT       180

CGTAATGAGC ACTGAAAGCA TGATCCGGGA CGTGGAGCTG GCCGAGGAGG CGCTCCCCAA       240

GAAGACAGGG GGGCCCCAGG GCTCCAGGCG GTGCTTGTTC CTCAGCCTCT TCTCCTTCCT       300

GATCGTGGCA GGCGCCACCA CGCTCTTCTG CCTGCTGCAC TTTGGAGTGA TCGGCCCCCA       360

GAGGGAAGAG TCCCCCAGGG ACCTCTCTCT AATCAGCCCT CTGGCCCAGG CAGTCAGATC       420

ATCTTCTCGA ACCCCGAGTG ACAAGCCTGT AGCCCATGTT GTAGCAAACC CTCAAGCTGA       480

GGGGCAGCTC CAGTGGCTGA ACCGCCGGGC CAATGCCCTC CTGGCCAATG GCGTGGAGCT       540

GAGAGATAAC CAGCTGGTGG TGCCATCAGA GGGCCTGTAC CTCATCTACT CCCAGGTCCT       600

CTTCAAGGGC CAAGGCTGCC CCTCCACCCA TGTGCTCCTC ACCCACACCA TCAGCCGCAT       660

CGCCGTCTCC TACCAGACCA AGGTCAACCT CCTCTCTGCC ATCAAGAGCC CCTGCCAGAG       720

GGAGACCCCA GAGGGGCTG AGGCCAAGCC CTGGTATGAG CCCATCTATC TGGGAGGGGT       780

CTTCCAGCTG GAGAAGGGTG ACCGACTCAG CGCTGAGATC AATCGGCCCG ACTATCTCGA       840

CTTTGCCGAG TCTGGGCAGG TCTACTTTGG GATCATTGCC CTGTGATTTT TATTGGGAGA       900

TCTAATTTAA TTTAATTTAT ATAACTTATT TTTTGAATAT ACTTTTA                     947
```

(2) INFORMATION FOR SEQ ID NO: 90:

(i) SEQUENCE CHARACTERISTICS:
    (A) LENGTH: 41 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 90:

GATCTGACTG CGGCTCCTCC ATTACGATAC AAACTTAACG G                     41

(2) INFORMATION FOR SEQ ID NO: 91:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 91:

GTGGGTAAGG GAATTCGGAT CCCCGGGTTA ATTAATTAGT GATAC                 45

(2) INFORMATION FOR SEQ ID NO: 92:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 92:

GTTTGTATCG TAATGGAGGA GCCGCAGTCA GATC                             34

(2) INFORMATION FOR SEQ ID NO: 93:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 93:

CATTACGATA CAAACTTAAC GGATATCGCG ACGCGTTCAC ACAGGGCAGG TCTTGGC    57

(2) INFORMATION FOR SEQ ID NO: 94:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 94:

TACTACCTCG AGCCCGGGAT AAAAAACGCG TTCAGTCTGA GTCAGGCCC             49

(2) INFORMATION FOR SEQ ID NO: 95:

(i) SEQUENCE CHARACTERISTICS:
        (A) LENGTH: 66 base pairs
        (B) TYPE: nucleic acid
        (C) STRANDEDNESS: single

```
            (D) TOPOLOGY: linear (ii) MOLECULE TYPE: cDNA (xi) SEQUENCE DESCRIPTION: SEQ ID NO: 95:

GTGTGAACGC GTCGCGATAT CCGTTAAGTT TGTATCGTAA TGCAGCTGCG TGGGCGTGAG      60

CGCTTC                                                                66

(2) INFORMATION FOR SEQ ID NO: 96:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 96:

ATCATCGGAT CCCCCGGGTT CTTTATTCTA TAC                                  33

(2) INFORMATION FOR SEQ ID NO: 97:

(i) SEQUENCE CHARACTERISTICS:
            (A) LENGTH: 66 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 97:

AGAAAAATCA GTTAGCTAAG ATCTCCCGGG CTCGAGGGTA CCGGATCCTG ATTAGTTAAT      60

TTTTGT                                                                66

(2) INFORMATION FOR SEQ ID NO: 98:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 98:

GATCACAAAA ATTAACTAAT CAGGATCCGG TACCCTCGAG CCCGGGAGAT CTTAGCTAAC      60

TGATTTTTCT                                                            70

(2) INFORMATION FOR SEQ ID NO: 99:

(i) SEQUENCE CHARACTERISTICS:
            (A) LENGTH: 1512 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 99:

GATTAAAGAA AGTTACTCTG AGACACAAAA GAGGTAGCTG AAGTGGTACT CTCAAAGGTA      60

CCCCCGGGTT AATTAATTAG TCATCAGGCA GGGCGAGAAC GAGACTATCT GCTCGTTAAT     120

TAATTAGGTC GACGGATCCC CGGGTTCTTT ATTCTATACT TAAAAAGTGA AAATAAATAC     180

AAAGGTTCTT GAGGGTTGTG TTAAATTGAA AGCGAGAAAT AATCATAAAT TATTTCATTA     240
```

```
TCGCGATATC CGTTAAGTTT GTATCGTAAT GGAGGAGCCG CAGTCAGATC CTAGCGTCGA      300

GCCCCCTCTG AGTCAGGAAA CATTTTCAGA CCTATGGAAA CTACTTCCTG AAAACAACGT      360

TCTGTCCCCC TTGCCGTCCC AAGCAATGGA TGATTTGATG CTGTCCCCGG ACGATATTGA      420

ACAATGGTTC ACTGAAGACC CAGGTCCAGA TGAAGCTCCC AGAATGCCAG AGGCTGCTCC      480

CCGCGTGGCC CCTGCACCAG CAGCTCCTAC ACCGGCGGCC CCTGCACCAG CCCCCTCCTG      540

GCCCCTGTCA TCTTCTGTCC CTTCCCAGAA AACCTACCAG GGCAGCTACG GTTTCCGTCT      600

GGGCTTCTTG CATTCTGGGA CAGCCAAGTC TGTGACTTGC ACGTACTCCC CTGCCCTCAA      660

CAAGATGTTT TGCCAACTGG CCAAGACCTG CCCTGTGCAG CTGTGGGTTG ATTCCACACC      720

CCCGCCCGGC ACCCGCGTCC GCGCCATGGC CATCTACAAG CAGTCACAGC ACATGACGGA      780

GGTTGTGAGG CGCTGCCCCC ACCATGAGCG CTGCTCAGAT AGCGATGGTC TGGCCCCTCC      840

TCAGCATCTT ATCCGAGTGG AAGGAAATTT GCGTGTGGAG TATTTGGATG ACAGAAACAC      900

TTTTCGACAT AGTGTGGTGG TGCCCTATGA GCCGCCTGAG GTTGGCTCTG ACTGTACCAC      960

CATCCACTAC AACTACATGT GTAACAGTTC CTGCATGGGC GGCATGAACC GGAGGCCCAT     1020

CCTCACCATC ATCACACTGG AAGACTCCAG TGGTAATCTA CTGGGACGGA ACAGCTTTGA     1080

GGTGCGTGTT TGTGCCTGTC CTGGGAGAGA CCGGCGCACA GAGGAAGAGA ATCTCCGCAA     1140

GAAAGGGGAG CCTCACCACG AGCTGCCCCC AGGGAGCACT AAGCGAGCAC TGCCCAACAA     1200

CACCAGCTCC TCTCCCCAGC CAAAGAAGAA ACCACTGGAT GGAGAATATT TCACCCTTCA     1260

GATCCGTGGG CGTGAGCGCT TCGAGATGTT CCGAGAGCTG AATGAGGCCT TGGAACTCAA     1320

GGATGCCCAG GCTGGGAAGG AGCCAGGGGG GAGCAGGGCT CACTCCAGCC ACCTGAAGTC     1380

CAAAAAGGGT CAGTCTACCT CCCGCCATAA AAAACTCATG TTCAAGACAG AAGGGCCTGA     1440

CTCAGACTGA ACGCGTTTTT ATCCCGGGCT CGAGTCTAGA ATCGATCCCG GGTTTTTATG     1500

ACTAGTTAAT CA                                                         1512

(2) INFORMATION FOR SEQ ID NO: 100:

(i) SEQUENCE CHARACTERISTICS:
         (A) LENGTH: 71 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 100:

CATCTTAATT AATTAGTCAT CAGGCAGGGC GAGAACGAAG ACTATCTGCT CGTTAATTAA       60

TTAGGTCGAC G                                                           71

(2) INFORMATION FOR SEQ ID NO: 101:

(i) SEQUENCE CHARACTERISTICS:
         (A) LENGTH: 69 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 101:

CATCCGTCGA CCTAATTAAT TAACGACGAC ATAGTCTCGT TCTCGCCTGC CTGATGACTA       60

ATTAATTAA                                                              69
```

(2) INFORMATION FOR SEQ ID NO: 102:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 102:

```
AATTGCGGCC GC                                                          12
```

(2) INFORMATION FOR SEQ ID NO: 103:

(i) SEQUENCE CHARACTERISTICS:
        (A) LENGTH: 1484 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 103:

```
GGTACGTGAC TAATTAGCTA TAAAAAGGAT CTTAATTAAT TAGTCATCAG GCAGGGCGAG        60
AACGAGACTA TCTGCTCGTT AATTAATTAG GTCGACGGAT CCCCCGGGTT CTTTATTCTA       120
TACTTAAAAA GTGAAAATAA ATACAAAGGT TCTTGAGGGT TGTGTTAAAT TGAAAGCGAG       180
AAATAATCAT AAATTATTTC ATTATCGCGA TATCCGTTAA GTTTGTATCG TAATGGAGGA       240
GCCGCAGTCA GATCCTAGCG TCGAGCCCCC TCTGAGTCAG GAAACATTTT CAGACCTATG       300
GAAACTACTT CCTGAAAACA ACGTTCTGTC CCCCTTGCCG TCCCAAGCAA TGGATGATTT       360
GATGCTGTCC CCGGACGATA TTGAACAATG GTTCACTGAA GACCCAGGTC CAGATGAAGC       420
TCCCAGAATG CCAGAGGCTG CTCCCCGCGT GGCCCCTGCA CCAGCAGCTC CTACACCGGC       480
GGCCCCTGCA CCAGCCCCCT CCTGGCCCCT GTCATCTTCT GTCCCTTCCC AGAAAACCTA       540
CCAGGGCAGC TACGGTTTCC GTCTGGGCTT CTTGCATTCT GGGACAGCCA AGTCTGTGAC       600
TTGCACGTAC TCCCCTGCCC TCAACAAGAT GTTTTGCCAA CTGGCCAAGA CCTGCCCTGT       660
GCAGCTGTGG GTTGATTCCA CACCCCCGCC CGGCACCCGC GTCCGCGCCA TGGCCATCTA       720
CAAGCAGTCA CAGCACATGA CGGAGGTTGT GAGGCGCTGC CCCCACCATG AGCGCTGCTC       780
AGATAGCGAT GGTCTGGCCC CTCCTCAGCA TCTTATCCGA GTGGAAGGAA ATTTGCGTGT       840
GGAGTATTTG GATGACAGAA ACACTTTTCG ACATAGTGTG GTGGTGCCCT ATGAGCCGCC       900
TGAGGTTGGC TCTGACTGTA CCACCATCCA CTACAACTAC ATGTGTAACA GTTCCTGCAT       960
GGGCGGCATG AACCGGAGGC CCATCCTCAC CATCATCACA CTGGAAGACT CCAGTGGTAA      1020
TCTACTGGGA CGGAACAGCT TTGAGGTGCG TGTTTGTGCC TGTCCTGGGA GAGACCGGCG      1080
CACAGAGGAA GAGAATCTCC GCAAGAAAGG GGAGCCTCAC CACGAGCTGC CCCCAGGGAG      1140
CACTAAGCGA GCACTGCCCA ACAACACCAG CTCCTCTCCC CAGCCAAAGA AGAAACCACT      1200
GGATGGAGAA TATTTCACCC TTCAGATCCG TGGGCGTGAG CGCTTCGAGA TGTTCCGAGA      1260
GCTGAATGAG GCCTTGGAAC TCAAGGATGC CCAGGCTGGG AAGGAGCCAG GGGGGAGCAG      1320
GGCTCACTCC AGCCACCTGA AGTCCAAAAA GGGTCAGTCT ACCTCCCGCC ATAAAAAACT      1380
CATGTTCAAG ACAGAAGGGC CTGACTCAGA CTGAACGCGT TTTTTATCCC GGGCTCGAGT      1440
CTAGAATCGA TCCCGGGTTT TTATGACTAG TTAATCACGG CCGC                      1484
```

(2) INFORMATION FOR SEQ ID NO: 104:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 104:

CAGACTCCTC TGCTCAAGAG ACATTACGAT ACAAACTTAA CG        42

(2) INFORMATION FOR SEQ ID NO: 105:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 105:

ATGTCTCTTG AGCAGAGGAG TCTG        24

(2) INFORMATION FOR SEQ ID NO: 106:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 106:

CAGGCCATCA TAGGAGAGAC C        21

(2) INFORMATION FOR SEQ ID NO: 107:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 107:

GTGGCTGATT TGGTTGGTTT TCTG        24

(2) INFORMATION FOR SEQ ID NO: 108:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 108:

ATCATCTCTA GAAAAAAAAT CACATAGCTG GTTTCAG        37

(2) INFORMATION FOR SEQ ID NO: 109:

(i) SEQUENCE CHARACTERISTICS:
        (A) LENGTH: 1094 base pairs (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 109:

| | | | | | |
|---|---|---|---|---|---|
| AAAAAGGATC | CGGGTTAATT | AATTAGTCAT | CAGGCAGGGC | GAGAACGAGA | CTATCTGCTC | 60 |
| GTTAATTAAT | TAGAGCTTCT | TTATTCTATA | CTTAAAAAGT | GAAATAAAT | ACAAAGGTTC | 120 |
| TTGAGGGTTG | TGTTAAATTG | AAAGCGAGAA | ATAATCATAA | ATTATTTCAT | TATCGCGATA | 180 |
| TCCGTTAAGT | TTGTATCGTA | ATGTCTCTTG | AGCAGAGGAG | TCTGCACTGC | AAGCCTGAGG | 240 |
| AAGCCCTTGA | GGCCCAACAA | GAGGCCCTGG | GCCTGGTGTG | TGTGCAGGCT | GCCACCTCCT | 300 |
| CCTCCTCTCC | TCTGGTCCTG | GCACCCTGG | AGGAGGTGCC | CACTGCTGGG | TCAACAGATC | 360 |
| CTCCCCAGAG | TCCTCAGGGA | GCCTCCGCCT | TTCCCACTAC | CATCAACTTC | ACTCGACAGA | 420 |
| GGCAACCCAG | TGAGGGTTCC | AGCAGCCGTG | AAGAGGAGG | GCCAAGCACC | TCTTGTATCC | 480 |
| TGGAGTCCTT | GTTCCGAGCA | GTAATCACTA | AGAAGGTGGC | TGATTTGGTT | GGTTTTCTGC | 540 |
| TCCTCAAATA | TCGAGCCAGG | GAGCCAGTCA | CAAAGGCAGA | AATGCTGGAG | AGTGTCATCA | 600 |
| AAAATTACAA | GCACTGTTTT | CCTGAGATCT | TCGGCAAAGC | CTCTGAGTCC | TTGCAGCTGG | 660 |
| TCTTTGGCAT | TGACGTGAAG | GAAGCAGACC | CCACCGGCCA | CTCCTATGTC | CTTGTCACCT | 720 |
| GCCTAGGTCT | CTCCTATGAT | GGCCTGCTGG | GTGATAATCA | GATCATGCCC | AAGACAGGCT | 780 |
| TCCTGATAAT | TGTCCTGGTC | ATGATTGCAA | TGGAGGCGG | CCATGCTCCT | GAGGAGGAAA | 840 |
| TCTGGGAGGA | GCTGAGTGTG | ATGGAGGTGT | ATGATGGGAG | GGAGCACAGT | GCCTATGGGG | 900 |
| AGCCCAGGAA | GCTGCTCACC | CAAGATTTGG | TGCAGGAAAA | GTACCTGGAG | TACGGCAGGT | 960 |
| GCCGGACAGT | GATCCCGCAC | GCTATGAGTT | CCTGTGGGGT | CCAAGGGCCC | TCGCTGAAAC | 1020 |
| CAGCTATGTG | ATTTTTATTC | TAGAATCGAT | CCCGGGTTTT | TATGACTAGT | TAATCACGGC | 1080 |
| CGCTTATAAA | GATC | | | | | 1094 |

(2) INFORMATION FOR SEQ ID NO: 110:

(i) SEQUENCE CHARACTERISTICS:
       (A) LENGTH: 1084 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 110:

| | | | | | |
|---|---|---|---|---|---|
| ATAAATCACT | TTTTATACTA | ATATTTAATT | AATTAAGCTT | GGTACCCTCG | AAGCTTCTTT | 60 |
| ATTCTATACT | TAAAAAGTGA | AAATAAATAC | AAAGGTTCTT | GAGGGTTGTG | TTAAATTGAA | 120 |
| AGCGAGAAAT | AATCATAAAT | TATTTCATTA | TCGCGATATC | CGTTAAGTTT | GTATCGTAAT | 180 |
| GTCTCTTGAG | CAGAGGAGTC | TGCACTGCAA | GCCTGAGGAA | GCCCTTGAGG | CCCAACAAGA | 240 |
| GGCCCTGGGC | CTGGTGTGTG | TGCAGGCTGC | CACCTCCTCC | TCCTCTCCTC | TGGTCCTGGG | 300 |
| CACCCTGGAG | GAGGTGCCCA | CTGCTGGGTC | AACAGATCCT | CCCCAGAGTC | CTCAGGGAGC | 360 |
| CTCCGCCTTT | CCCACTACCA | TCAACTTCAC | TCGACAGAGG | CAACCCAGTG | AGGGTTCCAG | 420 |
| CAGCCGTGAA | GAGGAGGGGC | CAAGCACCTC | TTGTATCCTG | GAGTCCTTGT | TCCGAGCAGT | 480 |
| AATCACTAAG | AAGGTGGCTG | ATTTGGTTGG | TTTTCTGCTC | CTCAAATATC | GAGCCAGGGA | 540 |
| GCCAGTCACA | AAGGCAGAAA | TGCTGGAGAG | TGTCATCAAA | AATTACAAGC | ACTGTTTTCC | 600 |

-continued

```
TGAGATCTTC GGCAAAGCCT CTGAGTCCTT GCAGCTGGTC TTTGGCATTG ACGTGAAGGA      660

AGCAGACCCC ACCGGCCACT CCTATGTCCT TGTCACCTGC CTAGGTCTCT CCTATGATGG      720

CCTGCTGGGT GATAATCAGA TCATGCCCAA GACAGGCTTC CTGATAATTG TCCTGGTCAT      780

GATTGCAATG GAGGGCGGCC ATGCTCCTGA GGAGGAAATC TGGGAGGAGC TGAGTGTGAT      840

GGAGGTGTAT GATGGGAGGG AGCACAGTGC CTATGGGGAG CCCAGGAAGC TGCTCACCCA      900

AGATTTGGTG CAGGAAAAGT ACCTGGAGTA CGGCAGGTGC CGGACAGTGA TCCCGCACGC      960

TATGAGTTCC TGTGGGGTCC AAGGGCCCTC GCTGAAACCA GCTATGTGAT TTTTATTCTA     1020

GAACTAGTGG ATCCCCCGGG TAGCTAGCTA ATTTTTCTTT TACGTATTAT ATATGTAATA     1080

AACG                                                                 1084
```

(2) INFORMATION FOR SEQ ID NO: 111:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 111:

```
TATCGCGATA TCCGTTAAGT TTGTATCGTA ATGGAGTCTC CCTCG                       45
```

(2) INFORMATION FOR SEQ ID NO: 112:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 112:

```
TGCTAGATCT TTATCTCTCG ACCACTGTAT G                                      31
```

(2) INFORMATION FOR SEQ ID NO: 113:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 113:

```
CTATGAGTGT GGAATCCAGA ACG                                               23
```

(2) INFORMATION FOR SEQ ID NO: 114:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 114:

```
TCAGAAGCTT CCCGGGTCTA GACTCGAGAT AAAAACTATA TCAGAGCAAC C                51
```

(2) INFORMATION FOR SEQ ID NO: 115:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 115:

```
GTCTCAGAAC GTGTTCATGT                                            20
```

(2) INFORMATION FOR SEQ ID NO: 116:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 116:

```
CACGGATCCA TGAAGTCATA TATTTCCTT                                  29
```

(2) INFORMATION FOR SEQ ID NO: 117:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 117:

```
GTGAAGCTTA ATCCATAATC TTCAATAATT                                 30
```

(2) INFORMATION FOR SEQ ID NO: 118:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 118:

```
GTGAAGCTTT TATACATAAC AGAAATAACA                                 30
```

(2) INFORMATION FOR SEQ ID NO: 119:

(i) SEQUENCE CHARACTERISTICS:
        (A) LENGTH: 2981 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 119:

```
ATGAAGTCAT ATATTTCCTT GTTTTTCATA TTGTGTGTTA TATTTAACAA AAATGTTATA    60

AAATGTACAG GAGAAAGTCA AACAGGTAAT ACAGGAGGAG GTCAAGCAGG TAATACAGGA   120

GGAGGTCAAG CAGGTAATAC AGTAGGAGAT CAAGCAGGTA GTACAGGAGG AAGTCCACAA   180

GGTAGTACGG GAGCAAGTCA ACCCGGAAGT TCCGAACCAA GCAATCCTGT AAGTTCCGGA   240
```

```
CATTCTGTAA GTACTGTATC AGTATCACAA ACTTCAACTT CTTCAGAAAA ACAGGATACA    300

ATTCAAGTAA AATCAGCTTT ATTAAAAGAT TATATGGGTT TAAAAGTTAC TGGTCCATGT    360

AACGAAAATT TCATAATGTT CTTAGTTCCT CATATATATA TTGATGTTGA TACAGAAGAT    420

ACTAATATCG AATTAAGAAC AACATTGAAA GAAACAAATA ATGCAATATC ATTTGAATCA    480

AACAGTGGTT CATTAGAAAA AAAAAAATAT GTAAAACTAC CATCAAATGG TACAACTGGT    540

GAACAAAGTT CTAGTTCAAG TTCAAGTTCT AGTTCAAATT CTAGTTCAAG TTCAAGTTCA    600

AGTTCAAGTT CTAGTTCAAG TTCAAGTTCA AGTTCTAGTT CAAGTTCTAG TTCAAGTTCA    660

GAAAGTCTTC CTGCTAATGG ACCTGATTCC CCTACTGTTA AACCGCCAAG AAATTTACAA    720

AATATATGTG AAACTGGAAA AAACTTCAAG TTGGTAGTAT ATATTAAGGA GAATACATTA    780

ATAATTAAAT GGAAAGTATA CGGAGAAACA AAAGATACTA CTGAAAATAA CAAAGTTGAT    840

GTAAGAAAGT ATTTGATAAA TGAAAAGGAA ACCCCATTTA CTAGTATACT AATACATGCG    900

TATAAAGAAC ATAATGGAAC AAACTTAATA GAAAGTAAAA ACTACGCATT AGGATCAGAC    960

ATTCCAGAAA AATGTGATAC CTTAGCTTCC AATTGCTTTT TAAGTGGTAA TTTTAACATT   1020

GAAAAATGCT TTCAATGTGC TCTTTTAGTA GAAAAGAAA ATAAAAATGA CGTATGTTAC    1080

AAATACCTAT CTGAAGATAT TGTAAGTAAA TTCAAAGAAA TAAAAGCTGA GACAGAAGAT   1140

GATGATGAAG ATGATTATAC TGAATATAAA TTAACAGAAT CTATTGATAA TATATTAGTA   1200

AAAATGTTTA AAACAAATGA AAATAATGAT AAATCAGAAT TAATAAAATT AGAAGAAGTA   1260

GATGATAGTT TGAAATTAGA ATTAATGAAT TACTGTAGTT TACTTAAAGA CGTAGATACA   1320

ACAGGTACCT TAGATAATTA TGGGATGGGA AATGAAATGG ATATATTTAA TAACTTAAAG   1380

AGATTATTAA TTTATCATTC AGAAGAAAAT ATTAATACTT TAAAAAATAA ATTCCGTAAT   1440

GCAGCTGTAT GTCTTAAAAA TGTTGATGAT TGGATTGTAA ATAAGAGAGG TTTAGTATTA   1500

CCTGAATTAA ATTATGATTT AGAATATTTC AATGAACATT TATATAATGA TAAAAATTCT   1560

CCAGAAGATA AAGATAATAA AGGAAAAGGT GTCGTACATG TTGATACAAC TTTAGAAAAA   1620

GAAGATACTT TATCATATGA TAACTCAGAT AATATGTTTT GTAATAAAGA ATATTGTAAC   1680

AGATTAAAAG ATGAAAATAA TTGTATATCT AATCTTCAAG TTGAAGATCA AGGTAATTGT   1740

GATACTTCAT GGATTTTTGC TTCAAAATAT CATTTAGAAA CTATTAGATG TATGAAAGGA   1800

TATGAACCTA CCAAAATTTC TGCTCTTTAT GTAGCTAATT GTTATAAAGG TGAACATAAA   1860

GATAGATGTG ATGAAGGTTC TAGTCCAATG GAATTCTTAC AAATTATTGA AGATTATGGA   1920

TTCTTACCAG CAGAATCAAA TTATCCATAT AACTATGTGA AGTTGGAGA ACAATGTCCA   1980

AAGGTAGAAG ATCACTGGAT GAATCTATGG GATAATGGAA AAATCTTACA TAACAAAAAT   2040

GAACCTAATA GTTTAGATGG TAAGGGATAT ACTGCATATG AAAGTGAAAG ATTTCATGAT   2100

AATATGGATG CATTTGTTAA AATTATTAAA ACTGAAGTAA TGAATAAAGG TTCAGTTATT   2160

GCATATATTA AAGCTGAAAA TGTTATGGGA TATGAATTTA GTGGAAAGAA AGTACAGAAC   2220

TTATGTGGTG ATGATACAGC TGATCATGCA GTTAATATTG TTGGTTATGG TAATTATGTG   2280

AATAGCGAAG GAGAAAAAAA ATCCTATTGG ATTGTAAGAA ACAGTTGGGG TCCATATTGG   2340

GGAGATGAAG GTTATTTTAA AGTAGATATG TATGGACCAA CTCATTGTCA TTTTAACTTT   2400

ATTCACAGTG TTGTTATATT CAATGTTGAT TTACCTATGA ATAATAAAAC AACTAAAAAA   2460

GAATCAAAAA TATATGATTA TTATTTAAAG GCCTCTCCAG AATTTTATCA TAACCTTTAC   2520

TTTAAGAATT TTAATGTTGG TAAGAAAAAT TTATTCTCTG AAAAGGAAGA TAATGAAAAC   2580
```

```
AACAAAAAAT TAGGTAACAA CTATATTATA TTCGGTCAAG ATACGGCAGG ATCAGGACAA    2640

AGTGGAAAGG AAAGCAATAC TGCATTAGAA TCTGCAGGAA CTTCAAATGA AGTCTCAGAA    2700

CGTGTTCATG TTTATCACAT ATTAAAACAT ATAAAGGATG GCAAAATAAG AATGGGTATG    2760

CGTAAATATA TAGATACACA AGATGTAAAT AAGAAACATT CTTGTACAAG ATCCTATGCA    2820

TTTAATCCAG AGAATTATGA AAAATGTGTA AATTTATGTA ATGTGAACTG GAAAACATGC    2880

GAGGAAAAAA CATCACCAGG ACTTTGTTTA TCCAAATTGG ATACAAATAA CGAATGTTAT    2940

TTCTGTTATG TATAAAATAA TATAACAAAA AAAAAAAAAA A                       2981
```

(2) INFORMATION FOR SEQ ID NO: 120:

(i) SEQUENCE CHARACTERISTICS:
  (A) LENGTH: 984 amino acids
  (B) TYPE: amino acid
  (C) STRANDEDNESS: single
  (D) TOPOLOGY: linear (ii) MOLECULE TYPE: peptide (v) FRAGMENT TYPE: internal (xi) SEQUENCE DESCRIPTION: SEQ ID NO: 120:

```
Met Lys Ser Tyr Ile Ser Leu Phe Phe Ile Leu Cys Val Ile Phe Asn
1               5                   10                  15

Lys Asn Val Ile Lys Cys Thr Gly Glu Ser Gln Thr Gly Asn Thr Gly
            20                  25                  30

Gly Gly Gln Ala Gly Asn Thr Gly Gly Gly Gln Ala Gly Asn Thr Val
        35                  40                  45

Gly Asp Gln Ala Gly Ser Thr Gly Gly Ser Pro Gln Gly Ser Thr Gly
    50                  55                  60

Ala Ser Gln Pro Gly Ser Ser Glu Pro Ser Asn Pro Val Ser Ser Gly
65                  70                  75                  80

His Ser Val Ser Thr Val Ser Val Ser Ser Thr Ser Thr Ser Ser Glu
                85                  90                  95

Lys Gln Asp Thr Ile Gln Val Lys Ser Ala Leu Leu Lys Asp Tyr Met
            100                 105                 110

Gly Leu Lys Val Thr Gly Pro Cys Asn Glu Asn Phe Ile Met Phe Leu
        115                 120                 125

Val Pro His Ile Tyr Ile Asp Val Asp Thr Glu Asp Thr Asn Ile Glu
    130                 135                 140

Leu Arg Thr Thr Leu Lys Glu Thr Asn Asn Ala Ile Ser Phe Glu Ser
145                 150                 155                 160

Asn Ser Gly Ser Leu Glu Lys Lys Lys Tyr Val Lys Leu Pro Ser Asn
                165                 170                 175

Gly Thr Thr Gly Glu Gln Ser Ser Ser Ser Ser Ser Ser Ser Ser Ser
            180                 185                 190

Asn Ser Ser Ser Ser Ser Ser Ser Ser Ser Ser Ser Ser Ser Ser Ser
        195                 200                 205

Ser Ser Ser Ser Ser Ser Ser Ser Ser Ser Glu Ser Leu Pro
    210                 215                 220

Ala Asn Gly Pro Asp Ser Pro Thr Val Lys Pro Pro Arg Asn Leu Gln
225                 230                 235                 240

Asn Ile Cys Glu Thr Gly Lys Asn Phe Lys Leu Val Val Tyr Ile Lys
                245                 250                 255

Glu Asn Thr Leu Ile Ile Lys Trp Lys Val Tyr Gly Glu Thr Lys Asp
            260                 265                 270
```

-continued

```
Thr Thr Glu Asn Asn Lys Val Asp Val Arg Lys Tyr Leu Ile Asn Glu
        275                 280                 285

Lys Glu Thr Pro Phe Thr Ser Ile Leu Ile His Ala Tyr Lys Glu His
    290                 295                 300

Asn Gly Thr Asn Leu Ile Glu Ser Lys Asn Tyr Ala Leu Gly Ser Asp
305                 310                 315                 320

Ile Pro Glu Lys Cys Asp Thr Leu Ala Ser Asn Cys Phe Leu Ser Gly
                325                 330                 335

Asn Phe Asn Ile Glu Lys Cys Phe Gln Cys Ala Leu Leu Val Glu Lys
            340                 345                 350

Glu Asn Lys Asn Asp Val Cys Tyr Lys Tyr Leu Ser Glu Asp Ile Val
        355                 360                 365

Ser Lys Phe Lys Glu Ile Lys Ala Glu Thr Glu Asp Asp Glu Asp
    370                 375                 380

Asp Tyr Thr Glu Tyr Lys Leu Thr Glu Ser Ile Asp Asn Ile Leu Val
385                 390                 395                 400

Lys Met Phe Lys Thr Asn Glu Asn Asn Asp Lys Ser Glu Leu Ile Lys
                405                 410                 415

Leu Glu Glu Val Asp Asp Ser Leu Lys Leu Glu Leu Met Asn Tyr Cys
            420                 425                 430

Ser Leu Leu Lys Asp Val Asp Thr Thr Gly Thr Leu Asp Asn Tyr Gly
        435                 440                 445

Met Gly Asn Glu Met Asp Ile Phe Asn Asn Leu Lys Arg Leu Leu Ile
    450                 455                 460

Tyr His Ser Glu Glu Asn Ile Asn Thr Leu Lys Asn Lys Phe Arg Asn
465                 470                 475                 480

Ala Ala Val Cys Leu Lys Asn Val Asp Asp Trp Ile Val Asn Lys Arg
                485                 490                 495

Gly Leu Val Leu Pro Glu Leu Asn Tyr Asp Leu Glu Tyr Phe Asn Glu
            500                 505                 510

His Leu Tyr Asn Asp Lys Asn Ser Pro Glu Asp Lys Asp Asn Lys Gly
        515                 520                 525

Lys Gly Val Val His Val Asp Thr Thr Leu Glu Lys Glu Asp Thr Leu
    530                 535                 540

Ser Tyr Asp Asn Ser Asp Asn Met Phe Cys Asn Lys Glu Tyr Cys Asn
545                 550                 555                 560

Arg Leu Lys Asp Glu Asn Asn Cys Ile Ser Asn Leu Gln Val Glu Asp
                565                 570                 575

Gln Gly Asn Cys Asp Thr Ser Trp Ile Phe Ala Ser Lys Tyr His Leu
            580                 585                 590

Glu Thr Ile Arg Cys Met Lys Gly Tyr Glu Pro Thr Lys Ile Ser Ala
        595                 600                 605

Leu Tyr Val Ala Asn Cys Tyr Lys Gly Glu His Lys Asp Arg Cys Asp
    610                 615                 620

Glu Gly Ser Ser Pro Met Glu Phe Leu Gln Ile Ile Glu Asp Tyr Gly
625                 630                 635                 640

Phe Leu Pro Ala Glu Ser Asn Tyr Pro Tyr Asn Tyr Val Lys Val Gly
                645                 650                 655

Glu Gln Cys Pro Lys Val Glu Asp His Trp Met Asn Leu Trp Asp Asn
            660                 665                 670

Gly Lys Ile Leu His Asn Lys Asn Glu Pro Asn Ser Leu Asp Gly Lys
        675                 680                 685
```

```
Gly Tyr Thr Ala Tyr Glu Ser Glu Arg Phe His Asp Asn Met Asp Ala
        690             695             700

Phe Val Lys Ile Ile Lys Thr Glu Val Met Asn Lys Gly Ser Val Ile
705             710             715             720

Ala Tyr Ile Lys Ala Glu Asn Val Met Gly Tyr Glu Phe Ser Gly Lys
            725             730             735

Lys Val Gln Asn Leu Cys Gly Asp Asp Thr Ala Asp His Ala Val Asn
            740             745             750

Ile Val Gly Tyr Gly Asn Tyr Val Asn Ser Glu Gly Glu Lys Lys Ser
            755             760             765

Tyr Trp Ile Val Arg Asn Ser Trp Gly Pro Tyr Trp Gly Asp Glu Gly
    770             775             780

Tyr Phe Lys Val Asp Met Tyr Gly Pro Thr His Cys His Phe Asn Phe
785             790             795             800

Ile His Ser Val Val Ile Phe Asn Val Asp Leu Pro Met Asn Asn Lys
            805             810             815

Thr Thr Lys Lys Glu Ser Lys Ile Tyr Asp Tyr Tyr Leu Lys Ala Ser
            820             825             830

Pro Glu Phe Tyr His Asn Leu Tyr Phe Lys Asn Phe Asn Val Gly Lys
        835             840             845

Lys Asn Leu Phe Ser Glu Lys Glu Asp Asn Glu Asn Asn Lys Lys Leu
850             855             860

Gly Asn Asn Tyr Ile Ile Phe Gly Gln Asp Thr Ala Gly Ser Gly Gln
865             870             875             880

Ser Gly Lys Glu Ser Asn Thr Ala Leu Glu Ser Ala Gly Thr Ser Asn
            885             890             895

Glu Val Ser Glu Arg Val His Val Tyr His Ile Leu Lys His Ile Lys
            900             905             910

Asp Gly Lys Ile Arg Met Gly Met Arg Lys Tyr Ile Asp Thr Gln Asp
            915             920             925

Val Asn Lys Lys His Ser Cys Thr Arg Ser Tyr Ala Phe Asn Pro Glu
            930             935             940

Asn Tyr Glu Lys Cys Val Asn Leu Cys Asn Val Asn Trp Lys Thr Cys
945             950             955             960

Glu Glu Lys Thr Ser Pro Gly Leu Cys Leu Ser Lys Leu Asp Thr Asn
            965             970             975

Asn Glu Cys Tyr Phe Cys Tyr Val
            980
```

(2) INFORMATION FOR SEQ ID NO: 121:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 121:

TAGAATCTGC AGGAACTTCA A                          21

(2) INFORMATION FOR SEQ ID NO: 122:

(i) SEQUENCE CHARACTERISTICS:
        (A) LENGTH: 54 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO: 122:

CTACACGAGC TCCCGGGCTC GAGATAAAAA TTATACATAA CAGAAATAAC ATTC         54

(2) INFORMATION FOR SEQ ID NO: 123:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 123:

CTAGAGAAGC TTCCCGGGAT CCTCAAAATT GAAAATATAT AATTACAATA TAAAATGAAG    60

TCATATATTT CCTTGT                                                   76

(2) INFORMATION FOR SEQ ID NO: 124:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 124:

ACTTCCGGGT TGACTTGCT                                                19

(2) INFORMATION FOR SEQ ID NO: 125:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 125:

GATCTTTTGT TAACAAAAAC TAATCAGCTA TCGCGAATCG ATTCCCGGGG GATCCGGTAC    60

CC                                                                  62

(2) INFORMATION FOR SEQ ID NO: 126:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 126:

TCGAGGGTAC CGGATCCCCC GGGAATCGAT TCGCGATAGC TGATTAGTTT TTGTTAACAA    60

AA                                                                  62

(2) INFORMATION FOR SEQ ID NO: 127:

(i) SEQUENCE CHARACTERISTICS:
        (A) LENGTH: 7351 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 127:

```
AGATATTTGT TAGCTTCTGC CGGAGATACC GTGAAAATCT ATTTTCTGGA AGGAAAGGGA      60
GGTCTTATCT ATTCTGTCAG CAGAGTAGGT TCCTCTAATG ACGAAGACAA TAGTGAATAC     120
TTGCATGAAG GTCACTGTGT AGAGTTCAAA ACTGATCATC AGTGTTTGAT AACTCTAGCG     180
TGTACGAGTC CTTCTAACAC TGTGGTTTAT TGGCTGGAAT AAAAGGATAA AGACACCTAT     240
ACTGATTCAT TTTCATCTGT CAACGTTTCT CTAAGAGATT CATAGGTATT ATTATTACAT     300
CGATCTAGAA GTCAATAAC TGCTAAGTAT ATTATTGGAT TTAACGCGCT ATAAACGCAT      360
CCAAAACCTA CAAATATAGG AGAAGCTTCT CTTATGAAAC TTCTTAAAGC TTTACTCTTA     420
CTATTACTAC TCAAAAGAGA TATTACATTA ATTATGTGAT GAGGCATCCA ACATATAAAG     480
AAGACTAAAG CTGTAGAAGC TGTTATGAAG AATATCTTAT CAGATATATT AGATGCATTG     540
TTAGTTCTGT AGATCAGTAA CGTATAGCAT ACGAGTATAA TTATCGTAGG TAGTAGGTAT     600
CCTAAAATAA ATCTGATACA GATAATAACT TTGTAAATCA ATTCAGCAAT TTCTCTATTA     660
TCATGATAAT GATTAATACA CAGCGTGTCG TTATTTTTTG TTACGATAGT ATTTCTAAAG    720
TAAAGAGCAG GAATCCCTAG TATAATAGAA ATAATCCATA TGAAAAATAT AGTAATGTAC    780
ATATTTCTAA TGTTAACATA TTTATAGGTA AATCCAGGAA GGGTAATTTT TACATATCTA    840
TATACGCTTA TTACAGTTAT TAAAAATATA CTTGCAAACA TGTTAGAAGT AAAAAAGAAA    900
GAACTAATTT TACAAAGTGC TTTACCAAAA TGCCAATGGA AATTACTTAG TATGTATATA    960
ATGTATAAAG GTATGAATAT CACAAACAGC AAATCGGCTA TTCCCAAGTT GAGAAACGGT   1020
ATAATAGATA TATTTCTAGA TACCATTAAT AACCTTATAA GCTTGACGTT TCCTATAATG   1080
CCTACTAAGA AAACTAGAAG ATACATACAT ACTAACGCCA TACGAGAGTA ACTACTCATC   1140
GTATAACTAC TGTTGCTAAC AGTGACACTG ATGTTATAAC TCATCTTTGA TGTGGTATAA   1200
ATGTATAATA ACTATATTAC ACTGGTATTT TATTTCAGTT ATATACTATA TAGTATTAAA   1260
AATTATATTT GTATAATTAT ATTATTATAT TCAGTGTAGA AAGTAAAATA CTATAAATAT   1320
GTATCTCTTA TTTATAACTT ATTAGTAAAG TATGTACTAT TCAGTTATAT TGTTTTATAA   1380
AAGCTAAATG CTACTAGATT GATATAAATG AATATGTAAT AAATTAGTAA TGTAGTATAC   1440
TAATATTAAC TCACATTATG AATACTACTA ATCACGAAGA ATGCAGTAAA ACATATGATA   1500
CAAACATGTT AACAGTTTTA AAAGCCATTA GTAATAAACA GTACAATATA ATTAAGTCTT   1560
TACTTAAAAA AGATATTAAT GTTAATAGAT TATTAACTAG TTATTCTAAC GAAATATATA   1620
AACATTTAGA CATTACATTA TGTAATATAC TTATAGAACG TGCAGCAGAC ATAAACATTA   1680
TAGATAAGAA CAATCGTACA CCGTTGTTTT ATGCGGTAAA GAATAATGAT TATGATATGG   1740
TTAAACTCCT ATTAAAAAAT GGCGCGAATG TAAATTTACA AGATAGTATA GGATATTCAT   1800
GTCTTCACAT CGCAGGTATA CATAATAGTA ACATAGAAAT AGTAGATGCA TTGATATCAT   1860
ACAAACCAGA TTTAAACTCC CGCGATTGGG TAGGTAGAAC ACCGCTACAT ATCTTCGTGA   1920
TAGAATCTAA CTTTGAAGCT GTGAAATTAT TATTAAAGTC AGGTGCATAT GTAGGTTTGA   1980
AAGACAAATG TAAGCATTTT CCTATACACC ATTCTGTAAT GAAATTAGAT CACTTAATAT   2040
CAGGATTGTT ATTAAAATAT GGAGCAAATC CAAATACAAT TAACGGCAAT GGAAAAACAT   2100
TATTAAGCAT TGCTGTAACA TCTAATAATA CACTACTGGT AGAACAGCTG CTGTTATATG   2160
```

```
GAGCAGAAGT TAATAATGGT GGTTATGATG TTCCAGCTCC TATTATATCC GCTGTCAGTG    2220

TTAACAATTA TGATATTGTT AAGATACTGA TACATAATGG TGCGAATATA AATGTATCCA    2280

CGGAAGATGG TAGAACGTCT TTACATACAG CTATGTTTTG GAATAACGCT AAAATAATAG    2340

ATGAGTTGCT TAACTATGGA AGTGACATAA ACAGCGTAGA TACTTATGGT AGAACTCCGT    2400

TATCTTGTTA TCGTAGCTTA AGTTATGATA TCGCTACTAA ACTAATATCA CGTATCATTA    2460

TAACAGATGT CTATCGTGAA GCACCAGTAA ATATCAGCGG ATTTATAATT AATTTAAAAA    2520

CTATAGAAAA TAATGATATA TTCAAATTAA TTAAAGATGA TTGTATTAAA GAGATAAACA    2580

TACTTAAAAG TATAACCCTT AATAAATTTC ATTCATCTGA CATATTTATA CGATATAATA    2640

CTGATATATG TTTATTAACG AGATTTATTC AACATCCAAA GATAATAGAA CTAGACAAAA    2700

AACTCTACGC TTATAAATCT ATAGTCAACG AGAGAAAAAT CAAAGCTACT TACAGGTATT    2760

ATCAAATAAA AAAGTATTA ACTGTACTAC CTTTTTCAGG ATATTTCTCT ATATTGCCGT     2820

TTGATGTGTT AGTATATATA CTTGAATTCA TCTATGATAA TAATATGTTG GTACTTATGA    2880

GAGCGTTATC ATTAAAATGA AATAAAAAGC ATACAAGCTA TTGCTTCGCT ATCGTTACAA    2940

AATGGCAGGA ATTTTGTGTA AACTAAGCCA CATACTTGCC AATGAAAAAA ATAGTAGAAA    3000

GGATACTATT TTAATGGGAT TAGATGTTAA GGTTCCTTGG GATTATAGTA ACTGGGCATC    3060

TGTTAACTTT TACGACGTTA GGTTAGATAC TGATGTTACA GATTATAATA ATGTTACAAT    3120

AAAATACATG ACAGGATGTG ATATTTTTCC TCATATAACT CTTGGAATAG CAAATATGGA    3180

TCAATGTGAT AGATTTGAAA ATTTCAAAAA GCAAATAACT GATCAAGATT TACAGACTAT    3240

TTCTATAGTC TGTAAAGAAG AGATGTGTTT TCCTCAGAGT AACGCCTCTA AACAGTTGGG    3300

AGCGAAAGGA TGCGCTGTAG TTATGAAACT GGAGGTATCT GATGAACTTA GAGCCCTAAG    3360

AAATGTTCTG CTGAATGCGG TACCCTGTTC GAAGGACGTG TTTGGTGATA TCACAGTAGA    3420

TAATCCGTGG AATCCTCACA TAACAGTAGG ATATGTTAAG GAGGACGATG TCGAAAACAA    3480

GAAACGCCTA ATGGAGTGCA TGTCCAAGTT TAGGGGGCAA GAAATACAAG TTCTAGGATG    3540

GTATTAATAA GTATCTAAGT ATTTGGTATA ATTTATTAAA TAGTATAATT ATAACAAATA    3600

ATAAATAACA TGATAACGGT TTTTATTAGA ATAAAATAGA GATAATATCA TAATGATATA    3660

TAATACTTCA TTACCAGAAA TGAGTAATGG AAGACTTATA AATGAACTGC ATAAAGCTAT    3720

AAGGTATAGA GATATAAATT TAGTAAGGTA TATACTTAAA AAATGCAAAT ACAATAACGT    3780

AAATATACTA TCAACGTCTT TGTATTTAGC CGTAAGTATT TCTGATATAG AAATGGTAAA    3840

ATTATTACTA GAACACGGTG CCGATATTTT AAAATGTAAA AATCCTCCTC TTCATAAAGC    3900

TGCTAGTTTA GATAATACAG AAATTGCTAA ACTACTAATA GATTCTGGCG CTGACATAGA    3960

ACAGATACAT TCTGGAAATA GTCCGTTATA TATTTCTGTA TATAGAAACA ATAAGTCATT    4020

AACTAGATAT TTATTAAAAA AAGGTGTTAA TTGTAATAGA TTCTTTCTAA ATTATTACGA    4080

TGTACTGTAT GATAAGATAT CTGATGATAT GTATAAAATA TTTATAGATT TTAATATTGA    4140

TCTTAATATA CAAACTAGAA ATTTTGAAAC TCCGTTACAT TACGCTATAA AGTATAAGAA    4200

TATAGATTTA ATTAGGATAT TGTTAGATAA TAGTATTAAA ATAGATAAAA GTTTATTTTT    4260

GCATAAACAG TATCTCATAA AGGCACTTAA AAATAATTGT AGTTACGATA TAATAGCGTT    4320

ACTTATAAAT CACGGAGTGC CTATAAACGA ACAAGATGAT TTAGGTAAAA CCCCATTACA    4380

TCATTCGGTA ATTAATAGAA GAAAAGATGT AACAGCACTT CTGTTAAATC TAGGAGCTGA    4440

TATAAACGTA ATAGATGACT GTATGGGCAG TCCCTTACAT TACGCTGTTT CACGTAACGA    4500
```

```
TATCGAAACA ACAAAGACAC TTTTAGAAAG AGGATCTAAT GTTAATGTGG TTAATAATCA    4560

TATAGATACC GTTCTAAATA TAGCTGTTGC ATCTAAAAAC AAAACTATAG TAAACTTATT    4620

ACTGAAGTAC GGTACTGATA CAAAGTTGGT AGGATTAGAT AAACATGTTA TTCACATAGC    4680

TATAGAAATG AAAGATATTA ATATACTGAA TGCGATCTTA TTATATGGTT GCTATGTAAA    4740

CGTCTATAAT CATAAAGGTT TCACTCCTCT ATACATGGCA GTTAGTTCTA TGAAAACAGA    4800

ATTTGTTAAA CTCTTACTTG ACCACGGTGC TTACGTAAAT GCTAAAGCTA AGTTATCTGG    4860

AAATACTCCT TTACATAAAG CTATGTTATC TAATAGTTTT AATAATATAA AATTACTTTT    4920

ATCTTATAAC GCCGACTATA ATTCTCTAAA TAATCACGGT AATACGCCTC TAACTTGTGT    4980

TAGCTTTTTA GATGACAAGA TAGCTATTAT GATAATATCT AAAATGATGT TAGAAATATC    5040

TAAAAATCCT GAAATAGCTA ATTCAGAAGG TTTTATAGTA AACATGGAAC ATATAAACAG    5100

TAATAAAAGA CTACTATCTA TAAAAGAATC ATGCGAAAAA GAACTAGATG TTATAACACA    5160

TATAAAGTTA AATTCTATAT ATTCTTTTAA TATCTTTCTT GACAATAACA TAGATCTTAT    5220

GGTAAAGTTC GTAACTAATC CTAGAGTTAA TAAGATACCT GCATGTATAC GTATATATAG    5280

GGAATTAATA CGGAAAAATA AATCATTAGC TTTTCATAGA CATCAGCTAA TAGTTAAAGC    5340

TGTAAAAGAG AGTAAGAATC TAGGAATAAT AGGTAGGTTA CCTATAGATA TCAAACATAT    5400

AATAATGGAA CTATTAAGTA ATAATGATTT ACATTCTGTT ATCACCAGCT GTTGTAACCC    5460

AGTAGTATAA AGTGATTTTA TTCAATTACG AAGATAAACA TTAAATTTGT TAACAGATAT    5520

GAGTTATGAG TATTTAACTA AAGTTACTTT AGGTACAAAT AAAATATTAT GTAATATAAT    5580

AGAAAATTAT CTTGAGTCTT CATTTCCATC ACCGTCTAAA TTTATTATTA AAACCTTATT    5640

ATATAAGGCT GTTGAGTTTA GAAATGTAAA TGCTGTAAAA AAAATATTAC AGAATGATAT    5700

TGAATATGTT AAAGTAGATA GTCATGGTGT CTCGCCTTTA CATATTATAG CTATGCCTTC    5760

AAATTTTTCT CTCATAGACG CTGACATGTA TTCAGAATTT AATGAAATTA GTAATAGACT    5820

TCAAAAATCT AAAGATAGTA ACGAATTTCA ACGAGTTAGT CTACTAAGGA CAATTATAGA    5880

ATATGGTAAT GATAGTGATA TTAATAAGTG TCTAACATTA GTAAAAACGG ATATACAGAG    5940

TAACGAAGAG ATAGATATTA TAGATCTTTT GATAAATAAA GGAATAGATA TAAATATTAA    6000

AGACGATTTA GGAAACACAG CTTTGCATTA CTCGTGTGAT TATGCTAAGG GATCAAAGAT    6060

AGCTAAAAAG TTACTAGATT GTGGAGCAGA TCCTAACATA GTTAATGATT TAGGTGTTAC    6120

ACCACTAGCG TGTGCCGTTA ATACTTGCAA CGAGATACTA GTAGATATTC TGTTAAATAA    6180

TGATGCGAAT CCTGATTCAT CTTCCTCATA TTTTTTAGGT ACTAATGTGT TACATACAGC    6240

CGTAGGTACC GGTAATATAG ATATTGTAAG ATCTTTACTT ACGGCTGGTG CCAATCCTAA    6300

TGTAGGAGAT AAATCTGGAG TTACTCCTTT GCACGTTGCT GCAGCTGATA AAGACAGTTA    6360

TCTGTTAATG GAGATGCTAC TAGATAGCGG GGCAGATCCA AATATAAAAT GCGCAAACGG    6420

TTTTACTCCT TTGTTTAATG CAGTATATGA TCATAACCGT ATAAAGTTAT TATTTCTTTA    6480

CGGGGCTGAT ATCAATATTA CTGACTCTTA CGGAAATACT CCTCTTACTT ATATGACTAA    6540

TTTTGATAAT AAATATGTAA ATTCAATAAT TATCTTACAA ATATATCTAC TTAAAAAAGA    6600

ATATAACGAT GAAAGATTGT TCCACCTGG TATGATAAAA AATTTAAACT TTATAGAATC    6660

AAACGATAGT CTTAAAGTTA TAGCTAAAAA GTGTAATTCG TTAATACGCT ATAAGAAAAA    6720

TAAAGACATA GATGCAGATA ACGTATTATT GGAGCTTTTA GAGGAAGAGG AAGAAGATGA    6780

AATAGACAGA TGGCATACTA CATGTAAAAT ATCTTAAATA GTAATTAAAT CATTGAAATA    6840

TTAACTTACA AGATGATCGA GGTCACTTAT TATACTCTTT AATAATGGGT ACAAAGAGTA    6900
```

```
TTCATACGTT AGTTAAATCT AACGATGTAA TACGTGTTCG TGAATTAATA AAGGATGATA    6960

GATGTTTGAT AAATAAAAGA AATAGAAGAA ATCAGTCACC TGTATATATA GCTATATACA    7020

AAGGACTTTA TGAAATGACT GAAATGTTAT TGCTAAATAA TGCAAGTCTA GATACTAAAA    7080

TACCTTCTTT AATTATAGCA GCTAAAAATA ATGACTTACC TATGATAAAA TTATTGATAC    7140

AATACGGGGC AAAATTAAAT GATATTTATT TAAGGGACAC AGCATTAATG ATAGCTCTCA    7200

GAAATGGTTA CCTAGATATA GCTGAATATT TACTTTCATT AGGAGCAGAA TTTGTTAAAT    7260

ACAGACATAA GGTAATATAT AAATATCTAT CAAAAGATGC GTATGAATTA CTTTTTAGAT    7320

TTAATTATGC AGTTAATATA ATAGATTGAG A                                   7351
```

(2) INFORMATION FOR SEQ ID NO: 128:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 128:

```
CAGTTGGTAC CACTGGTATT TTATTTCAG                                      29
```

(2) INFORMATION FOR SEQ ID NO: 129:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 129:

```
TATCTGAATT CCTGCAGCCC GGGTTTTTAT AGCTAATTAG TCAAATGTGA GTTAATATTA    60

G                                                                     61
```

(2) INFORMATION FOR SEQ ID NO: 130:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 130:

```
TCGCTGAATT CGATATCAAG CTTATCGATT TTTATGACTA GTTAATCAAA TAAAAAGCAT    60

ACAAGC                                                                66
```

(2) INFORMATION FOR SEQ ID NO: 131:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 131:

```
TTATCGAGCT CTGTAACATC AGTATCTAAC                              30
```

(2) INFORMATION FOR SEQ ID NO: 132:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 132:

```
TCCGGTACCG CGGCCGCAGA TATTTGTTAG CTTCTGC                      37
```

(2) INFORMATION FOR SEQ ID NO: 133:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 133:

```
TCGCTCGAGT AGGATACCTA CCTACTACCT ACG                          33
```

(2) INFORMATION FOR SEQ ID NO: 134:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 134:

```
TCGCTCGAGC TTTCTTGACA ATAACATAG                               29
```

(2) INFORMATION FOR SEQ ID NO: 135:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 135:

```
TAGGAGCTCT TTATACTACT GGGTTACAAC                              30
```

(2) INFORMATION FOR SEQ ID NO: 136:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 136:

```
AATTCCTCGA GGGATCC                                            17
```

(2) INFORMATION FOR SEQ ID NO: 137:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 137:

CGGGATCCCT CGAGG                                                         15

(2) INFORMATION FOR SEQ ID NO: 138:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 138:

CCGGTTAATT AATTAGTTAT TAGACAAGGT GAAAACGAAA CTATTTGTAG CTTAATTAAT         60

TAGGTCACC                                                                69

(2) INFORMATION FOR SEQ ID NO: 139:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 139:

CCGGGGTCGA CCTAATTAAT TAAGCTACAA ATAGTTTCGT TTTCACCTTG TCTAATAACT         60

AATTAATTAA                                                               70

(2) INFORMATION FOR SEQ ID NO: 140:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 140:

CCCCCCGAAT TCGTCGACGA TTGTTCATGA TGGCAAGAT                                39

(2) INFORMATION FOR SEQ ID NO: 141:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 141:

CCCGGGGGAT CCCTCGAGGG TACCAAGCTT AATTAATTAA ATATTAGTAT AAAAAGTGAT         60

TTATTTTT                                                                 68

(2) INFORMATION FOR SEQ ID NO: 142:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 142:

```
AAGCTTGGTA CCCTCGAGGG ATCCCCCGGG TAGCTAGCTA ATTTTTCTTT TACGTATTAT    60

ATATGTAATA AACGTTC                                                  77
```

(2) INFORMATION FOR SEQ ID NO: 143:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 143:

```
TTTTTTCTGC AGGTAAGTAT TTTTAAAACT TCTAACACC                           39
```

(2) INFORMATION FOR SEQ ID NO: 144:

(i) SEQUENCE CHARACTERISTICS:
        (A) LENGTH: 2434 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 144:

```
GAAGCAATAG CTTGTATGCT TTTTATTTGA TTAACTAGTC ATAAAAATCG GGATCCTTCT    60

TTATTCTATA CTTAAAAAGT GAAAATAAAT ACAAAGGTTC TTGAGGGTTG TGTTAAATTG   120

AAAGCGAGAA ATAATCATAA ATTATTTCAT TATCGCGATA TCCGTTAAGT TTGTATCGTA   180

ATGGAGTCTC CCTCGGCCCC TCCCCACAGA TGGTGCATCC CCTGGCAGAG GCTCCTGCTC   240

ACAGCCTCAC TTCTAACCTT CTGGAACCCG CCCACCACTG CCAAGCTCAC TATTGAATCC   300

ACGCCGTTCA ATGTCGCAGA GGGGAAGGAG GTGCTTCTAC TTGTCCACAA TCTGCCCCAG   360

CATCTTTTTG GCTACAGCTG GTACAAAGGT GAAAGAGTGG ATGGCAACCG TCAAATTATA   420

GGATATGTAA TAGGAACTCA ACAAGCTACC CCAGGGCCCG CATACAGTGG TCGAGAGATA   480

ATATACCCCA ATGCATCCCT GCTGATCCAG AACATCATCC AGAATGACAC AGGATTCTAC   540

ACCCTACACG TCATAAAGTC AGATCTTGTG AATGAAGAAG CAACTGGCCA GTTCCGGGTA   600

TACCCGGAGC TGCCCAAGCC CTCCATCTCC AGCAACAACT CCAAACCCGT GGAGGACAAG   660

GATGCTGTGG CCTTCACCTG TGAACCTGAG ACTCAGGACG CAACCTACCT GTGGTGGGTA   720

AACAATCAGA GCCTCCCGGT CAGTCCCAGG CTGCAGCTGT CCAATGGCAA CAGGACCCTC   780

ACTCTATTCA ATGTCACAAG AAATGACACA GCAAGCTACA AATGTGAAAC CCAGAACCCA   840

GTGAGTGCCA GGCGCAGTGA TTCAGTCATC CTGAATGTCC TCTATGGCCC GGATGCCCCC   900

ACCATTTCCC CTCTAAACAC ATCTTACAGA TCAGGGGAAA ATCTGAACCT CTCCTGCCAC   960

GCAGCCTCTA ACCCACCTGC ACAGTACTCT TGGTTTGTCA ATGGGACTTT CCAGCAATCC  1020
```

-continued

```
ACCCAAGAGC TCTTTATCCC CAACATCACT GTGAATAATA GTGGATCCTA TACGTGCCAA   1080

GCCCATAACT CAGACACTGG CCTCAATAGG ACCACAGTCA CGACGATCAC AGTCTATGCA   1140

GAGCCACCCA AACCCTTCAT CACCAGCAAC AACTCCAACC CCGTGGAGGA TGAGGATGCT   1200

GTAGCCTTAA CCTGTGAACC TGAGATTCAG AACACAACCT ACCTGTGGTG GGTAAATAAT   1260

CAGAGCCTCC CGGTCAGTCC CAGGCTGCAG CTGTCCAATG ACAACAGGAC CCTCACTCTA   1320

CTCAGTGTCA CAAGGAATGA TGTAGGACCC TATGAGTGTG GAATCCAGAA CGAATTAAGT   1380

GTTGACCACA GCGACCCAGT CATCCTGAAT GTCCTCTATG CCCAGACGA CCCCACCATT    1440

TCCCCCTCAT ACACCTATTA CCGTCCAGGG GTGAACCTCA GCCTCTCCTG CCATGCAGCC   1500

TCTAACCCAC CTGCACAGTA TTCTTGGCTG ATTGATGGGA ACATCCAGCA ACACACACAA   1560

GAGCTCTTTA TCTCCAACAT CACTGAGAAG AACAGCGGAC TCTATACCTG CCAGGCCAAT   1620

AACTCAGCCA GTGGCCACAG CAGGACTACA GTCAAGACAA TCACAGTCTC TGCGGAGCTG   1680

CCCAAGCCCT CCATCTCCAG CAACAACTCC AAACCCGTGG AGGACAAGGA TGCTGTGGCC   1740

TTCACCTGTG AACCTGAGGC TCAGAACACA ACCTACCTGT GGTGGGTAAA TGGTCAGAGC   1800

CTCCCAGTCA GTCCCAGGCT GCAGCTGTCC AATGGCAACA GGACCCTCAC TCTATTCAAT   1860

GTCACAAGAA ATGACGCAAG AGCCTATGTA TGTGGAATCC AGAACTCAGT GAGTGCAAAC   1920

CGCAGTGACC CAGTCACCCT GGATGTCCTC TATGGGCCGG ACACCCCCAT CATTTCCCCC   1980

CCAGACTCGT CTTACCTTTC GGGAGCGAAC CTCAACCTCT CCTGCCACTC GGCCTCTAAC   2040

CCATCCCCGC AGTATTCTTG GCGTATCAAT GGGATACCGC AGCAACACAC ACAAGTTCTC   2100

TTTATCGCCA AAATCACGCC AAATAATAAC GGGACCTATG CCTGTTTTGT CTCTAACTTG   2160

GCTACTGGCC GCAATAATTC CATAGTCAAG AGCATCACAG TCTCTGCATC TGGAACTTCT   2220

CCTGGTCTCT CAGCTGGGGC CACTGTCGGC ATCATGATTG GAGTGCTGGT TGGGGTTGCT   2280

CTGATATAGT TTTTATCTCG AGGAATTCCT GCAGCCCGGG GTGACCTAAT TAATTAAGCT   2340

ACAAATAGTT TCGTTTTCAC CTTGTCTAAT AACTAATTAA TTAACCGGGT TTTTATAGCT   2400

AATTAGTCAA ATGTGAGTTA ATATTAGTAT ACTA                               2434
```

(2) INFORMATION FOR SEQ ID NO: 145:

(i) SEQUENCE CHARACTERISTICS:
        (A) LENGTH: 2349 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 145:

```
TAAAAATAAA TCACTTTTTA TACTAATATT TAATTAATTA AGCTTGGTAC CCTCGAAGCT     60

TCTTTATTCT ATACTTAAAA AGTGAAAATA AATACAAAGG TTCTTGAGGG TTGTGTTAAA    120

TTGAAAGCGA GAAATAATCA TAAATTATTT CATTATCGCG ATATCCGTTA AGTTTGTATC    180

GTAATGGAGT CTCCCTCGGC CCCTCCCCAC AGATGGTGCA TCCCCTGGCA GAGGCTCCTG    240

CTCACAGCCT CACTTCTAAC CTTCTGGAAC CCGCCCACCA CTGCCAAGCT CACTATTGAA    300

TCCACGCCGT TCAATGTCGC AGAGGGGAAG GAGGTGCTTC TACTTGTCCA CAATCTGCCC    360

CAGCATCTTT TTGGCTACAG CTGGTACAAA GGTGAAAGAG TGGATGGCAA CCGTCAAATT    420

ATAGGATATG TAATAGGAAC TCAACAAGCT ACCCCAGGGC CCGCATACAG TGGTCGAGAG    480

ATAATATACC CCAATGCATC CCTGCTGATC CAGAACATCA TCCAGAATGA CACAGGATTC    540
```

-continued

```
TACACCCTAC ACGTCATAAA GTCAGATCTT GTGAATGAAG AAGCAACTGG CCAGTTCCGG      600

GTATACCCGG AGCTGCCCAA GCCCTCCATC TCCAGCAACA ACTCCAAACC CGTGGAGGAC      660

AAGGATGCTG TGGCCTTCAC CTGTGAACCT GAGACTCAGG ACGCAACCTA CCTGTGGTGG      720

GTAAACAATC AGAGCCTCCC GGTCAGTCCC AGGCTGCAGC TGTCCAATGG CAACAGGACC      780

CTCACTCTAT TCAATGTCAC AAGAAATGAC ACAGCAAGCT ACAAATGTGA AACCCAGAAC      840

CCAGTGAGTG CCAGGCGCAG TGATTCAGTC ATCCTGAATG TCCTCTATGG CCCGGATGCC      900

CCCACCATTT CCCCTCTAAA CACATCTTAC AGATCAGGGG AAAATCTGAA CCTCTCCTGC      960

CACGCAGCCT CTAACCCACC TGCACAGTAC TCTTGGTTTG TCAATGGGAC TTTCCAGCAA     1020

TCCACCCAAG AGCTCTTTAT CCCCAACATC ACTGTGAATA ATAGTGGATC CTATACGTGC     1080

CAAGCCCATA ACTCAGACAC TGGCCTCAAT AGGACCACAG TCACGACGAT CACAGTCTAT     1140

GCAGAGCCAC CCAAACCCTT CATCACCAGC AACAACTCCA ACCCCGTGGA GGATGAGGAT     1200

GCTGTAGCCT TAACCTGTGA ACCTGAGATT CAGAACACAA CCTACCTGTG GTGGGTAAAT     1260

AATCAGAGCC TCCCGGTCAG TCCCAGGCTG CAGCTGTCCA ATGACAACAG GACCCTCACT     1320

CTACTCAGTG TCACAAGGAA TGATGTAGGA CCCTATGAGT GTGGAATCCA GAACGAATTA     1380

AGTGTTGACC ACAGCGACCC AGTCATCCTG AATGTCCTCT ATGGCCCAGA CGACCCCACC     1440

ATTTCCCCCT CATACACCTA TTACCGTCCA GGGGTGAACC TCAGCCTCTC CTGCCATGCA     1500

GCCTCTAACC CACCTGCACA GTATTCTTGG CTGATTGATG GAACATCCA GCAACACACA      1560

CAAGAGCTCT TTATCTCCAA CATCACTGAG AAGAACAGCG GACTCTATAC CTGCCAGGCC     1620

AATAACTCAG CCAGTGGCCA CAGCAGGACT ACAGTCAAGA CAATCACAGT CTCTGCGGAG     1680

CTGCCCAAGC CCTCCATCTC CAGCAACAAC TCCAAACCCG TGGAGGACAA GGATGCTGTG     1740

GCCTTCACCT GTGAACCTGA GGCTCAGAAC ACAACCTACC TGTGGTGGGT AAATGGTCAG     1800

AGCCTCCCAG TCAGTCCCAG GCTGCAGCTG TCCAATGGCA ACAGGACCCT CACTCTATTC     1860

AATGTCACAA GAAATGACGC AAGAGCCTAT GTATGTGGAA TCCAGAACTC AGTGAGTGCA     1920

AACCGCAGTG ACCCAGTCAC CCTGGATGTC CTCTATGGGC CGGACACCCC CATCATTTCC     1980

CCCCCAGACT CGTCTTACCT TTCGGGAGCG AACCTCAACC TCTCCTGCCA CTCGGCCTCT     2040

AACCCATCCC CGCAGTATTC TTGGCGTATC AATGGGATAC CGCAGCAACA CACACAAGTT     2100

CTCTTTATCG CCAAAATCAC GCCAAATAAT AACGGGACCT ATGCCTGTTT TGTCTCTAAC     2160

TTGGCTACTG GCCGCAATAA TTCCATAGTC AAGAGCATCA CAGTCTCTGC ATCTGGAACT     2220

TCTCCTGGTC TCTCAGCTGG GGCCACTGTC GGCATCATGA TTGGAGTGCT GGTTGGGGTT     2280

GCTCTGATAT AGTTTTTATC TCGAGGGATC CCCCGGGTAG CTAGCTAATT TTTCTTTTAC     2340

GTATTATAT                                                            2349
```

(2) INFORMATION FOR SEQ ID NO: 146:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 146:

```
ATCATCGGAT CCCTGCAGCC CGGGTTAATT AATTAGTGAT AC                          42
```

(2) INFORMATION FOR SEQ ID NO: 147:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 147:

GAGCTGCATG CTGTACATTA CGATACAAAC TTAACGGA                                    38

(2) INFORMATION FOR SEQ ID NO: 148:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 148:

CGTTAAGTTT GTATCGTAAT GTACAGCATG CAGCTG                                      36

(2) INFORMATION FOR SEQ ID NO: 149:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 149:

GAGGAGGAAT TCCCCGGGTT ATTGAGGGCT TGTTGAGA                                    38

(2) INFORMATION FOR SEQ ID NO: 150:

(i) SEQUENCE CHARACTERISTICS:
            (A) LENGTH: 510 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 150:

ATGTACAGCA TGCAGCTCGC ATCCTGTGTC ACATTGACAC TTGTGCTCCT TGTCAACAGC            60

GCACCCACTT CAAGCTCCAC TTCAAGCTCT ACAGCGGAAG CACAGCAGCA GCAGCAGCAG           120

CAGCAGCAGC AGCAGCAGCA CCTGGAGCAG CTGTTGATGG ACCTACAGGA GCTCCTGAGC           180

AGGATGGAGA ATTACAGGAA CCTGAAACTC CCCAGGATGC TCACCTTCAA ATTTTACTTG           240

CCCAAGCAGG CCACAGAATT GAAAGATCTT CAGTGCCTAG AAGATGAACT TGGACCTCTG           300

CGGCATGTTC TGGATTTGAC TCAAAGCAAA AGCTTTCAAT TGGAAGATGC TGAGAATTTC           360

ATCAGCAATA TCAGAGTAAC TGTTGTAAAA CTAAAGGGCT CTGACAACAC ATTTGAGTGC           420

CAATTCGATG ATGAGTCAGC AACTGTGGTG GACTTTCTGA GGAGATGGAT AGCCTTCTGT           480

CAAAGCATCA TCTCAACAAG CCCTCAATAA                                           510

(2) INFORMATION FOR SEQ ID NO: 151:

(i) SEQUENCE CHARACTERISTICS:
            (A) LENGTH: 17 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 151:

GGCCGCGTCG ACATGCA                                                          17

(2) INFORMATION FOR SEQ ID NO: 152:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 152:

TGTCGACGC                                                                    9

(2) INFORMATION FOR SEQ ID NO: 153:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 153:

GGTCGACGGA TCCT                                                             14

(2) INFORMATION FOR SEQ ID NO: 154:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 154:

GATCAGGATC CGTCGACCTG CA                                                    22

(2) INFORMATION FOR SEQ ID NO: 155:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 155:

GAGTTGCATC CTGTACATTA CGATACAAAC TTAACGGA                                   38

(2) INFORMATION FOR SEQ ID NO: 156:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 156:

CGTTAAGTTT GTATCGTAAT GTACAGGATG CAACTC                                      36

(2) INFORMATION FOR SEQ ID NO: 157:

(i) SEQUENCE CHARACTERISTICS:
            (A) LENGTH: 79 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 157:

TTGTAGCTGT GTTTTCTTTG TAGAACTTGA AGTAGGTGCA CTGTTTGTGA CAAGTGCAAG             60

ACTTAGTGCA ATGCAAGAC                                                         79

(2) INFORMATION FOR SEQ ID NO: 158:

(i) SEQUENCE CHARACTERISTICS:
            (A) LENGTH: 79 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 158:

TTCTACAAAG AAAACACAGC TACAACTGGA GCATTTACTT CTGGATTTAC AGATGATTTT            60

GAATGGAATT AATAATTAC                                                         79

(2) INFORMATION FOR SEQ ID NO: 159:

(i) SEQUENCE CHARACTERISTICS:
            (A) LENGTH: 462 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 159:

ATGTACAGGA TGCAACTCCT GTCTTGCATT GCACTAAGTC TTGCACTTGT CACAAACAGT            60

GCACCTACTT CAAGTTCTAC AAAGAAAACA CAGCTACAAC TGGAGCATTT ACTTCTGGAT           120

TTACAGATGA TTTTGAATGG AATTAATAAT TACAAGAATC CCAAACTCAC CAGGATGCTC           180

ACATTTAAGT TTTACATGCC CAAGAAGGCC ACAGAACTGA ACATCTTCA GTGTCTAGAA            240

GAAGAACTCA AACCTCTGGA GGAAGTGCTA AATTTAGCTC AAAGCAAAAA CTTTCACTTA           300

AGACCCAGGG ACTTAATCAG CAATATCAAC GTAATAGTTC TGGAACTAAA GGGATCTGAA           360

ACAACATTCA TGTGTGAATA TGCTGATGAG ACAGCAACCA TTGTAGAATT TCTGAACAGA           420

TGGATTACCT TTTGTCAAAG CATCATCTCA ACACTGACTT GA                              462

(2) INFORMATION FOR SEQ ID NO: 160:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 160:

GAGGAGGAAT TCCCCGGGTC AAGTCAGTGT TGAGATGA                                       38

(2) INFORMATION FOR SEQ ID NO: 161:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 161:

TAATCATGAA CGCTACACAC TGC                                                       23

(2) INFORMATION FOR SEQ ID NO: 162:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 162:

CCCGGATCCC TGCAGTTATT GGGACAATCT CTT                                            33

(2) INFORMATION FOR SEQ ID NO: 163:

(i) SEQUENCE CHARACTERISTICS:
        (A) LENGTH: 598 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 163:

ACATCATGCA GTGGTTAAAC AAAAACATTT TTATTCTCAA ATGAGATAAA GTGAAAATAT                60

ATATCATTAT ATTACAAAGT ACAATTATTT AGGTTTAATC ATGAACGCTA CACACTGCAT              120

CTTGGCTTTG CAGCTCTTCC TCATGGCTGT TTCTGGCTGT TACTGCCACG GCACAGTCAT              180

TGAAAGCCTA GAAAGTCTGA ATAACTATTT TAACTCAAGT GGCATAGATG TGGAAGAAAA              240

GAGTCTCTTC TTGGATATCT GGAGGAACTG GCAAAAGGAT GGTGACATGA AAATCCTGCA              300

GAGCCAGATT ATCTCTTTCT ACCTCAGACT CTTTGAAGTC TTGAAAGACA ATCAGGCCAT              360

CAGCAACAAC ATAAGCGTCA TTGAATCACA CCTGATTACT ACCTTCTTCA GCAACAGCAA              420

GGCGAAAAAG GATGCATTCA TGAGTATTGC CAAGTTTGAG GTCAACAACC CACAGGTCCA              480

GCGCCAAGCA TTCAATGAGC TCATCCGAGT GGTCCACCAG CTGTTGCCGG AATCCAGCCT              540

CAGGAAGCGG AAAAGGAGTC GCTGCTGATT CGGGGTGGGG AAGAGATTGT CCCAATAA                598

(2) INFORMATION FOR SEQ ID NO: 164:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 164:

TAATCATGAA ATATACAAGT TATATCTTGG CTTTTCAGCT CTGCATCGTT TTGGGTTCTC          60

TTGGCTGTTA CTGCCAGGAC CCATATGTAA AAGAAGC          97

(2) INFORMATION FOR SEQ ID NO: 165:

(i) SEQUENCE CHARACTERISTICS:
        (A) LENGTH: 106 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 165:

TTCTTCAAAA TGCCTAAGAA AAGAGTTCCA TTATCCGCTA CATCTGAATG ACCTGCATTA          60

AAATATTTCT TAAGGTTTTC TGCTTCTTTT ACATATGGGT CCTGGC          106

(2) INFORMATION FOR SEQ ID NO: 166:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 166:

TCTTTTCTTA GGCATTTTGA AGAATTGGAA AGAGGAGAGT GACAG          45

(2) INFORMATION FOR SEQ ID NO: 167:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 167:

CCCGGATCCC TGCAGTTACT GGGATGCTCT TCGA          34

(2) INFORMATION FOR SEQ ID NO: 168:

(i) SEQUENCE CHARACTERISTICS:
        (A) LENGTH: 601 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 168:

ACATCATGCA GTGGTTAAAC AAAAACATTT TTATTCTCAA ATGAGATAAA GTGAAAATAT          60

ATATCATTAT ATTACAAAGT ACAATTATTT AGGTTTAATC ATGAAATATA CAAGTTATAT          120

CTTGGCTTTT CAGCTCTGCA TCGTTTTGGG TTCTCTTGGC TGTTACTGCC AGGACCCATA          180

TGTAAAAGAA GCAGAAAACC TTAAGAAATA TTTTAATGCA GGTCATTCAG ATGTAGCGGA          240

TAATGGAACT CTTTTCTTAG GCATTTTGAA GAATTGGAAA GAGGAGAGTG ACAGAAAAAT          300

AATGCAGAGC CAAATTGTCT CCTTTTACTT CAAACTTTTT AAAACTTTA AAGATGACCA          360

GAGCATCCAA AAGAGTGTGG AGACCATCAA GGAAGACATG AATGTCAAGT TTTTCAATAG          420

```
CAACAAAAAG AAACGAGATG ACTTCGAAAA GCTGACTAAT TATTCGGTAA CTGACTTGAA        480

TGTCCAACGC AAAGCAATAC ATGAACTCAT CCAAGTGATG GCTGAACTGT CGCCAGCAGC        540

TAAAACAGGG AAGCGAAAAA GGAGTCAGAT GCTGTTTCAA GGTCGAAGAG CATCCCAGTA        600

A                                                                       601
```

(2) INFORMATION FOR SEQ ID NO: 169:

(i) SEQUENCE CHARACTERISTICS:
        (A) LENGTH: 3063 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 169:

```
AAGCTTCTAT CAAAAGTCTT AATGAGTTAG GTGTAGATAG TATAGATATT ACTACAAAGG         60

TATTCATATT TCCTATCAAT TCTAAAGTAG ATGATATTAA TAACTCAAAG ATGATGATAG        120

TAGATAATAG ATACGCTCAT ATAATGACTG CAAATTTGGA CGGTTCACAT TTTAATCATC        180

ACGCGTTCAT AAGTTTCAAC TGCATAGATC AAAATCTCAC TAAAAAGATA GCCGATGTAT        240

TTGAGAGAGA TTGGACATCT AACTACGCTA AAGAAATTAC AGTTATAAAT AATACATAAT        300

GGATTTTGTT ATCATCAGTT ATATTTAACA TAAGTACAAT AAAAAGTATT AAATAAAAAT        360

ACTTACTTAC GAAAAAATGT CATTATTACA AAAACTATAT TTTACAGAAC AATCTATAGT        420

AGAGTCCTTT AAGAGTTATA ATTTAAAGA TAACCATAAT GTAATATTTA CCACATCAGA         480

TGATGATACT GTTGTAGTAA TAAATGAAGA TAATGTACTG TTATCTACAA GATTATTATC        540

ATTTGATAAA ATTCTGTTTT TTAACTCCTT TAATAACGGT TTATCAAAAT ACGAAACTAT        600

TAGTGATACA ATATTGATA TAGATACTCA TAATTATTAT ATACCTAGTT CTTCTTCTTT         660

GTTAGATATT CTAAAAAAAA GAGCGTGTGA TTTAGAATTA GAAGATCTAA ATTATGCGTT        720

AATAGGAGAC AATAGTAACT TATATTATAA AGATATGACT TACATGAATA ATTGGTTATT        780

TACTAAAGGA TTATTAGATT ACAAGTTTGT ATTATTGCGC GATGTAGATA AATGTTACAA        840

ACAGTATAAT AAAAAGAATA CTATAATAGA TATAATACAT CGCGATAACA GACAGTATAA        900

CATATGGGTT AAAAATGTTA TAGAATACTG TTCTCCTGGC TATATATTAT GGTTACATGA        960

TCTAAAAGCC GCTGCTGAAG ATGATTGGTT AAGATACGAT AACCGTATAA ACGAATTATC       1020

TGCGGATAAA TTATACACTT TCGAGTTCAT AGTTATATTA GAAAATAATA TAAAACATTT       1080

ACGAGTAGGT ACAATAATTG TACATCCAAA CAAGATAATA GCTAATGGTA CATCTAATAA       1140

TATACTTACT GATTTTCTAT CTTACGTAGA AGAACTAATA TATCATCATA ATTCATCTAT       1200

AATATTGGCC GGATATTTTT TAGAATTCTT TGAGACCACT ATTTTATCAG AATTTATTTC       1260

TTCATCTTCT GAATGGGTAA TGAATAGTAA CTGTTTAGTA CACCTGAAAA CAGGGTATGA       1320

AGCTATACTC TTTGATGCTA GTTTATTTTT CCAACTCTCT ACTAAAAGCA ATTATGTAAA       1380

ATATTGGACA AAGAAAACTT TGCAGTATAA GAACTTTTTT AAAGACGGTA ACAGTTAGC        1440

AAAATATATA ATTAAGAAAG ATAGTCAGGT GATAGATAGA GTATGTTATT TACACGCAGC       1500

TGTATATAAT CACGTAACTT ACTTAATGGA TACGTTAAA ATTCCTGGTT TTGATTTTAA        1560

ATTCTCCGGA ATGATAGATA TACTACTGTT TGGAATATTG CATAAGGATA ATGAGAATAT       1620

ATTTTATCCG AAACGTGTTT CTGTAACTAA TATAATATCA GAATCTATCT ATGCAGATTT       1680

TTACTTTATA TCAGATGTTA ATAAATTCAG TAAAAAGATA GAATATAAAA CTATGTTTCC       1740
```

-continued

```
TATACTCGCA GAAAACTACT ATCCAAAAGG AAGGCCCTAT TTTACACATA CATCTAACGA    1800

AGATCTTCTG TCTATCTGTT TATGCGAAGT AACAGTTTGT AAAGATATAA AAAATCCATT    1860

ATTATATTCT AAAAAGGATA TATCAGCAAA ACGATTCATA GGTTTATTTA CATCTGTCGA    1920

TATAAATACG GCTGTTGAGT TAAGAGGATA TAAAATAAGA GTAATAGGAT GTTTAGAATG    1980

GCCTGAAAAG ATAAAAATAT TTAATTCTAA TCCTACATAC ATTAGATTAT TACTAACAGA    2040

AAGACGTTTA GATATTCTAC ATTCCTATCT GCTTAAATTT AATATAACAG AGGATATAGC    2100

TACCAGAGAT GGAGTCAGAA ATAATTTACC TATAATTTCT TTTATCGTCA GTTATTGTAG    2160

ATCGTATACT TATAAATTAC TAAATTGCCA TATGTACAAT TCGTGTAAGA TAACAAAGTG    2220

TAAATATAAT CAGGTAATAT ATAATCCTAT ATAGGAGTAT ATATAATTGA AAAAGTAAAA    2280

TATAAATCAT ATAATAATGA AACGAAATAT CAGTAATAGA CAGGAACTGG CAGATTCTTC    2340

TTCTAATGAA GTAAGTACTG CTAAATCTCC AAAATTAGAT AAAAATGATA CAGCAAATAC    2400

AGCTTCATTC AACGAATTAC CTTTTAATTT TTTCAGACAC ACCTTATTAC AAACTAACTA    2460

AGTCAGATGA TGAGAAAGTA AATATAAATT TAACTTATGG GTATAATATA ATAAAGATTC    2520

ATGATATTAA TAATTTACTT AACGATGTTA ATAGACTTAT TCCATCAACC CCTTCAAACC    2580

TTTCTGGATA TTATAAAATA CCAGTTAATG ATATTAAAAT AGATTGTTTA AGAGATGTAA    2640

ATAATTATTT GGAGGTAAAG GATATAAAAT TAGTCTATCT TTCACATGGA AATGAATTAC    2700

CTAATATTAA TAATTATGAT AGGAATTTTT TAGGATTTAC AGCTGTTATA TGTATCAACA    2760

ATACAGGCAG ATCTATGGTT ATGGTAAAAC ACTGTAACGG GAAGCAGCAT TCTATGGTAA    2820

CTGGCCTATG TTTAATAGCC AGATCATTTT ACTCTATAAA CATTTTACCA CAAATAATAG    2880

GATCCTCTAG ATATTTAATA TTATATCTAA CAACAACAAA AAAATTTAAC GATGTATGGC    2940

CAGAAGTATT TTCTACTAAT AAAGATAAAG ATAGTCTATC TTATCTACAA GATATGAAAG    3000

AAGATAATCA TTTAGTAGTA GCTACTAATA TGGAAAGAAA TGTATACAAA AACGTGGAAG    3060

CTT                                                                  3063
```

(2) INFORMATION FOR SEQ ID NO: 170:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 170:

```
ATCATCGAGC TCGCGGCCGC CTATCAAAAG TCTTAATGAG TT                        42
```

(2) INFORMATION FOR SEQ ID NO: 171:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 171:

```
GAATTCCTCG AGCTGCAGCC CGGGTTTTTA TAGCTAATTA GTCATTTTTT CGTAAGTAAG    60

TATTTTTATT TAA                                                        73
```

(2) INFORMATION FOR SEQ ID NO: 172:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 172:

```
CCCGGGCTGC AGCTCGAGGA ATTCTTTTTA TTGATTAACT AGTCAAATGA GTATATATAA      60

TTGAAAAAGT AA                                                         72
```

(2) INFORMATION FOR SEQ ID NO: 173:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 173:

```
GATGATGGTA CCTTCATAAA TACAAGTTTG ATTAAACTTA AGTTG                      45
```

(2) INFORMATION FOR SEQ ID NO: 174:

(i) SEQUENCE CHARACTERISTICS:
        (A) LENGTH: 1615 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 174:

```
GAGCTCGCGG CCGCCTATCA AAAGTCTTAA TGAGTTAGGT GTAGATAGTA TAGATATTAC      60

TACAAAGGTA TTCATATTTC CTATCAATTC TAAAGTAGAT GATATTAATA ACTCAAAGAT     120

GATGATAGTA GATAATAGAT ACGCTCATAT AATGACTGCA AATTTGGACG GTTCACATTT     180

TAATCATCAC GCGTTCATAA GTTTCAACTG CATAGATCAA AATCTCACTA AAAAGATAGC     240

CGATGTATTT GAGAGAGATT GGACATCTAA CTACGCTAAA GAAATTACAG TTATAAATAA     300

TACATAATGG ATTTTGTTAT CATCAGTTAT ATTTAACATA AGTACAATAA AAAGTATTAA     360

ATAAAAATAC TTACTTACGA AAAATGACTA ATTAGCTATA AAAACCCGGG CTGCAGCTCG     420

AGGAATTCTT TTTATTGATT AACTAGTCAA ATGAGTATAT ATAATTGAAA AAGTAAAATA     480

TAAATCATAT AATAATGAAA CGAAATATCA GTAATAGACA GGAACTGGCA GATTCTTCTT     540

CTAATGAAGT AAGTACTGCT AAATCTCCAA AATTAGATAA AAATGATACA GCAAATACAG     600

CTTCATTCAA CGAATTACCT TTTAATTTTT TCAGACACAC CTTATTACAA ACTAACTAAG     660

TCAGATGATG AGAAAGTAAA TATAAATTTA ACTTATGGGT ATAATATAAT AAAGATTCAT     720

GATATTAATA ATTTACTTAA CGATGTTAAT AGACTTATTC CATCAACCCC TTCAAACCTT     780

TCTGGATATT ATAAAATACC AGTTAATGAT ATTAAAATAG ATTGTTTAAG AGATGTAAAT     840

AATTATTTGG AGGTAAAGGA TATAAAATTA GTCTATCTTT CACATGGAAA TGAATTACCT     900

AATATTAATA ATTATGATAG GAATTTTTTA GGATTTACAG CTGTTATATG TATCAACAAT     960

ACAGGCAGAT CTATGGTTAT GGTAAAACAC TGTAACGGGA AGCAGCATTC TATGGTAACT    1020
```

-continued

```
TGGCCTATGT TTAATAGCCA GATCATTTTA CTCTATAAAC ATTTTACCAC AAATAATAGG    1080

ATCCTCTAGA TATTTAATAT TATATCTAAC AACAACAAAA AAATTTAACG ATGTATGGCC    1140

AGAAGTATTT TCTACTAATA AAGATAAAGA TAGTCTATCT TATCTACAAG ATATGAAAGA    1200

AGATAATCAT TTAGTAGTAG CTACTAATAT GGAAAGAAAT GTATACAAAA ACGTGGAAGC    1260

TTTTATATTA AATAGCATAT TACTAGAAGA TTTAAAATCT AGACTTAGTA TAACAAAACA    1320

GTTAAATGCC AATATCGATT CTATATTTCA TCATAACAGT AGTACATTAA TCAGTGATAT    1380

ACTGAAACGA TCTACAGACT CAACTATGCA AGGAATAAGC AATATGCCAA TTATGTCTAA    1440

TATTTTAACT TTAGAACTAA AACGTTCTAC CAATACTAAA AATAGGATAC GTGATAGGCT    1500

GTTAAAAGCT GCAATAAATA GTAAGGATGT AGAAGAAATA CTTTGTTCTA TACCTTCGGA    1560

GGAAAGAACT TTAGAACAAC TTAAGTTTAA TCAAACTTGT ATTTATGAAG GTACC         1615
```

(2) INFORMATION FOR SEQ ID NO: 175:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 175:

```
TTAATCAGGA TCCTTAATTA ATTAGTTATT AGACAAGGTG AAACGAAACT ATTTGTAGCT    60

TAATTAATTA GCTGCAGCCC GGG                                            83
```

(2) INFORMATION FOR SEQ ID NO: 176:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 176:

```
CCCGGGCTGC AGCTAATTAA TTAAGCTACA AATAGTTTCG TTTTCACCTT GTCTAATAAC    60

TAATTAATTA AGGATCCTGA TTAA                                           84
```

(2) INFORMATION FOR SEQ ID NO: 177:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 177:

```
CAAAATTGAA AATATATAAT TACAATATAA A                                   31
```

(2) INFORMATION FOR SEQ ID NO: 178:

(i) SEQUENCE CHARACTERISTICS:
        (A) LENGTH: 490 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 178:

GAATTCGAAT AAAAAAATGA TAAAGTAGGT TCAGTTTTAT TGCTGGTTGT GTTAGTTCTC        60

TCTAAAAATG GGTCTCAACC CCCAGCTAGT TGTCATCCTG CTCTTCTTTC TCGAATGTAC       120

CAGGAGCCAT ATCCACGGAT GCGACAAAAA TCACTTGAGA GAGATCATCG GCATTTTGAA       180

CGAGGTCACA GGAGAAGGGA CGCCATGCAC GGAGATGGAT GTGCCAAACG TCCTCACAGC       240

AACGAAGAAC ACCACAGAGA GTGAGCTCGT CTGTAGGGCT TCCAAGGTGC TTCGTATATT       300

TTATTTAAAA CATGGGAAAA CTCCATGCTT GAAGAAGAAC TCTAGTGTTC TCATGGAGCT       360

GCAGAGACTC TTTCGGGCTT TTCGATGCCT GGATTCATCG ATAAGCTGCA CCATGAATGA       420

GTCCAAGTCC ACATCACTGA AAGACTTCCT GGAAAGCCTA AAGAGCATCA TGCAAATGGA       480

TTACTCGTAG                                                             490

(2) INFORMATION FOR SEQ ID NO: 179:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 179:

CTCACCCGGG TACCGAATTC GAATAAAAAA ATGATAAAGT AGGTTCAGTT TTATTGCTGG        60

TTGTGTTAGT TCTCTCTAAA AATGGGTCTC AACCCCCAG                              99

(2) INFORMATION FOR SEQ ID NO: 180:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 180:

TTAGGGATCC AGATCTCGAG ATAAAAACTA CGAGTAATCC ATTTGCATGA TGCTC             55

(2) INFORMATION FOR SEQ ID NO: 181:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 181:

GCTGGTTGTG TTAGTTCTCT CTAAAAATGG GTCTCACCTC CCAACTG                     47

(2) INFORMATION FOR SEQ ID NO: 182:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 182:

| | |
|---|---|
| ATCATCTCTA GAATAAAAAT CAGCTCGAAC ACTTTGAATA TTTCTCTCTC ATG | 53 |

(2) INFORMATION FOR SEQ ID NO: 183:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 183:

| | |
|---|---|
| ATCATCAAGC TTGAATAAAA AAATGATAAA GTAGGTTCAG TTTTATTGCT GGTTGTGTTA | 60 |
| GTTCTCTCTA AAA | 73 |

(2) INFORMATION FOR SEQ ID NO: 184:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 184:

| | |
|---|---|
| TTTTAGAGAG AACTAACACA ACCAGCAATA AAACTGAACC TACTTTATCA TTTTTTTATT | 60 |
| C | 61 |

(2) INFORMATION FOR SEQ ID NO: 185:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 185:

| | |
|---|---|
| ATCATCAAGC TTGAATAAAA AAATGATAAA GTAGGTTCAG | 40 |

(2) INFORMATION FOR SEQ ID NO: 186:

(i) SEQUENCE CHARACTERISTICS:
        (A) LENGTH: 523 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 186:

| | |
|---|---|
| GAATAAAAAA ATGATAAAGT AGGTTCAGTT TTATTGCTGG TTGTGTTAGT TCTCTCTAAA | 60 |
| AATGGGTCTC ACCTCCCAAC TGCTTCCCCC TCTGTTCTTC CTGCTAGCAT GTGCCGGCAA | 120 |
| CTTTGTCCAC GGACACAAGT GCGATATCAC CTTACAGGAG ATCATCAAAA CTTTGAACAG | 180 |
| CCTCACAGAG CAGAAGACTC TGTGCACCGA GTTGACCGTA ACAGACATCT TGCTGCCTC | 240 |
| CAAGAACACA ACTGAGAAGG AAACCTTCTG CAGGGCTGCG ACTGTGCTCC GGCAGTTCTA | 300 |
| CAGCCACCAT GAGAAGGACA CTCGCTGCCT GGGTGCGACT GCACAGCAGT TCCACAGGCA | 360 |
| CAAGCAGCTG ATCCGATTCC TGAAACGGCT CGACAGGAAC CTCTGGGGCC TGGCGGGCTT | 420 |

GAATTCCTGT CCTGTGAAGG AAGCCAACCA GAGTACGTTG GAAAACTTCT TGGAAAGGCT        480

AAAGACGATC ATGAGAGAGA AATATTCAAA GTGTTCGAGC TGA                         523

(2) INFORMATION FOR SEQ ID NO: 187:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 187:

GCTGGTTGTG TTAGTTCTCT CTAAAAATGT GGCTGCAGAG CCTGCTG                     47

(2) INFORMATION FOR SEQ ID NO: 188:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 188:

ATCATCCTCG AGATAAAAAT CACTCCTGGA CTGGCTCCCA GCAGTCAAAG GGG              53

(2) INFORMATION FOR SEQ ID NO: 189:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 189:

ATCATCCCCG GGGAATAAAA AAATGATAAA GTAGGTTCAG TTTTATTGCT GGTTGTGTTA       60

GTTCTCTCTA AAA                                                          73

(2) INFORMATION FOR SEQ ID NO: 190:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 190:

ATCATCCCCG GGGAATAAAA AAATGATAAA GTAGGTTCAG                             40

(2) INFORMATION FOR SEQ ID NO: 191:

(i) SEQUENCE CHARACTERISTICS:
        (A) LENGTH: 496 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 191:

```
GAATAAAAAA ATGATAAAGT AGGTTCAGTT TTATTGCTGG TTGTGTTAGT TCTCTCTAAA      60

AATGTGGCTG CAGAGCCTGC TGCTCTTGGG CACTGTGGCC TGCAGCATCT CTGCACCCGC     120

CCGCTCGCCC AGCCCCAGCA CGCAGCCCTG GGAGCATGTG AATGCCATCC AGGAGGCCCG     180

GCGTCTCCTG AACCTGAGTA GAGACACTGC TGCTGAGATG AATGAAACAG TAGAAGTCAT     240

CTCAGAAATG TTTGACCTCC AGGAGCCGAC CTGCCTACAG ACCCGCCTGG AGCTGTACAA     300

GCAGGGCCTG CGGGGCAGCC TCACCAAGCT CAAGGGCCCC TTGACCATGA TGGCCAGCCA     360

CTACAAGCAG CACTGCCCTC AACCCCGGA AACTTCCTGT GCAACCCAGA CTATCACCTT      420

TGAAAGTTTC AAAGAGAACC TGAAGGACTT TCTGCTTGTC ATCCCCTTTG ACTGCTGGGA     480

GCCAGTCCAG GAGTGA                                                    496

(2) INFORMATION FOR SEQ ID NO: 192:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 192:

CATCATATCG ATGGTACCTC AAAATTGAAA ATATATAATT ACAATATAAA ATGTGTCACC      60

AGCAGTTGG                                                             69

(2) INFORMATION FOR SEQ ID NO: 193:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 193:

TACTACGAGC TCTCAGATAG AAATTATATC TTTTTGGG                              38

(2) INFORMATION FOR SEQ ID NO: 194:

(i) SEQUENCE CHARACTERISTICS:
        (A) LENGTH: 1018 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 194:

CAAAATTGAA AATATATAAT TACAATATAA AATGTGTCAC CAGCAGTTGG TCATCTCTTG      60

GTTTTCCCTG GTTTTTCTGG CATCTCCCCT CGTGGCCATA TGGGAACTGA AGAAAGATGT     120

TTATGTCGTA GAATTGGATT GGTATCCGGA TGCCCCTGGA GAAATGGTGG TCCTCACCTG     180

TGACACCCCT GAAGAAGATG GTATCACCTG GACCTTGGAC CAGAGCAGTG AGGTCTTAGG     240

CTCTGGCAAA ACCCTGACCA TCCAAGTCAA AGAGTTTGGA GATGCTGGCC AGTACACCTG     300

TCACAAAGGA GGCGAGGTTC TAAGCCATTC GCTCCTGCTG CTTCACAAAA AGGAAGATGG     360

AATTTGGTCC ACTGATATTT TAAAGGACCA GAAAGAACCC AAAAATAAGA CCTTTCTAAG     420

ATGCGAGGCC AAGAATTATT CTGGACGTTT CACCTGCTGG TGGCTGACGA CAATCAGTAC     480
```

```
TGATTTGACA TTCAGTGTCA AAAGCAGCAG AGGCTCTTCT GACCCCCAAG GGGTGACGTG      540

CGGAGCTGCT ACACTCTCTG CAGAGAGAGT CAGAGGGGAC AACAAGGAGT ATGAGTACTC      600

AGTGGAGTGC CAGGAGGACA GTGCCTGCCC AGCTGCTGAG GAGAGTCTGC CCATTGAGGT      660

CATGGTGGAT GCCGTTCACA AGCTCAAGTA TGAAAACTAC ACCAGCAGCT TCTTCATCAG      720

GGACATCATC AAACCTGACC CACCCAAGAA CTTGCAGCTG AAGCCATTAA AGAATTCTCG      780

GCAGGTGGAG GTCAGCTGGG AGTACCCTGA CACCTGGAGT ACTCCACATT CCTACTTCTC      840

CCTGACATTC TGCGTTCAGG TCCAGGGCAA GAGCAAGAGA GAAAAGAAAG ATAGAGTCTT      900

CACGGACAAG ACCTCAGCCA CGGTCATCTG CCGCAAAAAT GCCAGCATTA GCGTGCGGGC      960

CCAGGACCGC TACTATAGCT CATCTTGGAG CGAATGGGCA TCTGTGCCCT GCAGTTAG      1018
```

(2) INFORMATION FOR SEQ ID NO: 195:

(i) SEQUENCE CHARACTERISTICS:
  (A) LENGTH: 63 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO: 195:

```
CATCATGGTA CCTCAAAATT GAAAATATAT AATTACAATA TAAAATGTGT CCAGCGCGCA       60

GCC                                                                     63
```

(2) INFORMATION FOR SEQ ID NO: 196:

(i) SEQUENCE CHARACTERISTICS:
  (A) LENGTH: 31 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO: 196:

```
TACTACATCG ATTTAGGAAG CATTCAGATA G                                      31
```

(2) INFORMATION FOR SEQ ID NO: 197:

(i) SEQUENCE CHARACTERISTICS:
  (A) LENGTH: 92 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO: 197:

```
CATCATGGTA CCGAATAAAA AAATGATAAA GTAGGTTCAG TTTTATTGCT GGTTGTGTTA       60

GTTCTCTCTA AAAATGTGTC CAGCGCGCAG CC                                     92
```

(2) INFORMATION FOR SEQ ID NO: 198:

(i) SEQUENCE CHARACTERISTICS:
  (A) LENGTH: 39 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO: 198:

| CATCATATCG ATTTAGGAAG CATTCAGATA GCTCGTCAC | 39 |

(2) INFORMATION FOR SEQ ID NO: 199:

(i) SEQUENCE CHARACTERISTICS:
        (A) LENGTH: 721 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 199:

| GAATAAAAAA ATGATAAAGT AGGTTCAGTT TTATTGCTGG TTGTGTTAGT TCTCTCTAAA | 60 |
| AATGTGTCCA GCGCGCAGCC TCCTCCTTGT GGCTACCCTG GTCCTCCTGG ACCACCTCAG | 120 |
| TTTGGCCAGA AACCTCCCCG TGGCCACTCC AGACCCAGGA ATGTTCCCAT GCCTTCACCA | 180 |
| CTCCCAAAAC CTGCTGAGGG CCGTCAGCAA CATGCTCCAG AAGGCCAGAC AAACTCTAGA | 240 |
| ATTTTACCCT TGCACTTCTG AAGAGATTGA TCATGAAGAT ATCACAAAAG ATAAAACCAG | 300 |
| CACAGTGGAG GCCTGTTTAC CATTGGAATT AACCAAGAAT GAGAGTTGCC TAAATTCCAG | 360 |
| AGAGACCTCT TTCATAACTA ATGGGAGTTG CCTGGCCTCC AGAAAGACCT CTTTTATGAT | 420 |
| GGCCCTGTGC CTTAGTAGTA TTTATGAAGA CTTGAAGATG TACCAGGTGG AGTTCAAGAC | 480 |
| CATGAATGCA AAGCTTCTGA TGGATCCTAA GAGGCAGATC TTTCTAGATC AAAACATGCT | 540 |
| GGCAGTTATT GATGAGCTGA TGCAGGCCCT GAATTTCAAC AGTGAGACTG TGCCACAAAA | 600 |
| ATCCTCCCTT GAAGAACCGG ATTTTTATAA AACTAAAATC AAGCTCTGCA TACTTCTTCA | 660 |
| TGCTTTCAGA ATTCGGGCAG TGACTATTGA CAGAGTGACG AGCTATCTGA ATGCTTCCTA | 720 |
| A | 721 |

(2) INFORMATION FOR SEQ ID NO: 200:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 200:

| TATCTGGAAT TCTATCGCGA TATCCGTTAA GTTTGTATCG TAATGGCTTG CAATTGTCAG | 60 |

(2) INFORMATION FOR SEQ ID NO: 201:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 201:

| ATCGTAAGCT TACTAAAGGA AGACGGTCTG | 30 |

(2) INFORMATION FOR SEQ ID NO: 202:

(i) SEQUENCE CHARACTERISTICS:
        (A) LENGTH: 921 base pairs
        (B) TYPE: nucleic acid (C) STRANDEDNESS: single
        (D) TOPOLOGY: linear (ii) MOLECULE TYPE: cDNA (xi) SEQUENCE DESCRIPTION: SEQ ID NO: 202:

| | | | | | |
|---|---|---|---|---|---|
| ATGGCTTGCA | ATTGTCAGTT | GATGCAGGAT | ACACCACTCC | TCAAGTTTCC | ATGTCCAAGG | 60
| CTCATTCTTC | TCTTTGTGCT | GCTGATTCGT | CTTTCACAAG | TGTCTTCAGA | TGTTGATGAA | 120
| CAACTGTCCA | AGTCAGTGAA | AGATAAGGTA | TTGCTGCCTT | GCCGTTACAA | CTCTCCTCAT | 180
| GAAGATGAGT | CTGAAGACCG | AATCTACTGG | CAAAAACATG | ACAAAGTGGT | GCTGTCTGTC | 240
| ATTGCTGGGA | AACTAAAAGT | GTGGCCCGAG | TATAAGAACC | GGACTTTATA | TGACAACACT | 300
| ACCTACTCTC | TTATCATCCT | GGGCCTGGTC | CTTTCAGACC | GGGGCACATA | CAGCTGTGTC | 360
| GTTCAAAAGA | AGGAAAGAGG | AACGTATGAA | GTTAAACACT | TGGCTTTAGT | AAAGTTGTCC | 420
| ATCAAAGCTG | ACTTCTCTAC | CCCCAACATA | ACTGAGTCTG | GAAACCCATC | TGCAGACACT | 480
| AAAAGGATTA | CCTGCTTTGC | TTCCGGGGGT | TTCCCAAAGC | CTCGCTTCTC | TTGGTTGGAA | 540
| AATGGAAGAG | AATTACCTGG | CATCAATACG | ACAATTTCCC | AGGATCCTGA | ATCTGAATTG | 600
| TACACCATTA | GTAGCCAACT | AGATTTCAAT | ACGACTCGCA | ACCACACCAT | TAAGTGTCTC | 660
| ATTAAATATG | GAGATGCTCA | CGTGTCAGAG | GACTTCACCT | GGGAAAAACC | CCCAGAAGAC | 720
| CCTCCTGATA | GCAAGAACAC | ACTTGTGCTC | TTTGGGGCAG | GATTCGGCGC | AGTAATAACA | 780
| GTCGTCGTCA | TCGTTGTCAT | CATCAAATGC | TTCTGTAAGC | ACAGAAGCTG | TTTCAGAAGA | 840
| AATGAGGCAA | GCAGAGAAAC | AAACAACAGC | CTTACCTTCG | GGCCTGAAGA | AGCATTAGCT | 900
| GAACAGACCG | TCTTCCTTTA | G | | | | 921

(2) INFORMATION FOR SEQ ID NO: 203:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 203:

CGACATTTGG ATTTCAAGCT TCTACG                                              26

(2) INFORMATION FOR SEQ ID NO: 204:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 204:

GATCCGTAGA AGCTTGAAAT CCAAATGTCG                                          30

(2) INFORMATION FOR SEQ ID NO: 205:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 205:

ATCGTAAGCT TATTATACAG GGCGTACACT TTC                                33

(2) INFORMATION FOR SEQ ID NO: 206:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 206:

TATCTGGAAT CTATCGCGA TATCCGTTAA GTTTGTATCG TAATGGGCCA CACACGGAGG     60

(2) INFORMATION FOR SEQ ID NO: 207:

(i) SEQUENCE CHARACTERISTICS:
        (A) LENGTH: 867 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 207:

ATGGGCCACA CACGGAGGCA GGGAACATCA CCATCCAAGT GTCCATACCT CAATTTCTTT     60

CAGCTCTTGG TGCTGGCTGG TCTTTCTCAC TTCTGTTCAG GTGTTATCCA CGTGACCAAG    120

GAAGTGAAAG AAGTGGCAAC GCTGTCCTGT GGTCACAATG TTTCTGTTGA AGAGCTGGCA    180

CAAACTCGCA TCTACTGGCA AAAGGAGAAG AAAATGGTGC TGACTATGAT GTCTGGGGAC    240

ATGAATATAT GGCCCGAGTA CAAGAACCGG ACCATCTTTG ATATCACTAA TAACCTCTCC    300

ATTGTGATCC TGGCTCTGCG CCCATCTGAC GAGGGCACAT ACGAGTGTGT TGTTCTGAAG    360

TATGAAAAAG ACGCTTTCAA GCGGGAACAC CTGGCTGAAG TGACGTTATC AGTCAAAGCT    420

GACTTCCCTA CACCTAGTAT ATCTGACTTT GAAATTCCAA CTTCTAATAT TAGAAGGATA    480

ATTTGCTCAA CCTCTGGAGG TTTTCCAGAG CCTCACCTCT CCTGGTTGGA AAATGGAGAA    540

GAATTAAATG CCATCAACAC AACAGTTTCC CAAGATCCTG AAACTGAGCT CTATGCTGTT    600

AGCAGCAAAC TGGATTTCAA TATGACAACC AACCACAGCT TCATGTGTCT CATCAAGTAT    660

GGACATTTAA GAGTGAATCA GACCTTCAAC TGGAATACAA CCAAGCAAGA GCATTTTCCT    720

GATAACCTGC TCCCATCCTG GCCATTACC TTAATCTCAG TAAATGGAAT TTTTGTGATA     780

TGCTGCCTGA CCTACTGCTT TGCCCCAAGA TGCAGAGAGA GAAGGAGGAA TGAGAGATTG    840

AGAAGGGAAA GTGTACGCCC TGTATAA                                       867

(2) INFORMATION FOR SEQ ID NO: 208:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 208:

ATTATTATTG GATCCTTAAT TAATTAGTGA TACGC                               35

-continued (2) INFORMATION FOR SEQ ID NO: 209:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 209:

CTCCTCCATG GCAGTCATTA CGATACAAAC TTAAC                            35

(2) INFORMATION FOR SEQ ID NO: 210:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 210:

CGTTAAGTTT GTATCGTAAT GACTGCCATG GAGGAGTC                         38

(2) INFORMATION FOR SEQ ID NO: 211:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 211:

TAGTAGTAGT AGTAGCTTCT GGAGGAAGTA GTTTCC                           36

(2) INFORMATION FOR SEQ ID NO: 212:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 212:

CAGAAGCTAC TACTACTACT ACCCACCTGC ACAAGCGCC                        39

(2) INFORMATION FOR SEQ ID NO: 213:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 213:

AACTACTGTC CCGGGATAAA AATCAGTCTG AGTCAGGCCC CAC                   43

(2) INFORMATION FOR SEQ ID NO: 214:

(i) SEQUENCE CHARACTERISTICS:
        (A) LENGTH: 1173 base pairs (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 214:

| | |
|---|---|
| ATGACTGCCA TGGAGGAGTC ACAGTCGGAT ATCAGCCTCG AGCTCCCTCT GAGCCAGGAG | 60 |
| ACATTTTCAG GCTTATGGAA ACTACTTCCT CCAGAAGATA TCCTGCCATC ACCTCACTGC | 120 |
| ATGGACGATC TGTTGCTGCC CCAGGATGTT GAGGAGTTTT TTGAAGGCCC AAGTGAAGCC | 180 |
| CTCCGAGTGT CAGGAGCTCC TGCAGCACAG GACCCTGTCA CCGAGACCCC TGGGCCAGTG | 240 |
| GCCCCTGCCC CAGCCACTCC ATGGCCCCTG TCATCTTTTG TCCCTTCTCA AAAAACTTAC | 300 |
| CAGGGCAACT ATGGCTTCCA CCTGGGCTTC CTGCAGTCTG GGACAGCCAA GTCTGTTATG | 360 |
| TGCACGTACT CTCCTCCCCT CAATAAGCTA TTCTGCCAGC TGGCGAAGAC GTGCCCTGTG | 420 |
| CAGTTGTGGG TCAGCGCCAC ACCTCCAGCT GGGAGCCGTG TCCGCGCCAT GGCCATCTAC | 480 |
| AAGAAGTCAC AGCACATGAC GGAGGTCGTG AGACGCTGCC CCCACCATGA GCGCTGCTCC | 540 |
| GATGGTGATG GCCTGGCTCC TCCCCAGCAT CTTATCCGGG TGGAAGGAAA TTTGTATCCC | 600 |
| GAGTATCTGG AAGACAGGCA GACTTTTCGC CACAGCGTGG TGGTACCTTA TGAGCCACCC | 660 |
| GAGGCCGGCT CTGAGTATAC CACCATCCAC TACAAGTACA TGTGTAATAG CTCCTGCATG | 720 |
| GGGGGCATGA ACCGCCGACC TATCCTTACC ATCATCACAC TGGAAGACTC CAGTGGGAAC | 780 |
| CTTCTGGGAC GGGACAGCTT TGAGGTTCGT GTTTGTGCCT GCCCTGGGAG AGACCGCCGT | 840 |
| ACAGAAGAAG AAAATTTCCG CAAAAAGGAA GTCCTTTGCC CTGAACTGCC CCCAGGGAGC | 900 |
| GCAAAGAGAG CGCTGCCCAC CTGCACAAGC GCCTCTCCCC CGCAAAAGAA AAAACCACTT | 960 |
| GATGGAGAGT ATTTCACCCT CAAGATCCGC GGGCGTAAAC GCTTCGAGAT GTTCCGGGAG | 1020 |
| CTGAATGAGG CCTTAGAGTT AAAGGATGCC CATGCTACAG AGGAGTCTGG AGACAGCAGG | 1080 |
| GCTCACTCCA GCTACCTGAA GACCAAGAAG GGCCAGTCTA CTTCCCGCCA TAAAAAAACA | 1140 |
| ATGGTCAAGA AAGTGGGGCC TGACTCAGAC TGA | 1173 |

(2) INFORMATION FOR SEQ ID NO: 215:

(i) SEQUENCE CHARACTERISTICS:
        (A) LENGTH: 1182 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 215:

| | |
|---|---|
| ATGGAGGAGC CGCAGTCAGA TCCTAGCGTC GAGCCCCCTC TGAGTCAGGA AACATTTTCA | 60 |
| GACCTATGGA AACTACTTCC TGAAAACAAC GTTCTGTCCC CCTTGCCGTC CCAAGCAATG | 120 |
| GATGATTTGA TGCTGTCCCC GGACGATATT GAACAATGGT TCACTGAAGA CCCAGGTCCA | 180 |
| GATGAAGCTC CCAGAATGCC AGAGGCTGCT CCCCGCGTGG CCCCTGCACC AGCAGCTCCT | 240 |
| ACACCGGCGG CCCCTGCACC AGCCCCCTCC TGGCCCCTGT CATCTTCTGT CCCTTCCCAG | 300 |
| AAAACCTACC AGGGCAGCTA CGGTTTCCGT CTGGGCTTCT TGCATTCTGG GACAGCCAAG | 360 |
| TCTGTGACTT GCACGTACTC CCCTGCCCTC AACAAGATGT TTGCCAACT GGCCAAGACC | 420 |
| TGCCCTGTGC AGCTGTGGGT TGATTCCACA CCCCCGCCCG GCACCCGCGT CCGCGCCATG | 480 |
| GCCATCTACA AGCAGTCACA GCACATGACG GAGGTTGTGA GGCGCTGCCC CCACCATGAG | 540 |

-continued

```
CGCTGCTCAG ATAGCGATGG TCTGGCCCCT CCTCAGCATC TTATCCGAGT GGAAGGAAAT        600

TTGCGTGTGG AGTATTTGGA TGACAGAAAC ACTTTTCGAC ATAGTGTGGT GGTGCCCTAT        660

GAGCCGCCTG AGGTTGGCTC TGACTGTACC ACCATCCACT ACAACTACAT GTGTAACAGT        720

TCCTGCATGG GCGGCATGAA CCGGAGGCCC ATCCTCACCA TCATCACACT GGAAGACTCC        780

AGTGGTAATC TACTGGGACG GAACAGCTTT GAGGTGCGTG TTTGTGCCTG TCCTGGGAGA        840

GACCGGCGCA CAGAGGAAGA GAATCTCCGC AAGAAAGGGG AGCCTCACCA CGAGCTGCCC        900

CCAGGGAGCA CTAAGCGAGC ACTGCCCAAC AACACCAGCT CCTCTCCCCA GCCAAAGAAG        960

AAACCACTGG ATGGAGAATA TTTCACCCTT CAGATCCGTG GGCGTGAGCG CTTCGAGATG       1020

TTCCGAGAGC TGAATGAGGC CTTGGAACTC AAGGATGCCC AGGCTGGGAA GGAGCCAGGG       1080

GGGAGCAGGG CTCACTCCAG CCACCTGAAG TCCAAAAAGG GTCAGTCTAC CTCCCGCCAT       1140

AAAAAACTCA TGTTCAAGAC AGAAGGGCCT GACTCAGACT GA                         1182

(2) INFORMATION FOR SEQ ID NO: 216:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 216:

CGATATCCGT TAAGTTTGTA TCGTAATGGA GCTCCTGCAG CCCGGGG                      47

(2) INFORMATION FOR SEQ ID NO: 217:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 217:

GATCCCCCGG GCTGCAGGAG CTCCATTACG ATACAAACTT AACGGATATC G                 51
```

POX VIRUS COMPRISING DNA SEQUENCES ENCODING CEA AND B7 ANTIGEN

CROSS REFERENCE TO RELATED APPLICATIONS

This application is a divisional application of Ser. No. 08/521,016 filed Aug. 30, 1995, abandoned, which is a continuation-in-part of Ser. No. 08/184,009 filed Jan. 19, 1994, now U.S. Pat. No. 5,833,975, which is a continuation-in-part of Ser. No. 08/007,115 filed Jan. 21, 1993, abandoned, which is a continuation-in-part of Ser. No. 07/847,977 filed Mar. 3, 1992, abandoned, which is a divisional of Ser. No. 07/478,179, filed Feb. 14, 1990, abandoned, which is a continuation-in-part of Ser. No. 07/320,471 filed Mar. 8, 1989, now U.S. Pat. No. 5,155,020; Ser. No. 07/805,567 filed Dec. 16, 1991, now U.S. Pat. No. 5,378,457, which is a continuation-in-part of Ser. No. 07/638,080 filed Jan. 7, 1991, abandoned; and, Ser. No. 07/847,951 filed Mar. 6, 1992, abandoned, which is a continuation-in-part of Ser. No. 07/713,967 filed Jun. 11, 1991, abandoned, which is a continuation-in-part of Ser. No. 07/666,056 filed Mar. 7, 1991, abandoned, all of which are hereby incorporated herein by reference.

FIELD OF THE INVENTION

The present invention relates to a modified poxvirus and to methods of making and using the same. More in particular, the invention relates to improved vectors for the insertion and expression of foreign genes for use as safe immunization vehicles to protect against a variety of pathogens, as well as for use in immunotherapy.

Several publications are referenced in this application. Full citation to these references is found at the end of the specification immediately preceding the claims or where the publication is mentioned; and each of these publications is hereby incorporated herein by reference. These publications relate to the art to which this invention pertains.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art and analogous to the methods for creating synthetic recombinants of poxviruses such as the vaccinia virus and avipox virus described in U.S. Pat. Nos. 4,769,330, 4,772,848, 4,603,112, 5,100,587, and 5,179,993, the disclosures of which are incorporated herein by reference.

First, the DNA gene sequence to be inserted into the virus, particularly an open reading frame from a non-pox source, is placed into an E. coli plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within E. coli bacteria (Clewell, 1972) and isolated (Clewell et al., 1969; Maniatis et al., 1982).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome. Additional strategies have recently been reported for generating recombinant vaccinia virus (Scheiflinger et al., 1992; Merchlinsky and Moss, 1992).

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

Vaccinia virus has been used successfully to immunize against smallpox, culminating in the worldwide eradication of smallpox in 1980. In the course of its history, many strains of vaccinia have arisen. These different strains demonstrate varying immunogenicity and are implicated to varying degrees with potential complications, the most serious of which are post-vaccinial encephalitis and generalized vaccinia (Behbehani, 1983).

With the eradication of smallpox, a new role for vaccinia became important, that of a genetically engineered vector for the expression of foreign genes. Genes encoding a vast number of heterologous antigens have been expressed in vaccinia, often resulting in protective immunity against challenge by the corresponding pathogen (reviewed in Tartaglia et al., 1990a,b).

The genetic background of the vaccinia vector has been shown to affect the protective efficacy of the expressed foreign immunogen. For example, expression of Epstein Barr Virus (EBV) gp340 in the Wyeth vaccine strain of vaccinia virus did not protect cottontop tamarins against EBV virus induced lymphoma, while expression of the same gene in the WR laboratory strain of vaccinia virus was protective (Morgan et al., 1988).

A fine balance between the efficacy and the safety of a vaccinia virus-based recombinant vaccine candidate is extremely important. The recombinant virus must present the immunogen(s) in a manner that elicits a protective immune response in the vaccinated animal but lacks any significant pathogenic properties. Therefore attenuation of the vector strain would be a highly desirable advance over the current state of technology.

A number of vaccinia genes have been identified which are non-essential for growth of the virus in tissue culture and whose deletion or inactivation reduces virulence in a variety of animal systems.

The gene encoding the vaccinia virus thymidine kinase (TK) has been mapped (Hruby et al., 1982) and sequenced (Hruby et al., 1983; Weir et al., 1983). Inactivation or complete deletion of the thymidine kinase gene does not prevent growth of vaccinia virus in a wide variety of cells in tissue culture. $TK^-$ vaccinia virus is also capable of replication in vivo at the site of inoculation in a variety of hosts by a variety of routes.

It has been shown for herpes simplex virus type 2 that intravaginal inoculation of guinea pigs with $TK^-$ virus resulted in significantly lower virus titers in the spinal cord than did inoculation with $TK^+$ virus (Stanberry et al., 1985). It has been demonstrated that herpesvirus encoded TK activity in vitro was not important for virus growth in actively metabolizing cells, but was required for virus growth in quiescent cells (Jamieson et al., 1974).

Attenuation of $TK^-$ vaccinia has been shown in mice inoculated by the intracerebral and intraperitoneal routes (Buller et al., 1985). Attenuation was observed both for the WR neurovirulent laboratory strain and for the Wyeth vaccine strain. In mice inoculated by the intradermal route, $TK^-$ recombinant vaccinia generated equivalent anti-vaccinia neutralizing antibodies as compared with the parental $TK^+$ vaccinia virus, indicating that in this test system the loss of TK function does not significantly decrease immunogenicity of the vaccinia virus vector. Following intranasal inoculation of mice with $TK^-$ and $TK^+$ recombinant vaccinia virus (WR strain), significantly less dissemination of virus to other locations, including the brain, has been found (Taylor et al., 1991a).

Another enzyme involved with nucleotide metabolism is ribonucleotide reductase. Loss of virally encoded ribonucleotide reductase activity in herpes simplex virus (HSV) by deletion of the gene encoding the large subunit was shown to have no effect on viral growth and DNA synthesis in dividing cells in vitro, but severely compromised the ability of the virus to grow on serum starved cells (Goldstein et al., 1988). Using a mouse model for acute HSV infection of the eye and reactivatable latent infection in the trigeminal ganglia, reduced virulence was demonstrated for HSV deleted of the large subunit of ribonucleotide reductase, compared to the virulence exhibited by wild type HSV (Jacobson et al., 1989).

Both the small (Slabaugh et al., 1988) and large (Schmitt et al., 1988) subunits of ribonucleotide reductase have been identified in vaccinia virus. Insertional inactivation of the large subunit of ribonucleotide reductase in the WR strain of vaccinia virus leads to attenuation of the virus as measured by intracranial inoculation of mice (Child et al., 1990).

The vaccinia virus hemagglutinin gene (HA) has been mapped and sequenced (Shida, 1986). The HA gene of vaccinia virus is nonessential for growth in tissue culture (Ichihashi et al., 1971). Inactivation of the HA gene of vaccinia virus results in reduced neurovirulence in rabbits inoculated by the intracranial route and smaller lesions in rabbits at the site of intradermal inoculation (Shida et al., 1988). The HA locus was used for the insertion of foreign genes in the WR strain (Shida et al., 1987), derivatives of the Lister strain (Shida et al., 1988) and the Copenhagen strain (Guo et al., 1989) of vaccinia virus. Recombinant $HA^-$ vaccinia virus expressing foreign genes have been shown to be immunogenic (Guo et al., 1989; Itamura et al., 1990; Shida et al., 1988; Shida et al., 1987) and protective against challenge by the relevant pathogen (Guo et al., 1989; Shida et al., 1987).

Cowpox virus (Brighton red strain) produces red (hemorrhagic) pocks on the chorioallantoic membrane of chicken eggs. Spontaneous deletions within the cowpox genome generate mutants which produce white pocks (Pickup et al., 1984). The hemorrhagic function (u) maps to a 38 kDa protein encoded by an early gene (Pickup et al., 1986). This gene, which has homology to serine protease inhibitors, has been shown to inhibit the host inflammatory response to cowpox virus (Palumbo et al., 1989) and is an inhibitor of blood coagulation.

The u gene is present in WR strain of vaccinia virus (Kotwal et al., 1989b). Mice inoculated with a WR vaccinia virus recombinant in which the u region has been inactivated by insertion of a foreign gene produce higher antibody levels to the foreign gene product compared to mice inoculated with a similar recombinant vaccinia virus in which the u gene is intact (Zhou et al., 1990). The u region is present in a defective nonfunctional form in Copenhagen strain of vaccinia virus (open reading frames B13 and B14 by the terminology reported in Goebel et al., 1990a,b).

Cowpox virus is localized in infected cells in cytoplasmic A type inclusion bodies (ATI) (Kato et al., 1959). The function of ATI is thought to be the protection of cowpox virus virions during dissemination from animal to animal (Bergoin et al., 1971). The ATI region of the cowpox genome encodes a 160 kDa protein which forms the matrix of the ATI bodies (Funahashi et al., 1988; Patel et al., 1987). Vaccinia virus, though containing a homologous region in its genome, generally does not produce ATI. In WR strain of vaccinia, the ATI region of the genome is translated as a 94 kDa protein (Patel et al., 1988). In Copenhagen strain of vaccinia virus, most of the DNA sequences corresponding to the ATI region are deleted, with the remaining 3' end of the region fused with sequences upstream from the ATI region to form open reading frame (ORF) A26L (Goebel et al., 1990a,b).

A variety of spontaneous (Altenburger et al., 1989; Drillien et al., 1981; Lai et al., 1989; Moss et al., 1981; Paez et al., 1985; Panicali et al., 1981) and engineered (Perkus et al., 1991; Perkus et al., 1989; Perkus et al., 1986) deletions have been reported near the left end of the vaccinia virus genome. A WR strain of vaccinia virus with a 10 kb spontaneous deletion (Moss et al., 1981; Panicali et al., 1981) was shown to be attenuated by intracranial inoculation in mice (Buller et al., 1985). This deletion was later shown to include 17 potential ORFs (Kotwal et al., 1988b). Specific genes within the deleted region include the virokine N1L and a 35 kDa protein (C3L, by the terminology reported in Goebel et al., 1990a,b). Insertional inactivation of N1L reduces virulence by intracranial inoculation for both normal and nude mice (Kotwal et al., 1989a). The 35 kDa protein is secreted like N1L into the medium of vaccinia virus infected cells. The protein contains homology to the family of complement control proteins, particularly the complement 4B binding protein (C4bp) (Kotwal et al., 1988a). Like the cellular C4bp, the vaccinia 35 kDa protein binds the fourth component of complement and inhibits the classical complement cascade (Kotwal et al., 1990). Thus the vaccinia 35 kDa protein appears to be involved in aiding the virus in evading host defense mechanisms.

The left end of the vaccinia genome includes two genes which have been identified as host range genes, K1L (Gillard et al., 1986) and C7L (Perkus et al., 1990). Deletion of both of these genes reduces the ability of vaccinia virus to grow on a variety of human cell lines (Perkus et al., 1990).

Two additional vaccine vector systems involve the use of naturally host-restricted poxviruses, avipoxviruses. Both fowlpoxvirus (FPV) and canarypoxvirus (CPV) have been engineered to express foreign gene products. Fowlpox virus (FPV) is the prototypic virus of the Avipox genus of the Poxvirus family. The virus causes an economically important disease of poultry which has been well controlled since the 1920's by the use of live attenuated vaccines. Replication of the avipox viruses is limited to avian species (Matthews, 1982b) and there are no reports in the literature of avipoxvirus causing a productive infection in any non-avian species including man. This host restriction provides an inherent safety barrier to transmission of the virus to other species and makes use of avipoxvirus based vaccine vectors in veterinary and human applications an attractive proposition.

FPV has been used advantageously as a vector expressing antigens from poultry pathogens. The hemagglutinin protein of a virulent avian influenza virus was expressed in an FPV recombinant (Taylor et al., 1988a). After inoculation of the recombinant into chickens and turkeys, an immune response was induced which was protective against either a homologous or a heterologous virulent influenza virus challenge (Taylor et al., 1988a). FPV recombinants expressing the surface glycoproteins of Newcastle Disease Virus have also been developed (Taylor et al., 1990; Edbauer et al., 1990).

Despite the host-restriction for replication of FPV and CPV to avian systems, recombinants derived from these viruses were found to express extrinsic proteins in cells of nonavian origin. Further, such recombinant viruses were shown to elicit immunological responses directed towards the foreign gene product and where appropriate were shown to afford protection from challenge against the corresponding pathogen (Tartaglia et al., 1993 a,b; Taylor et al., 1992; 1991b; 1988b).

In the past, viruses have been shown to have utility in cancer immunotherapy, in that, they provide a means of enhancing tumor immunoresponsiveness. Examples exist showing that viruses such as Newcastle disease virus (Cassel et al., 1983), influenza virus (Lindenmann, 1974; Lindenmann, 1967), and vaccinia virus (Wallack et al., 1986; Shimizu et al., 1988; Shimizu et al. 1984; Fujiwara et al., 1984) may act as tumor-modifying antigens or adjuvants resulting in inducing tumor-specific and tumor-nonspecific immune effector mechanisms. Due to advances in the fields of immunology, tumor biology, and molecular biology, however, such approaches have yielded to more directed immunotherapeutic approaches for cancer. Genetic modification of tumor cells and immune effector cells (i.e. tumor-infiltrating lymphocytes; TILs) to express, for instance cytokines, have provided encouraging results in animal models and humans with respect to augmenting tumor-directed immune responses (Pardoll, 1992; Rosenberg, 1992). Further, the definition of tumor-associated antigens (TAAs) has provided the opportunity to investigate their role in the immunobiology of certain cancers which may eventually be applied to their use in cancer prevention or therapy (van der Bruggen, 1992).

Advances in the use of eukaryotic vaccine vectors have provided a renewed interest in viruses in cancer prevention and therapy. Among the viruses engineered to express foreign gene products are adenoviruses, adeno-associated virus, baculovirus, herpesviruses, poxviruses, and retroviruses. Most notably, retrovirus-, adenovirus-, and poxvirus-based recombinant viruses have been developed with the intent of in vivo utilization in the areas of vector-based vaccines, gene therapy, and cancer therapy (Tartaglia, in press; Tartaglia, 1990).

Immunotherapeutic approaches to combat cancers or neoplasia can take the form of classical vaccination schemes or cell-based therapies. Immunotherapeutic vaccination is the concept of inducing or enhancing immune responses of the cancer patient to antigenic determinants that are uniquely expressed or expressed at increased levels on tumor cells. Tumor-associated antigens (TAAs) are usually of such weak immunogenicity as to allow progression of the tumor unhindered by the patient's immune system. Under normal circumstances, the severity of the disease-state associated with the tumor progresses more rapidly than the elaboration of immune responses, if any, to the tumor cells. Consequently, the patient may succumb to the neoplasia before a sufficient immune response is mounted to control and prevent growth and spread of the tumor.

Poxvirus vector technology has been utilized to elicit immunological responses to TAAs. Examples exist demonstrating the effectiveness of poxvirus-based recombinant viruses expressing TAAs in animal models in the immunoprophylaxis and immunotherapy of experimentally-induced tumors. The gene encoding carcinoembryonic antigen (CEA) was isolated from human colon tumor cells and inserted into the vaccinia virus genome (Kaufman et al., 1991). Inoculation of the vaccinia-based CEA recombinant elicited CEA-specific antibodies and an antitumor effect in a murine mouse model. This recombinant virus has been shown to elicit humoral and cell-mediated responses in rhesus macaques (Kantor et al., 1993). The human melanoma TAA, p97, has also been inserted into vaccinia virus and shown to protect mice from tumor transplants (Hu et al., 1988; Estin et al., 1988). A further example was described by Bernards et al. (1987). These investigators constructed a vaccinia recombinant that expressed the extracellular domain of the rat neu-encoded transmembrane glycoprotein, p185. Mice immunized with this recombinant virus developed a strong humoral response against the neu gene product and were protected against subsequent tumor challenge. Vaccinia virus recombinants expressing either a secreted or membrane-anchored form of a breast cancer-associated epithelial tumor antigen (ETA) have been generated for evaluation in the active immunotherapy of breast cancer (Hareuveni et al., 1991; 1990). These recombinant viruses have been shown to elicit anti-ETA antibodies in mice and to protect mice against a tumorigenic challenge with a ras-transformed Fischer rat fibroblast line expressing either form of ETA (Hareuveni et al., 1990). Further, vaccinia virus recombinants expressing the polyoma virus-derived T-Ag were shown efficacious for prevention and therapy in a mouse tumor model system (Lathe et al., 1987).

Recombinant vaccinia viruses have also been used to express cytokine genes (Reviewed by Ruby et al., 1992). Expression of certain cytokines (IL-2, IFN-γ, TNF-α) lead to self-limiting vaccinia virus infection in mice and, in essence, act to attenuate the virus. Expression of other cytokines (i.e. IL-5, IL-6) were found to modulate the immune response to co-expressed extrinsic immunogens (Reviewed by Ruby et al., 1992).

Frequently, immune responses against tumor cells are mediated by T cells, particularly cytotoxic T lymphocytes (CTLs); white blood cells capable of killing tumor cells and virus-infected cells (Greenberg, 1991). The behavior of CTLs is regulated by soluble factors termed cytokines. Cytokines direct the growth, differentiation, and functional properties of CTLs, as well as, other immune effector cells.

Cell-based immunotherapy has been shown to provide effective therapy for viruses and tumors in animal models (Greenberg, 1991; Pardoll, 1992; Riddel et al., 1992). Cytomegalovirus (CMV)-specific CTL clones from bone marrow donors have recently been isolated. These clones were propagated and expanded in vitro and ultimately returned to immunodeficient bone marrow patients. These transferred CMV-specific CTL clones provided no toxic-effects and provided persistent reconstitution of $CD8^+$ CMV-specific CTL responses preventing CMV infection in the transplant patient (Riddel et al., 1992).

There exists two forms of cell-based immunotherapy. These are adoptive immunotherapy, which involves the expansion of tumor reactive lymphocytes in vitro and reinfusion into the host, and active immunotherapy, which involves immunization of tumor cells to potentially enhance existing or to elicit novel tumor-specific immune responses and provide systemic anti-tumor immunity. Immunotherapeutic vaccination is the concept of inducing or enhancing immune responses of the cancer patient to antigenic determinants that are uniquely expressed or expressed at increased levels on tumor cells.

It can be appreciated that provision of novel strains, such as NYVAC, ALVAC, and TROVAC having enhanced safety would be a highly desirable advance over the current state of technology. For instance, so as to provide safer vaccines or safer products from the expression of a gene or genes by a virus.

OBJECTS OF THE INVENTION

It is therefore an object of this invention to provide modified recombinant viruses, which viruses have enhanced safety, and to provide a method of making such recombinant viruses.

It is an additional object of this invention to provide a recombinant poxvirus vaccine having an increased level of safety compared to known recombinant poxvirus vaccines.

It is a further object of this invention to provide a modified vector for expressing a gene product in a host, wherein the vector is modified so that it has attenuated virulence in the host.

It is another object of this invention to provide a method for expressing a gene product in a cell cultured in vitro using a modified recombinant virus or modified vector having an increased level of safety.

These and other objects and advantages of the present invention will become more readily apparent after consideration of the following.

STATEMENT OF THE INVENTION

In one aspect, the present invention relates to a modified recombinant virus having inactivated virus-encoded genetic functions so that the recombinant virus has attenuated virulence and enhanced safety. The functions can be non-essential, or associated with virulence. The virus is advantageously a poxvirus, particularly a vaccinia virus or an avipox virus, such as fowlpox virus and canarypox virus. The modified recombinant virus can include, within a non-essential region of the virus genome, a heterologous DNA sequence which encodes an antigenic protein, e.g., derived from a pathogen, a tumor associated antigen, a cytokine, or combination thereof.

In another aspect, the present invention relates to a vaccine for inducing an antigenic response in a host animal inoculated with the vaccine, said vaccine including a carrier and a modified recombinant virus having inactivated non-essential virus-encoded genetic functions so that the recombinant virus has attenuated virulence and enhanced safety. The virus used in the vaccine according to the present invention is advantageously a poxvirus, particularly a vaccinia virus or an avipox virus, such as fowlpox virus and canarypox virus. The modified recombinant virus can include, within a non-essential region of the virus genome, a heterologous DNA sequence which encodes an antigenic protein, e.g., derived from a pathogen, a tumor associated antigen, a cytokine, or combination thereof.

In yet another aspect, the present invention relates to an immunogenic composition containing a modified recombinant virus having inactivated nonessential virus-encoded genetic functions so that the recombinant virus has attenuated virulence and enhanced safety. The modified recombinant virus includes, within a non-essential region of the virus genome, a heterologous DNA sequence which encodes an antigenic protein (e.g., derived from a pathogen, a tumor associated antigen, a cytokine, or combination thereof) wherein the composition, when administered to a host, is capable of inducing an immunological response specific to the protein encoded by the pathogen.

In a further aspect, the present invention relates to a method for expressing a gene product in a cell cultured in vitro by introducing into the cell a modified recombinant virus having attenuated virulence and enhanced safety. The modified recombinant virus can include, within a non-essential region of the virus genome, a heterologous DNA sequence which encodes an antigenic protein, e.g., derived from a pathogen, a tumor associated antigen, a cytokine, or combination thereof.

In a still further aspect, the present invention relates to a modified recombinant virus having nonessential virus-encoded genetic functions inactivated therein so that the virus has attenuated virulence, and wherein the modified recombinant virus further contains DNA from a heterologous source in a nonessential region of the virus genome. The DNA can code for a tumor associated antigen, a cytokine, or a combination thereof. In particular, the genetic functions are inactivated by deleting an open reading frame encoding a virulence factor or by utilizing naturally host restricted viruses. The virus used according to the present invention is advantageously a poxvirus, particularly a vaccinia virus or an avipox virus, such as fowlpox virus and canarypox virus. Advantageously, the open reading frame is selected from the group consisting of J2R, B13R+B14R, A26L, A56R, C7L-K1L, and I4L (by the terminology reported in Goebel et al., 1990a,b); and, the combination thereof. In this respect, the open reading frame comprises a thymidine kinase gene, a hemorrhagic region, an A type inclusion body region, a hemagglutinin gene, a host range gene region or a large subunit, ribonucleotide reductase; or, the combination thereof. The modified Copenhagen strain of vaccinia virus is identified as NYVAC (Tartaglia et al., 1992).

In another aspect, the present invention relates to a recombinant vaccinia or avipox virus which contains exogenous DNA encoding at least one of human tumor necrosis factor; nuclear phosphoprotein p53, wildtype or mutant; human melanoma associated antigen; IL-2; IFNγ; IL-4; GMCSF; IL-12; B7; erb-B-2 and carcinoembryonic antigen (CEA). In yet another aspect, the present invention relates to a recombinant vaccinia virus such as NYVAC which contains exogenous DNA encoding B7 and CEA. In yet another aspect, the present invention relates to a recombinant avipox virus such as the canarypox ALVAC which contains exogenous DNA encoding B7 and CEA.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 7 schematically shows a method for the construction of plasmid pRW842 for insertion of rabies glycoprotein G gene into the TK deletion locus and generation of recombinant vaccinia virus vP879;

FIG. 8 shows the DNA sequence (SEQ ID NO:68) of a canarypox PvuII fragment containing the C5 ORF.

FIGS. 9A and 9B schematically show a method for the construction of recombinant canarypox virus vCP65 (ALVAC-RG);

FIG. 11 shows the nucleotide sequence (SEQ ID NO:77) of a fragment of TROVAC DNA containing an F8 ORF;

FIG. 12 shows the DNA sequence (SEQ ID NO:78) of a 2356 base pair fragment of TROVAC DNA containing the F7 ORF;

FIG. 14A to 14C show the nucleotide sequence of a 7351 bp fragment containing the ALVAC C3 insertion site (SEQ ID NO:127);

FIG. 15 shows the nucleotide sequences of H6/TNF-α expression cassette and flanking regions from vCP245 (SEQ ID NO:79);

FIG. 16 shows the nucleotide sequence of the H6/TNF-α expression cassette and flanking regions from vP1200 (SEQ ID NO:89);

FIG. 17 shows the nucleotide sequence of the H6/p53 (wildtype) expression cassette and flanking regions from vP1101 (SEQ ID NO:99);

FIG. 18 shows the nucleotide sequence of the H6/p53 (wildtype) expression cassette and flanking regions from vCP207 (SEQ ID NO:99);

FIG. 19 shows the nucleotide sequence of the H6/MAGE-1 expression cassette and flanking region from vCP235 (SEQ ID NO:109);

FIG. 20 shows the nucleotide sequence of the H6/MAGE-1 expression cassette and flanking regions from pMAW037 (SEQ ID NO:110);

FIGS. 21A and B show the nucleotide sequence of the p126.15 SERA cDNA insert along with the predicted amino acid sequence (SEQ ID NOS:119; 120);

FIG. 22 shows the nucleotide sequence of the H6/CEA expression cassette and flanking regions from pH6.CEA.C3.2 (SEQ ID NO:144);

FIG. 23 shows the nucleotide sequence of the H6/CEA expression cassette and flanking regions from pH6.CEA.HA (SEQ ID NO:145);

FIG. 24 shows the nucleotide sequence of murine IL-2 from the translation initiation codon through the stop codon (SEQ ID NO:150);

FIG. 25 shows the corrected nucleotide sequence of human IL-2 from the translation initiation codon through the stop codon (SEQ ID NO:159);

FIG. 26 shows the nucleotide sequence of the I3L/murine IFNα expression cassette (SEQ ID NO:163);

FIG. 27 shows the nucleotide sequence of the I3L/human IFNα expression cassette (SEQ ID NO:168);

FIG. 28 shows the nucleotide sequence of the canarypox insert in pC6HIII3kb (SEQ ID NO:169);

FIG. 29 shows the nucleotide sequence pC6L (SEQ ID NO:174);

FIG. 30 shows the nucleotide sequence of the E3L/murine IL-4 expression cassette (SEQ ID NO:178);

FIG. 31 shows the nucleotide sequence of the expression cassette comprising the E3L promoted human IL-4 gene (SEQ ID NO:186);

FIG. 32 shows the nucleotide sequence of the vaccinia E3L/hGMCSF expression cassette (SEQ ID NO:191);

FIG. 33 shows the sequence of the EPV 42 kDa/human IL-12 P40 expression cassette (SEQ ID NO:194);

FIG. 34 shows the nucleotide sequence of the vaccinia E3L/human IL-12 P35 expression cassette (SEQ ID NO:199);

FIG. 35 shows the nucleotide sequence of the murine B7 gene (SEQ ID NO:202);

FIG. 37 shows the nucleotide sequence for the human B7 gene (SEQ ID NO:207);

FIG. 38 shows the murine p53 gene (SEQ ID NO:214); and

FIG. 39 shows the coding sequence for the human p53 gene (SEQ ID NO:215).

FIG. 40 shows materials used in the study.

The data show a high level of production of IL2 by the prostate tumor cell line.

Figure 42:
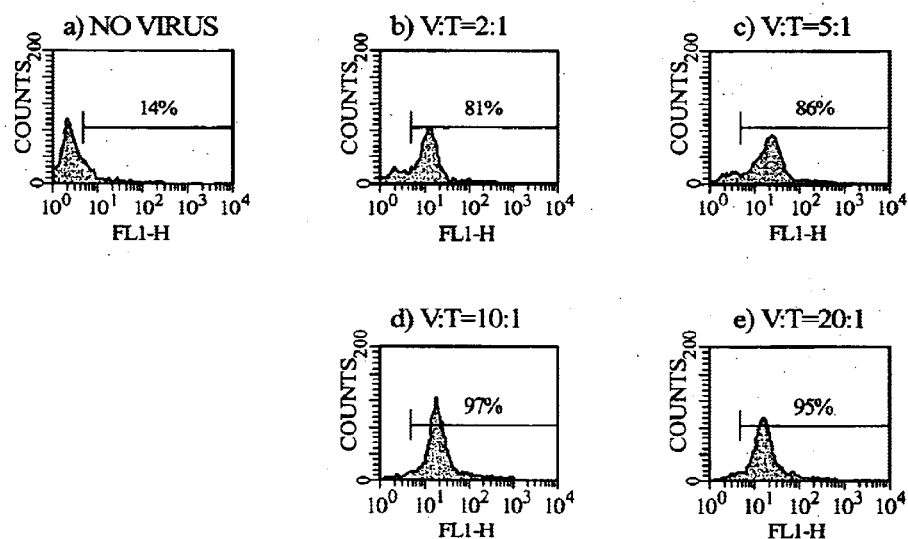

FIG. 42. Flow cytometry analysis of RM1 cells infected with ALVAC-B7. The data show a clear cell surface of B7 by the infected cells.

Figure 43:
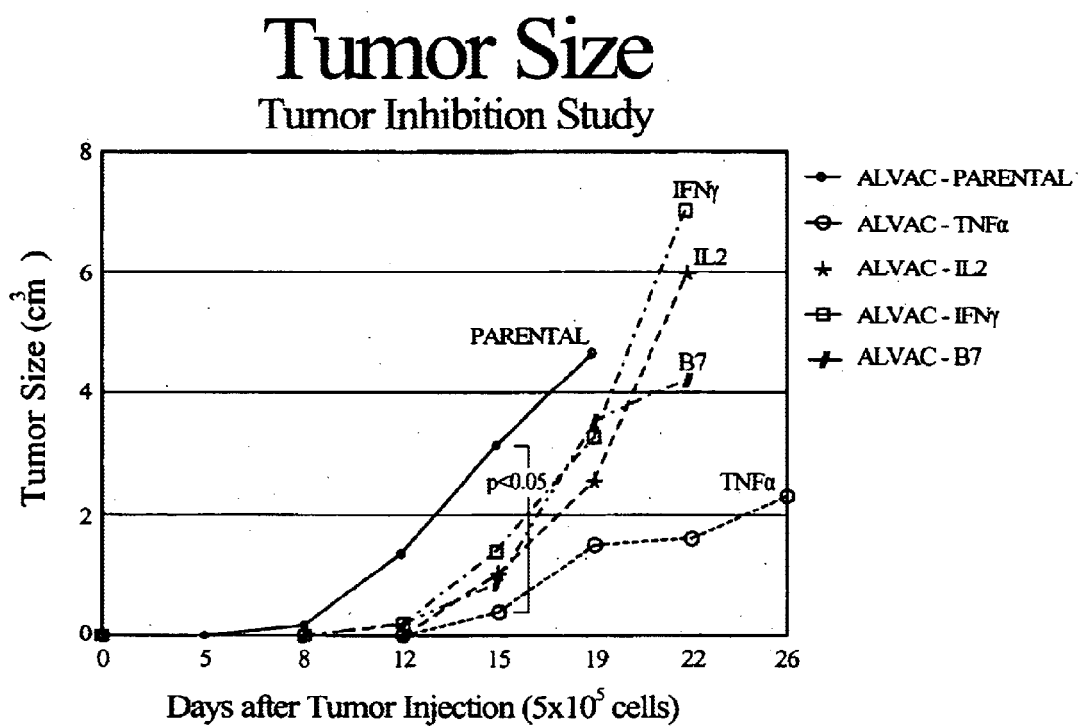

FIG. 43. Effects of various ALVAC cytokine recombinant on RM1 prostate tumor growth. These studies show that TNF-α is superior to interferon gamma, IL2 and B7. Further studies with these single agents are found in FIGS. 44 and 45.

Figure 44:
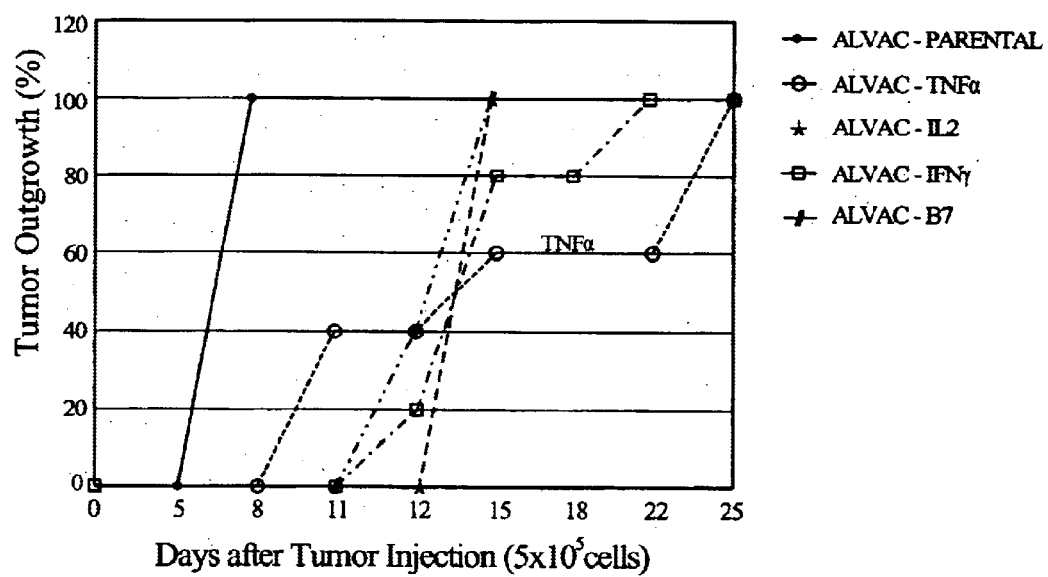

FIG. 44. FIG. 44 shows the incidents of tumor outgrowth for single agent vectors. Ultimately all animals develop tumors. However, TNFα exhibits the highest effects.

Figure 45:
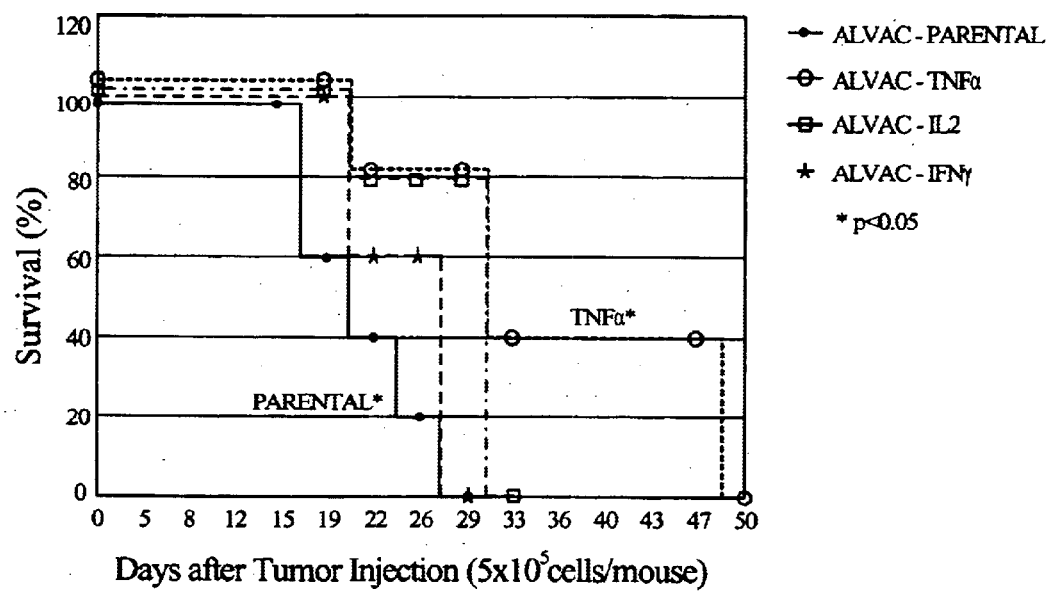

FIG. 45. FIG. 45 shows survival of animals in the experiments shown in FIGS. 43 and 44. All animals ultimately die of tumor, however, TNFα significantly prolonges survival.

Figure 46:
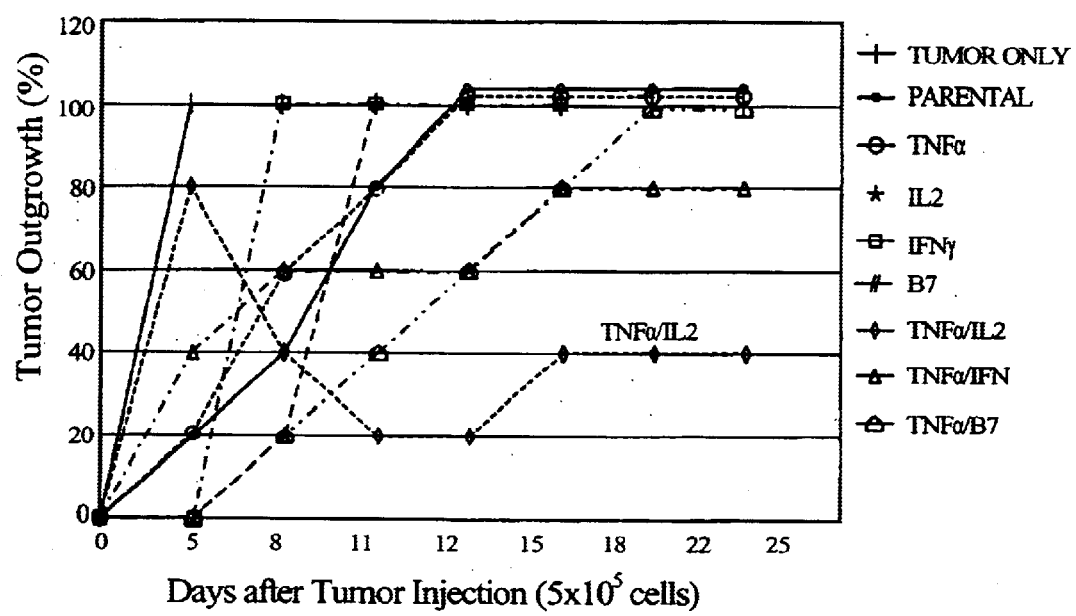

FIG. 46. Effects of combination of cytokine therapy on tumor outgrowth. Studies were performed to assess the effedts of single cytokine vector and combinations with the previously identified TNFα. The data show TNFα combined with IL2 to provide superior therapeutic efficacy. TNFα-IL2 combination therapy induces tumor regression in three (3) of five (5) animals who remain tumor-free for greater than 100 days.

Figure 47:
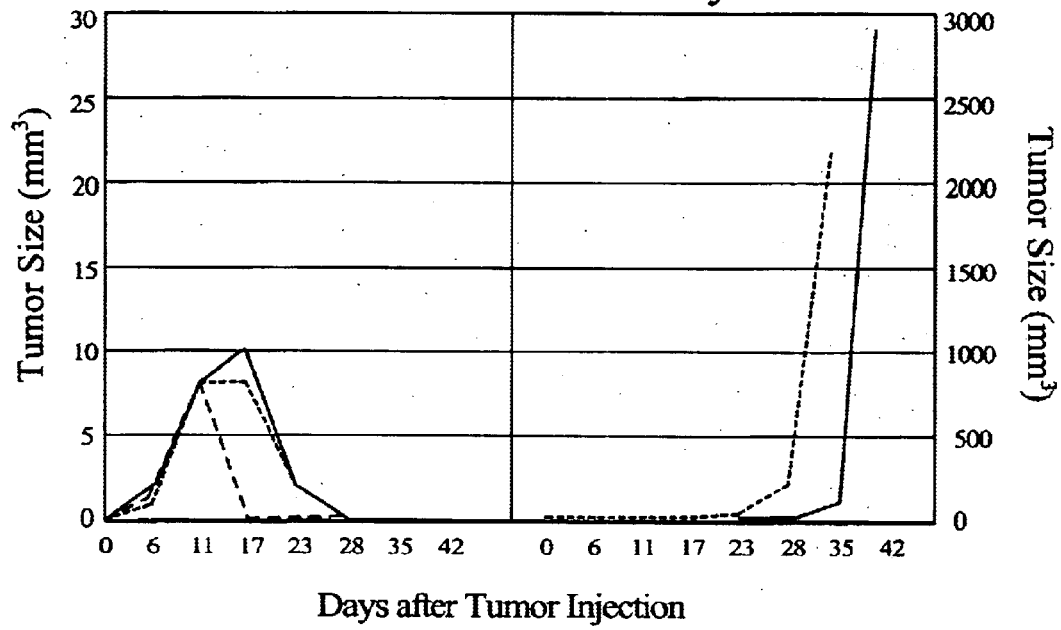

FIG. 47. Shows the growth of tumors (tumor size) in each animal treated with the combination TNFα+IL2. In some animals tumor exhibit an early growth phase with subsequent regression. These tumors never reappear (followed upto 100 days). A separated group of animals within this therapeutic group demonstrate delayed tumor outgrowth but ultimately succumbed to tumor. These observations have been confirmed in 40 mice.

Figure 48:
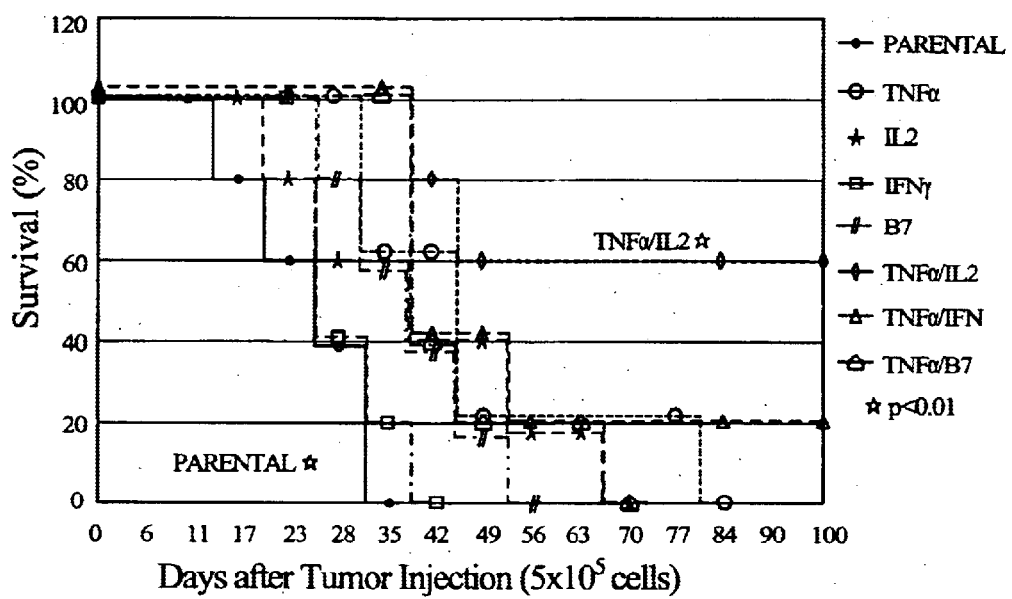

FIG. 48. Demonstrates the survival of animals treated as shown in FIGS. 46 and 47. Sixty percent of animals remain tumor-free for 10 days. These are the animals in which tumor regression was observed in FIG. 47.

Figure 49:
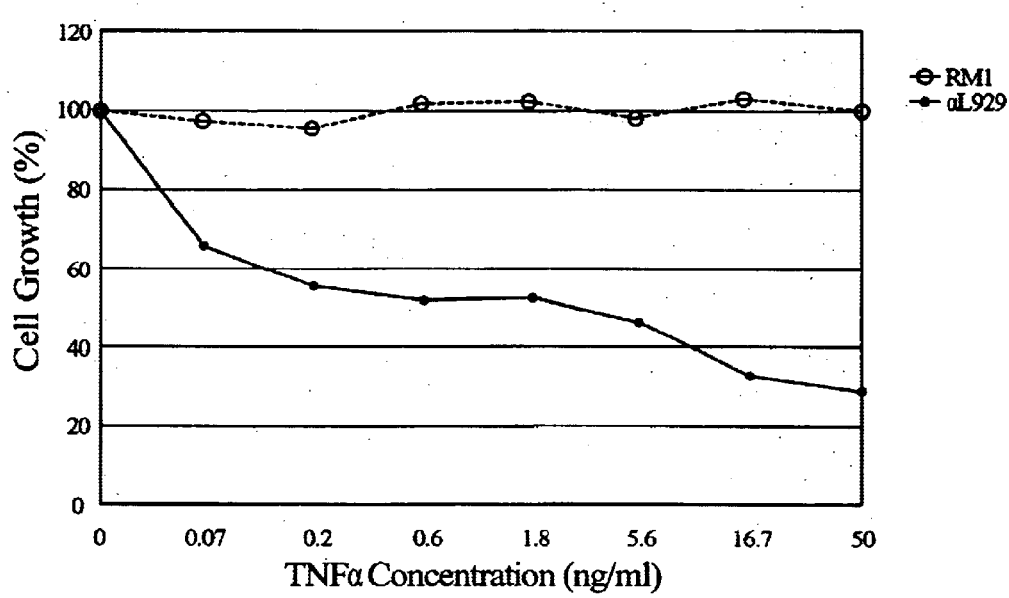

FIG. 49. In vitro studies to assess the effects of TNFα on RMI cells were performed. The data show that RMI cells are resistant to the direct effects of TNFα. The positive control of aL929 cells. Subsequent studies were performed with the new vectors ALVAC IL12 and ALVAC GMCSF. Studies were performed to assess the anti-tumor effects of these two vectors alone, and in combination with TNFα. The effectiveness was compared to TNFα plus IL2.

Figure 50:
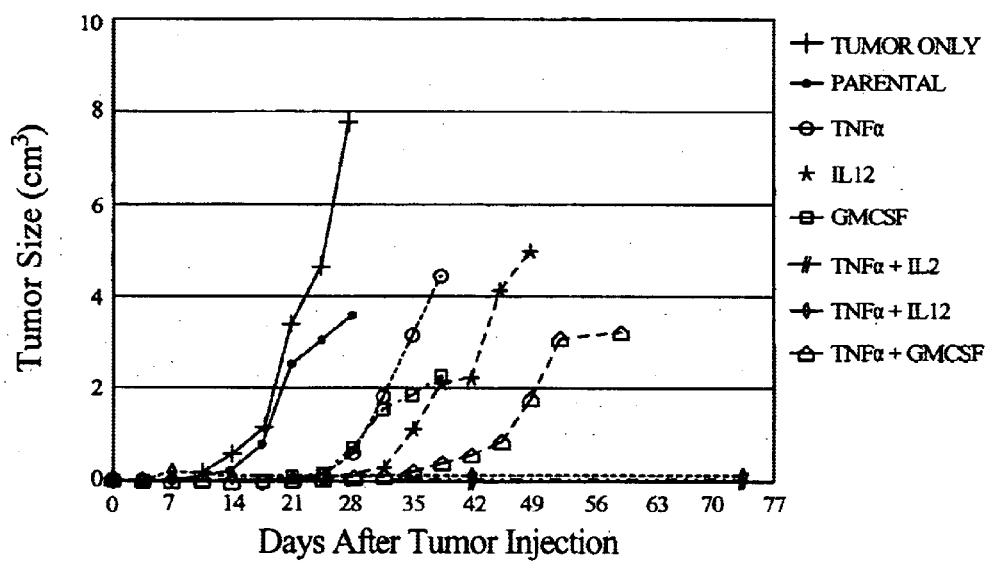

FIG. 50. The data in FIG. 50 showed delayed tumor outgrowth by all single agents (TNFα, IL12 and GMCSF). IL12 appeared to provide the most effective inhibition of tumor outgrowth as a single agent. TNFα combined with either IL2 completely inhibited tumor growth in this study. TNFα combined with GMCSF significantly inhibit tumor growth, but a reduction was inferior to TNFα plus IL2 or TNFα plus IL2. Tumor outgrowth and survival are shown in FIGS. 51 and 52 respectively.

Figure 51:
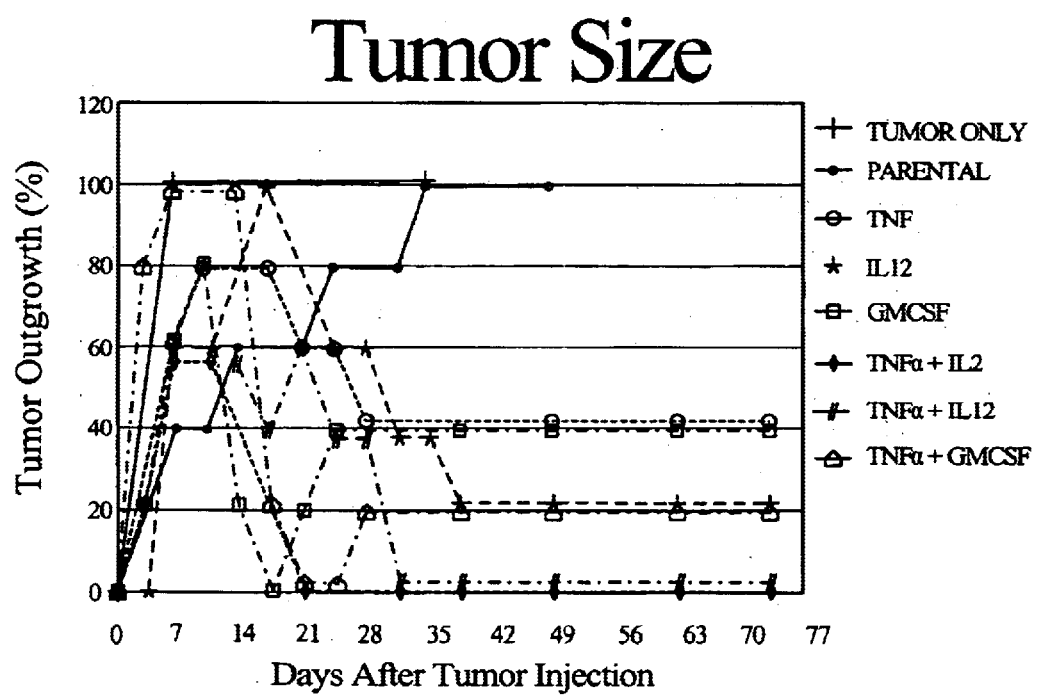
Figure 52:
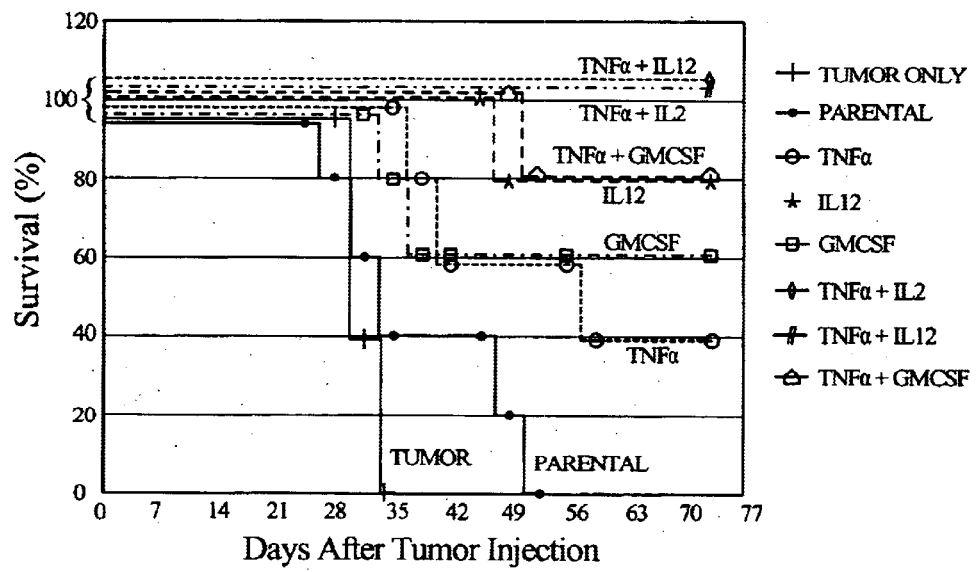

FIGS. 51 & 52. Tumors for all groups exhibited an initial growth phase followed by regression in varying number of animals depending on the vectors used. As stated above, the most effective combination were TNFα plus IL12. These survival curves (FIG. 52) clearly show TNFα plus IL12 and TNFα plus IL2 to provide 100 percent survival for 73 days. We are continuing to follow these immunological basis for the anti-tumor activity. The vectors were studied in SCID mice. The combination of TNFα plus IL2, IL12, or GMCSF was effective in SCID mice. These data suggest that combination therapy is independent of T or B cell immunity.

Figure 53:
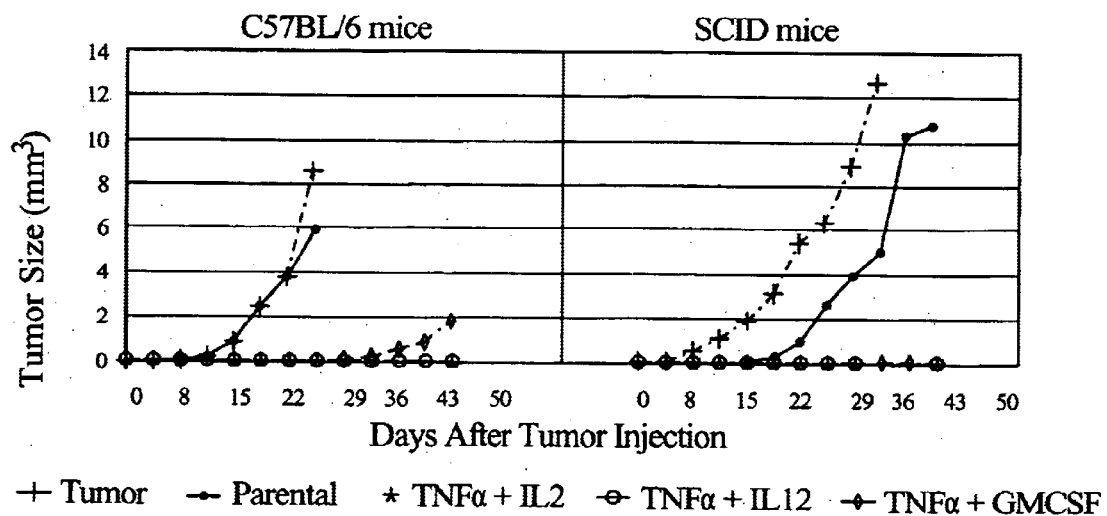

FIG. 53 shows the growth pattern of tumors in normal and Scid mice. There is an initial growth phase followed by regression as was seen in previous studies in FIG. 47.

Figure 54:
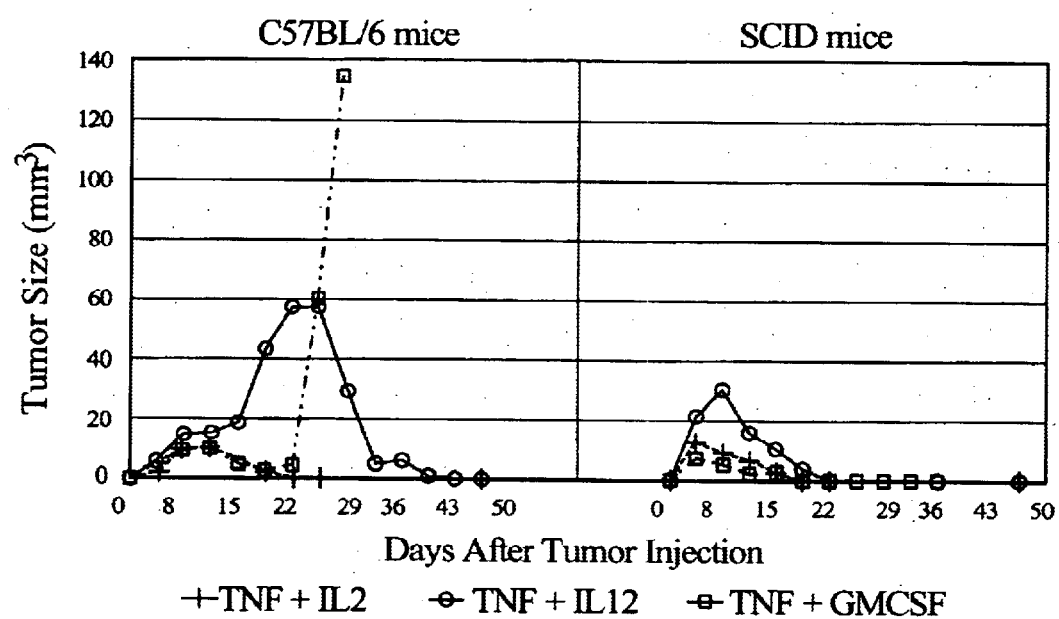

FIG. 54 provides studies or tumor size. There is a single animal in the TNF plus GMCSF group that developed a large tumor.

Figure 55:
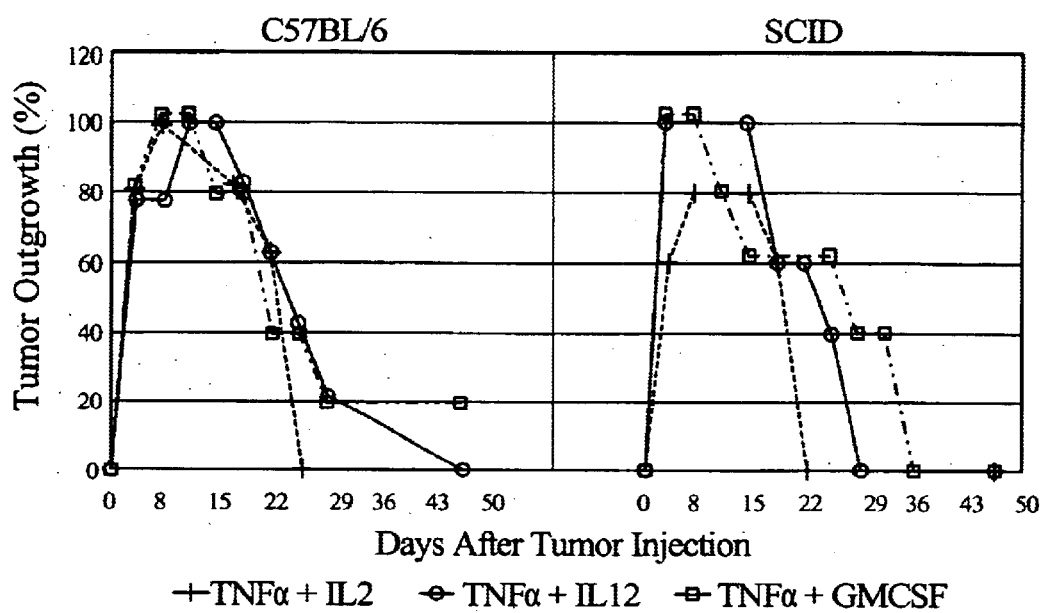
Figure 56:
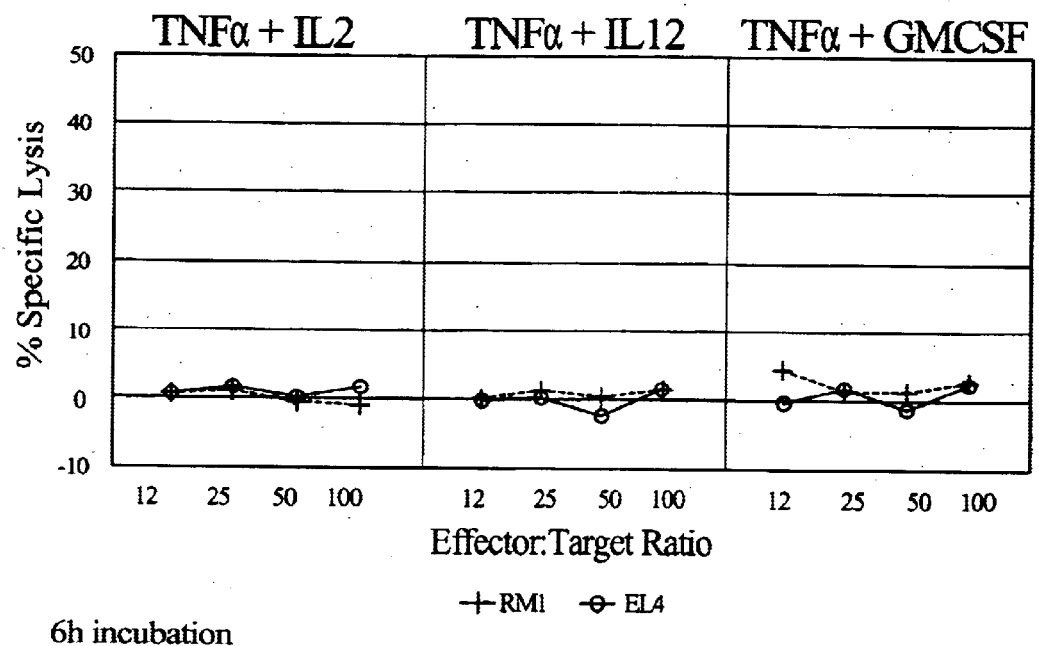
Figure 57:
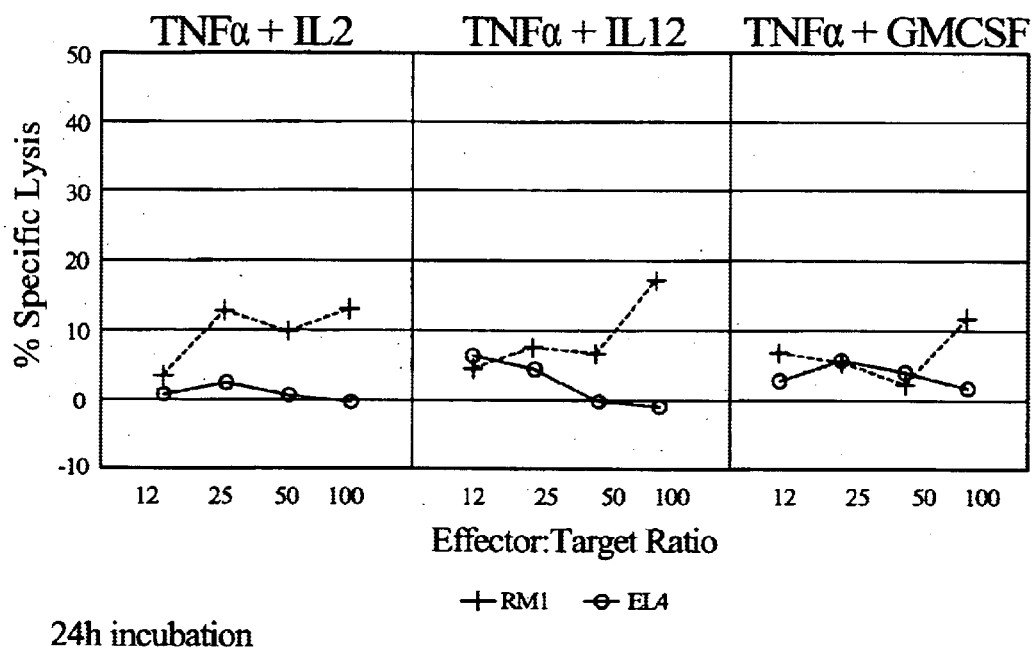
Figure 58:
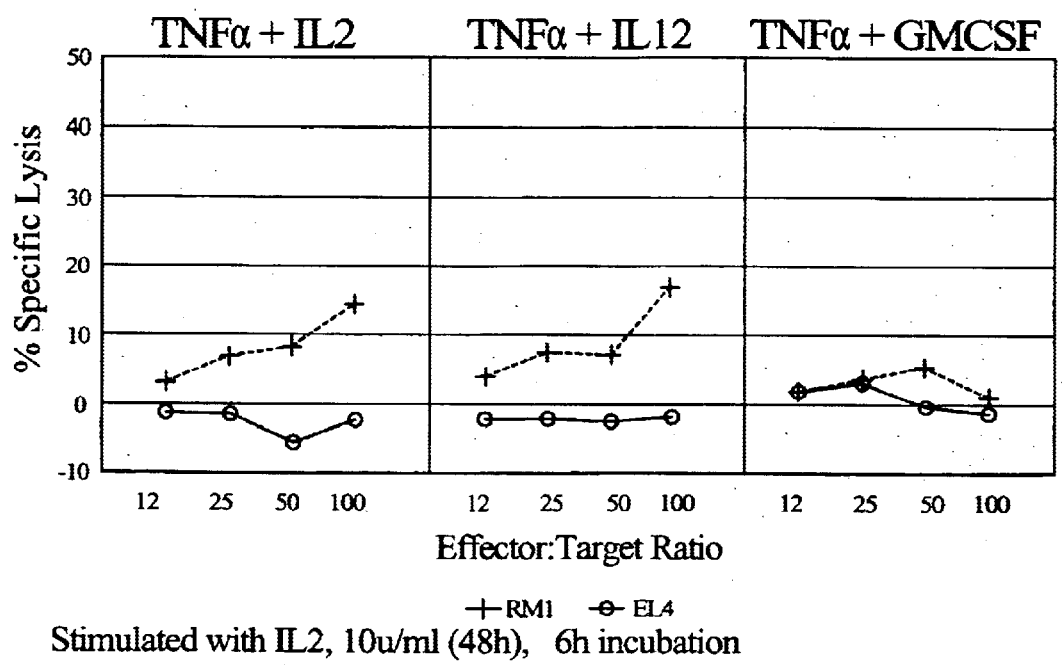
Figure 59:
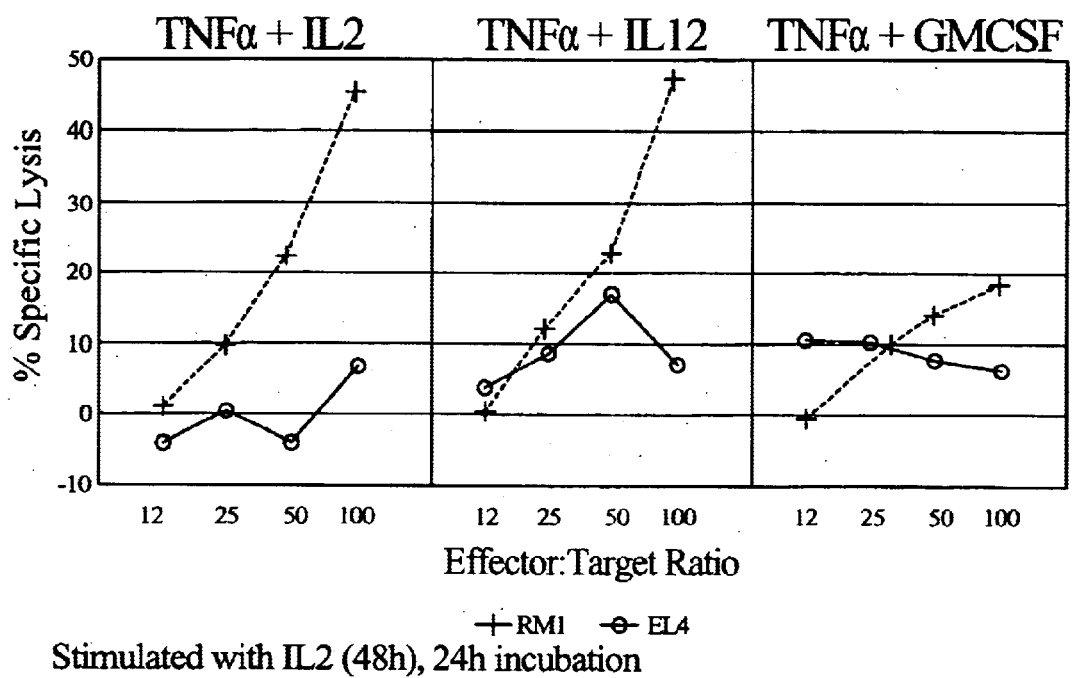

FIG. 55 is a representation of the same study in which tumor outgrowth is monitored. These date provide a clear indication of the growth and regression of the tumor in normal and scid mice.

FIGS. 56–59 are in vitro cytotoxic T lymphocyte assays performed on animals treated with the combinations of TNFα plus IL2, TNFα plus IL12, or TNFα plus GMCSF. Primary CTL assays were performed. These were assays performed on splenocytes immediately after harvest without in vitro stimulation. In a six hour 51 chromium release assay, no cytolytic activity is occurred in any group. If the assay is extended to 24 hours, significant lytic activity is observed for TNFα plus IL2. EL4, a antigenically distinct controlled target cell line were not lysed indicating specificity of lytic activity.

Figure 60:
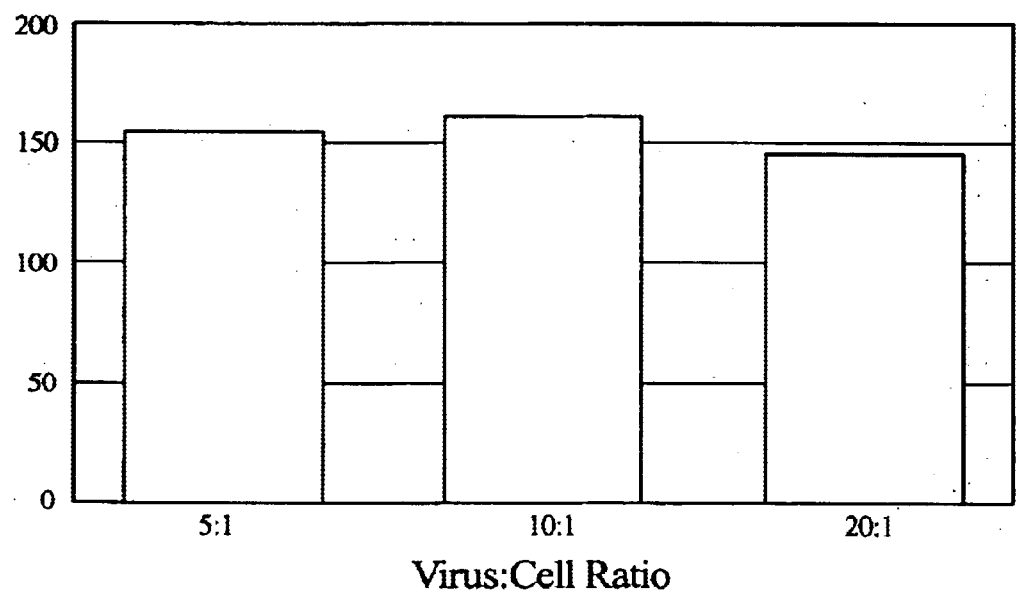

FIG. 60. Evaluation of IL-2 production by varying virus-to-cell ratios.

Figure 61:
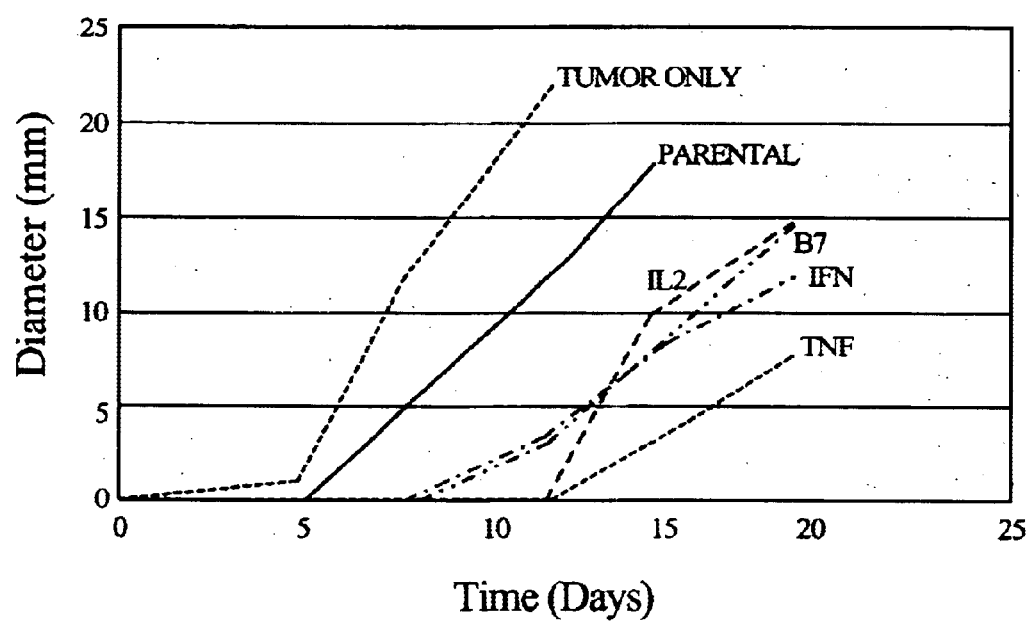

FIG. 61. Antitumor Effects of ALVAC Cytokine effectors.

Figure 62:
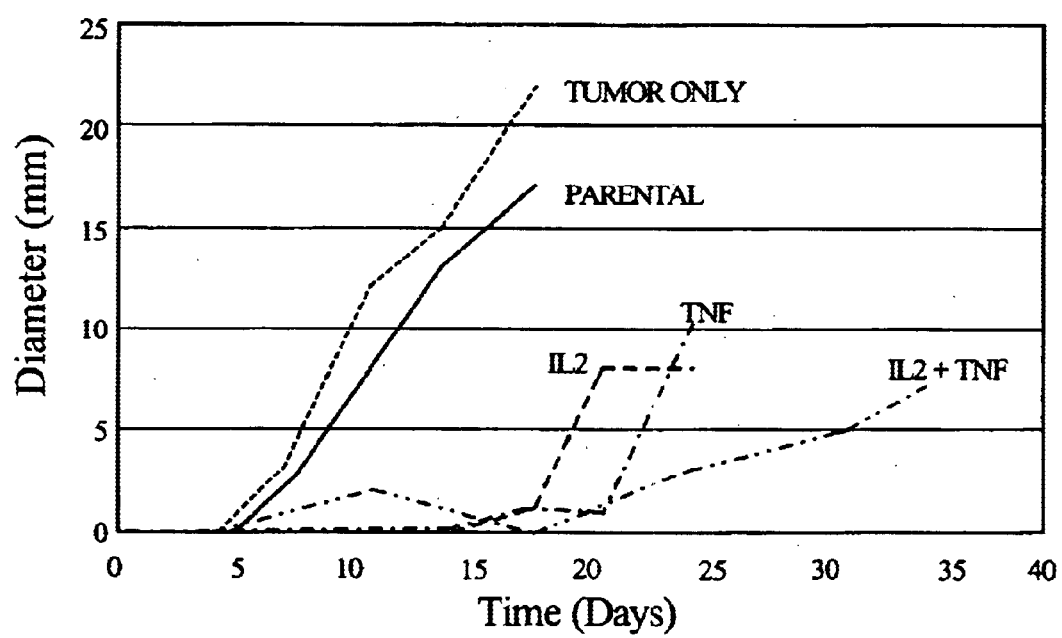

FIG. 62. Effect of Combination Therapy with ALVAC IL2 and TNFα.

Figure 63:
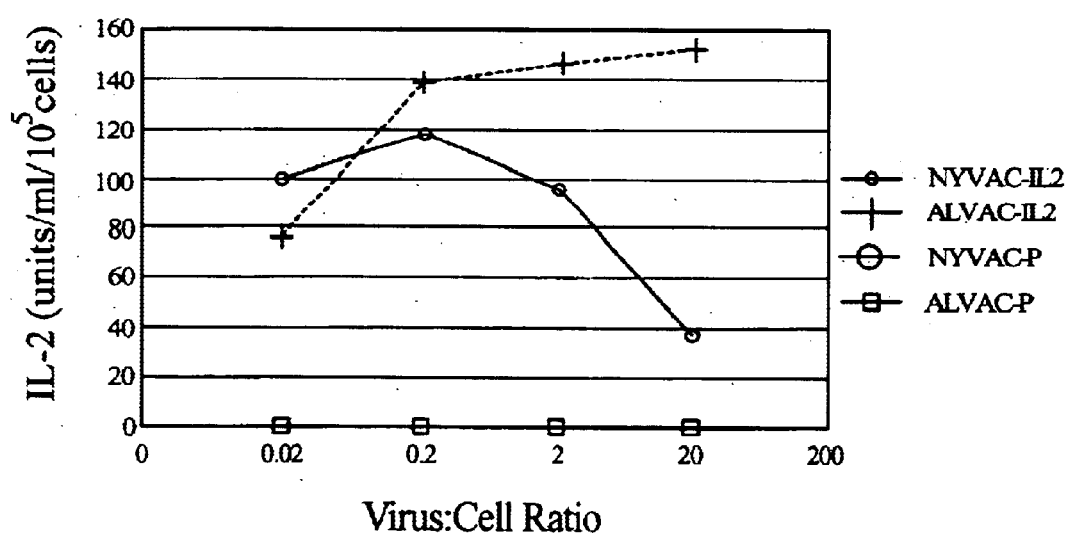

FIG. 63. Effect of varying virus-to-MBT2 cell ratios on the production of IL2.

Figure 64:
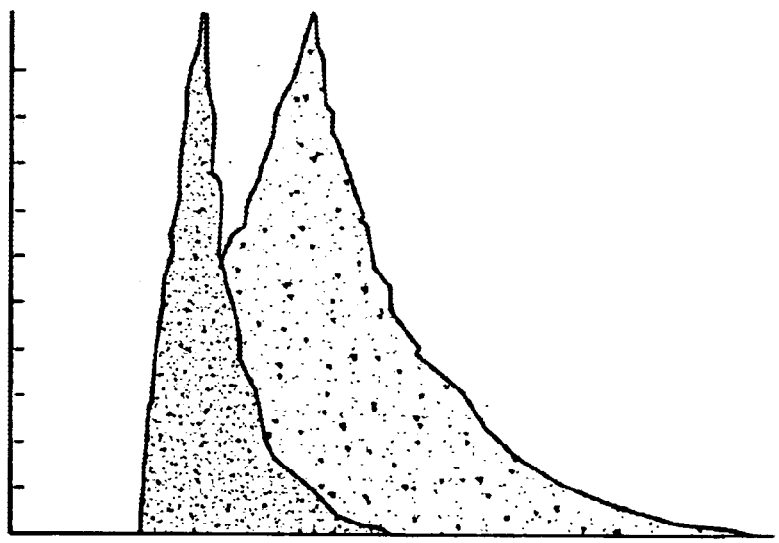

FIG. 64. Expression of B7 in MBT2 cells after infection with ALVAC-B7 at a ratio of 5:1 (virus:tumor cell).

Figure 65:
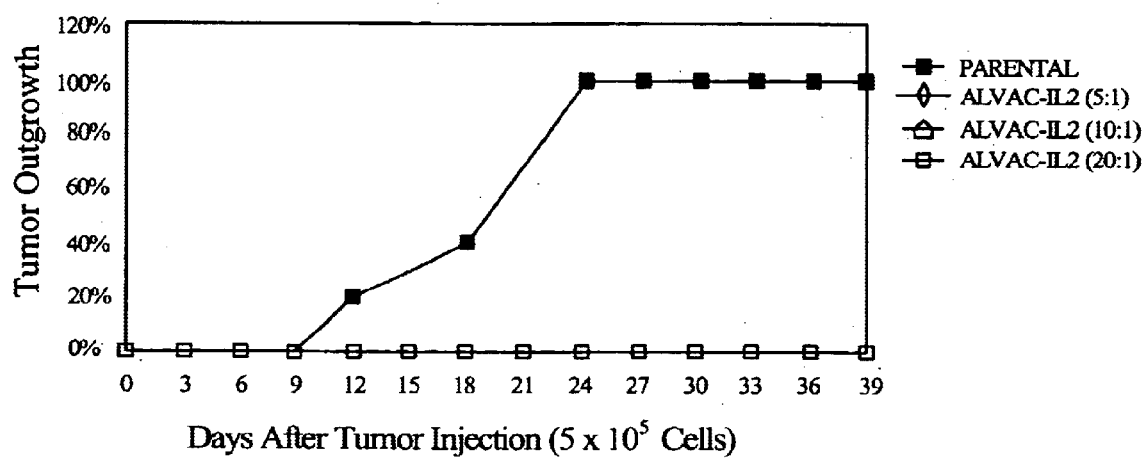

FIG. 65. Effect of varying ALVAC-IL2:MBT2 rations of tumor growth.

Figure 66:
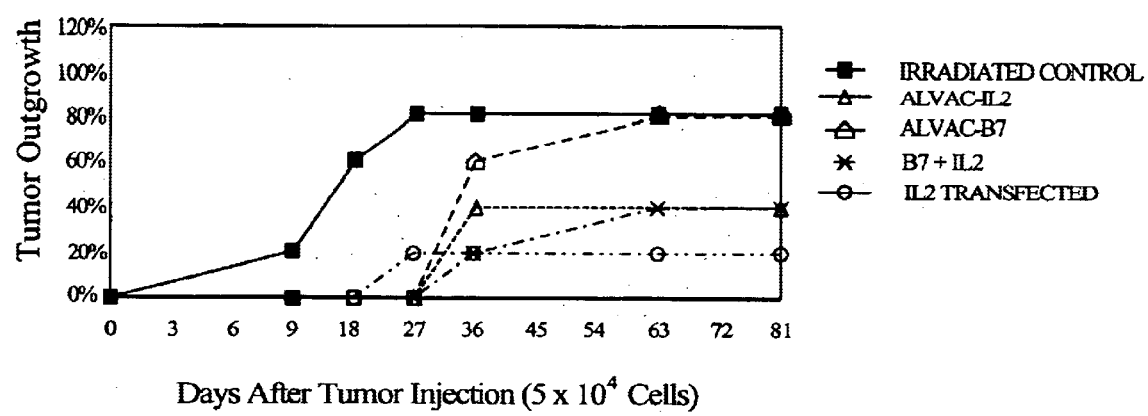

FIG. 66. Effect of immunization with ALVAC-IL2, ALVAC-B7 and the combination of ALVAC-IL2 and ALVAC-B7.

DETAILED DESCRIPTION OF THE INVENTION

To develop a new vaccinia vaccine strain, NYVAC (vP866), the Copenhagen vaccine strain of vaccinia virus was modified by the deletion of six nonessential regions of the genome encoding known or potential virulence factors. The sequential deletions are detailed below. All designations of vaccinia restriction fragments, open reading frames and nucleotide positions are based on the terminology reported in Goebel et al., 1990a,b.

The deletion loci were also engineered as recipient loci for the insertion of foreign genes.

The regions deleted in NYVAC are listed below. Also listed are the abbreviations and open reading frame designations for the deleted regions (Goebel et al., 1990a,b) and the designation of the vaccinia recombinant (vP) containing all deletions through the deletion specified:

(1) thymidine kinase gene (TK; J2R) vP410;
(2) hemorrhagic region (u; B13R+B14R) vP553;
(3) A type inclusion body region (ATI; A26L) vP618;
(4) hemagglutinin gene (HA; A56R) vP723;
(5) host range gene region (C7L–K1L) vP804; and
(6) large subunit, ribonucleotide reductase (I4L) vP866 (NYVAC).

NYVAC is a genetically engineered vaccinia virus strain that was generated by the specific deletion of eighteen open reading frames encoding gene products associated with virulence and host range. NYVAC is highly attenuated by a number of criteria including i) decreased virulence after intracerebral inoculation in newborn mice, ii) inocuity in genetically (nu$^+$/nu$^+$) or chemically (cyclophosphamide) immunocompromised mice, iii) failure to cause disseminated infection in immunocompromised mice, iv) lack of significant induration and ulceration on rabbit skin, v) rapid clearance from the site of inoculation, and vi) greatly reduced replication competency on a number of tissue culture cell lines including those of human origin. Nevertheless, NYVAC based vectors induce excellent responses to extrinsic immunogens and provided protective immunity.

TROVAC refers to an attenuated fowlpox that was a plaque-cloned isolate derived from the FP-1 vaccine strain of fowlpoxvirus which is licensed for vaccination of 1 day old chicks. ALVAC is an attenuated canarypox virus-based vector that was a plaque-cloned derivative of the licensed canarypox vaccine, Kanapox (Tartaglia et al., 1992). ALVAC has some general properties which are the same as some general properties of Kanapox. ALVAC-based recombinant viruses expressing extrinsic immunogens have also been demonstrated efficacious as vaccine vectors (Tartaglia et al., 1993 a,b). This avipox vector is restricted to avian species for productive replication. On human cell cultures, canarypox virus replication is aborted early in the viral replication cycle prior to viral DNA synthesis. Nevertheless, when engineered to express extrinsic immunogens, authentic expression and processing is observed in vitro in mammalian cells and inoculation into numerous mammalian species induces antibody and cellular immune responses to the extrinsic immunogen and provides protection against challenge with the cognate pathogen (Taylor et al., 1992; Taylor et al., 1991). Recent Phase I clinical trials in both Europe and the United States of a canarypox/rabies glycoprotein recombinant (ALVAC-RG) demonstrated that the experimental vaccine was well tolerated and induced protective levels of rabiesvirus neutralizing antibody titers (Cadoz et al., 1992; Fries et al., 1992). Additionally, peripheral blood mononuclear cells (PBMCs) derived from the ALVAC-RG vaccine demonstrated significant levels of lymphocyte proliferation when stimulated with purified rabies virus (Fries et al., 1992).

NYVAC, ALVAC and TROVAC have also been recognized as unique among all poxviruses in that the National Institutes of Health ("NIH")(U.S. Public Health Service), Recombinant DNA Advisory Committee, which issues guidelines for the physical containment of genetic material such as viruses and vectors, i.e., guidelines for safety procedures for the use of such viruses and vectors which are based upon the pathogenicity of the particular virus or vector, granted a reduction in physical containment level: from BL2 to BL1. No other poxvirus has a BL1 physical containment level. Even the Copenhagen strain of vaccinia virus—the common smallpox vaccine—has a higher physical containment level; namely, BL2. Accordingly, the art has recognized that NYVAC, ALVAC and TROVAC have a lower pathogenicity than any other poxvirus.

Both NYVAC- and ALVAC-based recombinant viruses have been shown to stimulate in vitro specific CD8$^+$ CTLs from human PBMCs (Tartaglia et al., 1993a). Mice immunized with NYVAC or ALVAC recombinants expressing various forms of the HIV-1 envelope glycoprotein generated both primary and memory HIV specific CTL responses which could be recalled by a second inoculation (Tartaglia et al., 1993a). ALVAC-env and NYVAC-env recombinants (expressing the HIV-1 envelope glycoprotein) stimulated strong HIV-specific CTL responses from peripheral blood mononuclear cells (PBMC) of HIV-1 infected individuals (Tartaglia et al., 1993a). Acutely infected autologous PBMC were used as stimulator cells for the remaining PBMC. After 10 days incubation in the absence of exogenous IL-2, the cells were evaluated for CTL activities. NYVAC-env and ALVAC-env stimulated high levels of anti-HIV activities. Thus, these vectors lend themselves well to ex vivo stimulation of antigen reactive lymphocytes; for example, adoptive immunotherapy such as the ex vivo expression of tumor reactive lymphocytes and reinfusion into the host (patient).

Immunization of the patient with NYVAC-, ALVAC-, or TROVAC-based recombinant viruses expressing TAAs produced by the patient's tumor cells can elicit anti-tumor immune responses more rapidly and to sufficient levels to impede or halt tumor spread and potentially eliminate the tumor burden.

Clearly based on the attenuation profiles of the NYVAC, ALVAC, and TROVAC vectors and their demonstrated ability to elicit both humoral and cellular immunological responses to extrinsic immunogens (Tartaglia et al., 1993a,b; Taylor et al., 1992; Konishi et al., 1992) such recombinant viruses offer a distinct advantage over previously described vaccinia-based recombinant viruses.

The immunization procedure for such recombinant viruses as immunotherapeutic vaccines or compositions may be via a parenteral route (intradermal, intramuscular or subcutaneous). Such an administration enables a systemic immune response against the specific TAA(s). Alternatively, the vaccine or composition may be administered directly into the tumor mass (intratumor). Such a route of administration can enhance the anti-tumor activities of lymphocytes specifically associated with tumors (Rosenberg, 1992). Immunization of the patient with NYVAC-, ALVAC- or TROVAC-based recombinant viruses expressing TAAs produced by the patient's tumor cells can elicit anti-tumor immune responses more rapidly and to sufficient levels to impede or halt tumor spread and potentially eliminate the tumor burden. The heightened tumor-specific immune response resulting from vaccinations with these poxvirus-based recombinant vaccines can result in remission of the tumor, including permanent remission of the tumor. Examples of known TAAs for which recombinant poxviruses can be generated and employed with immunotherapeutic value in accordance with this invention include, but are not limited to p53 (Hollstein et al., 1991), p21-ras (Almoguera et al., 1988), HER-2 (Fendly et al., 1990), and the melanoma-associated antigens (MAGE-1; MZE-2) (van der Bruggen et al., 1991), and p97 (Hu et al., 1988) and the carcinoembryonic antigen (CEA) associated with colorecteal cancer (Kantor et al., 1993; Fishbein et al., 1992; Kaufman et al., 1991).

More generally, the inventive vaccines or compositions (vaccines or compositions containing the poxvirus recombinants of the invention) can be prepared in accordance with standard techniques well known to those skilled in the pharmaceutical art. Such vaccines or compositions can be administered to a patient in need of such administration in dosages and by techniques well known to those skilled in the medical arts taking into consideration such factors as the age, sex, weight, and condition of the particular patient, and the route of administration. The vaccines or compositions can be co-administered or sequentially administered with other antineoplastic, anti-tumor or anti-cancer agents and/or with agents which reduce or alleviate ill effects of antineoplastic, anti-tumor or anti-cancer agents; again taking into consideration such factors as the age, sex, weight, and condition of the particular patient, and, the route of administration.

Examples of vaccines or compositions of the invention include liquid preparations for orifice, e.g., oral, nasal, anal, vaginal, etc., administration such as suspensions, syrups or elixirs; and, preparations for parental, subcutaneous, intradermal, intramuscular or intravenous administration (e.g., injectable administration) such as sterile suspensions or emulsions. In such compositions the recombinant poxvirus may be in admixture with a suitable carrier, diluent, or excipient such as sterile water, physiological saline, glucose or the like. The recombinant poxvirus of the invention can be provided in lyophilized form for reconstituting, for instance, in isotonic aqueous, saline buffer. Further, the invention also comprehends a kit wherein the recombinant poxvirus is provided. The kit can include a separate container containing a suitable carrier, diluent or excipient. The kit can also include an additional anti-cancer, anti-tumor or antineoplastic agent and/or an agent which reduces or alleviates ill effects of antineoplastic, anti-tumor or anti-cancer agents for co- or sequential-administration. Additionally, the kit can include instructions for mixing or combining ingredients and/or administration.

The poxvirus vector technology provides an appealing approach towards manipulating lymphocytes and tumor cells for use in cell-based immunotherapeutic modalities for cancer. Characteristics of the NYVAC, ALVAC and TROVAC vectors providing the impetus for such applications include 1) their apparent independence for specific receptors for entry into cells, 2) their ability to express foreign genes in cell substrates despite their species- or tissue-specific origin, 3) their ability to express foreign genes independent of host cell regulation, 4) the demonstrated ability of using poxvirus recombinant viruses to amplify specific CTL reactivities from peripheral blood mononuclear cells (PBMCs), and 5) their highly attenuated properties compared to existing vaccinia virus vaccine strains (Reviewed by Tartaglia et al., 1993a; Tartaglia et al., 1990).

The expression of specific cytokines or the co-expression of specific cytokines with TAAs by NYVAC-, ALVAC-, and TROVAC-based recombinant viruses can enhance the numbers and anti-tumor activities of CTLs associated with tumor cell depletion or elimination. Examples of cytokines which have a beneficial effect in this regard include tumor necrosis factor-α (TNF-α). interferon-gamma (INF-gamma), interleukin-2 (IL-2), interleukin-4 (IL-4), and interleukin-7 (IL-7) (reviewed by Pardoll, 1992). Cytokine interleukin 2 (IL-2) plays a major role in promoting cell mediated immunity. Secreted by the $T_H1$ subset of lymphocytes, IL-2 is a T cell growth factor which stimulates division of both $CD4^+$ and $CD8^+$ T cells. In addition, IL-2 also has been shown to activate B cells, monocytes and natural killer cells. To a large degree the biological effects of IL-2 are due to its role in inducing production of IFNa. Recombinant vaccinia virus expressing IL-2 is attenuated in mice compared to wild-type vaccinia virus. This is due to the ability of the vaccinia-expressed IL-2 to stimulate mouse NK cells to produce IFN a, which limits the growth of the recombinant vaccinia virus (Karupiah et al., 1990). Similarly, it has been shown that inoculation of immunodeficient athymic nude mice with recombinant vaccinia virus expressing both IL-2 and the HA gene of influenza can protect these mice from subsequent challenge with influenza virus (Karupiah et al., 1992).

Cytokine interferon γ (IFNγ) is secreted by the $T_H1$ subset of lymphocytes. IFNγ promotes the $T_H1$ cell mediated immune response, while inhibiting the $T_H2$ (antibody) response. IFNγ induces the expression of major histocompatibility complex (MHC) molecules on antigen presenting cells, and induces the expression of the B7 costimulatory molecule on macrophages. In addition to enhancing the phagocytic activity of macrophages, IFNγ enhances the cytotoxic activity of NK cells. When expressed in replicating recombinant vaccinia virus, IFNa limits the growth of the recombinant virus. This allows T cell immunodeficient mice to resolve the infection (Kohonen-Corish et al., 1990).

Cytokine interleukin 4 (IL-4) is secreted by the $T_H2$ subset of lymphocytes. IL-4 promotes the $T_H2$ (antibody) response, while inhibiting the $T_H1$ cell mediated immune response. Recombinant vaccinia virus expressing IL-4 shows increased pathogenicity in mice compared to wild-type vaccinia virus (Ramshaw et al., 1992).

Cytokine granulocyte macrophage colony stimulating factor (GMCSF) is pleiotropic. In addition to stimulating the proliferation of cells of both the granulocyte and macrophage cell lineages, GMCSF, in cross-competition with interleukins 3 and 5 (IL-3 and IL-5), influences many other aspects of hematopoiesis and may play a role in facilitation of tumor cell growth (Lopez et al., 1992). GMCSF is used clinically for hematopoietic reconstitution following bone marrow transplantation.

Cytokine interleukin 12 (IL-12), formerly known as natural killer (NK) cell stimulatory factor, is a heterodimer composed of 35 kDa and 40 kDa subunits. IL-12 is produced by monocytes, macrophages, B cells and other accessory cells. IL-12 has pleiotropic effects on both NK cells and T cells. Partly through its role in inducing IFNγ production, IL-12 plays a major role in promoting the $T_H1$ cell mediated immune response, while inhibiting the $T_H2$ response (reviewed in Trinchieri, 1993). Recently, recombinant murine IL-12 has been demonstrated to have potent antitumor and antimetastatic effects in mice (Brunda et al., 1993).

B7 (BB-1), a member of the immunoglobin superfamily, is present on the surface of antigen presenting cells. Interaction of the B7 molecule on antigen presenting cells with its receptors on T cells provides costimulatory signals, including IL-2, which are necessary for T cell activation (Schwartz, 1992). Recently it was shown that experimental co-expression of B7 along with a tumor antigen on murine melanoma cells can lead to regression of tumors in mice. This was accomplished by the B7-assisted activation of tumor-specific cytotoxic T cells (Chen et al, 1992).

The c-erb-B-2 gene, which is conserved among vertebrates, encodes a possible receptor protein. The 185 kDa translation product contains a kinase domain which is highly homologous to the kinase domain of the epidermal growth factor (EGF) receptor. The c-erb-B-2 gene is conserved among vertebrates, and is the same as the rat neu gene, which has been detected in a number of rat neuro/glioblastomas. The human c-erb-B-2 gene, also known as HER2, is amplified in certain neoplasias, most notably breast cancer. In the gastric cancer cell line, MKN-7, both the normal 4.6 kb transcript encoding c-erb-B-2 and a 2.3 kb transcript which specifies only the extracellular domain of the putative receptor are synthesized at elevated levels (Yamamoto et al., 1986). The extracellular domain has been suggested as a potential immunogen for active specific immunotherapy of breast cancer (Fendly et al., 1990).

Utility of NYVAC-, ALVAC-, and TROVAC-based recombinant viruses expressing TAAs plus or minus specific cytokines for adoptive immunotherapy can take several forms. For one, genetic modification of PBMCs can be accomplished by vector-mediated introduction of TAAs, cytokine genes, or other genes and then directly reintroduced into the patient. Such administration relies on the drainage or movement of modified PBMCs to lymphoid tissue (i.e. spleen; lymph nodes) via the reticuloendothelial system (RES) for elicitation of the tumor-specific immune response. PBMCs modified by infection with the pertinent NYVAC-, ALVAC-, and TROVAC-based recombinant can be employed, for instance, in vitro, to expand TAA-specific CTLs for reinfusion into the patient. Tumor-infiltrating lymphocytes (TILs) derived from the tumor mass can be isolated, expanded, and modified to express pertinent genes using NYVAC-, ALVAC-, or TROVAC-based recombinants viruses prior to reinfusion into the patient. TILs retain the capability of returning to tumors (homing) when re-introduced into the subject (Rosenberg, 1992). Thus, they provide a convenient vehicle for delivery of cytotoxic or cytostatic cytokines to tumor masses.

Cell-based active immunotherapy can also take on several potential modalities using the NYVAC-, ALVAC-, and TRO-VAC vectors. Tumor cells can be modified to express TAAs, cytokines, or other novel antigens (i.e. class I or class II major histocompatibility genes). Such modified tumor cells can subsequently be utilized for active immunization. The therapeutic potential for such an administration is based on the ability of these modified tumor cells to secrete cytokines and to alter the presentation of TAAs to achieve systemic anti-tumor activity. The modified tumor cells can also be utilized to expand tumor-specific CTLs in vitro for reinfusion into the patient.

A better understanding of the present invention and of its many advantages will be had from the following examples, given by way of illustration.

EXAMPLES

DNA Cloning and Synthesis. Plasmids were constructed, screened and grown by standard procedures (Maniatis et al., 1982; Perkus et al., 1985; Piccini et al., 1987). Restriction endonucleases were obtained from Bethesda Research Laboratories, Gaithersburg, Md., New England Biolabs, Beverly, Mass.; and Boehringer Mannheim Biochemicals, Indianapolis, Ind. Klenow fragment of *E. coli* polymerase was obtained from Boehringer Mannheim Biochemicals. BAL-31 exonuclease and phage T4 DNA ligase were obtained from New England Biolabs. The reagents were used as specified by the various suppliers.

Synthetic oligodeoxyribonucleotides were prepared on a Biosearch 8750 or Applied Biosystems 380B DNA synthesizer as previously described (Perkus et al., 1989). DNA sequencing was performed by the dideoxy-chain termination method (Sanger et al., 1977) using Sequenase (Tabor et al., 1987) as previously described (Guo et al., 1989). DNA amplification by polymerase chain reaction (PCR) for sequence verification (Engelke et al., 1988) was performed using custom synthesized oligonucleotide primers and GeneAmp DNA amplification Reagent Kit (Perkin Elmer Cetus, Norwalk, Conn.) in an automated Perkin Elmer Cetus DNA Thermal Cycler. Excess DNA sequences were deleted from plasmids by restriction endonuclease digestion followed by limited digestion by BAL-31 exonuclease and mutagenesis (Mandecki, 1986) using synthetic oligonucleotides.

Cells, Virus, and Transfection. The origins and conditions of cultivation of the Copenhagen strain of vaccinia virus has been previously described (Guo et al., 1989). Generation of recombinant virus by recombination, in situ hybridization of nitrocellulose filters and screening for B-galactosidase activity are as previously described (Piccini et al., 1987).

The origins and conditions of cultivation of the Copenhagen strain of vaccinia virus and NYVAC has been previously described (Guo et al., 1989; Tartaglia et al., 1992).

Generation of recombinant virus by recombination, in situ hybridization of nitrocellulose filters and screening for B-galactosidase activity are as previously described (Panicali et al., 1982; Perkus et al., 1989).

The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

The strain of fowlpox virus (FPV) designated FP-1 has been described previously (Taylor et al., 1988a). It is an attenuated vaccine strain useful in vaccination of day old chickens. The parental virus strain Duvette was obtained in France as a fowlpox scale from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established.

NYVAC, ALVAC and TROVAC viral vectors and their derivatives were propagated as described previously (Piccini et al., 1987; Taylor et al., 1988a,b). Vero cells and chick embryo fibroblasts (CEF) were propagated as described previously (Taylor et al., 1988a,b).

Example 1

Construction of Plasmid pSD460 for Deletion of Thymidine Kinase Gene (J2R)

Figure 1:
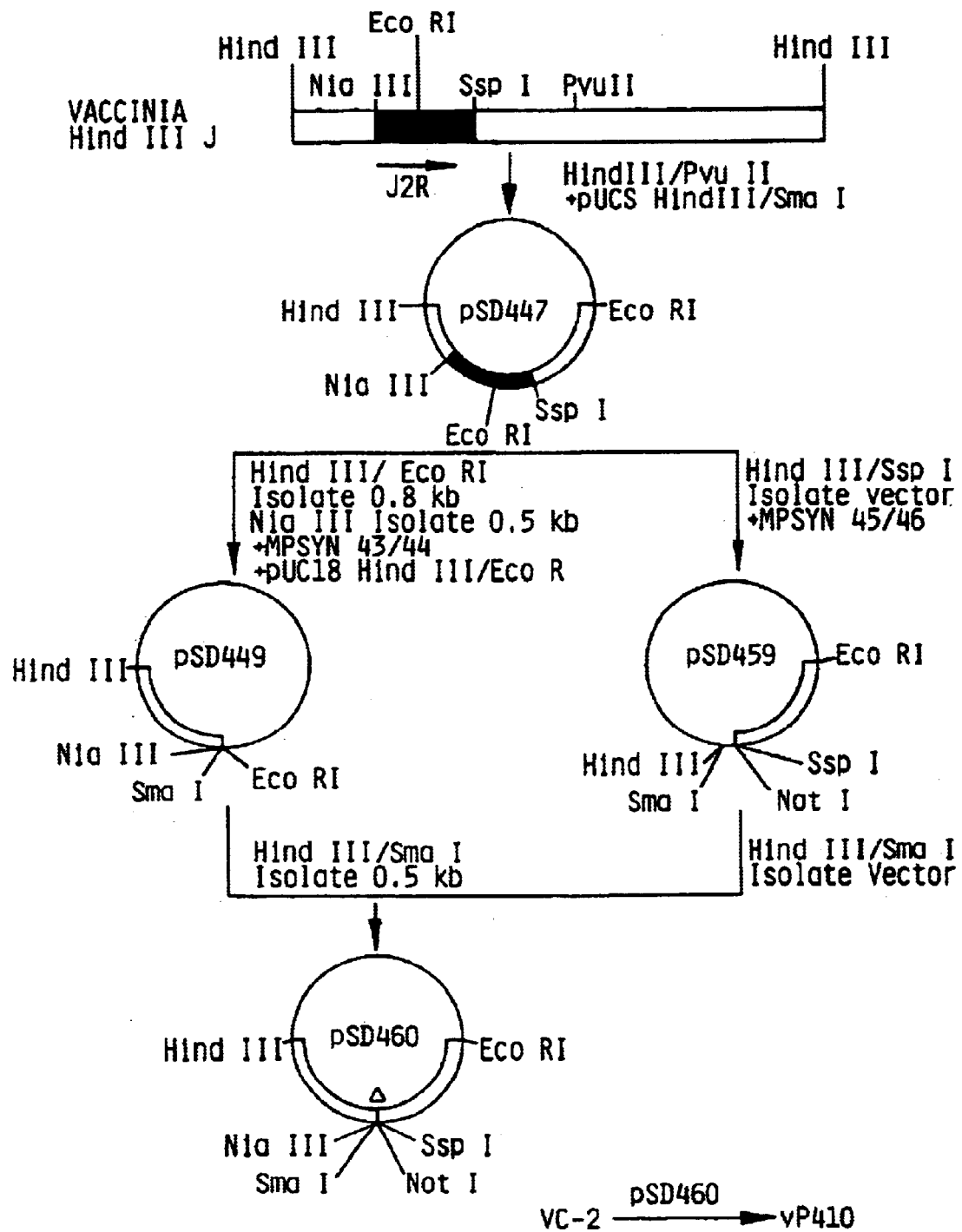
FIG. 1 schematically shows a method for the construction of plasmid pSD460 for deletion of thymidine kinase gene and generation of recombinant vaccinia virus vP410.

Referring now to FIG. 1, plasmid pSD406 contains vaccinia HindIII J (pos. 83359–88377) cloned into pUC8. pSD406 was cut with HindIII and PvuII, and the 1.7 kb fragment from the left side of HindIII J cloned into pUC8 cut with HindIII/SmaI, forming pSD447. pSD447 contains the entire gene for J2R (pos. 83855–84385). The initiation codon is contained within an NlaIII site and the termination codon is contained within an SspI site. Direction of transcription is indicated by an arrow in FIG. 1.

To obtain a left flanking arm, a 0.8 kb HindIII/EcoRI fragment was isolated from pSD447, then digested with NlaIII and a 0.5 kb HindIII/NlaIII fragment isolated. Annealed synthetic oligonucleotides MPSYN43/MPSYN44 (SEQ ID NO:1/SEQ ID NO:2)

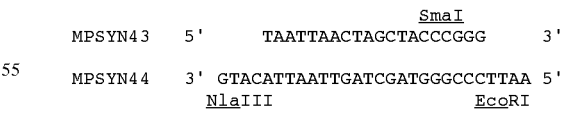

were ligated with the 0.5 kb HindIII/NlaIII fragment into pUC18 vector plasmid cut with HindIII/EcoRI, generating plasmid pSD449.

To obtain a restriction fragment containing a vaccinia right flanking arm and pUC vector sequences, pSD447 was cut with SspI (partial) within vaccinia sequences and HindIII at the pUC/vaccinia junction, and a 2.9 kb vector fragment isolated. This vector fragment was ligated with annealed synthetic oligonucleotides MPSYN45/MPSYN46 (SEQ ID NO:3/SEQ ID NO:4)

```
                HindIII  SmaI
MPSYN45  5' AGCTTCCCGGGTAAGTAATACGTCAAGGAGAAAACGAA

MPSYN46  3'     AGGGCCCATTCATTATGCAGTTCCTCTTTTGCTT

NotI            SspI
         ACGATCTGTAGTTAGCGGCCGCCTAATTAACTAAT 3' MPSYN45

TGCTAGACATCAATCGCCGGCGGATTAATTGATTA 5' MPSYN46
``` generating pSD459.

To combine the left and right flanking arms into one plasmid, a 0.5 kb HindIII/SmaI fragment was isolated from pSD449 and ligated with pSD459 vector plasmid cut with HindIII/SmaI, generating plasmid pSD460. pSD460 was used as donor plasmid for recombination with wild type parental vaccinia virus Copenhagen strain VC-2. $^{32}$P labelled probe was synthesized by primer extension using MPSYN45 (SEQ ID NO:3) as template and the complementary 20 mer oligonucleotide MPSYN47 (SEQ ID NO:5) (5' TTAGTTAATTAGGCGGCCGC 3') as primer. Recombinant virus vP410 was identified by plaque hybridization.

Example 2

Construction of Plasmid pSD486 For Deletion of Hemorrhagic Region (B13R+B14R)

Figure 2:
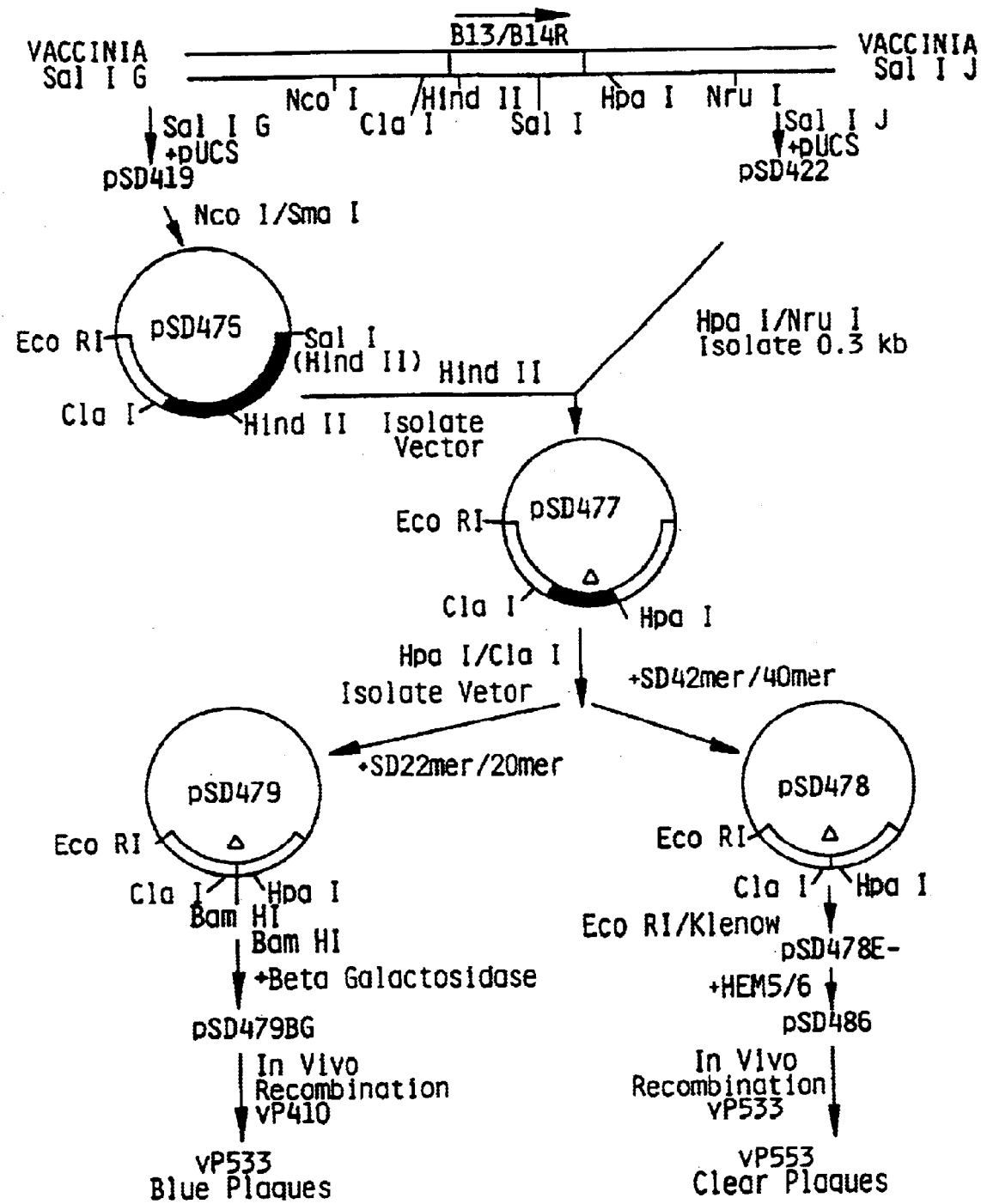
FIG. 2 schematically shows a method for the construction of plasmid pSD486 for deletion of hemorrhagic region and generation of recombinant vaccinia virus vP553.

Referring now to FIG. 2, plasmid pSD419 contains vaccinia SalI G (pos. 160,744–173,351) cloned into pUC8. pSD422 contains the contiguous vaccinia SalI fragment to the right, SalI J (pos. 173,351–182,746) cloned into pUCB. To construct a plasmid deleted for the hemorrhagic region, u, B13R–B14R (pos. 172,549–173,552), pSD419 was used as the source for the left flanking arm and pSD422 was used as the source of the right flanking arm. The direction of transcription for the u region is indicated by an arrow in FIG. 2.

To remove unwanted sequences from pSD419, sequences to the left of the NcoI site (pos. 172,253) were removed by digestion of pSD419 with NcoI/SmaI followed by blunt ending with Klenow fragment of E. coli polymerase and ligation generating plasmid pSD476. A vaccinia right flanking arm was obtained by digestion of pSD422 with HpaI at the termination codon of B14R and by digestion with NruI 0.3 kb to the right. This 0.3 kb fragment was isolated and ligated with a 3.4 kb HincII vector fragment isolated from pSD476, generating plasmid pSD477. The location of the partial deletion of the vaccinia u region in pSD477 is indicated by a triangle. The remaining B13R coding sequences in pSD477 were removed by digestion with ClaI/HpaI, and the resulting vector fragment was ligated with annealed synthetic oligonucleotides SD22 mer/SD20 mer (SEQ ID NO:6/SEQ ID NO:7)

```
                    ClaI       BamHI HpaI
    SD22mer   5' CGATTACTATGAAGGATCCGTT 3'

SD20mer   3'    TAATGATACTTCCTAGGCAA 5'
``` generating pSD479. pSD479 contains an initiation codon (underlined) followed by a BamHI site. To place E. coli Beta-galactosidase in the B13–B14 (u) deletion locus under the control of the u promoter, a 3.2 kb BamHI fragment containing the Beta-galactosidase gene (Shapira et al., 1983) was inserted into the BamHI site of pSD479, generating pSD479BG. pSD479BG was used as donor plasmid for recombination with vaccinia virus vP410. Recombinant vaccinia virus vP533 was isolated as a blue plaque in the presence of chromogenic substrate X-gal. In vP533 the B13R–B14R region is deleted and is replaced by Beta-galactosidase.

To remove Beta-galactosidase sequences from vP533, plasmid pSD486, a derivative of pSD477 containing a polylinker region but no initiation codon at the u deletion junction, was utilized. First the ClaI/HpaI vector fragment from pSD477 referred to above was ligated with annealed synthetic oligonucleotides SD42 mer/SD40 mer (SEQ ID NO:8/SEQ ID NO:9)

```
              ClaI       SacI      XhoI        HpaI
SD42mer  5' CGATTACTAGATCTGAGCTCCCCGGGCTCGAGGGATCCGTT 3'

SD40mer  3'    TAATGATCTAGACTCGAGGGGCCCGAGCTCCCTAGGCAA 5'
                  BglII       SmaI        BamHI
``` generating plasmid pSD478. Next the EcoRI site at the pUC/vaccinia junction was destroyed by digestion of pSD478 with EcoRI followed by blunt ending with Klenow fragment of E. coli polymerase and ligation, generating plasmid pSD478E⁻. pSD478E⁻ was digested with BamHI and HpaI and ligated with annealed synthetic oligonucleotides HEM5/HEM6 (SEQ ID NO:10/SEQ ID NO:11)

```
                    BamHI EcoRI   HpaI
       HEM5    5'  GATCCGAATTCTAGCT  3'

HEM6    3'      GCTTAAGATCGA  5'
``` generating plasmid pSD486. pSD486 was used as donor plasmid for recombination with recombinant vaccinia virus vP533, generating vP553, which was isolated as a clear plaque in the presence of X-gal.

Example 3

Construction of Plasmid pMP494Ä for Deletion of ATI Region (A26L)

Figure 3:
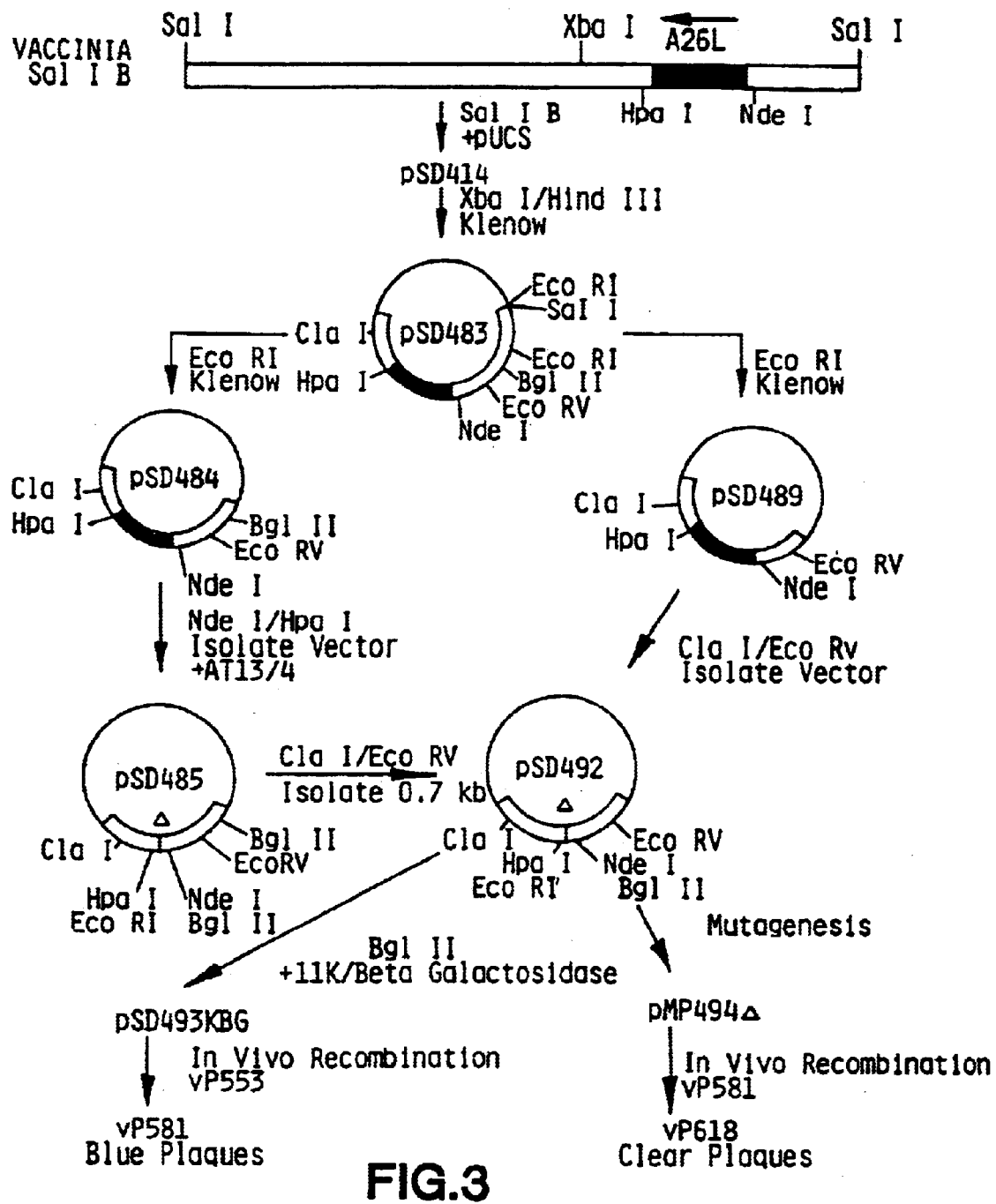
FIG. 3 schematically shows a method for the construction of plasmid pMP494Δ for deletion of ATI region and generation of recombinant vaccinia virus vP618.

Referring now to FIG. 3, pSD414 contains SalI B cloned into pUC8. To remove unwanted DNA sequences to the left of the A26L region, pSD414 was cut with XbaI within vaccinia sequences (pos. 137,079) and with HindIII at the pUC/vaccinia junction, then blunt ended with Klenow fragment of E. coli polymerase and ligated, resulting in plasmid pSD483. To remove unwanted vaccinia DNA sequences to the right of the A26L region, pSD483 was cut with EcoRI (pos. 140,665 and at the pUC/vaccinia junction) and ligated, forming plasmid pSD484. To remove the A26L coding region, pSD484 was cut with NdeI (partial) slightly upstream from the A26L ORF (pos. 139,004) and with HpaI (pos. 137,889) slightly downstream from the A26L ORF. The 5.2 kb vector fragment was isolated and ligated with annealed synthetic oligonucleotides ATI3/ATI4 (SEQ ID NO:12/SEQ ID NO:13)

```
              NdeI                                                  BglII EcoRI HpaI
ATI3 5' TATGAGTAACTTAACTCTTTTGTTAATTAAAAGTATATTCAAAAAATAAGTTATATAAATAGATCTGAATTCGTT 3'    ATI3

ATI4 3'     ACTCATTGAATTGAGAAAACAATTAATTTTCATATAAGTTTTTTATTCAATATATTTATCTAGACTTAAGCAA 5'    ATI4
``` reconstructing the region upstream from A26L and replacing the A26L ORF with a short polylinker region containing the restriction sites BglII, EcoRI and HpaI, as indicated above. The resulting plasmid was designated pSD485. Since the BglII and EcoRI sites in the polylinker region of pSD485 are not unique, unwanted BglII and EcoRI sites were removed from plasmid pSD483 (described above) by digestion with BglII (pos. 140,136) and with EcoRI at the pUC/vaccinia junction, followed by blunt ending with Klenow fragment of E. coli polymerase and ligation. The resulting plasmid was designated pSD489. The 1.8 kb ClaI (pos. 137,198)/EcoRV (pos. 139,048) fragment from pSD489 containing the A26L ORF was replaced with the corresponding 0.7 kb polylinker-containing ClaI/EcoRV fragment from pSD485, generating by digestion of pSD419 with HindIII within vaccinia sequences and at the pUC/vaccinia junction followed by ligation. The resulting plasmid, pSD456, contains the HA gene, A56R, flanked by 0.4 kb of vaccinia sequences to the left and 0.4 kb of vaccinia sequences to the right. A56R coding sequences were removed by cutting pSD456 with RsaI (partial; pos. 161,090) upstream from A56R coding sequences, and with EagI (pos. 162,054) near the end of the gene. The 3.6 kb RsaI/EagI vector fragment from pSD456 was isolated and ligated with annealed synthetic oligonucleotides MPSYN59 (SEQ ID NO:15), MPSYN62 (SEQ ID NO:16), MPSYN60 (SEQ ID NO:17), and MPSYN61 (SEQ ID NO:18)

```
                  RsaI
MPSYN59  5'  ACACGAATGATTTTCTAAAGTATTTGGAAAGTTTTATAGGTAGTTGATAGAACAAAATACATAATTT 3'

MPSYN62  3'  TGTGCTTACTAAAAGATTTCATAAACCTTTCAAAATATCCATCAACTATCT 5'

BglII SmaI PstI EagI
MPSYN60  5'                TGTAAAAATAAATCACTTTTTATACTAAGATCTCCCGGGCTGCAGC           3'

MPSYN61  3'  TGTTTTATGTATTAAAACATTTTTATTTAGTGAAAAATATGATTCTAGAGGGCCCGACGTCGCCGG 5'
``` pSD492. The BglII and EcoRI sites in the polylinker region of pSD492 are unique.

A 3.3 kb BglII cassette containing the E. coli Beta-galactosidase gene (Shapira et al., 1983) under the control of the vaccinia 11 kDa promoter (Bertholet et al., 1985; Perkus et al., 1990) was inserted into the BglII site of pSD492, forming pSD493KBG. Plasmid pSD493KBG was used in recombination with rescuing virus vP553. Recombinant vaccinia virus, vP581, containing Beta-galactosidase in the A26L deletion region, was isolated as a blue plaque in the presence of X-gal.

To generate a plasmid for the removal of Beta-galactosidase sequences from vaccinia recombinant virus vP581, the polylinker region of plasmid pSD492 was deleted by mutagenesis (Mandecki, 1986) using synthetic oligonucleotide MPSYN177 (SEQ ID NO:14) (5' AAAATGGGCGTGGATTGTTAACTT-TATATAACTTATTTTTTGAATATAC 3'). In the resulting plasmid, pMP494Ä, vaccinia DNA encompassing positions [137,889–138,937], including the entire A26L ORF is deleted. Recombination between the pMP494Ä and the Beta-galactosidase containing vaccinia recombinant, vP581, resulted in vaccinia deletion mutant vP618, which was isolated as a clear plaque in the presence of X-gal.

Example 4

Construction of Plasmid pSD467 FOR Deletion of Hemagglutinin Gene (A56R)

Figure 4:
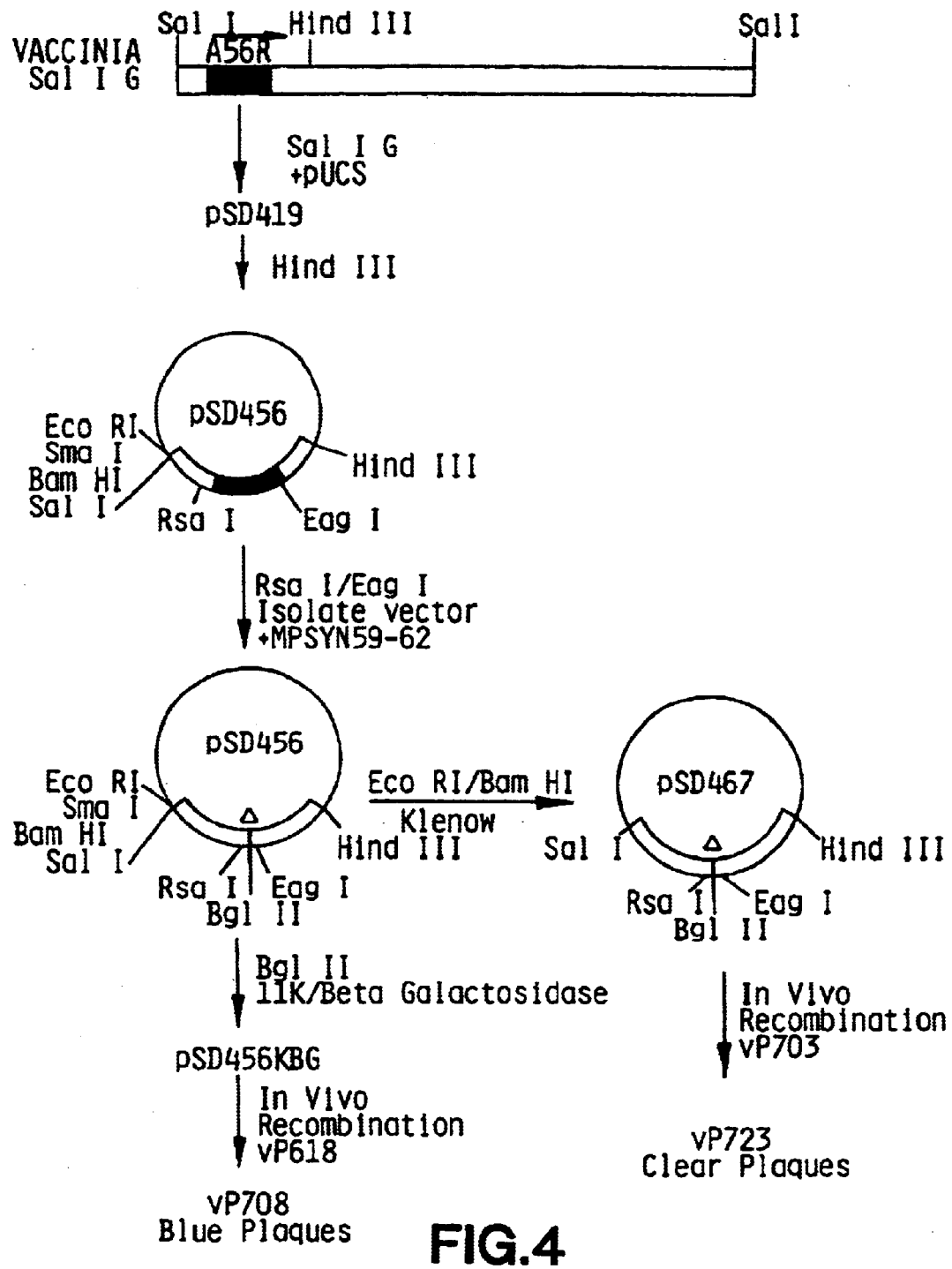
FIG. 4 schematically shows a method for the construction of plasmid pSD467 for deletion of hemagglutinin gene and generation of recombinant vaccinia virus vP723.

Referring now to FIG. 4, vaccinia SalI G restriction fragment (pos. 160,744–173,351) crosses the HindIII A/B junction (pos. 162,539). pSD419 contains vaccinia SalI G cloned into pUC8. The direction of transcription for the hemagglutinin (HA) gene is indicated by an arrow in FIG. 4. Vaccinia sequences derived from HindIII B were removed reconstructing the DNA sequences upstream from the A56R ORF and replacing the A56R ORF with a polylinker region as indicated above. The resulting plasmid is pSD466. The vaccinia deletion in pSD466 encompasses positions [161,185–162,053]. The site of the deletion in pSD466 is indicated by a triangle in FIG. 4.

A 3.2 kb BglII/BamHI (partial) cassette containing the E. coli Beta-galactosidase gene (Shapira et al., 1983) under the control of the vaccinia 11 kDa promoter (Bertholet et al., 1985; Guo et al., 1989) was inserted into the BglII site of pSD466, forming pSD466KBG. Plasmid pSD466KBG was used in recombination with rescuing virus vP618. Recombinant vaccinia virus, vP708, containing Beta-galactosidase in the A56R deletion, was isolated as a blue plaque in the presence of X-gal.

Beta-galactosidase sequences were deleted from vP708 using donor plasmid pSD467. pSD467 is identical to pSD466, except that EcoRI, SmaI and BamHI sites were removed from the pUC/vaccinia junction by digestion of pSD466 with EcoRI/BamHI followed by blunt ending with Klenow fragment of E. coli polymerase and ligation. Recombination between vP708 and pSD467 resulted in recombinant vaccinia deletion mutant, vP723, which was isolated as a clear plaque in the presence of X-gal.

Example 5

Construction of Plasmid pMPCSK1Ä for Deletion of Open Reading Frames [C7L-K1L]

Figure 5:
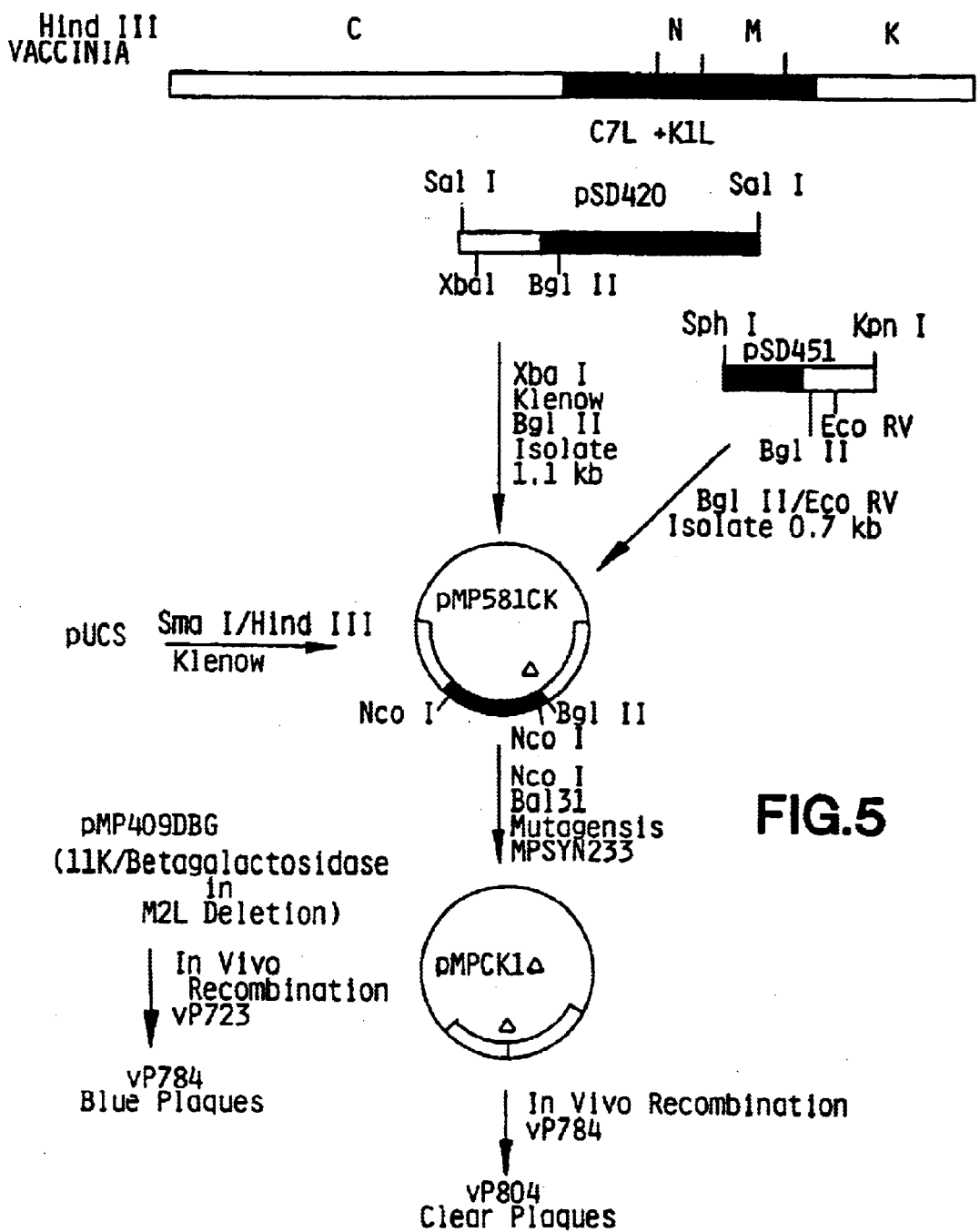
FIG. 5 schematically shows a method for the construction of plasmid pMPCK1Δ for deletion of gene cluster [C7L-K1L] and generation of recombinant vaccinia virus vP804.

Referring now to FIG. 5, the following vaccinia clones were utilized in the construction of pMPCSK1Ä. pSD420 is SalI H cloned into pUCB. pSD435 is KpnI F cloned into pUC18. pSD435 was cut with SphI and religated, forming pSD451. In pSD451, DNA sequences to the left of the SphI site (pos. 27,416) in HindIII M are removed (Perkus et al., 1990). pSD409 is HindIII M cloned into pUCB.

To provide a substrate for the deletion of the [C7L-K1L] gene cluster from vaccinia, E. coli Beta-galactosidase was first inserted into the vaccinia M2L deletion locus (Guo et al., 1990) as follows. To eliminate the BglII site in pSD409, the plasmid was cut with BglII in vaccinia sequences (pos. 28,212) and with BamHI at the pUC/vaccinia junction, then ligated to form plasmid pMP409B. pMP409B was cut at the unique SphI site (pos. 27,416). M2L coding sequences were removed by mutagenesis (Guo et al., 1990; Mandecki, 1986) using synthetic oligonucleotide

```
            MPSYN82 (SEQ ID NO:19)
                                 BglII
         5' TTTCTGTATATTTGCACCAATTTAGATCTT-

ACTCAAAATATGTAACAATA 3'
```

The resulting plasmid, pMP409D, contains a unique BglII site inserted into the M2L deletion locus as indicated above. A 3.2 kb BamHI (partial)/BglII cassette containing the E. coli Beta-galactosidase gene (Shapira et al., 1983) under the control of the 11 kDa promoter (Bertholet et al., 1985) was inserted into pMP409D cut with BglII. The resulting plasmid, pMP409DBG (Guo et al., 1990), was used as donor plasmid for recombination with rescuing vaccinia virus vP723. Recombinant vaccinia virus, vP784, containing Beta-galactosidase inserted into the M2L deletion locus, was isolated as a blue plaque in the presence of X-gal.

A plasmid deleted for vaccinia genes [C7L-K1L] was assembled in pUC8 cut with SmaI, HindIII and blunt ended with Klenow fragment of E. coli polymerase. The left flanking arm consisting of vaccinia HindIII C sequences was obtained by digestion of pSD420 with XbaI (pos. 18,628) followed by blunt ending with Klenow fragment of E. coli polymerase and digestion with BglII (pos. 19,706). The right flanking arm consisting of vaccinia HindIII K sequences was obtained by digestion of pSD451 with BglII (pos. 29,062) and EcoRV (pos. 29,778). The resulting plasmid, pMP581CK is deleted for vaccinia sequences between the BglII site (pos. 19,706) in HindIII C and the BglII site (pos. 29,062) in HindIII K. The site of the deletion of vaccinia sequences in plasmid pMP581CK is indicated by a triangle in FIG. 5.

To remove excess DNA at the vaccinia deletion junction, plasmid pMP581CK, was cut at the NcoI sites within vaccinia sequences (pos. 18,811; 19,655), treated with Bal-31 exonuclease and subjected to mutagenesis (Mandecki, 1986) using synthetic oligonucleotide MPSYN233 (SEQ ID NO:20) 5'-TGTCATTTAACACTATACTCATATTAA TAAAAATAATATTTATT-3'. The resulting plasmid, pMPCSK1Å, is deleted for vaccinia sequences positions 18,805–29,108, encompassing 12 vaccinia open reading frames [C7L - K1L]. Recombination between pMPCSK1Å and the Beta-galactosidase containing vaccinia recombinant, vP784, resulted in vaccinia deletion mutant, vP804, which was isolated as a clear plaque in the presence of X-gal.

Example 6

Construction of Plasmid pSD548 for Deletion of Large Subunit, Ribonucleotide Reductase (I4L)

Figure 6:
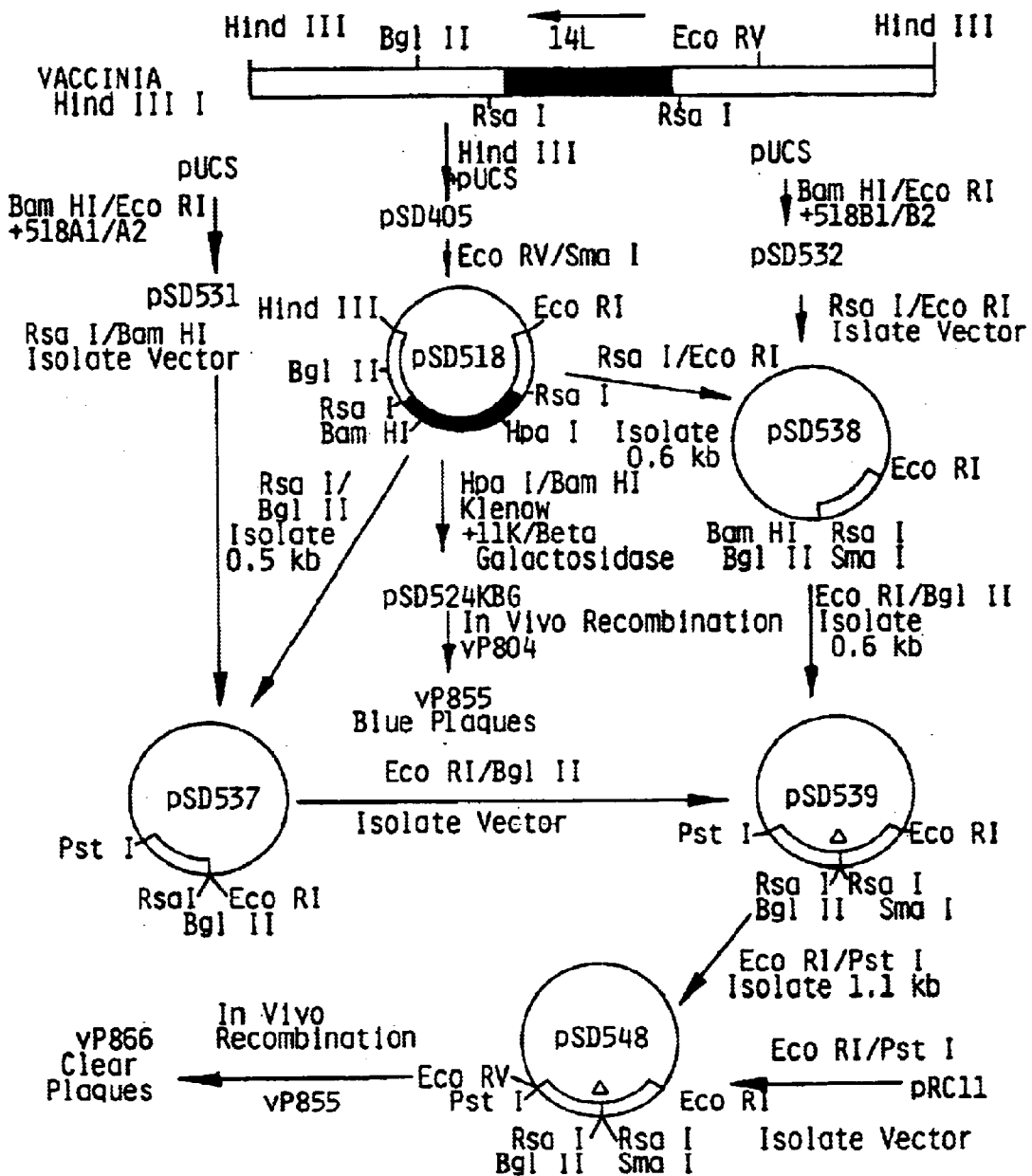
FIG. 6 schematically shows a method for the construction of plasmid pSD548 for deletion of large subunit, ribonucleotide reductase and generation of recombinant vaccinia virus vP866 (NYVAC)

Referring now to FIG. 6, plasmid pSD405 contains vaccinia HindIII I (pos. 63, 875–70,367) cloned in pUC8. pSD405 was digested with EcoRV within vaccinia sequences (pos. 67,933) and with SmaI at the pUC/vaccinia junction, and ligated, forming plasmid pSD518. pSD518 was used as the source of all the vaccinia restriction fragments used in the construction of pSD548.

The vaccinia I4L gene extends from position 67,371–65,059. Direction of transcription for I4L is indicated by an arrow in FIG. 6. To obtain a vector plasmid fragment deleted for a portion of the I4L coding sequences, pSD518 was digested with BamHI (pos. 65,381) and HpaI (pos. 67,001) and blunt ended using Klenow fragment of E. coli polymerase. This 4.8 kb vector fragment was ligated with a 3.2 kb SmaI cassette containing the E. coli Beta-galactosidase gene (Shapira et al., 1983) under the control of the vaccinia 11 kDa promoter (Bertholet et al., 1985; Perkus et al., 1990), resulting in plasmid pSD524KBG. pSD524KBG was used as donor plasmid for recombination with vaccinia virus vP804. Recombinant vaccinia virus, vP855, containing Beta-galactosidase in a partial deletion of the I4L gene, was isolated as a blue plaque in the presence of X-gal.

To delete Beta-galactosidase and the remainder of the I4L ORF from vP855, deletion plasmid pSD548 was constructed. The left and right vaccinia flanking arms were assembled separately in pUC8 as detailed below and presented schematically in FIG. 6.

To construct a vector plasmid to accept the left vaccinia flanking arm, pUC8 was cut with BamHI/EcoRI and ligated with annealed synthetic oligonucleotides 518A1/518A2 (SEQ ID NO:21/SEQ ID NO:22)

```
              BamHI   RsaI                                                     BglII    EcoRI
    518A1 5' GATCCTGAGTACTTTGTAATATAATGATATATATTTTCACTTTATCTCATTTGAGAATAAAAAGATCTTAGG    3' 518A1

518A2 3'     GACTCATGAAACATTATATTACTATATATAAAAGTGAAATAGAGTAAACTCTTATTTTTCTAGAATCCTTAA 5' 518A2
``` forming plasmid pSD531. pSD531 was cut with RsaI (partial) and BamHI and a 2.7 kb vector fragment isolated. pSD518 was cut with BglII (pos. 64,459)/RsaI (pos. 64,994) and a 0.5 kb fragment isolated. The two fragments were ligated together, forming pSD537, which contains the complete vaccinia flanking arm left of the I4L coding sequences.

To construct a vector plasmid to accept the right vaccinia flanking arm, pUC8 was cut with BamHI/EcoRI and ligated with annealed synthetic oligonucleotides 518B1/518B2 (SEQ ID NO:23/SEQ ID NO:24)

```
              BamHI BglII SmaI                                          RsaI    EcoRI
    518B1 5' GATCCAGATCTCCCGGGAAAAAATTATTTAACTTTTCATTAATAGGGATTTGACGTATGTAGCGTACTAGG      3' 518B1

518B2 3'     GTCTAGAGGGCCCTTTTTTTAATAAATTGAAAAGTAATTATCCCTAAACTGCATACTACGCATGATCCTTAA 5' 518B2
``` forming plasmid pSD532. pSD532 was cut with RsaI (partial)/EcoRI and a 2.7 kb vector fragment isolated. pSD518 was cut with RsaI within vaccinia sequences (pos. 67,436) and EcoRI at the vaccinia/pUC junction, and a 0.6 kb fragment isolated. The two fragments were ligated together, forming pSD538, which contains the complete vaccinia flanking arm to the right of I4L coding sequences.

The right vaccinia flanking arm was isolated as a 0.6 kb EcoRI/BglII fragment from pSD538 and ligated into pSD537 vector plasmid cut with EcoRI/BglII. In the resulting plasmid, pSD539, the I4L ORF (pos. 65, 047–67,386) is replaced by a polylinker region, which is flanked by 0.6 kb vaccinia DNA to the left and 0.6 kb vaccinia DNA to the right, all in a pUC background. The site of deletion within vaccinia sequences is indicated by a triangle in FIG. 6. To avoid possible recombination of Beta-galactosidase sequences in the pUC-derived portion of pSD539 with Beta-galactosidase sequences in recombinant vaccinia virus vP855, the vaccinia I4L deletion cassette was moved from pSD539 into pRC11, a pUC derivative from which all Beta-galactosidase sequences have been removed and replaced with a polylinker region (Colinas et al., 1990). pSD539 was cut with EcoRI/PstI and the 1.2 kb fragment isolated. This fragment was ligated into pRC11 cut with EcoRI/PstI (2.35 kb), forming pSD548. Recombination between pSD548 and the Beta-galactosidase containing vaccinia recombinant, vP855, resulted in vaccinia deletion mutant vP866, which was isolated as a clear plaque in the presence of X-gal.

DNA from recombinant vaccinia virus vP866 was analyzed by restriction digests followed by electrophoresis on an agarose gel. The restriction patterns were as expected. Polymerase chain reactions (PCR) (Engelke et al., 1988) using vP866 as template and primers flanking the six deletion loci detailed above produced DNA fragments of the expected sizes. Sequence analysis of the PCR generated fragments around the areas of the deletion junctions confirmed that the junctions were as expected. Recombinant vaccinia virus vP866, containing the six engineered deletions as described above, was designated vaccinia vaccine strain "NYVAC."

Example 7

Insertion of a Rabies Glycoprotein G Gene into NYVAC

The gene encoding rabies glycoprotein G under the control of the vaccinia H6 promoter (Taylor et al., 1988a,b) was inserted into TK deletion plasmid pSD513. pSD513 is identical to plasmid pSD460 (FIG. 1) except for the presence of a polylinker region.

Referring now to FIG. 7, the polylinker region was inserted by cutting pSD460 with SmaI and ligating the plasmid vector with annealed synthetic oligonucleotides VQ1A/VQ1B (SEQ ID NO:25/SEQ ID NO:26)

```
       SmaI  BglII  XhoI  PstI   NarI   BamHI
VQ1A 5' GGGAGATCTCTCGAGCTGCAGGGCGCCGGATCCTTTTTCT 3'

VQ1B 3' CCCTCTAGAGAGCTCGACGTCCCGCGGCCTAGGAAAAAGA 5'
``` to form vector plasmid pSD513. pSD513 was cut with SmaI and ligated with a SmaI ended 1.8 kb cassette containing the gene encoding the rabies glycoprotein G gene under the control of the vaccinia H6 promoter (Taylor et al., 1988a,b). The resulting plasmid was designated pRW842. pRW842 was used as donor plasmid for recombination with NYVAC rescuing virus (vP866). Recombinant vaccinia virus vP879 was identified by plaque hybridization using $^{32}$P-labelled DNA probe to rabies glycoprotein G coding sequences.

The modified recombinant viruses of the present invention provide advantages as recombinant vaccine vectors. The attenuated virulence of the vector advantageously reduces the opportunity for the possibility of a runaway infection due to vaccination in the vaccinated individual and also diminishes transmission from vaccinated to unvaccinated individuals or contamination of the environment.

The modified recombinant viruses are also advantageously used in a method for expressing a gene product in a cell cultured in vitro by introducing into the cell the modified recombinant virus having foreign DNA which codes for and expresses gene products in the cell.

Example 8

Construction of TROVAC-NDV Expressing the Fusion and Hemagglutinin-Neuraminidase Glycoproteins of Newcastle Disease Virus This example describes the development of TROVAC, a fowlpox virus vector and, of a fowlpox Newcastle Disease Virus recombinant designated TROVAC-NDV and its safety and efficacy. A fowlpox virus (FPV) vector expressing both F and HN genes of the virulent NDV strain Texas was constructed. The recombinant produced was designated TROVAC-NDV. TROVAC-NDV expresses authentically processed NDV glycoproteins in avian cells infected with the recombinant virus and inoculation of day old chicks protects against subsequent virulent NDV challenge.

Cells and Viruses. The Texas strain of NDV is a velogenic strain. Preparation of cDNA clones of the F and HN genes has been previously described (Taylor et al., 1990; Edbauer et al., 1990). The strain of FPV designated FP-1 has been described previously (Taylor et al., 1988a). It is a vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established. The stock virus used in the in vitro recombination test to produce TROVAC-NDV had been subjected to twelve passages in primary CEF cells from the plaque isolate.

Construction of a Cassette for NDV-F. A 1.8 kbp BamHI fragment containing all but 22 nucleotides from the 5' end of the F protein coding sequence was excised from pNDV81 (Taylor et al., 1990) and inserted at the BamHI site of pUC18 to form pCE13. The vaccinia virus H6 promoter previously described (Taylor et al., 1988a,b; Guo et al., 1989; Perkus et al., 1989) was inserted into pCE13 by digesting pCE13 with SalI, filling in the sticky ends with Klenow fragment of *E. coli* DNA polymerase and digesting with HindIII. A HindIII-EcoRV fragment containing the H6 promoter sequence was then inserted into pCE13 to form pCE38. A perfect 5' end was generated by digesting pCE38 with KpnI and NruI and inserting the annealed and kinased oligonucleotides CE75 (SEQ ID NO:27) and CE76 (SEQ ID NO:28) to generate pCE47.

CE75: CGATATCCGTTAAGTTTGTATCG-TAATGGGCTCCAGATCTTCTACCAG-GATCCCGGTAC

CE76: CGGGATCCTGGTAGAAGATCTGGAGC-CCATTACGATACAAACTTAACGGATATCG.

In order to remove non-coding sequence from the 3' end of the NDV-F a SmaI to PstI fragment from pCE13 was inserted into the SmaI and PstI sites of pUC18 to form pCE23. The non-coding sequences were removed by sequential digestion of pCE23 with SacI, BamHI, Exonuclease III, SI nuclease and EcoRI. The annealed and kinased oligonucleotides CE42 (SEQ ID NO:29) and CE43 (SEQ ID NO:30) were then inserted to form pCE29.

CE42: AATTCGAGCTCCCCGGG
CE43: CCCGGGGAGCTCG

The 3' end of the NDV-F sequence was then inserted into plasmid pCE20 already containing the 5' end of NDV-F by cloning a PstI-SacI fragment from pCE29 into the PstI and SacI sites of pCE20 to form pCE32. Generation of pCE20 has previously been described in Taylor et al., 1990.

In order to align the H6 promoter and NDV-F 5' sequences contained in pCE47 with the 3' NDV-F sequences contained in pCE32, a HindIII-PstI fragment of pCE47 was inserted into the HindIII and PstI sites of pCE32 to form pCE49. The H6 promoted NDV-F sequences were then transferred to the de-ORFed F8 locus (described below) by cloning a HindIII-NruI fragment from pCE49 into the HindIII and SmaI sites of pJCA002 (described below) to form pCE54. Transcription stop signals were inserted into pCE54 by digesting pCE54 with SacI, partially digesting with BamHI and inserting the annealed and kinased oligonucleotides CE166 (SEQ ID NO:31) and CE167 (SEQ ID NO:32) to generate pCE58.

CE166: CTTTTTATAAAAAGTTAACTACGTAG
CE167: GATCCTACGTAGTTAACTTTTTATAAAAAGAGCT

A perfect 3' end for NDV-F was obtained by using the polymerase chain reaction (PCR) with pCE54 as template and oligonucleotides CE182 (SEQ ID NO:33) and CE183 (SEQ ID NO:34) as primers.

CE182: CTTAACTCAGCTGACTATCC
CE183: TACGTAGTTAACTTTTTATAAAAAT-CATATTTTTGTAGTGGCTC

The PCR fragment was digested with PvuII and HpaI and cloned into pCE58 that had been digested with HpaI and partially digested with PvuII. The resulting plasmid was designated pCE64. Translation stop signals were inserted by cloning a HindIII-HpaI fragment which contains the complete H6 promoter and F coding sequence from pCE64 into the HindIII and HpaI sites of pRW846 to generate pCE71, the final cassette for NDV-F. Plasmid pRW846 is essentially equivalent to plasmid pJCA002 (described below) but containing the H6 promoter and transcription and translation stop signals. Digestion of pRW846 with HindIII and HpaI eliminates the H6 promoter but leaves the stop signals intact.

Construction of Cassette for NDV-HN. Construction of plasmid pRW802 was previously described in Edbauer et al., 1990. This plasmid contains the NDV-HN sequences linked to the 3' end of the vaccinia virus H6 promoter in a pUC9 vector. A HindIII-EcoRV fragment encompassing the 5' end of the vaccinia virus H6 promoter was inserted into the HindIII and EcoRV sites of pRW802 to form pRW830. A perfect 3' end for NDV-HN was obtained by inserting the annealed and kinased oligonucleotides CE162 (SEQ ID NO:35) and CE163 (SEQ ID NO:36) into the EcoRI site of pRW830 to form pCE59, the final cassette for NDV-HN.

CE162: AATTCAGGATCGTTCCTTTACTAGT-TGAGATTCTCAAGGATGATGGGATT-TAATTTTTATAAGCTTG
CE163: AATTCAAGCTTATAAAAATTAAATC-CCATCATCCTTGAGAATCTCAACTAG-TAAAGGAACGATCCTG

Construction of FPV Insertion Vector. Plasmid pRW731-15 contains a 10 kb PvuII-PvuII fragment cloned from genomic DNA. The nucleotide sequence was determined on both strands for a 3660 bp PvuII-EcoRV fragment. The limits of an open reading frame designated here as F8 were determined. Plasmid pRW761 is a sub-clone of pRW731-15 containing a 2430 bp EcoRV-EcoRV fragment. The F8 ORF was entirely contained between an XbaI site and an SspI site in pRW761. In order to create an insertion plasmid which on recombination with TROVAC genomic DNA would eliminate the F8 ORF, the following steps were followed. Plasmid pRW761 was completely digested with XbaI and partially digested with SspI. A 3700 bp XbaI-SspI band was isolated from the gel and ligated with the annealed double-stranded oligonucleotides JCA017 (SEQ ID NO:37) and JCA018 (SEQ ID NO:38).

JCA017: 5' CTAGACACTTTATGTTTTTAATATCCG-GTCTTAAAAGCTTCCCGGGGATCCT-TATACGGGGAATAAT
JCA018: 5' ATTATTCCCCGTATAAGGATCCCCCGG-GAAGCTTTTAAGACCGGATATTAAAAAA-CATAAAGTGT

The plasmid resulting from this ligation was designated pJCA002.

Construction of Double Insertion Vector for NDV F and HN. The H6 promoted NDV-HN sequence was inserted into the H6 promoted NDV-F cassette by cloning a HindIII fragment from pCE59 that had been filled in with Klenow fragment of *E. coli* DNA polymerase into the HpaI site of pCE71 to form pCE80. Plasmid pCE80 was completely digested with NdeI and partially digested with BglII to generate an NdeI-BglII 4760 bp fragment containing the NDV F and HN genes both driven by the H6 promoter and linked to F8 flanking arms. Plasmid pJCA021 was obtained by inserting a 4900 bp PvuII-HindII fragment from pRW731-15 into the SmaI and HindII sites of pBSSK+. Plasmid pJCA021 was then digested with NdeI and BglII and ligated to the 4760 bp NdeI-BglII fragment of pCE80 to form pJCA024. Plasmid pJCA024 therefore contains the NDV-F and HN genes inserted in opposite orientation with 3' ends adjacent between FPV flanking arms. Both genes are linked to the vaccinia virus H6 promoter. The right flanking arm adjacent to the NDV-F sequence consists of 2350 bp of FPV sequence. The left flanking arm adjacent to the NDV-HN sequence consists of 1700 bp of FPV sequence.

Development of TROVAC-NDV. Plasmid pJCA024 was transfected into TROVAC infected primary CEF cells by using the calcium phosphate precipitation method previously described (Panicali et al., 1982; Piccini et al., 1987). Positive plaques were selected on the basis of hybridization to specific NDV-F and HN radiolabelled probes and subjected to five sequential rounds of plaque purification until a pure population was achieved. One representative plaque was then amplified and the resulting TROVAC recombinant was designated TROVAC-NDV (vFP96).

Immunofluorescence. Indirect immunofluorescence was performed as described (Taylor et al., 1990) using a polyclonal anti-NDV serum and, as mono-specific reagents, sera produced in rabbits against vaccinia virus recombinants expressing NDV-F or NDV-HN.

Immunoprecipitation. Immunoprecipitation reactions were performed as described (Taylor et al., 1990) using a polyclonal anti-NDV serum obtained from SPAFAS Inc., Storrs, Conn.

The stock virus was screened by in situ plaque hybridization to confirm that the F8 ORF was deleted. The correct insertion of the NDV genes into the TROVAC genome and the deletion of the F8 ORF was also confirmed by Southern blot hybridization.

In NDV-infected cells, the F glycoprotein is anchored in the membrane via a hydrophobic transmembrane region near the carboxyl terminus and requires post-translational cleavage of a precursor, $F_0$, into two disulfide linked polypeptides $F_1$ and $F_2$. Cleavage of $F_0$ is important in determining the pathogenicity of a given NDV strain (Homma and Ohuchi, 1973; Nagai et al., 1976; Nagai et al., 1980), and the sequence of amino acids at the cleavage site is therefore critical in determining viral virulence. It has been determined that amino acids at the cleavage site in the NDV-F sequence inserted into FPV to form recombinant vFP29 had the sequence Arg-Arg-Gln-Arg-Arg (SEQ ID NO:39) (Taylor et al., 1990) which conforms to the sequence found to be a requirement for virulent NDV strains (Chambers et al., 1986; Espion et al., 1987; Le et al., 1988; McGinnes and Morrison, 1986; Toyoda et al., 1987). The HN glycoprotein synthesized in cells infected with virulent strains of NDV is an uncleaved glycoprotein of 74 kDa. Extremely avirulent strains such as Ulster and Queensland encode an HN precursor (HNo) which requires cleavage for activation (Garten et al., 1980).

The expression of F and HN genes in TROVAC-NDV was analyzed to confirm that the gene products were authentically processed and presented. Indirect-immunofluorescence using a polyclonal anti-NDV chicken serum confirmed that immunoreactive proteins were presented on the infected cell surface. To determine that both proteins were presented on the plasma membrane, mono-specific rabbit sera were produced against vaccinia recombinants expressing either the F or HN glycoproteins. Indirect immunofluorescence using these sera confirmed the surface presentation of both proteins.

Immunoprecipitation experiments were performed by using ($^{35}$S) methionine labeled lysates of CEF cells infected with parental and recombinant viruses. The expected values of apparent molecular weights of the glycolysated forms of $F_1$ and $F_2$ are 54.7 and 10.3 kDa respectively (Chambers et al., 1986). In the immunoprecipitation experiments using a polyclonal anti-NDV serum, fusion specific products of the appropriate size were detected from the NDV-F single recombinant vFP29 (Taylor et al., 1990) and the TROVAC-NDV double recombinant vFP96. The HN glycoprotein of appropriate size was also detected from the NDV-HN single recombinant VFP-47 (Edbauer et al., 1990) and TROVAC-NDV. No NDV specific products were detected from uninfected and parental TROVAC infected CEF cells.

In CEF cells, the F and HN glycoproteins are appropriately presented on the infected cell surface where they are recognized by NDV immune serum. Immunoprecipitation analysis indicated that the $F_0$ protein is authentically cleaved to the $F_1$ and $F_2$ components required in virulent strains. Similarly, the HN glycoprotein was authentically processed in CEF cells infected with recombinant TROVAC-NDV.

Previous reports (Taylor et al., 1990; Edbauer et al., 1990; Boursnell et al., 1990a,b,c; Ogawa et al., 1990) would indicate that expression of either HN or F alone is sufficient to elicit protective immunity against NDV challenge. Work on other paramyxoviruses has indicated, however, that antibody to both proteins may be required for full protective immunity. It has been demonstrated that SV5 virus could spread in tissue culture in the presence of antibody to the HN glycoprotein but not to the F glycoprotein (Merz et al., 1980). In addition, it has been suggested that vaccine failures with killed measles virus vaccines were due to inactivation of the fusion component (Norrby et al., 1975). Since both NDV glycoproteins have been shown to be responsible for eliciting virus neutralizing antibody (Avery et al., 1979) and both glycoproteins, when expressed individually in a fowlpox vector are able to induce a protective immune response, it can be appreciated that the most efficacious NDV vaccine should express both glycoproteins.

Example 9

Construction of ALVAC Recombinants Expressing Rabies Virus Glycoprotein G

This example describes the development of ALVAC, a canarypox virus vector and, of a canarypox-rabies recombinant designated as ALVAC-RG (vCP65) and its safety and efficacy.

Cells and Viruses. The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

Construction of a Canarypox Insertion Vector. An 880 bp canarypox PvuII fragment was cloned between the PvuII sites of pUC9 to form pRW764.5. The sequence of this fragment is shown in FIG. 8 between positions 1372 and 2251. The limits of an open reading frame designated as C5 were defined. It was determined that the open reading frame was initiated at position 166 within the fragment and terminated at position 487. The C5 deletion was made without interruption of open reading frames. Bases from position 167 through position 455 were replaced with the sequence (SEQ ID NO:39) GCTTCCCGGGAAT-TCTAGCTAGCTAGTTT. This replacement sequence contains HindIII, SmaI and EcoRI insertion sites followed by translation stops and a transcription termination signal recognized by vaccinia virus RNA polymerase (Yuen et al., 1987). Deletion of the C5 ORF was performed as described below. Plasmid pRW764.5 was partially cut with RsaI and the linear product was isolated. The RsaI linear fragment was recut with BglII and the pRW764.5 fragment now with a RsaI to BglII deletion from position 156 to position 462 was isolated and used as a vector for the following synthetic oligonucleotides:

RW145 (SEQ ID NO:40): ACTCTCAAAAGCTTCCCGG-GAATTCTAGCTAGCTAGTTTTTATAAA

RW146 (SEQ ID NO:41): GATCTTTATAAAAAC-TAGCTAGCTAGAATTCCCGG-GAAGCTTTTGAGAGT

Oligonucleotides RW145 and RW146 were annealed and inserted into the pRW 764.5 RsaI and BglII vector described above. The resulting plasmid is designated pRW831.

Construction of Insertion Vector Containing the Rabies G Gene. Construction of pRW838 is illustrated below. Oligonucleotides A through E, which overlap the translation initiation codon of the H6 promoter with the ATG of rabies G, were cloned into pUC9 as pRW737. Oligonucleotides A through E contain the H6 promoter, starting at NruI, through the HindIII site of rabies G followed by BglII. Sequences of oligonucleotides A through E ((SEQ ID NO:42)–(SEQ ID NO:46)) are:

A (SEQ ID NO:42): CTGAAATTATTTCATTATCGC-GATATCCGTTAAGTTTGTATCGTAATG-GTTCCTCAGGCTCTCCTGTTTGT

B (SEQ ID NO:43): CATTACGATACAAACTTAACG-GATATCGCGATAATGAAATAATTTCAG

C (SEQ ID NO:44): ACCCCTTCTGGTTTTTCCGT-TGTGTTTTGGGAAATTCCCTATTTACAC-GATCCCAGACAAGCTTAGATCTCAG

D (SEQ ID NO:45): CTGAGATCTAAGCTTGTCTGG-
GATCGTGTAAATAGGGAATTTCCCAAAACA

E (SEQ ID NO:46): CAACGGAAAAACCA-
GAAGGGGTACAAACAGGAGAGCCTGAGGAAC

The diagram of annealed oligonucleotides A through E is as follows:

Oligonucleotides A through E were kinased, annealed (95° C. for 5 minutes, then cooled to room temperature), and inserted between the PvuII sites of pUC9. The resulting plasmid, pRW737, was cut with HindIII and BqlII and used as a vector for the 1.6 kbp HindIII-BqlII fragment of ptg155PRO (Kieny et al., 1984) generating pRW739. The ptg155PRO HindIII site is 86 bp downstream of the rabies G translation initiation codon. BqlII is downstream of the rabies G translation stop codon in ptg155PRO. pRW739 was partially cut with NruI, completely cut with BqlII, and a 1.7 kbp NruI-BqlII fragment, containing the 3' end of the H6 promoter previously described (Taylor et al., 1988a,b; Guo et al., 1989; Perkus et al., 1989) through the entire rabies G gene, was inserted between the NruI and BamHI sites of pRW824. The resulting plasmid is designated pRW832. Insertion into pRW824 added the H6 promoter 5' of NruI. The pRW824 sequence of BamHI followed by SmaI is (SEQ ID NO:47): GGATCCCCGGG. pRW824 is a plasmid that contains a nonpertinent gene linked precisely to the vaccinia virus H6 promoter. Digestion with NruI and BamHI completely excised this nonpertinent gene. The 1.8 kbp pRW832 SmaI fragment, containing H6 promoted rabies G, was inserted into the SmaI of pRW831, to form plasmid pRW838.

Development of ALVAC-RG. Plasmid pRW838 was transfected into ALVAC infected primary CEF cells by using the calcium phosphate precipitation method previously described (Panicali et al., 1982; Piccini et al., 1987). Positive plaques were selected on the basis of hybridization to a specific rabies G probe and subjected to 6 sequential rounds of plaque purification until a pure population was achieved. One representative plaque was then amplified and the resulting ALVAC recombinant was designated ALVAC-RG (vCP65) (see also FIG. 9). The correct insertion of the rabies G gene into the ALVAC genome without subsequent mutation was confirmed by sequence analysis.

Immunofluorescence. During the final stages of assembly of mature rabies virus particles, the glycoprotein component is transported from the golgi apparatus to the plasma membrane where it accumulates with the carboxy terminus extending into the cytoplasm and the bulk of the protein on the external surface of the cell membrane. In order to confirm that the rabies glycoprotein expressed in ALVAC-RG was correctly presented, immunofluorescence was performed on primary CEF cells infected with ALVAC or ALVAC-RG. Immunofluorescence was performed as previously described (Taylor et al., 1990) using a rabies G monoclonal antibody. Strong surface fluorescence was detected on CEF cells infected with ALVAC-RG but not with the parental ALVAC.

Immunoprecipitation. Preformed monolayers of primary CEF, Vero (a line of African Green monkey kidney cells ATCC # CCL81) and MRC-5 cells (a fibroblast-like cell line derived from normal human fetal lung tissue ATCC # CCL171) were inoculated at 10 pfu per cell with parental virus ALVAC and recombinant virus ALVAC-RG in the presence of radiolabelled $^{35}$S-methionine and treated as previously described (Taylor et al., 1990). Immunoprecipitation reactions were performed using a rabies G specific monoclonal antibody. Efficient expression of a rabies specific glycoprotein with a molecular weight of approximately 67 kDa was detected with the recombinant ALVAC-RG. No rabies specific products were detected in uninfected cells or cells infected with the parental ALVAC virus.

Sequential Passaging Experiment. In studies with ALVAC virus in a range of non-avian species no proliferative infection or overt disease was observed (Taylor et al., 1991b). However, in order to establish that neither the parental nor recombinant virus could be adapted to grow in non-avian cells, a sequential passaging experiment was performed.

The two viruses, ALVAC and ALVAC-RG, were inoculated in sequential blind passages in three cell lines:

(1) Primary chick embryo fibroblast (CEF) cells produced from 11 day old white leghorn embryos;

(2) Vero cells—a continuous line of African Green monkey kidney cells (ATCC # CCL81); and (3) MRC-5 cells—a diploid cell line derived from human fetal lung tissue (ATCC # CCL171).

The initial inoculation was performed at an m.o.i. of 0.1 pfu per cell using three 60mm dishes of each cell line containing 2×10⁶ cells per dish. One dish was inoculated in the presence of 40 ìg/ml of Cytosine arabinoside (Ara C), an inhibitor of DNA replication. After an absorption period of 1 hour at 37° C., the inoculum was removed and the monolayer washed to remove unabsorbed virus. At this time the medium was replaced with 5 ml of EMEM+2% NBCS on two dishes (samples t0 and t7) and 5 ml of EMEM+2% NBCS containing 40 ìg/ml Ara C on the third (sample t7A). Sample to was frozen at −70° C. to provide an indication of the residual input virus. Samples t7 and t7A were incubated at 37° C. for 7 days, after which time the contents were harvested and the cells disrupted by indirect sonication.

One ml of sample t7 of each cell line was inoculated undiluted onto three dishes of the same cell line (to provide samples t0, t7 and t7A) and onto one dish of primary CEF cells. Samples t0, t7 and t7A were treated as for passage one. The additional inoculation on CEF cells was included to provide an amplification step for more sensitive detection of virus which might be present in the non-avian cells.

This procedure was repeated for 10 (CEF and MRC-5) or 8 (Vero) sequential blind passages. Samples were then frozen and thawed three times and assayed by titration on primary CEF monolayers.

Virus yield in each sample was then determined by plaque titration on CEF monolayers under agarose. Summarized results of the experiment are shown in Tables 1 and 2.

The results indicate that both the parental ALVAC and the recombinant ALVAC-RG are capable of sustained replication on CEF monolayers with no loss of titer. In Vero cells, levels of virus fell below the level of detection after 2 passages for ALVAC and 1 passage for ALVAC-RG. In MRC-5 cells, a similar result was evident, and no virus was detected after 1 passage. Although the results for only four passages are shown in Tables 1 and 2 the series was continued for 8 (Vero) and 10 (MRC-5) passages with no detectable adaptation of either virus to growth in the non-avian cells.

In passage 1 relatively high levels of virus were present in the t7 sample in MRC-5 and Vero cells. However this level of virus was equivalent to that seen in the t0 sample and the t7A sample incubated in the presence of Cytosine arabinoside in which no viral replication can occur. This demonstrated that the levels of virus seen at 7 days in non-avian cells represented residual virus and not newly replicated virus.

In order to make the assay more sensitive, a portion of the 7 day harvest from each cell line was inoculated onto a permissive CEF monolayer and harvested at cytopathic effect (CPE) or at 7 days if no CPE was evident. The results of this experiment are shown in Table 3. Even after amplification through a permissive cell line, virus was only detected in MRC-5 and Vero cells for two additional passages. These results indicated that under the conditions used, there was no adaptation of either virus to growth in Vero or MRC-5 cells.

Inoculation of Macaques. Four HIV seropositive macaques were initially inoculated with ALVAC-RG as described in Table 4. After 100 days these animals were re-inoculated to determine a booster effect, and an additional seven animals were inoculated with a range of doses. Blood was drawn at appropriate intervals and sera analyzed, after heat inactivation at 56° C. for 30 minutes, for the presence of anti-rabies antibody using the Rapid Fluorescent Focus Inhibition Assay (Smith et al., 1973).

Inoculation of Chimpanzees. Two adult male chimpanzees (50 to 65 kg weight range) were inoculated intramuscularly or subcutaneously with $1 \times 10^7$ pfu of vCP65. Animals were monitored for reactions and bled at regular intervals for analysis for the presence of anti-rabies antibody with the RFFI test (Smith et al., 1973). Animals were re-inoculated with an equivalent dose 13 weeks after the initial inoculation.

Inoculation of Mice. Groups of mice were inoculated with 50 to 100 ìl of a range of dilutions of different batches of vCP65. Mice were inoculated in the footpad. On day 14, mice were challenged by intracranial inoculation of from 15 to 43 mouse $LD_{50}$ of the virulent CVS strain of rabies virus. Survival of mice was monitored and a protective dose 50% ($PD_{50}$) calculated at 28 days post-inoculation.

Inoculation of Dogs and Cats. Ten beagle dogs, 5 months old, and 10 cats, 4 months old, were inoculated subcutaneously with either 6.7 or 7.7 $\log_{10}$ $TCID_{50}$ of ALVAC-RG. Four dogs and four cats were not inoculated. Animals were bled at 14 and 28 days post-inoculation and anti-rabies antibody assessed in an RFFI test. The animals receiving 6.7 $\log_{10}$ $TCID_{50}$ of ALVAC-RG were challenged at 29 days post-vaccination with 3.7 $\log_{10}$ mouse $LD_{50}$ (dogs) or 4.3 $\log_{10}$ mouse $LD_{50}$ (cats) of the NYGS rabies virus challenge strain.

Inoculation of Squirrel Monkeys. Three groups of four squirrel monkeys (*Saimiri sciureus*) were inoculated with one of three viruses (a) ALVAC, the parental canarypox virus, (b) ALVAC-RG, the recombinant expressing the rabies G glycoprotein or (c) vCP37, a canarypox recombinant expressing the envelope glycoprotein of feline leukemia virus. Inoculations were performed under ketamine anaesthesia. Each animal received at the same time: (1) 20 ìl instilled on the surface of the right eye without scarification; (2) 100 ìl as several droplets in the mouth; (3) 100 ìl in each of two intradermal injection sites in the shaven skin of the external face of the right arm; and (4) 100 ìl in the anterior muscle of the right thigh.

Four monkeys were inoculated with each virus, two with a total of 5.0 $\log_{10}$ pfu and two with a total of 7.0 $\log_{10}$ pfu. Animals were bled at regular intervals and sera analyzed for the presence of antirabies antibody using an RFFI test (Smith et al., 1973). Animals were monitored daily for reactions to vaccination. Six months after the initial inoculation the four monkeys receiving ALVAC-RG, two monkeys initially receiving vCP37, and two monkeys initially receiving ALVAC, as well as one naive monkey were inoculated with 6.5 $\log_{10}$ pfu of ALVAC-RG subcutaneously. Sera were monitored for the presence of rabies neutralizing antibody in an RFFI test (Smith et al., 1973).

Inoculation of Human Cell Lines with ALVAC-RG. In order to determine whether efficient expression of a foreign gene could be obtained in non-avian cells in which the virus does not productively replicate, five cell types, one avian and four non-avian, were analyzed for virus yield, expression of the foreign rabies G gene and viral specific DNA accumulation. The cells inoculated were:

(a) Vero, African Green monkey kidney cells, ATCC # CCL81;
(b) MRC-5, human embryonic lung, ATCC # CCL 171;
(c) WISH human amnion, ATCC # CCL 25;
(d) Detroit-532, human foreskin, Downs's syndrome, ATCC # CCL 54; and
(e) Primary CEF cells.

Chicken embryo fibroblast cells produced from 11 day old white leghorn embryos were included as a positive control. All inoculations were performed on preformed monolayers of $2 \times 10^6$ cells as discussed below.

A. Methods for DNA Analysis

Three dishes of each cell line were inoculated at 5 pfu/cell of the virus under test, allowing one extra dish of each cell line un-inoculated. One dish was incubated in the presence of 40 ìg/ml of cytosine arabinoside (Ara C). After an adsorption period of 60 minutes at 37+ C., the inoculum was removed and the monolayer washed twice to remove unadsorbed virus. Medium (with or without Ara C) was then replaced. Cells from one dish (without Ara C) were harvested as a time zero sample. The remaining dishes were incubated at 37° C. for 72 hours, at which time the cells were harvested and used to analyze DNA accumulation. Each sample of $2 \times 10^6$ cells was resuspended in 0.5 ml phosphate buffered saline (PBS) containing 40 mM EDTA and incubated for 5 minutes at 37° C. An equal volume of 1.5% agarose prewarmed at 42° C. and containing 120 mM EDTA was added to the cell suspension and gently mixed. The suspension was transferred to an agarose plug mold and allowed to harden for at least 15 min. The agarose plugs were then removed and incubated for 12–16 hours at 50° C. in a volume of lysis buffer (1% sarkosyl, 100 ìg/ml proteinase K, 10 mM Tris HCl pH 7.5, 200 mM EDTA) that completely covers the plug. The lysis buffer was then replaced with 5.0 ml sterile 0.5×TBE (44.5 mM Tris-borate, 44.5 mM boric acid, 0.5 mM EDTA) and equilibrated at 4° C. for 6 hours with 3 changes of TBE buffer. The viral DNA within the plug was fractionated from cellular RNA and DNA using a pulse field electrophoresis system. Electrophoresis was performed for 20 hours at 180 V with a ramp of 50–90 sec at 15° C. in 0.5×TBE. The DNA was run with lambda DNA molecular weight standards. After electrophoresis the viral DNA band was visualized by staining with ethidium bromide. The DNA was then transferred to a nitrocellulose membrane and probed with a radiolabelled probe prepared from purified ALVAC genomic DNA.

B. Estimation of Virus Yield

Dishes were inoculated exactly as described above, with the exception that input multiplicity was 0.1 pfu/cell. At 72 hours post infection, cells were lysed by three successive cycles of freezing and thawing. Virus yield was assessed by plaque titration on CEF monolayers.

C. Analysis of Expression of Rabies G Gene

Dishes were inoculated with recombinant or parental virus at a multiplicity of 10 pfu/cell, allowing an additional dish as an uninfected virus control. After a one hour absorption period, the medium was removed and replaced with methionine free medium. After a 30 minute period, this medium was replaced with methionine-free medium containing 25 uCi/ml of $^{35}$S-Methionine. Infected cells were labelled overnight (approximately 16 hours), then lysed by the addition of buffer A lysis buffer. Immunoprecipitation was performed as previously described (Taylor et al., 1990) using a rabies G specific monoclonal antibody.

Results: Estimation of Viral Yield. The results of titration for yield at 72 hours after inoculation at 0.1 pfu per cell are shown in Table 5. The results indicate that while a productive infection can be attained in the avian cells, no increase in virus yield can be detected by this method in the four non-avian cell systems.

Analysis of Viral DNA Accumulation. In order to determine whether the block to productive viral replication in the non-avian cells occurred before or after DNA replication, DNA from the cell lysates was fractionated by electrophoresis, transferred to nitrocellulose and probed for the presence of viral specific DNA. DNA from uninfected CEF cells, ALVAC-RG infected CEF cells at time zero, ALVAC-RG infected CEF cells at 72 hours post-infection and ALVAC-RG infected CEF cells at 72 hours post-infection in the presence of 40 ìg/ml of cytosine arabinoside all showed some background activity, probably due to contaminating CEF cellular DNA in the radiolabelled ALVAC DNA probe preparation. However, ALVAC-RG infected CEF cells at 72 hours post-infection exhibited a strong band in the region of approximately 350 kbp representing ALVAC-specific viral DNA accumulation. No such band is detectable when the culture is incubated in the presence of the DNA synthesis inhibitor, cytosine arabinoside. Equivalent samples produced in Vero cells showed a very faint band at approximately 350 kbp in the ALVAC-RG infected Vero cells at time zero. This level represented residual virus. The intensity of the band was amplified at 72 hours post-infection indicating that some level of viral specific DNA replication had occurred in Vero cells which had not resulted in an increase in viral progeny. Equivalent samples produced in MRC-5 cells indicated that no viral specific DNA accumulation was detected under these conditions in this cell line. This experiment was then extended to include additional human cell lines, specifically WISH and Detroit-532 cells. ALVAC infected CEF cells served as a positive control. No viral specific DNA accumulation was detected in either WISH or Detroit cells inoculated with ALVAC-RG. It should be noted that the limits of detection of this method have not been fully ascertained and viral DNA accumulation may be occurring, but at a level below the sensitivity of the method. Other experiments in which viral DNA replication was measured by $^3$H-thymidine incorporation support the results obtained with Vero and MRC-5 cells.

Analysis of Rabies Gene Expression. To determine if any viral gene expression, particularly that of the inserted foreign gene, was occurring in the human cell lines even in the absence of viral DNA replication, immunoprecipitation experiments were performed on $^{35}$S-methionine labelled lysates of avian and non-avian cells infected with ALVAC and ALVAC-RG. The results of immunoprecipitation using a rabies G specific monoclonal antibody illustrated specific immunoprecipitation of a 67 kDa glycoprotein in CEF, Vero and MRC-5, WISH and Detroit cells infected with ALVAC-RG. No such specific rabies gene products were detected in any of the uninfected and parentally infected cell lysates.

The results of this experiment indicated that in the human cell lines analyzed, although the ALVAC-RG recombinant was able to initiate an infection and express a foreign gene product under the transcriptional control of the H6 early/late vaccinia virus promoter, the replication did not proceed through DNA replication, nor was there any detectable viral progeny produced. In the Vero cells, although some level of ALVAC-RG specific DNA accumulation was observed, no viral progeny was detected by these methods. These results would indicate that in the human cell lines analyzed the block to viral replication occurs prior to the onset of DNA replication, while in Vero cells, the block occurs following the onset of viral DNA replication.

In order to determine whether the rabies glycoprotein expressed in ALVAC-RG was immunogenic, a number of animal species were tested by inoculation of the recombinant. The efficacy of current rabies vaccines is evaluated in a mouse model system. A similar test was therefore performed using ALVAC-RG. Nine different preparations of virus (including one vaccine batch (J) produced after 10 serial tissue culture passages of the seed virus) with infectious titers ranging from 6.7 to 8.4 $\log_{10}$ TCID$_{50}$ per ml were serially diluted and 50 to 100 ìl of dilutions inoculated into the footpad of four to six week old mice. Mice were challenged 14 days later by the intracranial route with 300 ìl of the CVS strain of rabies virus containing from 15 to 43 mouse LD$_{50}$ as determined by lethality titration in a control group of mice. Potency, expressed as the PD$_{50}$ (Protective dose 50%), was calculated at 14 days post-challenge. The results of the experiment are shown in Table 6. The results indicated that ALVAC-RG was consistently able to protect mice against rabies virus challenge with a PD$_{50}$ value ranging from 3.33 to 4.56 with a mean value of 3.73 (STD 0.48). As an extension of this study, male mice were inoculated intracranially with 50 ìl of virus containing 6.0 $\log_{10}$ TCID$_{50}$ of ALVAC-RG or with an equivalent volume of an uninfected cell suspension. Mice were sacrificed on days 1, 3 and 6 post-inoculation and their brains removed, fixed and sectioned. Histopathological examination showed no evidence for neurovirulence of ALVAC-RG in mice.

In order to evaluate the safety and efficacy of ALVAC-RG for dogs and cats, a group of 14, 5 month old beagles and 14, 4 month old cats were analyzed. Four animals in each species were not vaccinated. Five animals received 6.7 $\log_{10}$ TCID$_{50}$ subcutaneously and five animals received 7.7 $\log_{10}$ TCID$_{50}$ by the same route. Animals were bled for analysis for anti-rabies antibody. Animals receiving no inoculation or 6.7 $\log_{10}$ TCID$_{50}$ of ALVAC-RG were challenged at 29 days post-vaccination with 3.7 $\log_{10}$ mouse LD$_{50}$ (dogs, in the temporal muscle) or 4.3 $\log_{10}$ mouse LD$_{50}$ (cats, in the neck) of the NYGS rabies virus challenge strain. The results of the experiment are shown in Table 7.

No adverse reactions to inoculation were seen in either cats or dogs with either dose of inoculum virus. Four of 5 dogs immunized with 6.7 $\log_{10}$ TCID$_{50}$ had antibody titers on day 14 post-vaccination and all dogs had titers at 29 days. All dogs were protected from a challenge which killed three out of four controls. In cats, three of five cats receiving 6.7 $\log_{10}$ TCID$_{50}$ had specific antibody titers on day 14 and all cats were positive on day 29 although the mean antibody titer was low at 2.9 IU. Three of five cats survived a challenge which killed all controls. All cats immunized with 7.7 $\log_{10}$ TCID$_{50}$ had antibody titers on day 14 and at day 29 the Geometric Mean Titer was calculated as 8.1 International Units.

The immune response of squirrel monkeys (*Saimiri sciureus*) to inoculation with ALVAC, ALVAC-RG and an unrelated canarypox virus recombinant was examined. Groups of monkeys were inoculated as described above and sera analyzed for the presence of rabies specific antibody. Apart from minor typical skin reactions to inoculation by the intradermal route, no adverse reactivity was seen in any of the monkeys. Small amounts of residual virus were isolated from skin lesions after intradermal inoculation on days two and four post-inoculation only. All specimens were negative on day seven and later. There was no local reaction to intra-muscular injection. All four monkeys inoculated with ALVAC-RG developed anti-rabies serum neutralizing antibodies as measured in an RFFI test. Approximately six months after the initial inoculation all monkeys and one additional naive monkey were re-inoculated by the subcutaneous route on the external face of the left thigh with 6.5 $\log_{10}$ TCID$_{50}$ of ALVAC-RG. Sera were analyzed for the presence of anti-rabies antibody. The results are shown in Table 8.

Four of the five monkeys naive to rabies developed a serological response by seven days post-inoculation with ALVAC-RG. All five monkeys had detectable antibody by 11 days post-inoculation. Of the four monkeys with previous exposure to the rabies glycoprotein, all showed a significant increase in serum neutralization titer between days 3 and 7 post-vaccination. The results indicate that vaccination of squirrel monkeys with ALVAC-RG does not produce adverse side-effects and a primary neutralizing antibody response can be induced. An amnanestic response is also induced on re-vaccination. Prior exposure to ALVAC or to a canarypox recombinant expressing an unrelated foreign gene does not interfere with induction of an anti-rabies immune response upon re-vaccination.

The immunological response of HIV-2 seropositive macaques to inoculation with ALVAC-RG was assessed. Animals were inoculated as described above and the presence of anti-rabies serum neutralizing antibody assessed in an RFFI test. The results, shown in Table 9, indicated that HIV-2 positive animals inoculated by the subcutaneous route developed anti-rabies antibody by 11 days after one inoculation. An anamnestic response was detected after a booster inoculation given approximately three months after the first inoculation. No response was detected in animals receiving the recombinant by the oral route. In addition, a series of six animals were inoculated with decreasing doses of ALVAC-RG given by either the intra-muscular or subcutaneous routes. Five of the six animals inoculated responded by 14 days post-vaccination with no significant difference in antibody titer.

Two chimpanzees with prior exposure to HIV were inoculated with 7.0 $\log_{10}$ pfu of ALVAC-RG by the subcutaneous or intra-muscular route. At 3 months post-inoculations both animals were re-vaccinated in an identical fashion. The results are shown in Table 10.

No adverse reactivity to inoculation was noted by either intramuscular or subcutaneous routes. Both chimpanzees responded to primary inoculation by 14 days and a strongly rising response was detected following re-vaccination.

TABLE 1

Sequential Passage of ALVAC in Avian and non-Avian Cells.

| | | CEF | Vero | MRC-5 |
|---|---|---|---|---|
| Pass 1 | | | | |
| Sample | t0[a] | 2.4 | 3.0 | 2.6 |
| | t7[b] | 7.0 | 1.4 | 0.4 |
| | t7A[c] | 1.2 | 1.2 | 0.4 |
| Pass 2 | | | | |
| Sample | t0 | 5.0 | 0.4 | N.D.[d] |
| | t7 | 7.3 | 0.4 | N.D. |
| | t7A | 3.9 | N.D. | N.D. |
| Pass 3 | | | | |
| Sample | t0 | 5.4 | 0.4 | N.D. |
| | t7 | 7.4 | N.D. | N.D. |
| | t7A | 3.8 | N.D. | N.D. |
| Pass 4 | | | | |
| Sample | t0 | 5.2 | N.D. | N.D. |
| | t7 | 7.1 | N.D. | N.D. |
| | t7A | 3.9 | N.D. | N.D. |

[a]This sample was harvested at zero time and represents the residual input virus. The titer is expressed as $\log_{10}$ pfu per ml.
[b]This sample was harvested at 7 days post-infection.
[c]This sample was inoculated in the presence of 40 ìg/ml of Cytosine arabinoside and harvested at 7 days post infection.
[d]Not detectable

TABLE 2

Sequential Passage of ALVAC-RG in Avian and non-Avian Cells

| | | CEF | Vero | MRC-5 |
|---|---|---|---|---|
| Pass 1 | | | | |
| Sample | t0[a] | 3.0 | 2.9 | 2.9 |
| | t7[b] | 7.1 | 1.0 | 1.4 |
| | t7A[c] | 1.8 | 1.4 | 1.2 |
| Pass 2 | | | | |
| Sample | t0 | 5.1 | 0.4 | 0.4 |
| | t7 | 7.1 | N.D.[d] | N.D. |
| | t7A | 3.8 | N.D. | N.D. |
| Pass 3 | | | | |
| Sample | t0 | 5.1 | 0.4 | N.D. |
| | t7 | 7.2 | N.D. | N.D. |
| | t7A | 3.6 | N.D. | N.D. |
| Pass 4 | | | | |
| Sample | t0 | 5.1 | N.D. | N.D. |
| | t7 | 7.0 | N.D. | N.D. |
| | t7A | 4.0 | N.D. | N.D |

[a]This sample was harvested at zero time and represents the residual input virus. The titer is expressed as $\log_{10}$ pfu per ml.
[b]This sample was harvested at 7 days post-infection.
[c]This sample was inoculated in the presence of 40 ìg/ml of Cytosine arabinoside and harvested at 7 days post-infection.
[d]Not detectable.

TABLE 3

Amplification of residual virus by passage in CEF cells

| | | CEF | Vero | MRC-5 |
|---|---|---|---|---|
| a) ALVAC | | | | |
| Pass | 2[a] | 7.0[b] | 6.0 | 5.2 |
| | 3 | 7.5 | 4.1 | 4.9 |

TABLE 3-continued

Amplification of residual virus by passage in CEF cells

| | | CEF | Vero | MRC-5 |
|---|---|---|---|---|
| | 4 | 7.5 | N.D.[c] | N.D. |
| | 5 | 7.1 | N.D. | N.D. |
| b) ALVAC-RG | | | | |
| Pass | 2[a] | 7.2 | 5.5 | 5.5 |
| | 3 | 7.2 | 5.0 | 5.1 |
| | 4 | 7.2 | N.D. | N.D. |
| | 5 | 7.2 | N.D. | N.D. |

[a]Pass 2 represents the amplification in CEF cells of the 7 day sample from Pass 1.
[b]Titer expressed as $\log_{10}$ pfu per ml
[c]Not Detectable

TABLE 4

Schedule of inoculation of rhesus macaques with ALVAC-RG (vCP65)

| Animal | Inoculation | |
|---|---|---|
| 176L | Primary: | $1 \times 10^8$ pfu of vCP65 orally in TANG |
| | Secondary: | $1 \times 10^7$ pfu of vCP65 plus $1 \times 10^7$ pfu of vCP82[a] by SC route |
| 185 L | Primary: | $1 \times 10^8$ pfu of vCP65 orally in Tang |
| | Secondary: | $1 \times 10^7$ pfu of vCP65 plus $1 \times 10^7$ pfu of vCP82 by SC route |
| 177 L | Primary: | $5 \times 10^7$ pfu SC of vCP65 by SC route |
| | Secondary: | $1 \times 10^7$ pfu of vCP65 plus $1 \times 10^7$ pfu of vCP82 by SC route |
| 186L | Primary: | $5 \times 10^7$ pfu of vCP65 by SC route |
| | Secondary: | $1 \times 10^7$ pfu of vCP65 plus $1 \times 10^7$ pfu of vCP82 by SC route |
| 178L | Primary: | $1 \times 10^7$ pfu of vCP65 by SC route |
| 182L | Primary: | $1 \times 10^7$ pfu of vCP65 by IM route |
| 179L | Primary: | $1 \times 10^6$ pfu of vCP65 by SC route |
| 183L | Primary: | $1 \times 10^6$ pfu of vCP65 by IM route |
| 180L | Primary: | $1 \times 10^6$ pfu of vCP65 by SC route |
| 184L | Primary: | $1 \times 10^5$ pfu of vCP65 by IM route |
| 187L | Primary | $1 \times 10^7$ pfu of vCP65 orally |

[a]vCP82 is a canarypox virus recombinant expressing the measles virus fusion and hemagglutinin genes.

TABLE 5

Analysis of yield in avian and non-avian cells inoculated with ALVAC-RG

| | Sample Time | | |
|---|---|---|---|
| Cell Type | t0 | t72 | t72A[b] |
| Expt 1 | | | |
| CEF | 3.3[a] | 7.4 | 1.7 |
| Vero | 3.0 | 1.4 | 1.7 |
| MRC-5 | 3.4 | 2.0 | 1.7 |
| Expt 2 | | | |
| CEF | 2.9 | 7.5 | <1.7 |
| WISH | 3.3 | 2.2 | 2.0 |
| Detroit-532 | 2.8 | 1.7 | <1.7 |

[a]Titer expressed as $\log_{10}$ pfu per ml
[b]Culture incubated in the presence of 40 μg/ml of Cytosine arabinoside

TABLE 6

Potency of ALVAC-RG as tested in mice

| Test | Challenge Dose[a] | PD$_{50}$[b] |
|---|---|---|
| Initial seed | 43 | 4.56 |
| Primary seed | 23 | 3.34 |
| Vaccine Batch H | 23 | 4.52 |
| Vaccine Batch I | 23 | 3.33 |
| Vaccine Batch K | 15 | 3.64 |
| Vaccine Batch L | 15 | 4.03 |
| Vaccine Batch M | 15 | 3.32 |
| Vaccine Batch N | 15 | 3.39 |
| Vaccine Batch J | 23 | 3.42 |

[a]Expressed as mouse LD$_{50}$
[b]Expressed as $\log_{10}$ TCID$_{50}$

TABLE 7

Efficacy of ALVAC-RG in dogs and cats

| Dose | Dogs Antibody[a] | Survival[b] | Cats Antibody | Survival |
|---|---|---|---|---|
| 6.7 | 11.9 | 5/5 | 2.9 | 3/5 |
| 7.7 | 10.1 | N.T. | 8.1 | N.T. |

[a]Antibody at day 29 post inoculation expressed as the geometric mean titer in International Units.
[b]Expressed as a ratio of survivors over animals challenged

TABLE 8

Anti-rabies serological response of Squirrel monkeys inoculated with canarypox recombinants

| Monkey # | Previous Exposure | Rabies serum-neutralizing antibody[a] | | | | | |
|---|---|---|---|---|---|---|---|
| | | −196[b] | 0 | 3 | 7 | 11 | 21 | 28 |
| 22 | ALVAC[c] | NT[g] | <1.2 | <1.2 | <1.2 | 2.1 | 2.3 | 2.2 |
| 51 | ALVAC[c] | NT | <1.2 | <1.2 | 1.7 | 2.2 | 2.2 | 2.2 |
| 39 | vCP37[d] | NT | <1.2 | <1.2 | 1.7 | 2.1 | 2.2 | N.T.[g] |
| 55 | vCP37[d] | NT | <1.2 | <1.2 | 1.7 | 2.2 | 2.1 | N.T. |
| 37 | ALVAC-RG[e] | 2.2 | <1.2 | <1.2 | 3.2 | 3.5 | 3.5 | 3.2 |
| 53 | ALVAC-RG[e] | 2.2 | <1.2 | <1.2 | 3.6 | 3.6 | 3.6 | 3.4 |
| 38 | ALVAC-RG[f] | 2.7 | <1.7 | <1.7 | 3.2 | 3.8 | 3.6 | N.T. |

TABLE 8-continued

Anti-rabies serological response of Squirrel monkeys inoculated with canarypox recombinants

| Monkey # | Previous Exposure | Rabies serum-neutralizing antibody[a] | | | | | | |
|---|---|---|---|---|---|---|---|---|
| | | −196[b] | 0 | 3 | 7 | 11 | 21 | 28 |
| 54 | ALVAC-RG[f] | 3.2 | <1.7 | <1.5 | 3.6 | 4.2 | 4.0 | 3.6 |
| 57 | None | NT | <1.2 | <1.2 | 1.7 | 2.7 | 2.7 | 2.3 |

[a]As determined by RFFI test on days indicated and expressed in International Units
[b]Day-196 represents serum from day 28 after primary vaccination
[c]Animals received 5.0 $\log_{10}$ $TCID_{50}$ of ALVAC
[d]Animals received 5.0 $\log_{10}$ $TCID_{50}$ of vCP37
[e]Animals received 5.0 $\log_{10}$ $TCID_{50}$ of ALVAC-RG
[f]Animals received 7.0 $\log_{10}$ $TCID_{50}$ of ALVAC-RG
[g]Not tested.

TABLE 9

Inoculation of rhesus macaques with ALVAC-RG[a]

| Days post-Inoculation | Route of primary Inoculation | | | | | | | | | |
|---|---|---|---|---|---|---|---|---|---|---|
| | or/Tang | | SC | SC | SC | IM | SC | IM | SC | IM | OR |
| | 176L[b] | 185L | 177L | 186L | 178L | 182L | 179L | 183L | 180L | 184L | 187L[b] |
| −84 | — | — | | | | | | | | | |
| −9 | — | — | — | — | | | | | | | |
| 3 | — | — | — | — | | | | | | | |
| 6 | — | — | ± | ± | | | | | | | |
| 11 | — | — | 16[d] | 128 | | | | | | | |
| 19 | — | — | 32 | 128 | — | | — | | | | |
| 35 | — | — | 32 | 512 | | | | | | | |
| 59 | — | — | 64 | 256 | | | | | | | |
| 75 | — | — | 64 | 128 | | | | | | | |
| 99[c] | — | — | 64 | 256 | — | — | — | — | — | — | — |
| 2 | — | — | 32 | 256 | — | — | — | — | — | — | — |
| 6 | — | — | 512 | 512 | — | — | — | — | — | — | — |
| 15 | 16 | 16 | 512 | 512 | 64 | 32 | 64 | 128 | 32 | — | |
| 29 | 16 | 32 | 256 | 256 | 64 | 64 | 32 | 128 | 32 | — | |
| 55 | | 32 | | | | 32 | | 32 | 16 | — | |
| 57 | 16 | | 128 | 128 | 16 | | 16 | | | | — |

[a]See Table 9 for schedule of inoculations.
[b]Animals 176L and 185L received 8.0 $\log_{10}$ pfu by the oral route in 5 ml Tang. Animal 187L received 7.0 $\log_{10}$ pfu by oral route not in Tang.
[c]Day of re-vaccination for animals 176L, 185L, 177L and 186L by S.C. route, and primary vaccination for animals 178L, 182L, 179L, 183L, 180L, 184L and 187L.
[d]Titers expressed as reciprocal of last dilution showing inhibition of fluorescence in an RFFI test.

TABLE 10

Inoculation of chimpanzees with ALVAC-RG

| Weeks post-Inoculation | Animal 431 I.M. | Animal 457 S.C. |
|---|---|---|
| 0 | <8[a] | <8 |
| 1 | <8 | <8 |
| 2 | 8 | 32 |
| 4 | 16 | 32 |
| 8 | 16 | 32 |
| 12[b]/0 | 16 | 8 |
| 13/1 | 128 | 128 |
| 15/3 | 256 | 512 |
| 20/8 | 64 | 128 |
| 26/12 | 32 | 128 |

[a]Titer expressed as reciprocal of last dilution showing inhibition of fluorescence in an RFFI test
[b]Day of re-inoculation Example 10

Immunization of Humans Using Canarypox Expressing Rabies Glycoprotein (ALVAC-RG; vCP65)

Figure 9A:
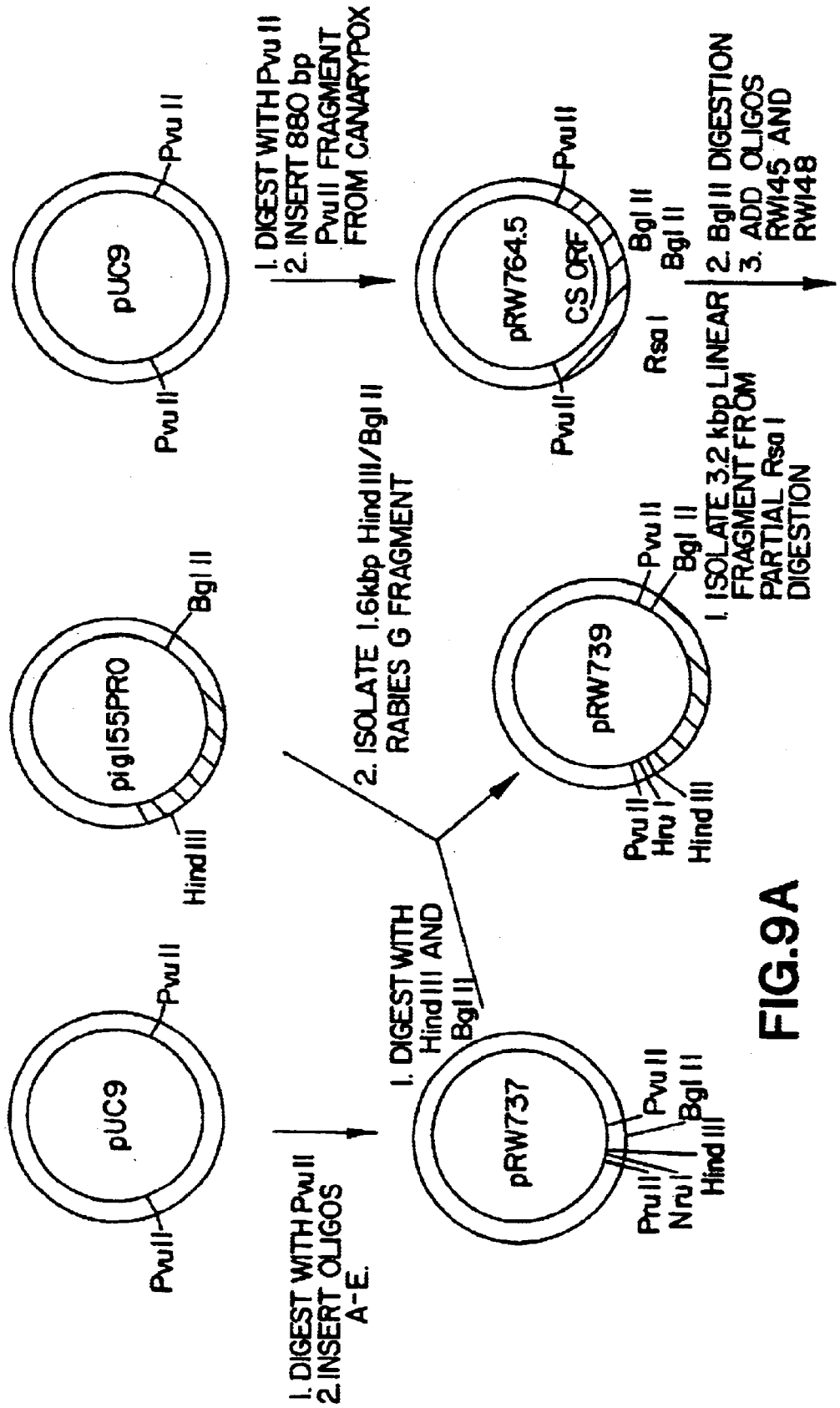

ALVAC-RG (vCP65) was generated as described in Example 9 and FIGS. 9A and 9B. For scaling-up and vaccine manufacturing ALVAC-RG (vCP65) was grown in primary CEF derived from specified pathogen free eggs. Cells were infected at a multiplicity of 0.01 and incubated at 37° C. for three days.

The vaccine virus suspension was obtained by ultrasonic disruption in serum free medium of the infected cells; cell debris were then removed by centrifugation and filtration. The resulting clarified suspension was supplemented with lyophilization stabilizer (mixture of amino-acids), dispensed in single dose vials and freeze dried. Three batches of decreasing titer were prepared by ten-fold serial dilutions of the virus suspension in a mixture of serum free medium and lyophilization stabilizer, prior to lyophilization.

Quality control tests were applied to the cell substrates, media and virus seeds and final product with emphasis on the search for adventitious agents and innocuity in laboratory rodents. No undesirable trait was found.

Preclinical data. Studies in vitro indicated that VERO or MRC-5 cells do not support the growth of ALVAC-RG (vCP65); a series of eight (VERO) and 10 (MRC) blind serial passages caused no detectable adaptation of the virus to grow in these non avian lines. Analyses of human cell lines (MRC-5, WISH, Detroit 532, HEL, HNK or EBV-transformed lymphoblastoid cells) infected or inoculated with ALVAC-RG (vCP65) showed no accumulation of virus specific DNA suggesting that in these cells the block in replication occurs prior to DNA synthesis. Significantly, however, the expression of the rabies virus glycoprotein gene in all cell lines tested indicating that the abortive step in the canarypox replication cycle occurs prior to viral DNA replication.

The safety and efficacy of ALVAC-RG (vCP65) were documented in a series of experiments in animals. A number of species including canaries, chickens, ducks, geese, laboratory rodents (suckling and adult mice), hamsters, guinea-pigs, rabbits, cats and dogs, squirrel monkeys, rhesus macaques and chimpanzees, were inoculated with doses ranging from $10^5$ to $10^8$ pfu. A variety of routes were used, most commonly subcutaneous, intramuscular and intradermal but also oral (monkeys and mice) and intracerebral (mice).

In canaries, ALVAC-RG (vCP65) caused a "take" lesion at the site of scarification with no indication of disease or death. Intradermal inoculation of rabbits resulted in a typical poxvirus inoculation reaction which did not spread and healed in seven to ten days. There was no adverse side effects due to canarypox in any of the animal tests. Immunogenicity was documented by the development of anti-rabies antibodies following inoculation of ALVAC-RG (vCP65) in rodents, dogs, cats, and primates, as measured by Rapid Fluorescent Focus Inhibition Test (RFFIT). Protection was also demonstrated by rabies virus challenge experiments in mice, dogs, and cats immunized with ALVAC-RG (vCP65).

Volunteers. Twenty-five healthy adults aged 20–45 with no previous history of rabies immunization were enrolled. Their health status was assessed by complete medical histories, physical examinations, hematological and blood chemistry analyses. Exclusion criteria included pregnancy, allergies, immune depression of any kind, chronic debilitating disease, cancer, injection of immune globins in the past three months, and seropositivity to human immunodeficiency virus (HIV) or to hepatitis B virus surface antigen.

Study design. Participants were randomly allocated to receive either standard Human Diploid Cell Rabies Vaccine (HDC) batch no E0751 (Pasteur Merieux Serums & Vaccine, Lyon, France) or the study vaccine ALVAC-RG (vCP65).

The trial was designated as a dose escalation study. Three batches of experimental ALVAC-RG (vCP65) vaccine were used sequentially in three groups of volunteers (Groups A, B and C) with two week intervals between each step. The concentration of the three batches was $10^{3.5}$, $10^{4.5}$, $10^{5.5}$ Tissue Culture Infectious Dose ($TCID_{50}$) per dose, respectively.

Each volunteer received two doses of the same vaccine subcutaneously in the deltoid region at an interval of four weeks. The nature of the injected vaccine was not known by the participants at the time of the first injection but was known by the investigator.

In order to minimize the risk of immediate hypersensitivity at the time of the second injection, the volunteers of Group B allocated to the medium dose of experimental vaccine were injected 1 h previously with the lower dose and those allocated to the higher dose (Group C) received successively the lower and the medium dose at hourly intervals.

Six months later, the recipients of the highest dosage of ALVAC-RG (vCP65) (Group C) and HDC vaccine were offered a third dose of vaccine; they were then randomized to receive either the same vaccine as previously or the alternate vaccine. As a result, four groups were formed corresponding to the following immunization scheme: 1. HDC, HDC-HDC; 2. HDC, HDC-ALVAC-RG (vCP65); 3. ALVAC-RG (vCP65), ALVAC-RG (vCP65)-HDC; 4. ALVAC-RG (vCP65), ALVAC-RG (vCP65), ALVAC-RG (vCP65).

Monitoring of Side Effects. All subjects were monitored for 1 h after injection and re-examined every day for the next five days. They were asked to record local and systemic reactions for the next three weeks and were questioned by telephone two times a week.

Laboratory Investigators. Blood specimens were obtained before enrollment and two, four and six days after each injection. Analysis included complete blood cell count, liver enzymes and creatine kinase assays.

Antibody assays. Antibody assays were performed seven days prior to the first injection and at days 7, 28, 35, 56, 173, 187 and 208 of the study.

The levels of neutralizing antibodies to rabies were determined using the Rapid Fluorescent Focus Inhibition test (RFFIT) (Smith & Yaeger, In Laboratory Techniques on Rabies). Canarypox antibodies were measured by direct ELISA. The antigen, a suspension of purified canarypox virus disrupted with 0.1% Triton X100, was coated in microplates. Fixed dilutions of the sera were reacted for two hours at room temperature and reacting antibodies were revealed with a peroxidase labelled anti-human IgG goat serum. The results are expressed as the optical density read at 490 nm.

Analysis. Twenty-five subjects were enrolled and completed the study. There were 10 males and 15 females and the mean age was 31.9 (21 to 48). All but three subjects had evidence of previous smallpox vaccination; the three remaining subjects had no typical scar and vaccination history. Three subjects received each of the lower doses of experimental vaccine ($10^{3.5}$ and $10^{4.5}$ $TCID_{50}$), nine subjects received $10^{5.5}$ $TCID_{50}$ and ten received the HDC vaccine.

Safety (Table 11). During the primary series of immunization, fever greater than 37.7° C. was noted within 24 hours after injection in one HDC recipient (37.8° C.) and in one vCP65 $10^{5.5}$ $TCID_{50}$ recipient (38° C.). No other systemic reaction attributable to vaccination was observed in any participant.

Local reactions were noted in 9/10 recipients of HDC vaccine injected subcutaneously and in 0/3, 1/3 and 9/9 recipients of vCP65 $10^{3.5}$, $10^{4.5}$, $10^{5.5}$ $TCID_{50}$, respectively.

Tenderness was the most common symptoms and was always mild. Other local symptoms included redness and induration which were also mild and transient. All symptoms usually subsided within 24 hours and never lasted more than 72 hours.

There was no significant change in blood cell counts, liver enzymes or creatine kinase values.

Immune Responses; Neutralizing Antibodies to Rabies (Table 12). Twenty eight days after the first injection all the HDC recipients had protective titers ($\geq 0.5$ IU/ml). By contrast none in groups A and B ($10^{3.5}$ and $10^{4.5}$ TCID$_{50}$) and only 2/9 in group C ($10^{5.5}$ TCID$_{50}$) ALVAC-RG (vCP65) recipients reached this protective titer.

At day 56 (i.e. 28 days after the second injection) protective titers were achieved in 0/3 of Group A, 2/3 of Group B and 9/9 of Group C recipients of ALVAC-RG (vCP65) vaccine and persisted in all 10 HDC recipients.

At day 56 the geometric mean titers were 0.05, 0.47, 4.4 and 11.5 IU/ml in groups A, B, C and HDC respectively.

At day 180, the rabies antibody titers had substantially decreased in all subjects but remained above the minimum protective titer of 0.5 IU/ml in 5/10 HCD recipients and in 5/9 ALVAC-RG (vCP65) recipients; the geometric mean titers were 0.51 and 0.45 IU/ml in groups HCD and C, respectively.

Antibodies to the Canarypox virus (Table 13). The preimmune titers observed varied widely with titers varying from 0.22 to 1.23 O.D. units despite the absence of any previous contact with canary birds in those subjects with the highest titers. When defined as a greater than two-fold increase between preimmunization and post second injection titers, a seroconversion was obtained in 1/3 subjects in group B and in 9/9 subjects in group C whereas no subject seroconverted in groups A or HDC.

Booster Injection. The vaccine was similarly well tolerated six months later, at the time of the booster injection: fever was noted in 2/9 HDC booster recipients and in 1/10 ALVAC-RG (vCP65) booster recipients. Local reactions were present in 5/9 recipients of HDC booster and in 6/10 recipients of the ALVAC-RG (vCP65) booster.

Observations. FIG. 13 shows graphs of rabies neutralizing antibody titers (Rapid Fluorescent Focus Inhibition Test or RFFIT, IU/ml): Booster effect of HDC and vCP65 ($10^{5.5}$ TCID$_{50}$) in volunteers previously immunized with either the same or the alternate vaccine. Vaccines were given at days 0, 28 and 180. Antibody titers were measured at days 0, 7, 28, 35, 56, 173, and 187 and 208.

As shown in FIGS. 13A to 13D, the booster dose given resulted in a further increase in rabies antibody titers in every subject whatever the immunization scheme. However, the ALVAC-RG (vCP65) booster globally elicited lower immune responses than the HDC booster and the ALVAC-RG (vCP65), ALVAC-RG (vCP65)-ALVAC-RG (vCP65) group had significantly lower titers than the three other groups. Similarly, the ALVAC-RG (vCP65) booster injection resulted in an increase in canarypox antibody titers in 3/5 subjects who had previously received the HDC vaccine and in all five subjects previously immunized with ALVAC-RG (vCP65).

In general, none of the local side effects from administration of vCP65 was indicative of a local replication of the virus. In particular, lesions of the skin such as those observed after injection of vaccine were absent. In spite of the apparent absence of replication of the virus, the injection resulted in the volunteers generating significant amounts of antibodies to both the canarypox vector and to the expressed rabies glycoprotein.

Rabies neutralizing antibodies were assayed with the Rapid Fluorescent Focus Inhibition Test (RFFIT) which is known to correlate well with the sero neutralization test in mice. Of 9 recipients of $10^{5.5}$ TCID$_{50}$, five had low level responses after the first dose. Protective titers of rabies antibodies were obtained after the second injection in all recipients of the highest dose tested and even in 2 of the 3 recipients of the medium dose. In this study, both vaccines were given subcutaneously as usually recommended for live vaccines, but not for the inactivated HDC vaccine. This route of injection was selected as it best allowed a careful examination of the injection site, but this could explain the late appearance of antibodies in HDC recipients: indeed, none of the HDC recipients had an antibody increase at day 7, whereas, in most studies where HDC vaccine is give intramuscularly a significant proportion of subjects do (Klietmann et al., Int'l Green Cross—Geneva, 1981; Kuwert et al., Int'l Green Cross—Geneva, 1981). However, this invention is not necessarily limited to the subcutaneous route of administration.

The GMT (geometric mean titers) of rabies neutralizing antibodies was lower with the investigational vaccine than with the HDC control vaccine, but still well above the minimum titer required for protection. The clear dose effect response obtained with the three dosages used in this study suggest that a higher dosage might induce a stronger response. Certainly from this disclosure the skilled artisan can select an appropriate dosage for a given patient.

The ability to boost the antibody response is another important result of this Example; indeed, an increase in rabies antibody titers was obtained in every subject after the 6 month dose whatever the immunization scheme, showing that preexisting immunity elicited by either the canarypox vector or the rabies glycoprotein had no blocking effect on the booster with the recombinant vaccine candidate or the conventional HDC rabies vaccine. This contrasts findings of others with vaccinia recombinants in humans that immune response may be blocked by pre-existing immunity (Cooney et al., Lancet 1991, 337:567–72; Etlinger et al., Vaccine 9:470–72, 1991).

Thus, this Example clearly demonstrates that a non-replicating poxvirus can serve as an immunizing vector in humans, with all of the advantages that replicating agents confer on the immune response, but without the safety problem created by a fully permissive virus.

TABLE 11

Reactions in the 5 days following vaccination

| vCP65 dosage (TCID50) | $10^{3.5}$ | | $10^{4.5}$ | | $10^{5.5}$ | | H D C control | |
|---|---|---|---|---|---|---|---|---|
| Injection | 1st | 2nd | 1st | 2nd | 1st | 2nd | 1st | 2nd |
| No. vaccinees | 3 | 3 | 3 | 3 | 9 | 9 | 10 | 10 |
| temp >37.7° C. | 0 | 0 | 0 | 0 | 0 | 1 | 1 | 0 |
| soreness | 0 | 0 | 1 | 1 | 6 | 8 | 8 | 6 |
| redness | 0 | 0 | 0 | 0 | 0 | 4 | 5 | 4 |
| induration | 0 | 0 | 0 | 0 | 0 | 4 | 5 | 4 |

TABLE 12

Rabies neutralizing antibodies (REFIT; IU/ml)
Individual titers and geometric mean titers (GMT)

| No. | TCID50/ dose | Days | | | | |
|---|---|---|---|---|---|---|
| | | 0 | 7 | 28 | 35 | 56 |
| 1 | $10^{3.5}$ | <0.1 | <0.1 | <0.1 | <0.1 | 0.2 |
| 3 | $10^{3.5}$ | <0.1 | <0.1 | <0.1 | <0.1 | <0.1 |
| 4 | $10^{3.5}$ | <0.1 | <0.1 | <0.1 | <0.1 | <0.1 |
| | G.M.T. | <0.1 | <0.1 | <0.1 | <0.1 | <0.1 |
| 6 | $10^{4.5}$ | <0.1 | <0.1 | <0.1 | <0.1 | <0.1 |
| 7 | $10^{4.5}$ | <0.1 | <0.1 | <0.1 | 2.4 | 1.9 |
| 10 | $10^{4.5}$ | <0.1 | <0.1 | <0.1 | 1.6 | 1.1 |

TABLE 12-continued

Rabies neutralizing antibodies (REFIT; IU/ml)
Individual titers and geometric mean titers (GMT)

| No. | TCID50/ dose | Days 0 | 7 | 28 | 35 | 56 |
|---|---|---|---|---|---|---|
|  | G.M.T. | <0.1 | <0.1 | <0.1 | 0.58 | 0.47 |
| 11 | $10^{5.5}$ | <0.1 | <0.1 | 1.0 | 3.2 | 4.3 |
| 13 | $10^{5.5}$ | <0.1 | <0.1 | 0.3 | 6.0 | 8.8 |
| 14 | $10^{5.5}$ | <0.1 | <0.1 | 0.2 | 2.1 | 9.4 |
| 17 | $10^{5.5}$ | <0.1 | <0.1 | <0.1 | 1.2 | 2.5 |
| 18 | $10^{5.5}$ | <0.1 | <0.1 | 0.7 | 8.3 | 12.5 |
| 20 | $10^{5.5}$ | <0.1 | <0.1 | <0.1 | 0.3 | 3.7 |
| 21 | $10^{5.5}$ | <0.1 | <0.1 | 0.2 | 2.6 | 3.9 |
| 23 | $10^{5.5}$ | <0.1 | <0.1 | <0.1 | 1.7 | 4.2 |
| 25 | $10^{5.5}$ | <0.1 | <0.1 | <0.1 | 0.6 | 0.9 |
|  | G.M.T. | <0.1 | <0.1 | 0.16 | 1.9 | 4.4* |
| 2 | HDC | <0.1 | <0.1 | 0.8 | 7.1 | 7.2 |
| 5 | HDC | <0.1 | <0.1 | 9.9 | 12.8 | 18.7 |
| 8 | HDC | <0.1 | <0.1 | 12.7 | 21.1 | 16.5 |
| 9 | HDC | <0.1 | <0.1 | 6.0 | 9.9 | 14.3 |
| 12 | HDC | <0.1 | <0.1 | 5.0 | 9.2 | 25.3 |
| 15 | HDC | <0.1 | <0.1 | 2.2 | 5.2 | 8.6 |
| 16 | HDC | <0.1 | <0.1 | 2.7 | 7.7 | 20.7 |
| 19 | HDC | <0.1 | <0.1 | 2.6 | 9.9 | 9.1 |
| 22 | HDC | <0.1 | <0.1 | 1.4 | 8.6 | 6.6 |
| 24 | HDC | <0.1 | <0.1 | 0.8 | 5.8 | 4.7 |
|  | G.M.T. | <0.1 | <0.1 | 2.96 | 9.0 | 11.5* |

*p = 0.007 student t test

TABLE 13

Canarypox antibodies: ELISA Geometric Mean Titers*

| vCP65 dosage TCID50/dose | Days 0 | 7 | 28 | 35 | 56 |
|---|---|---|---|---|---|
| $10^{3.5}$ | 0.69 | ND | 0.76 | ND | 0.68 |
| $10^{4.5}$ | 0.49 | 0.45 | 0.56 | 0.63 | 0.87 |
| $10^{5.5}$ | 0.38 | 0.38 | 0.77 | 1.42 | 1.63 |
| HDC control | 0.45 | 0.39 | 0.40 | 0.35 | 0.39 |

*optical density at 1/25 dilution

Example 11

Comparison of the $LD_{50}$ of ALVAC and NYVAC with Various Vaccinia Virus Strains Mice. Male outbred Swiss Webster mice were purchased from Taconic Farms (Germantown, N.Y.) and maintained on mouse chow and water ad libitum until use at 3 weeks of age ("normal" mice). Newborn outbred Swiss Webster mice were of both sexes and were obtained following timed pregnancies performed by Taconic Farms. All newborn mice used were delivered within a two day period.

Viruses. ALVAC was derived by plaque purification of a canarypox virus population and was prepared in primary chick embryo fibroblast cells (CEF). Following purification by centrifugation over sucrose density gradients, ALVAC was enumerated for plaque forming units in CEF cells. The WR(L) variant of vaccinia virus was derived by selection of large plaque phenotypes of WR (Panicali et al., 1981). The Wyeth New York State Board of Health vaccine strain of vaccinia virus was obtained from Pharmaceuticals Calf Lymph Type vaccine Dryvax, control number 302001B. Copenhagen strain vaccinia virus VC-2 was obtained from Institut Merieux, France. Vaccinia virus strain NYVAC was derived from Copenhagen VC-2. All vaccinia virus strains except the Wyeth strain were cultivated in Vero African green monkey kidney cells, purified by sucrose gradient density centrifugation and enumerated for plaque forming units on Vero cells. The Wyeth strain was grown in CEF cells and enumerated in CEF cells.

Inoculations. Groups of 10 normal mice were inoculated intracranially (ic) with 0.05 ml of one of several dilutions of virus prepared by 10-fold serially diluting the stock preparations in sterile phosphate-buffered saline. In some instances, undiluted stock virus preparation was used for inoculation.

Groups of 10 newborn mice, 1 to 2 days old, were inoculated ic similarly to the normal mice except that an injection volume of 0.03 ml was used.

All mice were observed daily for mortality for a period of 14 days (newborn mice) or 21 days (normal mice) after inoculation. Mice found dead the morning following inoculation were excluded due to potential death by trauma.

The lethal dose required to produce mortality for 50% of the experimental population ($LD_{50}$) was determined by the proportional method of Reed and Muench.

Comparison of the $LD_{50}$ of ALVAC and NYVAC with Various Vaccinia Virus Strains for Normal, Young Outbred Mice by the ic Route. In young, normal mice, the virulence of NYVAC and ALVAC were several orders of magnitude lower than the other vaccinia virus strains tested (Table 14). NYVAC and ALVAC were found to be over 3,000 times less virulent in normal mice than the Wyeth strain; over 12,500 times less virulent than the parental VC-2 strain; and over 63,000,000 times less virulent than the WR(L) variant. These results would suggest that NYVAC is highly attenuated compared to other vaccinia strains, and that ALVAC is generally nonvirulent for young mice when administered intracranially, although both may cause mortality in mice at extremely high doses ($3.85 \times 10^8$ PFUs, ALVAC and $3 \times 10^8$ PFUs, NYVAC) by an undetermined mechanism by this route of inoculation.

Comparison of the $LD_{50}$ of ALVAC and NYVAC with Various Vaccinia Virus Strains for Newborn Outbred Mice by the ic Route. The relative virulence of 5 poxvirus strains for normal, newborn mice was tested by titration in an intracranial (ic) challenge model system (Table 15). With mortality as the endpoint, $LD_{50}$ values indicated that ALVAC is over 100,000 times less virulent than the Wyeth vaccine strain of vaccinia virus; over 200,000 times less virulent than the Copenhagen VC-2 strain of vaccinia virus; and over 25,000,000 times less virulent than the WR-L variant of vaccinia virus. Nonetheless, at the highest dose tested, $6.3 \times 10^7$ PFUs, 100% mortality resulted. Mortality rates of 33.3% were observed at $6.3 \times 10^6$ PFUs. The cause of death, while not actually determined, was not likely of toxicological or traumatic nature since the mean survival time (MST) of mice of the highest dosage group (approximately 6.3 $LD_{50}$) was 6.7±1.5 days. When compared to WR(L) at a challenge dose of 5 $LD_{50}$, wherein MST is 4.8±0.6 days, the MST of ALVAC challenged mice was significantly longer (P=0.001).

Relative to NYVAC, Wyeth was found to be over 15,000 times more virulent; VC-2, greater than 35,000 times more virulent; and WR(L), over 3,000,000 times more virulent. Similar to ALVAC, the two highest doses of NYVAC, $6 \times 10^8$ and $6 \times 10^7$ PFUs, caused 100% mortality. However, the MST of mice challenged with the highest dose, corresponding to 380 $LD_{50}$, was only 2 days (9 deaths on day 2 and 1 on day 4). In contrast, all mice challenged with the highest dose of WR-L, equivalent to 500 $LD_{50}$, survived to day 4.

TABLE 14

Calculated 50% Lethal Dose for mice by various vaccinia virus strains and for canarypox virus (ALVAC) by the ic route.

| POXVIRUS STRAIN | CALCULATED LD$_{50}$ (PFUs) |
|---|---|
| WR (L) | 2.5 |
| VC-2 | $1.26 \times 10^4$ |
| WYETH | $5.00 \times 10^4$ |
| NYVAC | $1.58 \times 10^8$ |
| ALVAC | $1.58 \times 10^8$ |

TABLE 15

Calculated 50% Lethal Dose for newborn mice by various vaccinia virus strains and for canarypox virus (ALVAC) by the ic route.

| POXVIRUS STRAIN | CALCULATED LD$_{50}$ (PFUs) |
|---|---|
| WR (L) | 0.4 |
| VC-2 | 0.1 |
| WYETH | 1.6 |
| NYVAC | $1.58 \times 10^6$ |
| ALVAC | $1.00 \times 10^7$ |

Example 12

Evaluation of NYVAC (vP866) and NYVAC-RG (vP879)

Immunoprecipitations. Preformed monolayers of avian or non-avian cells were inoculated with 10 pfu per cell of parental NYVAC (vP866) or NYVAC-RG (vP879) virus. The inoculation was performed in EMEM free of methionine and supplemented with 2% dialyzed fetal bovine serum. After a one hour incubation, the inoculum was removed and the medium replaced with EMEM (methionine free) containing 20 ìCi/ml of $^{35}$S-methionine. After an overnight incubation of approximately 16 hours, cells were lysed by the addition of Buffer A (1% Nonidet P-40, 10 mM Tris pH7.4, 150 mM NaCl, 1 mM EDTA, 0.01% sodium azide, 500 units per ml of aprotinin, and 0.02% phenyl methyl sulfonyl fluoride). Immunoprecipitation was performed using a rabies glycoprotein specific monoclonal antibody designated 24-3F10 supplied by Dr. C. Trinarchi, Griffith Laboratories, New York State Department of Health, Albany, N.Y., and a rat anti-mouse conjugate obtained from Boehringer Mannheim Corporation (Cat. #605-500). Protein A Sepharose CL-48 obtained from Pharmacia LKB Biotechnology Inc., Piscataway, N.J., was used as a support matrix. Immunoprecipitates were fractionated on 10% polyacrylamide gels according to the method of Dreyfuss et. al. (1984). Gels were fixed, treated for fluorography with 1M Na-salicylate for one hour, and exposed to Kodak XAR-2 film to visualize the immunoprecipitated protein species.

Sources of Animals. New Zealand White rabbits were obtained from Hare-Marland (Hewitt, N.J.). Three week old male Swiss Webster outbred mice, timed pregnant female Swiss Webster outbred mice, and four week old Swiss Webster nude (nu$^+$nu$^+$) mice were obtained from Taconic Farms, Inc. (Germantown, N.Y.). All animals were maintained according to NIH guidelines. All animal protocols were approved by the institutional IACUC. When deemed necessary, mice which were obviously terminally ill were euthanized.

Evaluation of Lesions in Rabbits. Each of two rabbits was inoculated intradermally at multiple sites with 0.1 ml of PBS containing $10^4$, $10^5$, $10^6$, $10^7$, or $10^8$ pfu of each test virus or with PBS alone. The rabbits were observed daily from day 4 until lesion resolution. Indurations and ulcerations were measured and recorded.

Virus Recovery from Inoculation Sites. A single rabbit was inoculated intradermally at multiple sites of 0/1 ml of PBS containing $10^6$, $10^7$, or $10^8$ pfu of each test virus or with PBS alone. After 11 days, the rabbit was euthanized and skin biopsy specimens taken from each of the inoculation sites were aseptically prepared by mechanical disruption and indirect sonication for virus recovery. Infectious virus was assayed by plaque titration on CEF monolayers.

Virulence in Mice. Groups of ten mice, or five in the nude mice experiment, were inoculated ip with one of several dilutions of virus in 0.5 ml of sterile PBS. Reference is also made to Example 11.

Cyclophosphamide (CY) Treatment. Mice were injected by the ip route with 4 mg (0.02 ml) of CY (SIGMA) on day −2, followed by virus injection on day 0. On the following days post infection, mice were injected ip with CY: 4 mg on day 1; 2 mg on days 4, 7 and 11; 3 mg on days 14, 18, 21, 25 and 28. Immunosuppression was indirectly monitored by enumerating white blood cells with a Coulter Counter on day 11. The average white blood cell count was 13,500 cells per ìl for untreated mice (n=4) and 4,220 cells per ìl for CY-treated control mice (n=5).

Calculation of LD$_{50}$. The lethal dose required to produce 50% mortality (LD$_{50}$) was determined by the proportional method of Reed and Muench (Reed and Muench 1938).

Potency Testing of NYVAC-RG in Mice. Four to six week old mice were inoculated in the footpad with 50 to 100 ìl of a range of dilutions (2.0–8.0 log$_{10}$ tissue culture infective dose 50% (TCID$_{50}$)) of either VV-RG (Kieny et al., 1984), ALVAC-RG (Taylor et al., 1991b), or the NYVAC-RG. Each group consisted of eight mice. At 14 days post-vaccination, the mice were challenged by intracranial inoculation with 15 LD$_{50}$ of the rabies virus CVS strain (0.03 ml). On day 28, surviving mice were counted and protective does 50% (PD$_{50}$) calculated.

Figure 10:
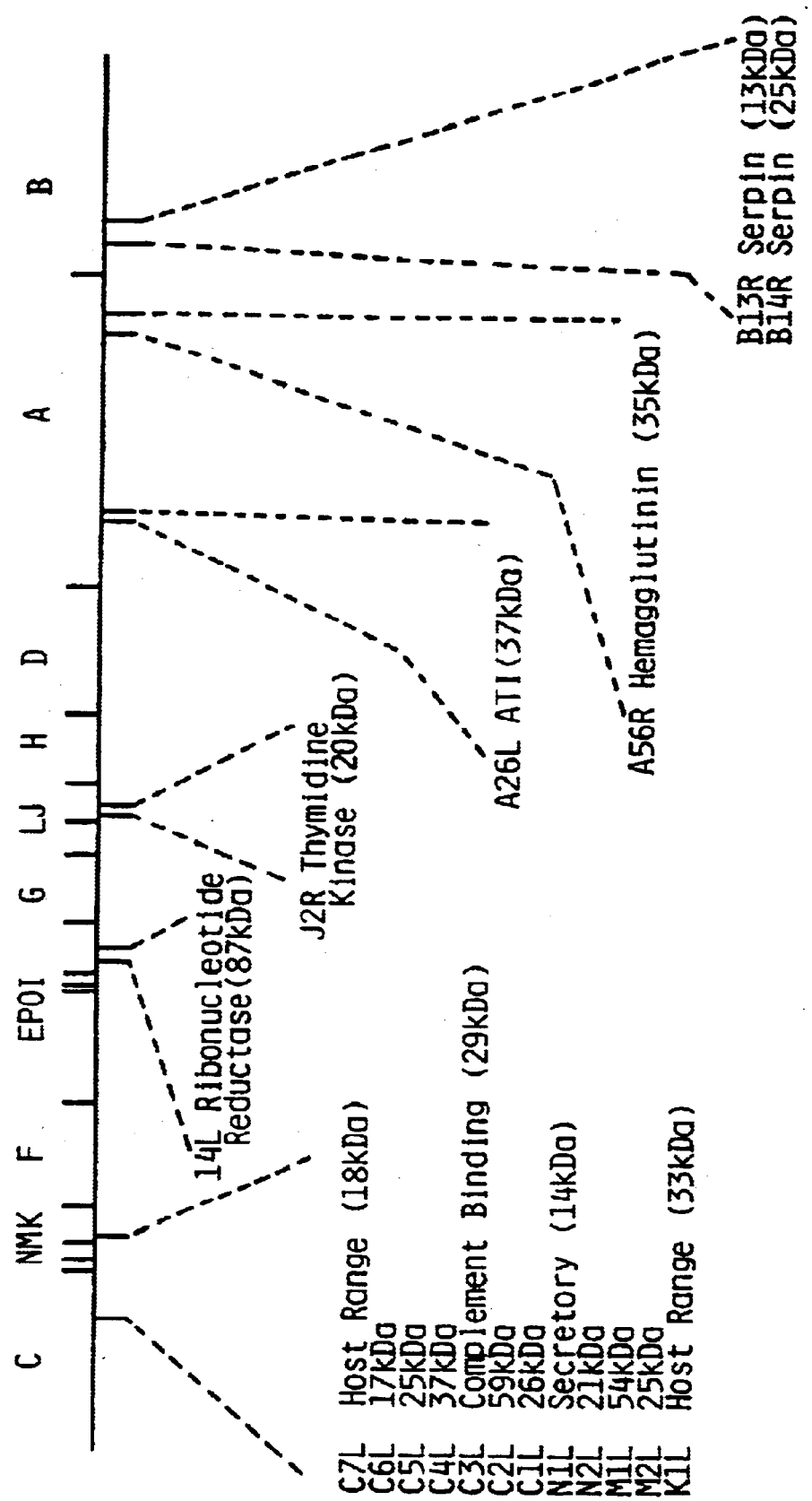
FIG. 10 shows schematically the ORFs deleted to generate NYVAC.
Figure 13A:
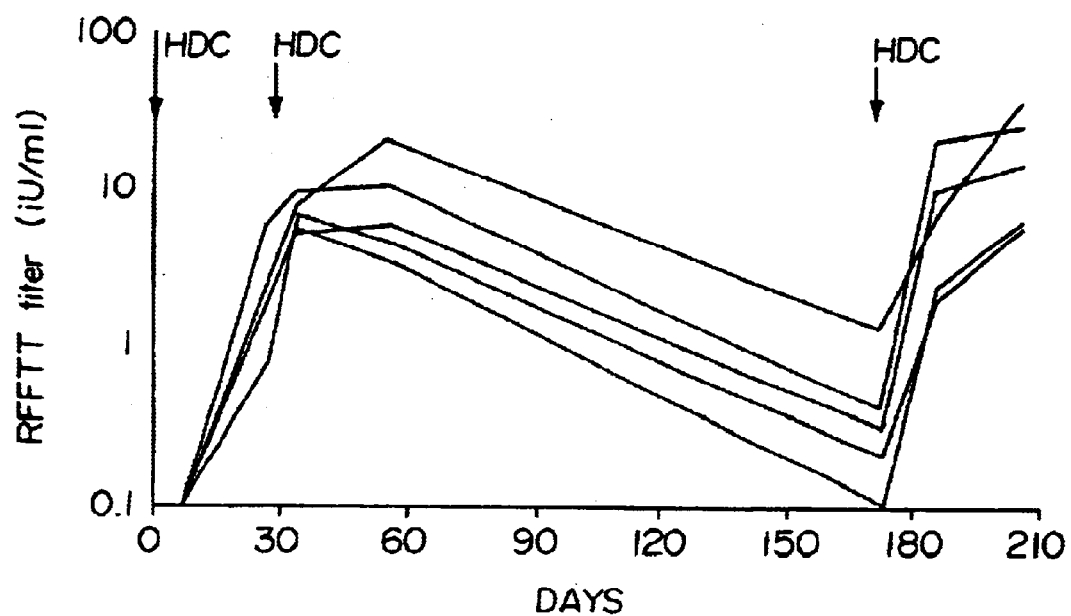
FIGS. 13A to 13D show graphs of rabies neutralizing antibody titers (RFFIT, IU/ml), booster effect of HDC and vCP65 ($10^{5.5}$ TCID50) in volunteers previously immunized with either the same or the alternate vaccine (vaccines given at days 0, 28 and 180, antibody titers measured at days 0, 7, 28, 35, 56, 173, 187 and 208)
Figure 13C:
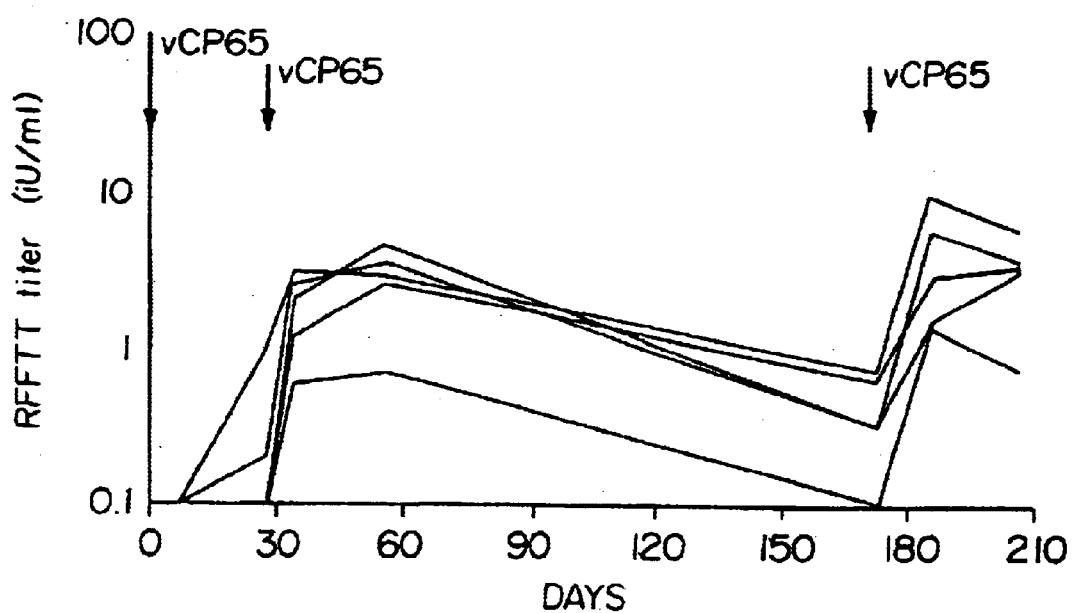
Figure 13B:
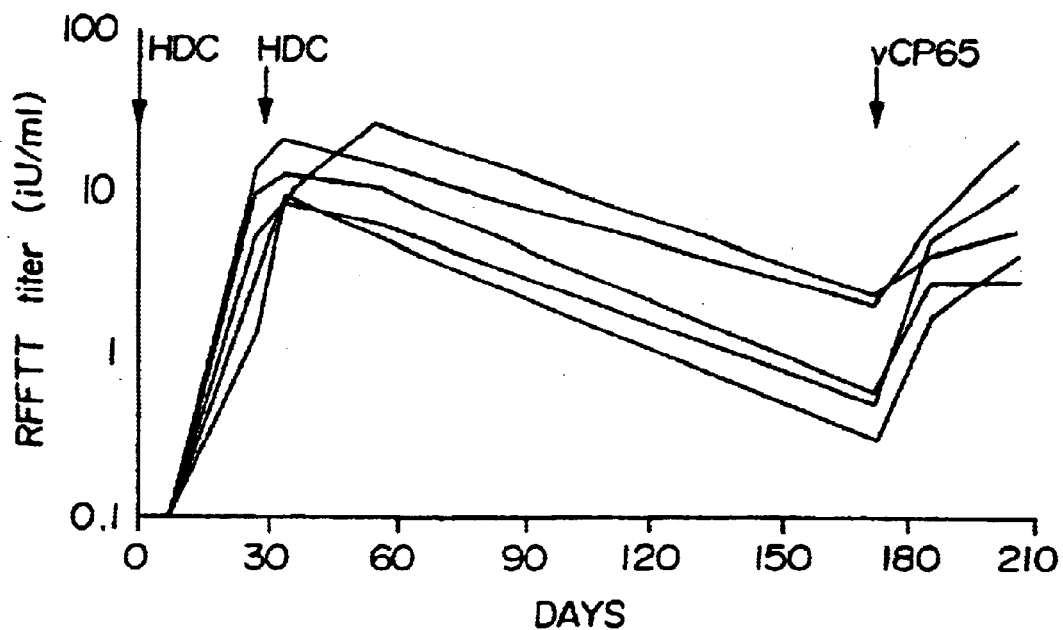
Figure 13D:
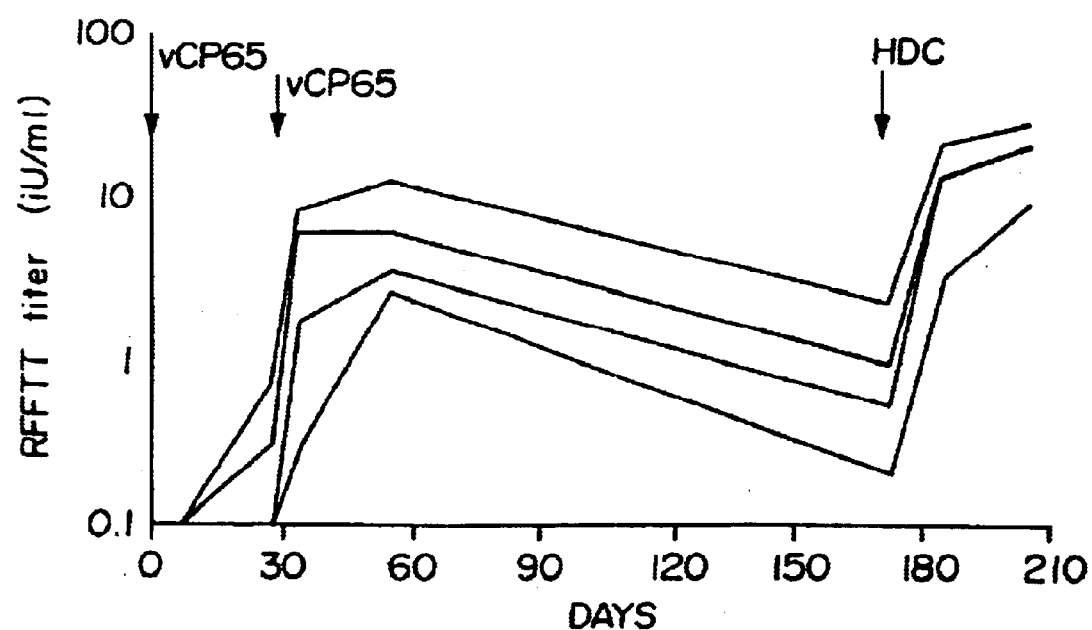

Derivation of NYVAC (vP866). The NYVAC strain of vaccinia virus was generated from VC-2, a plaque cloned isolate of the COPENHAGEN vaccine strain. To generate NYVAC from VC-2, eighteen vaccinia ORFs, including a number of viral functions associated with virulence, were precisely deleted in a series of sequential manipulations as described earlier in this disclosure. These deletions were constructed in a manner designed to prevent the appearance of novel unwanted open reading frames. FIG. 10 schematically depicts the ORFs deleted to generate NYVAC. At the top of FIG. 10 is depicted the HindIII restriction map of the vaccinia virus genome (VC-2 plaque isolate, COPENHAGEN strain). Expanded are the six regions of VC-2 that were sequentially deleted in the generation of NYVAC. The deletions were described earlier in this disclosure (Examples 1 through 6). Below such deletion locus is listed the ORFs which were deleted from that locus, along with the functions or homologies and molecular weight of their gene products.

Replication Studies of NYVAC and ALVAC on Human Tissue Cell Lines. In order to determine the level of replication of NYVAC strain of vaccinia virus (vP866) in cells of human origin, six cell lines were inoculated at an input multiplicity of 0.1 pfu per cell under liquid culture and incubated for 72 hours. The COPENHAGEN parental clone (VC-2) was inoculated in parallel. Primary chick embryo fibroblast (CEF) cells (obtained from 10–11 day old embryonated eggs of SPF origin, Spafas, Inc., Storrs, Conn.) were included to represent a permissive cell substrate for all viruses. Cultures were analyzed on the basis of two criteria: the occurrence of productive viral replication and expression of an extrinsic antigen.

The replication potential of NYVAC in a number of human derived cells are shown in Table 16. Both VC-2 and NYVAC are capable of productive replication in CEF cells, although NYVAC with slightly reduced yields. VC-2 is also capable of productive replication in the six human derived cell lines tested with comparable yields except in the EBV transformed lymphoblastoid cell line JT-1 (human lymphoblastoid cell line transformed with Epstein-Barr virus, see Rickinson et al., 1984). In contract, NYVAC is highly attenuated in its ability to productively replicate in any of the human derived cell lines tested. Small increases of infectious virus above residual virus levels were obtained from NYVAC-infected MRC-5 (ATCC #CCL171, human embryonic lung origin), DETROIT 532 (ATCC #CCL54, human foreskin, Downs Syndrome), HEL 299 (ATCC #CCL137, human embryonic lung cells) and HNK (human neonatal kidney cells, Whittiker Bioproducts, Inc. Walkersville, MD, Cat #70-151) cells. Replication on these cell lines was significantly reduced when compared to virus yields obtained from NYVAC-infected CEF cells or with parental VC-2 (Table 16). It should be noted that the yields at 24 hours in CEF cells for both NYVAC and VC-2 is equivalent to the 72-hour yield. Allowing the human cell line cultures to incubate an additional 48 hours (another two viral growth cycles) may, therefore, have amplified the relative virus yield obtained.

Consistent with the low levels of virus yields obtained in the human-derived cell lines, MRC-5 and DETROIT 532, detectable but reduced levels of NYVAC-specific DNA accumulation were noted. The level of DNA accumulation in the MRC-5 and DETROIT 532 NYVAC-infected cell lines relative to that observed in NYVAC-infected CEF cells paralleled the relative virus yields. NYVAC-specific viral DNA accumulation was not observed in any of the other human-derived cells.

An equivalent experiment was also performed using the avipox virus, ALVAC. The results of virus replication are also shown in Table 16. No progeny virus was detectable in any of the human cell lines consistent with the host range restriction of canarypox virus to avian species. Also consistent with a lack of productive replication of ALVAC in these human-derived cells is the observation that no ALVAC-specific DNA accumulation was detectable in any of the human-derived cell lines.

Expression of Rabies Glycoprotein by NYVAC-RG (vP879) in Human Cells. In order to determine whether efficient expression of a foreign gene could be obtained in the absence of significant levels of productive viral replication, the same cell lines were inoculated with the NYVAC recombinant expressing the rabies virus glycoprotein (vP879, Example 7) in the presence of 35S- methionine. Immunoprecipitation of the rabies glycoprotein was performed from the radiolabelled culture lysate using a monoclonal antibody specific for the rabies glycoprotein. Immunoprecipitation of a 67 kDa protein was detected consistent with a fully glycosylated form of the rabies glycoprotein. No serologically crossreactive product was detected in uninfected or parental NYVAC infected cell lysates. Equivalent results were obtained with all other human cells analyzed.

Inoculations on the Rabbit Skin. The induction and nature of skin lesions on rabbits following intradermal (id) inoculations has been previously used as a measure of pathogenicity of vaccinia virus strains (Buller et al., 1988; Child et al., 1990; Fenner, 1958, Flexner et al., 1987; Ghendon and Chernos 1964). Therefore, the nature of lesions associated with id inoculations with the vaccinia strains WR (ATCC #VR119 plaque purified on CV-1 cells, ATCC #CCL70, and a plaque isolate designated L variant, ATCC #VR2035 selected, as described in Panicali et al., 1981)), WYETH (ATCC #VR325 marketed as DRYVAC by Wyeth Laboratories, Marietta, Pa.), COPENHAGEN (VC-2), and NYVAC was evaluated by inoculation of two rabbits (A069 and A128). The two rabbits displayed different overall sensitivities to the viruses, with rabbit A128 displaying less severe reactions than rabbit A069. In rabbit A128, lesions were relatively small and resolved by 27 days post-inoculation. On rabbit A069, lesions were intense, especially for the WR inoculation sites, and resolved only after 49 days. Intensity of the lesions was also dependent on the location of the inoculation sites relative to the lymph drainage network. In particular, all sites located above the backspine displayed more intense lesions and required longer times to resolve the lesions located on the flanks. All lesions were measured daily from day 4 to the disappearance of the last lesion, and the means of maximum lesion size and days to resolution were calculated (Table 17). No local reactions were observed from sites injected with the control PBS. Ulcerative lesions were observed at sites injected with WR, VC-2 and WYETH vaccinia virus strains. Significantly, no induration or ulcerative lesions were observed at sites of inoculation with NYVAC.

Persistence of Infectious Virus at the Site of Inoculation. To assess the relative persistence of these viruses at the site of inoculation, a rabbit was inoculated intradermally at multiple sites with 0.1 ml PBS containing $10^6$, $10^7$ or $10^8$ pfu of VC-2, WR, WYETH or NYVAC. For each virus, the $10^7$ pfu dose was located above the backspine, flanked by the $10^6$ and $10^8$ doses. Sites of inoculation were observed daily for 11 days. WR elicited the most intense response, followed by VC-2 and WYETH (Table 18). Ulceration was first observed at day 9 for WR and WYETH and day 10 for VC-2. Sites inoculated with NYVAC or control PBS displayed no induration or ulceration. At day 11 after inoculation, skin samples from the sites of inoculation were excised, mechanically disrupted, and virus was titrated on CEF cells. The results are shown in Table 18. In no case was more virus recovered at this timepoint than was administered. Recovery of vaccinia strain, WR, was approximately $10^6$ pfu of virus at each site irrespective of amount of virus administered. Recovery of vaccinia strains WYETH and VC-2 was $10^3$ to $10^4$ pfu regardless of amount administered. No infectious virus was recovered from sites inoculated with NYVAC.

Inoculation of Genetically or Chemically Immune Deficient Mice. Intraperitoneal inoculation of high doses of NYVAC ($5 \times 10^8$ pfu) or ALVAC ($10^9$ pfu) into nude mice caused no deaths, no lesions, and no apparent disease through the 100 day observation period. In contrast, mice inoculated with WR ($10^3$ to $10^4$ pfu), WYETH ($5 \times 10^7$ or $5 \times 10^8$ pfu) or VC-2 ($10^4$ to $10^9$ pfu) displayed disseminated lesions typical of poxviruses first on the toes, then on the tail, followed by severe orchitis in some animals. In mice infected with WR or WYETH, the appearance of disseminated lesions generally led to eventual death, whereas most mice infected with VC-2 eventually recovered. Calculated $LD_{50}$ values are given in Table 19.

In particular, mice inoculated with VC-2 began to display lesions on their toes (red papules) and 1 to 2 days later on the tail. These lesions occurred between 11 and 13 days post-inoculation (pi) in mice given the highest doses ($10^9$, $10^8$, $10^7$ and $10^6$ pfu), on day 16 pi in mice given $10^5$ pfu and on day 21 pi in mice given $10^4$ pfu. No lesions were observed in mice inoculated with $10^3$ and $10^2$ pfu during the 100 day observation period. Orchitis was noticed on day 23 pi in mice given $10^9$ and $10^8$ pfu, and approximately 7 days later in the other groups ($10^7$ to $10^4$ pfu). Orchitis was especially intense in the $10^9$ and $10^8$ pfu groups and, although receding, was observed until the end of the 100 day observation period. Some pox-like lesions were noticed on the skin of a few mice, occurring around 30–35 days pi. Most pox lesions healed normally between 60–90 days pi. Only one mouse died in the group inoculated with $10^9$ pfu (Day 34 pi) and one mouse died in the group inoculated with $10^8$ pfu (Day 94 pi). No other deaths were observed in the VC-2 inoculated mice.

Mice inoculated with $10^4$ pfu of the WR strain of vaccinia started to display pox lesions on Day 17 pi. These lesions appeared identical to the lesions displayed by the VC-2 injected mice (swollen toes, tail). Mice inoculated with $10^3$ pfu of the WR strain did not develop lesions until 34 days pi. Orchitis was noticed only in the mice inoculated with the highest dose of WR ($10^4$ pfu). During the latter stages of the observation period, lesions appeared around the mouth and the mice stopped eating. All mice inoculated with $10^4$ pfu of WR died or were euthanized when deemed necessary between 21 days and 31 days pi. Four out of the 5 mice injected with $10^3$ pfu of WR died or were euthanized when deemed necessary between 35 days and 57 days pi. No deaths were observed in mice inoculated with lower doses of WR (1 to 100 pfu).

Mice inoculated with the WYETH strain of vaccinia virus at higher doses $5 \times 10^7$ and $5 \times 10^8$ pfu) showed lesions on toes and tails, developed orchitis, and died. Mice injected with $5 \times 10^6$ pfu or less of WYETH showed no signs of disease or lesions.

As shown in Table 19, CY-treated mice provided a more sensitive model for assaying poxvirus virulence than did nude mice. $LD_{50}$ values for the WR, WYETH, and VC-2 vaccinia virus strains were significantly lower in this model system than in the nude mouse model. Additionally, lesions developed in mice injected with WYETH, WR and VC-2 vaccinia viruses, as noted below, with higher doses of each virus resulting in more rapid formation of lesions. As was seen with nude mice, CY-treated mice injected with NYVAC or ALVAC did not develop lesions. However, unlike nude mice, some deaths were observed in CY-treated mice challenged with NYVAC or ALVAC, regardless of the dose. These random incidences are suspect as to the cause of death.

Mice injected with all doses of WYETH ($9.5 \times 10^4$ to $9.5 \times 10^8$ pfu) displayed pox lesions on their tail and/or on their toes between 7 and 15 days pi. In addition, the tails and toes were swollen. Evolution of lesions on the tail was typical of pox lesions with formation of a papule, ulceration and finally formation of a scab. Mice inoculated with all doses of VC-2 ($1.65 \times 10^5$ to $1.65 \times 10^9$) also developed pox lesions on their tails and/or their toes analogous to those of WYETH injected mice. These lesions were observed between 7–12 days post inoculation. No lesions were observed on mice injected with lower doses of WR virus, although deaths occurred in these groups.

Potency Testing of NYVAC-RG. In order to determine that attenuation of the COPENHAGEN strain of vaccinia virus had been effected without significantly altering the ability of the resulting NYVAC strain to be a useful vector, comparative potency tests were performed. In order to monitor the immunogenic potential of the vector during the sequential genetic manipulations performed to attenuate the virus, a rabiesvirus glycoprotein was used as a reporter extrinsic antigen. The protective efficacy of the vectors expressing the rabies glycoprotein gene was evaluated in the standard NIH mouse potency test for rabies (Seligmann, 1973). Table 20 demonstrates that the $PD_{50}$ values obtained with the highly attenuated NYVAC vector are identical to those obtained using a COPENHAGEN-based recombinant containing the rabies glycoprotein gene in the tk locus (Kieny et al., 1984) and similar to $PD_{50}$ values obtained with ALVAC-RG, a canarypox based vector restricted to replication to avian species.

Observations. NYVAC, deleted of known virulence genes and having restricted in vitro growth characteristics, was analyzed in animal model systems to assess its attenuation characteristics. These studies were performed in comparison with the neurovirulent vaccinia virus laboratory strain, WR, two vaccinia virus vaccine strains, WYETH (New York City Board of Health) and COPENHAGEN (VC-2), as well as with a canarypox virus strain, ALVAC (See also Example 11). Together, these viruses provided a spectrum of relative pathogenic potentials in the mouse challenge model and the rabbit skin model, with WR being the most virulent strain, WYETH and COPENHAGEN (VC-2) providing previously utilized attenuated vaccine strains with documented characteristics, and ALVAC providing an example of a poxvirus whose replication is restricted to avian species. Results from these in vivo analyses clearly demonstrate the highly attenuated properties of NYVAC relative to the vaccinia virus strains, WR, WYETH and COPENHAGEN (VC-2) (Tables 14–20). Significantly, the $LD_{50}$ values for NYVAC were comparable to those observed with the avian host restricted avipoxvirus, ALVAC. Deaths due to NYVAC, as well as ALVAC, were observed only when extremely high doses of virus were administered via the intracranial route (Example 11, Tables 14, 15, 19). It has not yet been established whether these deaths were due to nonspecific consequences of inoculation of a high protein mass. Results from analyses in immunocompromised mouse models (nude and CY-treated) also demonstrate the relatively high attenuation characteristics of NYVAC, as compared to WR, WYETH and COPENHAGEN strains (Tables 17 and 18). Significantly, no evidence of disseminated vaccinia infection or vaccinial disease was observed in NYVAC-inoculated animals or ALVAC-inoculated animals over the observation period. The deletion of multiple virulence-associated genes in NYVAC shows a synergistic effect with respect to pathogenicity. Another measure of the innocuity of NYVAC was provided by the intradermal administration on rabbit skin (Tables 17 and 18). Considering the results with ALVAC, a virus unable to replicate in nonavian species, the ability to replicate at the site of inoculation is not the sole correlate with reactivity, since intradermal inoculation of ALVAC caused areas of induration in a dose dependent manner. Therefore, it is likely that factors other than the replicative capacity of the virus contribute to the formation of the lesions. Deletion of genes in NYVAC prevents lesion occurrence.

Together, the results in this Example and in foregoing Examples, including Example 11, demonstrate the highly attenuated nature of NYVAC relative to WR, and the previously utilized vaccinia virus vaccine strains, WYETH and COPENHAGEN. In fact, the pathogenic profile of NYVAC, in the animal model systems tested, was similar to that of ALVAC, a poxvirus known to productively replicate only in avian species. The apparently restricted capacity of NYVAC to productively replicate on cells derived from humans (Table 16) and other species, including the mouse, swine, dog and horse, provides a considerable barrier that limits or prevents potential transmission to unvaccinated contacts or to the general environment in addition to providing a vector with reduced probability of dissemination within the vaccinated individual.

Significantly, NYVAC-based vaccine candidates have been shown to be efficacious. NYVAC recombinants expressing foreign gene products from a number of pathogens have elicited immunological responses towards the foreign gene products in several animal species, including primates. In particular, a NYVAC-based recombinant expressing the rabies glycoprotein was able to protect mice against a lethal rabies challenge. The potency of the NYVAC-based rabies glycoprotein recombinant was comparable to the $PD_{50}$ value for a COPENHAGEN-based recombinant containing the rabies glycoprotein in the tk locus (Table 20). NYVAC-based recombinants have also been shown to elicit measles virus neutralizing antibodies in rabbits and protection against pseudorabies virus and Japanese encephalitis virus challenge in swine. The highly attenuated NYVAC strain confers safety advantages with human and veterinary applications (Tartaglia et al., 1990). Furthermore, the use of NYVAC as a general laboratory expression vector system may greatly reduce the biological hazards associated with using vaccinia virus.

By the following criteria, the results of this Example and the Examples herein, including Example 11, show NYVAC to be highly attenuated: a) no detectable induration or ulceration at site of inoculation (rabbit skin); b) rapid clearance of infectious virus from intradermal site of inoculation (rabbit skin); c) absence of testicular inflammation (nude mice); d) greatly reduced virulence (intracranial challenge, both three-week old and newborn mice); e) greatly reduced pathogenicity and failure to disseminate in immunodeficient subjects (nude and cyclophosphamide treated mice); and f) dramatically reduced ability to replicate on a variety of human tissue culture cells. Yet, in spite of being highly attenuated, NYVAC, as a vector, retains the ability to induce strong immune responses to extrinsic antigens.

TABLE 16

Replication of COPENHAGEN (VC-2), NYVAC and ALVAC in avian or human derived cell lines

| Cells | Hours post-infection | Yield[a] VC-2 | NYVAC | ALVAC | % Yield |
|---|---|---|---|---|---|
| CEF | 0 | 3.8[b] | 3.7 | 4.5 | |
| | 24 | 8.3 | 7.8 | 6.6 | |
| | 48 | 8.6 | 7.9 | 7.7 | |
| | 72 | 8.3 | 7.7 | 7.5 | 25 |
| | 72A[c] | <1.4 | 1.8 | 3.1 | |
| MRC-5 | 0 | 3.8 | 3.8 | 4.7 | |
| | 72 | 7.2 | 4.6 | 3.8 | 0.25 |
| | 72A | 2.2 | 2.2 | 3.7 | |
| WISH* | 0 | 3.4 | 3.4 | 4.3 | |
| | 72 | 7.6 | 2.2 | 3.1 | 0.0004 |
| | 72A | —[d] | 1.9 | 2.9 | |
| DETROIT | 0 | 3.8 | 3.7 | 4.4 | |
| | 72 | 7.2 | 5.4 | 3.4 | 1.6 |
| | 72A | 1.7 | 1.7 | 2.9 | |
| HEL | 0 | 3.8 | 3.5 | 4.3 | |
| | 72 | 7.5 | 4.6 | 3.3 | 0.125 |
| | 72A | 2.5 | 2.1 | 3.6 | |
| JT-1 | 0 | 3.1 | 3.1 | 4.1 | |
| | 72 | 6.5 | 3.1 | 4.2 | 0.039 |
| | 72A | 2.4 | 2.1 | 4.4 | |

TABLE 16-continued

Replication of COPENHAGEN (VC-2), NYVAC and ALVAC in avian or human derived cell lines

| Cells | Hours post-infection | Yield[a] VC-2 | NYVAC | ALVAC | % Yield |
|---|---|---|---|---|---|
| HNK | 0 | 3.8 | 3.7 | 4.7 | |
| | 72 | 7.6 | 4.5 | 3.6 | 0.079 |
| | 72A | 3.1 | 2.7 | 3.7 | |

[a]Yield of NYVAC at 72 hours post-injection expressed as a percentage of yield of VAC-2 after 72 hours on the same cell line.
[b]Titer expressed as $LOG_{50}$ pfu per ml.
[c]Sample was incubated in the presence of 40 ig/ml of cytosine arabinoside.
[d]Not determined.
*ATCC #CCL25 Human amnionic cells.

TABLE 17

Induration and ulceration at the site of intradermal inoculation of the rabbit skin

| VIRUS STRAIN | DOSE[a] | INDURATION Size[b] | Days[c] | ULCERATION Size | Days |
|---|---|---|---|---|---|
| WR | $10^4$ | 386 | 30 | 88 | 30 |
| | $10^5$ | 622 | 35 | 149 | 32 |
| | $10^6$ | 1057 | 34 | 271 | 34 |
| | $10^7$ | 877 | 35 | 204 | 35 |
| | $10^8$ | 581 | 25 | 88 | 26 |
| WYETH | $10^4$ | 32 | 5 | —[d] | — |
| | $10^5$ | 116 | 15 | — | — |
| | $10^6$ | 267 | 17 | 3 | 15 |
| | $10^7$ | 202 | 17 | 3 | 24 |
| | $10^8$ | 240 | 29 | 12 | 31 |
| VC-2 | $10^4$ | 64 | 7 | — | — |
| | $10^5$ | 86 | 8 | — | — |
| | $10^6$ | 136 | 17 | — | — |
| | $10^7$ | 167 | 21 | 6 | 10 |
| | $10^8$ | 155 | 32 | 6 | 8 |
| NYVAC | $10^4$ | — | — | — | — |
| | $10^5$ | — | — | — | — |
| | $10^6$ | — | — | — | — |
| | $10^7$ | — | — | — | — |
| | $10^8$ | — | — | — | — |

[a]pfu of indicated vaccinia virus in 0.1 ml PBS inoculated intradermally into one site.
[b]mean maximum size of lesions (mm$^2$)
[c]mean time after inoculation for complete healing of lesion.
[d]no lesions discernable.

TABLE 18

Persistence of poxviruses at the site of intradermal inoculation

| Virus | Inoculum Dose | Total Virus Recovered |
|---|---|---|
| WR | 8.0[a] | 6.14 |
| | 7.0 | 6.26 |
| | 6.0 | 6.21 |
| WYETH | 8.0 | 3.66 |
| | 7.0 | 4.10 |
| | 6.0 | 3.59 |
| VC-2 | 8.0 | 4.47 |
| | 7.0 | 4.74 |
| | 6.0 | 3.97 |
| NYVAC | 8.0 | 0 |
| | 7.0 | 0 |
| | 6.0 | 0 |

[a]expressed as $\log_{10}$ pfu.

TABLE 19

Virulence studies in immunocompromised mice

| Poxvirus Strain | LD$_{50}$$^a$ | |
|---|---|---|
| | Nude mice | Cyclophosphamide treated mice |
| WR | 422 | 42 |
| VC-2 | >10$^9$ | <1.65 × 10$^5$ |
| WYETH | 1.58 × 10$^7$ | 1.83 × 10$^6$ |
| NYVAC | >5.50 × 10$^8$ | 7.23 × 10$^8$ |
| ALVAC | >10$^9$ | ≧5.00 × 10$^{8b}$ |

$^a$Calculated 50% lethal dose (pfu) for nude or cyclophosphamide treated mice by the indicated vaccinia viruses and for ALVAC by intraperitoneal route.
$^b$5 out of 10 mice died at the highest dose of 5 × 10$^8$ pfu.

TABLE 20

Comparative efficacy of NYVAC-RG and ALVAC-RG in mice

| Recombinant | PD$_{50}$$^a$ |
|---|---|
| VV-RG | 3.74 |
| ALVAC-RG | 3.86 |
| NYVAC-RG | 3.70 |

$^a$Four to six week old mice were inoculated in the footpad with 50–100 ìl of a range of dilutions (2.0–8.0 log$_{10}$ tissue culture infection dose 50% (TCID$_{50}$) of either the VV-RG (Kieny et al., 1984), ALVAC-RG (vCP65) or NYVAC-RG (vP879). At day 14, mice of each group were challenged by intracranial inoculation of 30 ìl of a live CVS strain rabies virus corresponding to 15 lethal dose 50% (LD$_{50}$) per mouse. At day 28, surviving mice were counted and a protective dose 50% (PD$_{50}$) was calculated.

Example 13

Construction of TROVAC Recombinants Expressing the Hemagglutinin Glycoproteins of Avian Influenza Viruses This Example describes the development of fowlpox virus recombinants expressing the hemagglutinin genes of three serotypes of avian influenza virus.

Cells and Viruses. Plasmids containing cDNA clones of the H4, H5 and H7 hemagglutinin genes were obtained from Dr. Robert Webster, St. Jude Children's Research Hospital, Memphis, Tenn. The strain of FPV designated FP-1 has been described previously (Taylor et al., 1988a, b). It is a vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chick embryo fibroblast (CEF) cells. This virus was obtained in September 1980 by Rhone Merieux, Lyon, France, and a master viral seed established. The virus was received by Virogenetics in September 1989, where it was subjected to four successive plaque purifications. One plaque isolate was further amplified in primary CEF cells and a stock virus, designated as TROVAC, was established. The stock virus used in the in vitro recombination test to produce TROVAC-AIH5 (vFP89) and TROVAC-AIH4 (vFP92) had been further amplified though 8 passages in primary CEF cells. The stock virus used to produce TROVAC-AIH7 (vFP100) had been further amplified through 12 passages in primary CEF cells.

Construction of Fowlpox Insertion Plasmid at F8 Locus. Plasmid pRW731.15 contains a 10 kbp PvuII-PvuII fragment cloned from TROVAC genomic DNA. The nucleotide sequence was determined on both strands for a 3659 bp PvuII-EcoRV fragment. This sequence is shown in FIG. 11 (SEQ ID NO:77). The limits of an open reading frame designated in this laboratory as F8 were determined within this sequence. The open reading frame is initiated at position 495 and terminates at position 1887. A deletion was made from position 779 to position 1926, as described below.

Plasmid pRW761 is a sub-clone of pRW731.15 containing a 2430 bp EcoRV-EcoRV fragment. Plasmid pRW761 was completely digested with XbaI and partially digested with SspI. A 3700 bp XbaI-SspI band was isolated and ligated with the annealed double-stranded oligonucleotides JCA017 (SEQ ID NO:37) and JCA018 (SEQ ID NO:38).

JCA017 (SEQ ID NO:37) 5' CTAGACACTTTATGTTTTT-TAATATCCGGTCTTAAAAGCTTCCCGGG-GATCCTTATACGGGGAATAAT 3'

JCA018 (SEQ ID NO:38) 5' ATTATTCCCCGTATAAG-GATCCCCCGGGAAGCTTTTAAGACCG-GATATTAAAAAACATAAAGTGT 3'

The plasmid resulting from this ligation was designated pJCA002. Plasmid pJCA004 contains a non-pertinent gene linked to the vaccinia virus H6 promoter in plasmid pJCA002. The sequence of the vaccinia virus H6 promoter has been previously described (Taylor et al., 1988a, b; Guo et al. 1989; Perkus et al., 1989). Plasmid pJCA004 was digested with EcoRV and BamHI which deletes the non-pertinent gene and a portion of the 3' end of the H6 promoter. Annealed oligonucleotides RW178 (SEQ ID NO:48) and RW179 (SEQ ID NO:49) were cut with EcoRV and BamHI and inserted between the EcoRV and BamHI sites of JCA004 to form pRW846.

RW178 (SEQ ID NO:48): 5' TCATTATCGCGATATCCGT-GTTAACTAGCTAGCTAATTTTTATTC-CCGGGATCCTTATCA 3'

RW179 (SEQ ID NO:49): 5' GTATAAGGATCCCGG-GAATAAAAATTAGCTAGCTAGTTAA-CACGGATATCGCGATAATGA 3'

Plasmid pRW846 therefore contains the H6 promoter 5' of EcoRV in the de-ORFed F8 locus. The HincII site 3' of the H6 promoter in pRW846 is followed by translation stop codons, a transcriptional stop sequence recognized by vaccinia virus early promoters (Yuen et al., 1987) and a SmaI site.

Construction of Fowlpox Insertion Plasmid at F7 Locus. The original F7 non-de-ORFed insertion plasmid, pRW731.13, contained a 5.5 kb FP genomic PvuII fragment in the PvuII site of pUC9. The insertion site was a unique HincII site within these sequences. The nucleotide sequence shown in FIG. 12 (SEQ ID NO:78) was determined for a 2356 bp region encompassing the unique HincII site. Analysis of this sequence revealed that the unique HincII site (FIG. 12, underlined) was situated within an ORF encoding a polypeptide of 90 amino acids. The ORF begins with an ATG at position 1531 and terminates at position 898 (positions marked by arrows in FIG. 12).

The arms for the de-ORFed insertion plasmid were derived by PCR using pRW731.13 as template. A 596 bp arm (designated as HB) corresponding to the region upstream from the ORF was amplified with oligonucleotides F73PH2 (SEQ ID NO:50) (5'-GACAATCTAAGTCCTATATTAGAC-3') and F73PB (SEQ ID NO:51) (5'-GGATTTTTAGGTAGACAC-3'). A 270 bp arm (designated as EH) corresponding to the region downstream from the ORF was amplified using oligonucleotides F75PE (SEQ ID NO:52) (5'-TCATCGTCTTCATCATCG-3') and F73PH1 (SEQ ID NO:53) (5'-GTCTTAAACTTATTGTAAGGGTATACCTG-3').

Fragment EH was digested with EcoRV to generate a 126 bp fragment. The EcoRV site is at the 3'-end and the 5'-end was formed, by PCR, to contain the 3' end of a HincII site. This fragment was inserted into pBS-SK (Stratagene, La Jolla, Calif.) digested with HincII to form plasmid pF7D1. The sequence was confirmed by dideoxynucleotide sequence analysis. The plasmid pF7D1 was linearized with ApaI, blunt-ended using T4 DNA polymerase, and ligated to the 596 bp HB fragment. The resultant plasmid was designated as pF7D2. The entire sequence and orientation were confirmed by nucleotide sequence analysis.

The plasmid pF7D2 was digested with EcoRV and BglII to generate a 600 bp fragment. This fragment was inserted into pBS-SK that was digested with ApaI, blunt-ended with T4 DNA polymerase, and subsequently digested with BamHI. The resultant plasmid was designated as pF7D3. This plasmid contains an HB arm of 404 bp and a EH arm of 126 bp.

The plasmid pF7D3 was linearized with XhoI and blunt-ended with the Klenow fragment of the E. coli DNA polymerase in the presence of 2 mM dNTPs. This linearized plasmid was ligated with annealed oligonucleotides F7MCSB (SEQ ID NO:54) (5'-AACGATTAGTTAGTTACTAAAAGCTTGCTGCAGCCCGGGTTTTTTATTAGTTTAGTTAGTC-3') and F7MCSA (SEQ ID NO:55) (5'-GACTAACTAACTAATAAAAAACCCGGGCTGCAGCAAGCTTTTTGTAACTAACTAATCGTT-3'). This was performed to insert a multiple cloning region containing the restriction sites for HindIII, PstI and SmaI between the EH and HB arms. The resultant plasmid was designated as pF7D0.

Construction of Insertion Plasmid for the H4 Hemagglutinin at the F8 Locus. A cDNA copy encoding the avian influenza H4 derived from A/Ty/Min/833/80 was obtained from Dr. R. Webster in plasmid pTM4H833. The plasmid was digested with HindIII and NruI and blunt-ended using the Klenow fragment of DNA polymerase in the presence of dNTPs. The blunt-ended 2.5 kbp HindIII-NruI fragment containing the H4 coding region was inserted into the HincII site of pIBI25 (International Biotechnologies, Inc., New Haven, Conn.). The resulting plasmid pRW828 was partially cut with BanII, the linear product isolated and recut with HindIII. Plasmid pRW828 now with a 100 bp HindIII-BanII deletion was used as a vector for the synthetic oligonucleotides RW152 (SEQ ID NO:56) and RW153 (SEQ ID NO:57). These oligonucleotides represent the 3' portion of the H6 promoter from the EcoRV site and align the ATG of the promoter with the ATG of the H4 cDNA.

RW152 (SEQ ID NO:56): 5' GCACGGAACAAAGCTTATCGCGATATCCGTTAAGTTTGTATCGTAATGCTATCAATCACGATTCTGTTCCTGCTCATAGCAGAGGGCTCATCTCAGAAT 3'

RW153 (SEQ ID NO:57): 5' ATTCTGAGATGAGCCCTCTGCTATGAGCAGGAACAGAATCGTGATTGATAGCATTACGATACAAACTTAACGGATATCGCGATAAGCTTTGTTCCGTGC 3'

The oligonucleotides were annealed, cut with BanII and HindIII and inserted into the HindIII-BanII deleted pRW828 vector described above. The resulting plasmid pRW844 was cut with EcoRV and DraI and the 1.7 kbp fragment containing the 3' H6 promoted H4 coding sequence was inserted between the EcoRV and HincII sites of pRW846 (described previously) forming plasmid pRW848. Plasmid pRW848 therefore contains the H4 coding sequence linked to the vaccinia virus H6 promoter in the de-ORFed F8 locus of fowlpox virus.

Construction of Insertion Plasmid for H5 Hemagglutinin at the F8 Locus. A cDNA clone of avian influenza H5 derived from A/Turkey/Ireland/1378/83 was received in plasmid pTH29 from Dr. R. Webster. Synthetic oligonucleotides RW10 (SEQ ID NO:58) through RW13 (SEQ ID NO:61) were designed to overlap the translation initiation codon of the previously described vaccinia virus H6 promoter with the ATG of the H5 gene. The sequence continues through the 5' SalI site of the H5 gene and begins again at the 3' H5 DraI site containing the H5 stop codon.

RW10 (SEQ ID NO:58): 5' GAAAAATTTAAAGTCGACCTGTTTTGTTGAGTTGTTTGCGTGGTAACCAATGCAAATCTGGTCACT 3'

RW11 (SEQ ID NO:59): 5' TCTAGCAAGACTGACTATTGCAAAAAGAAGCACTATTTCCTCCATTACGATACAAACTTAACGGAT 3'

RW12 (SEQ ID NO:60): 5' ATCCGTTAAGTTTGTATCGTAATGGAGGAAATAGTGCTTCTTTTTGCAATAGTCAGTCTTGCTAGAAGTGACCAGATTTGCATTGGT 3'

RW13 (SEQ ID NO:61): 5' TACCACGCAAACAACTCAACAAAACAGGTCGACTTTAAATTTTTCTGCA 3'

The oligonucleotides were annealed at 95° C. for three minutes followed by slow cooling at room temperature. This results in the following double strand structure with the indicated ends.

```
EcoRV                                                PstI
|        RW12         |           RW13              |
|   RW11              |          RW10               
```

Cloning of oligonucleotides between the EcoRV and PstI sites of pRW742B resulted in pRW744. Plasmid pRW742B contains the vaccinia virus H6 promoter linked to a non-pertinent gene inserted at the HincII site of pRW731.15 described previously. Digestion with PstI and EcoRV eliminates the non-pertinent gene and the 3'-end of the H6 promoter. Plasmid pRW744 now contains the 3' portion of the H6 promoter overlapping the ATG of avian influenza H5. The plasmid also contains the H5 sequence through the 5' SalI site and the 3' sequence from the H5 stop codon (containing a DraI site). Use of the DraI site removes the H5 3' non-coding end. The oligonucleotides add a transcription termination signal recognized by early vaccinia virus RNA polymerase (Yuen et al., 1987). To complete the H6 promoted H5 construct, the H5 coding region was isolated as a 1.6 kpb SalI-DraI fragment from pTH29. Plasmid pRW744 was partially digested with DraI, the linear fragment isolated, recut with SalI and the plasmid now with eight bases deleted between SalI and DraI was used as a vector for the 1.6 kpb pTH29 SalI and DraI fragment. The resulting plasmid pRW759 was cut with EcoRV and DraI. The 1.7 kbp PRW759 EcoRV-DraI fragment containing the 3' H6 promoter and the H5 gene was inserted between the EcoRV and HincII sites of pRW846 (previously described). The resulting plasmid pRW849 contains the H6 promoted avian influenza virus H5 gene in the de-ORFed F8 locus.

Construction of Insertion Vector for H7 Hemagglutinin at the F7 Locus. Plasmid pCVH71 containing the H7 hemagglutinin from A/CK/VIC/1/85 was received from Dr. R. Webster. An EcoRI-BamHI fragment containing the H7 gene was blunt-ended with the Klenow fragment of DNA polymerase and inserted into the HincII site of pIBI25 as PRW827. Synthetic oligonucleotides RW165 (SEQ ID NO:62) and RW166 (SEQ ID NO:63) were annealed, cut with HincII and StyI and inserted between the EcoRV and StyI sites of pRW827 to generate pRW845.

RW165 (SEQ ID NO:62): 5' GTACAGGTCGACAAGCTTCCCGGGTATCGCGATATCCGTTAAGTTTGTATCGTAATGAATACTCAAATTCTAATACTCACTCTTGTGGCAGCCATTCACACAAATGCAGACAAAATCTGCCTTGGACATCAT 3'

RW166 (SEQ ID NO:63): 5' ATGATGTCCAAGGCAGATTTTGTCTGCATTTGTGTGAATGGCTGCCACAAGAGTGAGTATTAGAATTTGAGTATTCATTACGATACAAACTTAACGGATATCGCGATACCCGGGAAGCTTGTCGACCTGTAC 3'

Oligonucleotides RW165 (SEQ ID NO:62) and RW166 (SEQ ID NO:63) link the 3' portion of the H6 promoter to the H7 gene. The 3' non-coding end of the H7 gene was removed by isolating the linear product of an ApaLI digestion of pRW845, recutting it with EcoRI, isolating the largest fragment and annealing with synthetic oligonucleotides RW227 (SEQ ID NO:64) and RW228 (SEQ ID NO:65). The resulting plasmid was pRW854.

RW227 (SEQ ID NO:64): 5' ATAACATGCGGTGCACCATTTGTATATAAGTTAACGAATTCCAAGTCAAGC 3'

RW228 (SEQ ID NO:65): 5' GCTTGACTTGGAATTCGTTAACTTATATACAAATGGTGCACCGCATGTTAT 3'

The stop codon of H7 in PRW854 is followed by an HpaI site. The intermediate H6 promoted H7 construct in the de-ORFed F7 locus (described below) was generated by moving the pRW854 EcoRV-HpaI fragment into pRW858 which had been cut with EcoRV and blunt-ended at its PstI site. Plasmid pRW858 (described below) contains the H6 promoter in an F7 de-ORFed insertion plasmid.

The plasmid pRW858 was constructed by insertion of an 850 bp SmaI/HpaI fragment, containing the H6 promoter linked to a non-pertinent gene, into the SmaI site of pF7D0 described previously. The non-pertinent sequences were excised by digestion of pRW858 with EcoRV (site 24 bp upstream of the 3'-end of the H6 promoter) and PstI. The 3.5 kb resultant fragment was isolated and blunt-ended using the Klenow fragment of the E. coli DNA polymerase in the presence of 2 mM dNTPs. This blunt-ended fragment was ligated to a 1700 bp EcoRV/HpaI fragment derived from pRW854 (described previously). This EcoRV/HpaI fragment contains the entire AIV HA (H7) gene juxtaposed 3' to the 3'-most 24 bp of the VV H6 promoter. The resultant plasmid was designated pRW861.

The 126 bp EH arm (defined previously) was lengthened in pRW861 to increase the recombination frequency with genomic TROVAC DNA. To accomplish this, a 575 bp AccI/SnaBI fragment was derived from pRW 731.13 (defined previously). The fragment was isolated and inserted between the AccI and NaeI sites of pRW861. The resultant plasmid, containing an EH arm of 725 bp and a HB arm of 404 bp flanking the AIV H7 gene, was designated as pRW869. Plasmid pRW869 therefore consists of the H7 coding sequence linked at its 5' end to the vaccinia virus H6 promoter. The left flanking arm consists of 404 bp of TROVAC sequence and the right flanking arm of 725 bp of TROVAC sequence which directs insertion to the de-ORFed F7 locus.

Development of TROVAC-Avian Influenza Virus Recombinants. Insertion plasmids containing the avian influenza virus HA coding sequences were individually transfected into TROVAC infected primary CEF cells by using the calcium phosphate precipitation method previously described (Panicali et al., 1982; Piccini et al., 1987). Positive plaques were selected on the basis of hybridization to HA specific radiolabelled probes and subjected to sequential rounds of plaque purification until a pure population was achieved. One representative plaque was then amplified to produce a stock virus. Plasmid pRW849 was used in an in vitro recombination test to produce recombinant TROVAC-AIH5 (vFP89) expressing the H5 hemagglutinin. Plasmid pRW848 was used to produce recombinant TROVAC-AIH4 (vFP92) expressing the H4 hemagglutinin. Plasmid pRW869 was used to produce recombinant TROVAC-AIH7 (vFP100) expressing the H7 hemagglutinin.

Immunofluorescence. In influenza virus infected cells, the HA molecule is synthesized and glycosylated as a precursor molecule at the rough endoplasmic reticulum. During passage to the plasma membrane it undergoes extensive post-translational modification culminating in proteolytic cleavage into the disulphide linked $HA_1$ and $HA_2$ subunits and insertion into the host cell membrane where it is subsequently incorporated into mature viral envelopes. To determine whether the HA molecules produced in cells infected with the TROVAC-AIV recombinant viruses were expressed on the cell surface, immunofluorescence studies were performed. Indirect immunofluorescence was performed as described (Taylor et al., 1990). Surface expression of the H5 hemagglutinin in TROVAC-AIH5, H4 hemagglutinin in TROVAC-AIH4 and H7 hemagglutinin in TROVAC-AIH7 was confirmed by indirect immunofluorescence. Expression of the H5 hemagglutinin was detected using a pool of monoclonal antibodies specific for the H5HA. Expression of the H4HA was analyzed using a goat monospecific anti-H4 serum. Expression of the H7HA was analyzed using a H7 specific monoclonal antibody preparation.

Immunoprecipitation. It has been determined that the sequence at and around the cleavage site of the hemagglutinin molecule plays an important role in determining viral virulence since cleavage of the hemagglutinin polypeptide is necessary for virus particles to be infectious. The hemagglutinin proteins of the virulent H5 and H7 viruses possess more than one basic amino acid at the carboxy terminus of HA1. It is thought that this allows cellular proteases which recognize a series of basic amino acids to cleave the hemagglutinin and allow the infectious virus to spread both in vitro and in vivo. The hemagglutinin molecules of H4 avirulent strains are not cleaved in tissue culture unless exogenous trypsin is added.

In order to determine that the hemagglutinin molecules expressed by the TROVAC recombinants were authentically processed, immunoprecipitation experiments were performed as described (Taylor et al., 1990) using the specific reagents described above.

Immunoprecipitation analysis of the H5 hemagglutinin expressed by TROVAC-AIH5 (vFP89) showed that the glycoprotein is evident as the two cleavage products $HA_1$ and $HA_2$ with approximate molecular weights of 44 and 23 kDa, respectively. No such proteins were precipitated from uninfected cells or cells infected with parental TROVAC. Similarly immunoprecipitation analysis of the hemagglutinin expressed by TROVAC-AIH7 (vFP100) showed specific precipitation of the $HA_2$ cleavage product. The $HA_1$ cleavage product was not recognized. No proteins were specifically precipitated from uninfected CEF cells or TROVAC infected CEF cells. In contrast, immunoprecipitation analysis of the expression product of TROVAC-AIH4 (vFP92) showed expression of only the precursor protein $HA_0$. This is in agreement with the lack of cleavage of the hemagglutinins of avirulent subtypes in tissue culture. No H4 specific proteins were detected in uninfected CEF cells or cells infected with TROVAC. Generation of recombinant virus by recombination, in situ hybridization of nitrocellulose filters and screening for B-galactosidase activity are as previously described (Panicali et al., 1982; Perkus et al., 1989).

Example 14

Generation of NYVAC- and ALVAC-Based Recombinant Containing the Gene Encoding Human Tumor Necrosis Factor-α (TNF-α)

TNF-α is a cytokine produced by CTLs. It is one of the products of these cells that is responsible for killing tumor cells during an immune response. It has previously been shown that the injection of recombinant TNF could mediate the necrosis and regression of a variety of established murine cancers (Asher et al., 1987). The exact mechanisms for this anti-tumor activity remain unclear, although TNF apparently affects the vascular supply of tumors (Asher et al., 1987). Both the secreted and membrane-bound forms of TNF-α may be critical for its anti-tumor activities (Kriegler et al., 1987).

Plasmid pE4, containing the human necrosis factor-α gene was extracted from *E. coli* transformed with this plasmid. The pE4 transformed *E. coli* were obtained from ATCC (ATCC #CLN-39894). PCR fragment PCR-TNF4 (755 bp) was generated using pE4 as template and oligonucleotides TNF3 (SEQ ID NO:66); 5'-ATCATCTCGCGATATCCGTTAAGTTTGTATCGTA ATGAGCACTGAAAGCATGATC-3') containing the 3'-most region of the vaccinia H6 promoter (from the NruI site to the end; Perkus et al., 1989) and the first 21 bp of the TNF-α coding sequence, and oligonucleotide TNF2 (SEQ ID NO:67) (5'-ATCATCTCTAGAATAAAAATCACAGGGCAATGAT CCC-3'), containing the last 15 bp of the TNF-α coding sequence, a vaccinia early transcription termination signal (T₅NT; Yuen and Moss, 1986), and an XbaI restriction site. A complete NruI/XbaI digestion was performed and the resultant 735 bp fragment was isolated and inserted into the 4.8 kb NruI/XbaI fragment obtained by the digestion of the generic insertion plasmid pVQH6C5LSP. The resultant plasmid was designated pMAW048. The nucleotide sequence of the entire H6-TNF-α expression cassette was confirmed as described by Goebel et al. (1990).

Plasmid pVQH6C5LSP was derived in the following manner:

A C5 insertion vector containing 1535 bp upstream of C5, polylinker containing KpnI, SmaI, XbaI, and NotI sites, and 404 bp of canarypox DNA (31 bp of C5 coding sequence and 373 bp of downstream sequence) was derived in the following manner. A genomic library of canarypox DNA was constructed in the cosmid vector pVK102 (Knauf et al., 1982) probed with pRW764.5 and a clone containing a 29 kb insert identified (pHCOS1). A 3.3 kb ClaI fragment from pHCOS1 containing the C5 region was identified. Sequence analysis of the ClaI fragment was used to extend the sequence in FIG. 8 (SEQ ID NO:68) from nucleotides 1–1372.

The C5 insertion vector was constructed as follows. The 1535 bp upstream sequence was generated by PCR amplification using oligonucleotides C5A (SEQ ID NO:69) (5'-ATCATCGAATTCTGAATGTTAAATGTTATACTTG-3') and C5B (SEQ ID NO:75) (5'-GGGGGTACCTTTGAGAGTACCACTTCAG-3') and purified genomic canarypox DNA as template. This fragment was digested with EcoRI (within oligo C5A) and cloned into EcoRI/SmaI digested pUC8 generating pC5LAB. The 404 bp arm was generated by PCR amplification using oligonucleotides C5C (SEQ ID NO:71) (5'-GGGTCTAGAGCGGCCGCTTATAAAGATCTAAAAT GCATAATTTC-3') and C5DA (SEQ ID NO:72) (5'-ATCATCCTGCAGGTATTCTAAACTAGGAATAGATG-3'). This fragment was digested with PstI (within oligo C5DA) and cloned into SmaI/PstI digested pC5LAB generating pC5L. pC5L was digested within the polylinker with Asp718 and NotI, treated with alkaline phosphatase and ligated to kinased and annealed oligonucleotides CP26 (SEQ ID NO:73) (5'-GTACGTGACTAATTAGCTAT AAAAAGGA TCCGGTACCCTCGAGTCTAGAATC GATCCCGGGTTTTTATGACTAGTTAATCAC-3') and CP27 (SEQ ID NO:74) (5'-GGCCGTGATTAACTAGTCATAAAAACCC GGGATC-GATTCTAGACTCGAGGGTACCGGATCC TTTTTATAGCTAATTAGTCAC-3') (containing a disabled Asp718 site, translation stop codons in six reading frames, vaccinia early transcription termination signal (Yuen and Moss, 1987), BamHI, KpnI, XhoI, XbaI, ClaI, and SmaI restriction sites, vaccinia early transcription termination signal, translation stop codons in six reading frames, and a disabled NotI site) generating plasmid pC5LSP.

The early/late H6 vaccinia virus promoter (Perkus et al., 1989) was derived by PCR from a plasmid containing the promoter using oligonucleotides CP30 (SEQ ID NO:75) (5'-TCGGGATCCGGGTTAATTAATTAGTCATCA GGCAGGGCG-3') and CP31 (SEQ ID NO:76) (5'-TAGCTCGAGGGTACCTACGATACAAACTTAACGG ATATCG-3'). The PCR product was digested with BamHI and XhoI (sites created at the 5' and 3' termini by the PCR) and ligated to similarly digested pC5LSP generating pVQH6C5LSP.

Plasmid pMAW048 was used in in vitro recombination assays with ALVAC (CPpp) as rescue virus to yield recombinant virus vCP245. Insertion with this plasmid replaces the two copies of the C5 open reading frame with the human TNF-α expression cassette. FIG. 15 presents the nucleotide sequence of the H6/TNFα sequence and flanking regions within vCP245 (SEQ ID NO:79). The H6 promoter starts at position 74. The TNF-α start codon is at position 201, and the TNF-α stop codon is at position 902. Positions 1 through 73 and positions 903 through 965 flank the H6/TNF-α expression cassette.

PCR fragment PCR-TNFH6 (156 bp) was amplified from plasmid pBSH6 using oligonucleotides H65PH (SEQ ID NO:80) (5'-ATCATCAAGCTTGATTCTTTATTCTATAC-3') containing a HindIII site in the initial 21 bp of the H6 promoter region and TNFH6 (SEQ ID NO:81) (5'-CATGCTTTCAGTGCTCATTACGATACAAACTTAAC GG-3') containing the 3'-most 19 nucleotides of the H6 promoter and the 5'-most 18 nucleotides of the TNF coding sequence.

Plasmid pBSH6 was generated in the following manner. The vaccinia H6 promoter through the EcoRV site was derived from a plasmid containing the synthetic H6 promoter (Perkus et al., 1989) using PCR and primers H6PCR2 (SEQ ID NO:82) (5'-TTAACGGATATCGCGATAATG-3') and H6PCR1 (SEQ ID NO:83) (5'-ACTACTAAGCTTCTTTATTCTATACTTAAAAAGTG-3') creating a 5' HindIII site. This 122 bp PCR-derived fragment was digested with HindIII and EcoRV followed by ligation to similarly digested pBS-SK⁺ (Stratagene, La Jolla, Calif.) generating plasmid pBSH6. The insert was confirmed by nucleotide sequence analysis.

PCR fragment PCR-TNF (721 bp) was amplified from plasmid pE4 using oligonucleotides TNF1 (SEQ ID NO:84) (5'-ATGAGCACTGAAAGCATG-3') containing the initial 18 nucleotides of the TNF-α coding sequence and TNF2

(SEQ ID NO:67). The PCR fragment, PCR-TNF fusion (859 bp), was generated using PCR-TNFH6 and PCR-TNF as templates and oligonucleotides H65PH (SEQ ID NO:80) and TNF2 (SEQ ID NO:67) as primers. PCR-TNF fusion was digested with HindIII and XbaI and the resultant 841 bp fragment was inserted into pBS-SK+ (Stratagene, La Jolla, Calif.) digested with HindIII and XbaI. The resultant plasmid was designated pMAW047 and the H6-TNF cassette was confirmed by nucleotide sequence analysis as described previously (Goebel et al., 1990).

The 841 bp HindIII/XbaI fragment containing the H6-TNF-α expression cassette was isolated from pMAW047, blunt-ended using the Klenow fragment of the E. coli DNA polymerase in the presence of 2 mM dNTPs, and inserted into the vaccinia insertion plasmid pSD541. The resultant plasmid was designated pMAW049.

Plasmid pSD541 was derived in the following manner. Flanking arms for the ATI region were generated by PCR using subclones of the Copenhagen HindIII A region as template. Oligonucleotides MPSYN267 (SEQ ID NO:85) (5'-GGGCTCAAGCTTGCGGCCGCTCATTAGA CAAGCGAATGAGGGAC-3') and MPSYN268 (SEQ ID NO:86) (5'-AGATCTCCCGGGCTCGAGTAATTAATTAA TTTTTA TTACACCAGAAAAGACGGCTTGAGATC-3') were used to derive the 420 bp vaccinia arm to the right of the ATI deletion. Synthetic oligonucleotides MPSYN269 (SEQ ID NO:87) (5'-TAATTACTCGAGCCCGGGAGATCTA ATTTAATTTA ATTTATATAACTCATTTTTTGAATATACT-3') and MPSYN270 (SEQ ID NO:88) (5'-TATCTCGAATTCCCGCGGCTTTAAATGGACGGAAC TCTTTTCCCC-3') were used to derive the 420 bp vaccinia arm to the left of the deletion. The left and right arms were fused together by PCR and are separated by a polylinker region specifying restriction sites for BglII, SmaI, and XhoI. The PCR-generated fragment was digested with HindIII and EcoRI to yield sticky ends, and ligated into pUC8 digested with HindIII and EcoRI to generate pSD541.

The plasmid pMAW047 was used in in vitro recombination assays (Piccini et al., 1987) with NYVAC (vP866; Tartaglia et al., 1992) as the rescue virus. Recombination with this plasmid replaces the ATI open reading frame with the H6-TNF-α expression cassette. The NYVAC recombinant virus containing the H6-TNF-α cassette was designated vP1200. FIG. 16 presents the nucleotide sequence of the H6/TNF-α expression cassette incorporated into the NYVAC recombinant, vP1200, and flanking NYVAC sequences (SEQ ID NO:89). The H6 promoter starts at position 59. The TNF-α start codon is at position 185, and the TNF-α stop codon is at position 884. Positions 1 through 58 and positions 885 through 947 flank the H6/TNF-α expression cassette.

TABLE 21

Expression of Human TNF-α by vP1200 and vCP245

| Sample | Description | TNF-α (ng/ml) |
|---|---|---|
| vP1196 | NYVAC-CMVgB+pp65 | 0 |
| vP1200 | NYVAC-TNF-α | >240 |
| CPpp | ALVAC | 0 |
| vCP245 | ALVAC-TNF-α | 59 |

Expression of TNF-α by vP1200 (NYVAC-TNF-α) and vCP245 (ALVAC-TNF-α) was measured by ELISA assay, using a commercially available kit (Genzyme Diagnostics, Cambridge, Mass., cat.#1915-01). Samples were prepared by infection of Vero cells (NYVAC recombinants) or primary chick embryo fibroblasts (ALVAC) with recombinant or parent virus. The cells were harvested when CPE was complete and the infected cell lysates were used for the ELISA assay, after sonication and clarification by centrifugation at 500×g for 10 min. One control, vP1196, which expresses two cytomegalovirus proteins, gB and pp65, was prepared in the same manner as the TNF-α recombinants. The other control, ALVAC parent, was a partially purified virus stock. All samples contained approximately $10^7$ PFU/ml of virus. The results, shown in Table 21, indicate that both vP1200 and vCP245 are expressing human TNF-α. Expression of such levels in vivo can be therapeutic.

Example 15

NYVAC and ALVAC-Based p53 Recombinant Viruses

The nuclear phosphoprotein, p53, is found in normal cells at very low steady state levels. Expression of p53 is tightly regulated throughout the cell cycle and may be involved in controlling cell proliferation. The molecular mechanisms by which p53 exerts its tumor suppressor activity remain unknown, although p53 appears to exist in two conformational states. One form is unique to wildtype p53 and is associated with the ability to block cell cycle progression while the second form is associated with the ability to promote cell proliferation and is common to wildtype and mutant forms (reviewed by Ulrich et al., 1992). p53 is the gene most frequently found to be mutated in a wide variety of human tumors (reviewed by Hollstein et al., 1991).

Probably the most studied cancer associated with p53 mutation is breast cancer. It is known that p53 mutation results in the overexpression of the p53 gene product in primary breast cancer patients (Davidoff et al., 1991). The basis for p53 overexpression was found to result from a post-transcriptional mechanism, since p53-specific mRNA levels were similar in tumors with high and low level protein expression. Further, the p53 mRNA from overexpressing tumors were found to contain missense mutations in highly conserved regions of the gene. These mutations were subsequently found to give rise to more stable p53 protein forms which form complexes with heat shock protein 70 (HSP-70). Since HSP-70 proteins have been implicated in antigen processing, not only may the humoral response to p53 observed in a subset of breast cancer patients have resulted from unique processing/presentation modes for complexes, such an association may also elicit cellular anti-p53 protein responses (Davidoff et al., 1992). Such anti-p53 cellular immune responses may be more germane to the eventual immunotherapy of such cancers.

Generation of Poxvirus-based Recombinant Viruses Expressing Wildtype and Mutant Forms of the Human p53 Gene Product Three plasmids, p53wtXbaISP6/T3, p53-217XbaI, and p53-238XbaI containing wildtype human p53 gene sequences, and two mutant forms of p53, respectively, were obtained from Dr. Jeffrey Marks (Duke University). The p53-217XbaI contains a p53 gene encoding a p53 product lacking codon 217 while p53-238XbaI encodes a p53 gene product with an cysteine to arginine substitution at amino acid 238. The sequence of the wildtype p53 cDNA and the deduced amino acid sequence was described previously (Lamb and Crawford, 1986; FIG. 3).

All three p53 genes were individually juxtaposed 3' to the modified vaccinia virus H6 promoter described by Perkus et al., 1989. These manipulations were performed in the following manner. A 227 bp PCR-derived fragment was generated using oligonucleotides MM002 (SEQ ID NO:90) (5'-GATCTGACTGCGGCTCCTCCATTACGATAC AAACTTAACGG-3') and RW425 (SEQ ID NO:91) (5'-GTGGGTAAGGGAATTCGGATCCCCGGGTTAATTAA TTAGTGATAC-3') and plasmid pRW825 as template. PCR using these oligonucleotides amplifies the vaccinia H6 promoter sequences from pRW825 such that the 3' end of the promoter is precisely linked to the 5'most region of the p53 coding sequence. Plasmid pRW825 contains the vaccinia virus H6 promoter (Perkus et al., 1989) linked to a nonpertinent gene.

PCR was also used to generate a 480 bp and 250 bp fragment from p53wtXbaISP6/T3. The 480 bp fragment was derived with oligonucleotides MM003 (SEQ ID NO:92) (5'-GTTTGTATCGTAATGGAGGAGCCGCAGTCA GATC-3') and MM008 (SEQ ID NO:93) (5'-CATTACGATACAAACTTAACGGATATCGCGACGCG TTCACACAGGGCAGGTCTTGGC-3'). This fragment contains the 3' portion of the vaccinia virus H6 promoter sequences and the 5' portion of the p53 coding sequences through the SgrAI site. The 250 bp fragment was derived by amplification with oligonucleotides MM005 (SEQ ID NO:94) (5'-TACTACCTCGAGCCCGGGATAAAAAA CGCGTTCAGTCTGAGTCAGGCCC-3') and MM007 (SEQ ID NO:95) (5'-GTGTGAACGCGTCGCGATATCCGTTAAGTTTGTAT CGTAATGCAGCTGCGTGGGCGTGAGCGCTTC-3'). This PCR fragment contains the 3' end of the p53 coding sequences beginning at the StuI restriction site. The 480 bp and 250 bp PCR fragments were generated such that the 5' end of the MM005/MM007-derived (SEQ ID NO:94/95) fragment overlaps the 3' end of the MM003/MM008-derived (SEQ ID NO:92/93) fragment.

The 227 bp, 480 bp, and 250 bp PCR-derived fragments were pooled and fused by PCR using oligonucleotides MM006 (SEQ ID NO:96) (5'-ATCATCGGATCCCCCGGGTTCTTTATTCTATAC-3') and MM005 (SEQ ID NO:94). The 783 bp fused PCR product contains the H6 promoter juxtaposed 5' to the 5' portion of the p53 coding sequence (through the SgrAI restriction site) followed by the end of the p53 coding sequence beginning at the StuI site. Following the end of the p53 coding sequence, a $T_5NT$ sequence motif providing early vaccinia transcription termination (Yuen and Moss, 1986) and a unique XhoI site were added. It should be noted that the final H6-p53 PCR fusion product (783 bp) does not contain the p53 coding sequences between the SgrAI and StuI restriction sites.

The 783 bp fusion was digested with BamHI (5' end) and XhoI (3' end) and inserted into plasmid pSD550 to yield plasmid pMM105. Plasmid pSD550 enables the insertion of foreign genes into the vaccinia I4L locus by replacing the I4L coding sequence. This plasmid was derived from pSD548 (Tartaglia et al., 1992) by first digesting this plasmid with BglII and SmaI. This digested plasmid was then ligated to annealed oligonucleotides 539A (SEQ ID NO:97) (5'-AGAAAAATCAGTTAGCTAAGATCTCCCGGG CTCGAGGGTACCGGATCCTGATTAGTTAATTTTTGT-3') and 539B (SEQ ID NO:98) (5'-GATCACAAAAATTAACTAATCAGGATCCGGTACCC TCGAGCCCGGGAGATCTTAGCTAACTGATTTTTCT-3) to generate pSD550.

Plasmids containing intact p53 gene (wildtype or mutant forms) juxtaposed 3' to the H6 promoter were generated by first digesting pMM105 with SgrAI and StuI. A 795 bp SgrAI/StuI fragment was isolated from p53wtXbaISP6/T3 and p53–238XbaI, while a 792 bp fragment was isolated from p53-217XbaI. These fragments were individually ligated to the SgrAI/StuI digested pMM105 plasmid to yield pMM106, pMM108, and pMM107, respectively.

Plasmids pMM106, pMM107, and pMM108 were used in standard in vitro recombination experiments (Piccini et al., 1987) with NYVAC (vP866; Tartaglia et al., 1992) as the rescue virus to generate recombinant viruses vP1101, vP1096, and vP1098, respectively. FIG. 17 presents the nucleotide sequence of the wildtype p53 expression cassette and flanking regions within vP1101 (SEQ ID NO:99). The H6 promoter starts at position 145. The p53 start codon is at position 269, and the p53 stop codon is at position 1450. Positions 1 through 144 and positions 1451 through 1512 flank the H6/p53 expression cassette. The sequences within vP1096 and vP1098 are identical except vP1096 contains a 3 base deletion from nucleotide 920 to 922 while vP1101 contains a point mutation at nucleotide 980 (T or C).

Both immunofluorescence and immunoprecipitation assays were performed using a p53-specific monoclonal antibody (pAB1801, Oncogene Science provided by Dr. J. Marks) to demonstrate expression of p53 in vP1101, vP1098 and vP1096 infected Vero cells. These assays were performed as described previously (Taylor et al., 1990). Immunofluorescence assay demonstrated p53-specific fluorescent staining of cells infected with vP1101, vP1096, or vP1098. The p53 antigen was located in both the nucleus and cytoplasm of the infected cells. The nuclear staining, however, was more intense in vP1101 infected cells. These results are similar to those reported by Ronen et al. (1992) using replication-competent vaccinia to express wildtype and mutant forms of p53. No p53-specific fluorescent staining was observed in Vero cells infected with the parental NYVAC virus, vP866.

ALVAC (CPpp) p53 insertion plasmids were engineered by excising the p53 expression cassettes from pMM106, pMM107, and pMM108 by digestion with BamHI and XhoI and inserting them individually into BamHI/XhoI digested pNVQC5LSP-7. The 1320 bp BamHI/XhoI fragment containing the H6-p53 expression cassette from pMM106 and pMM108 was inserted into pNVQC5LSP-7 to yield pMM110 and pMM112, respectively, while the 1317 bp BamHI/XhoI fragment derived from pMM107 and inserted into pNVQC5LSP-7 yielded pMM111.

The plasmid pNVQC5LSP-7 was derived in the following manner. pC5LSP (defined in Example 1) was digested with BamHI and ligated to annealed oligonucleotides CP32 (SEQ ID NO:100) (5'-CATCTTAATT AATTAGTCATCAG-GCAGGG CGAGAACGAAGACTATCTGCTCGTTAAT-TAATTA GGTCGACG-3') and CP33 (SEQ ID NO:101) (5'-CATCCGTCGACCTAATTAATTAACGACGACA TAGT CTCGTTCTCGCCTGCCTGATGACTAATTAA TTAA-3') to generate pVQC5LSP6. pVQC5LSP6 was digested with EcoRI, treated with alkaline phosphatase and ligated to self-annealed kinased oligonucleotide CP29 (SEQ ID NO:102) (5'-AATTGCGGCCGC-3'), digested with NotI and linear was purified followed by self-ligation. This procedure introduced a NotI site to pVQC5LSP6, generating pNVQC5LSP-7.

Insertion plasmids pMM110, pMM111, and pMM112 were used in standard in vitro recombination experiments (Piccini et al., 1987) with ALVAC (CPpp) as the rescue virus to yield vCP207, vCP193 and vCP191, respectively. Confirmation of expression of the p53 gene product was accomplished by immunoprecipitation assays performed as described above. FIG. 18 presents the nucleotide sequence of the H6/p53 (wildtype) expression cassette and flanking regions from vCP207 (SEQ ID NO:103). The H6 promoter starts at position 109. The p53 start codon is at position 233, and the p53 stop codon is at position 1414. Positions 1 through 232 and positions 1415 through 1483 flank the H6/p53 expression cassette. The nucleotide sequence is identical to that within vCP193 and vCP191 except vCP193 contains a 3 nucleotide deletion from nucleotide 973 to 975 while vCP191 contains a point mutation at nucleotide 94 to (T to C).

A listing of the NYVAC- and ALVAC-based p53 recombinant viruses is provided in Table 22.

TABLE 22

NYVAC and ALVAC-based p53 recombinant viruses

| Recombinant Virus | Parent Virus | Gene Insert |
| --- | --- | --- |
| vP1101 | NYVAC | w.t. 53 |
| vP1096 | NYVAC | p53 (–aa 217) |
| vP1098 | NYVAC | p53 (aa238; C to R) |
| vCP207 | ALVAC | w.t. 53 |
| vCP193 | ALVAC | p53 (–aa 217) |
| vCP191 | ALVAC | p53 (aa 238; C to R) |

Example 16

Utility of NYVAC- and ALVAC-Based Recombinant Viruses Containing the Mage-1 Gene Human melanoma-associated antigen MZ2-E is encoded by the MAGE-1 gene (Reviewed by van der Bruggen and Van der Eynde, 1992). MAGE-1 is expressed in primary melanoma tumor cells, melanoma-derived cell lines, and certain tumors of non-melanoma origins but not in normal cells except in testis (Coulie et al., 1993). Of interest from an immunological perspective, CTLs from melanoma-bearing patients that are of the HLA-A1 MHC haplotype are known to recognize a nonapeptide from the MZ2-E gene product (Traveseri et al., 1992). Therefore, definition of such an antigen provides a mechanism for targeted immunotherapy for HLA-typed (HLA-A1) melanoma patients.
Generation of NYVAC- and ALVAC-based Recombinant Viruses Containing the MAGE-1 Gene PCR fragment PCR-H6 (162 bp) was synthesized using pBSH6 (described in Example 14) as template and oligonucleotides H65PH (SEQ ID NO:80) and M1-4 (SEQ ID NO:104) (5'-CAGACTCCTCTGCTCAAGAGACATTA CGATACAAACTTAACG-3') which contains the last 18 bp of the H6 promoter and the initial 24 nucleotides of the MAGE-1 gene. A second PCR fragment (PCR-M1) was amplified from plasmid pTZ18RMAGE1 using oligonucleotides M1-1 (SEQ ID NO:105) (5'-ATGTCTCTTGAGCAGAGGAGTCTG-3' and M1-2 (SEQ ID NO:106) (5'-CAGGCCATCATAGGAGAGACC-3'). The resultant PCR fragment represents the initial 546 bp of the MAGE-1 coding sequence.

Plasmid pTZ18RMAGE-1 contains a cDNA clone of the MAGE-1 gene. This gene encodes the MZE-2 human melanoma rejection antigen. This plasmid was provided by Dr. Lloyd Old (Memorial Sloan-Kettering, NY, N.Y.) who obtained the plasmid originally from Dr. Thierry Boon (Ludwig Inst. for Cancer Research, Brussels, Belgium).

PCR fusion product, PCR-H6M1 was generated using PCR-H6 and PCR-M1 as templates and oligonucleotides H65PH (SEQ ID NO:80) and M1-2 (SEQ ID NO:106) as primers. A complete HindIII/BglII digestion of PCR-H6M1 was performed and the resultant 556 bp was purified for subsequent cloning steps.

PCR fragment PCR-M3' (535 bp) was amplified from pTZ18RMAGE-1 using oligonucleotides M1-3 (SEQ ID NO:107) (5'-GTGGCTGATTTGGTTGGTTTTCTG-3') which contains 24 nucleotides complementary to the MAGE-1 gene at a region approximately 200 bp upstream of the M1-2 oligonucleotide sequence and M1-5 (SEQ ID NO:108) (5'-ATCATCTCTAGAAAAAAAATCACATAGC TGGTTTCAG-3') containing the terminal 15 nucleotides of the MAGE-1 coding sequence, a vaccinia early transcription termination signal ($T_5NT$; Yuen and Moss, 1986) and an XbaI restriction site. PCR-M3' was digested with BglII and XbaI. The resultant 414 bp fragment was isolated and co-inserted into HindIII/XbaI digested pBS-SK(+) with the 556 bp HindIII/BglII digested PCR fragment PCR-H6M1. The resultant plasmid containing the entire H6-MAGE-1 expression cassette was designated pMAW034. The H6-MAGE-1 cassette was confirmed by nucleotide sequence analysis as per Goebel et al., 1990).

The 864 bp NruI/XbaI fragment from pMAW034 was isolated and inserted into pVQH6C5LSP (described in Example 14) that was digested in a similar fashion. The resultant plasmid was designated pMAW036. This plasmid served as the insertion plasmid for replacing the two C5 ORFs in the ALVAC genome with the H6-MAGE-1 expression cassette.

Plasmid pMAW036 was used in standard in vitro recombination experiments with ALVAC as the rescuing virus. Recombinant virus were identified by an in situ plaque hybridization assay using MAGE-1-specific radiolabeled DNA probes. Recombinant plaques were plaque purified and amplified. The resultant ALVAC-based recombinant containing the MAGE-1 gene was designated vCP235. FIG. 19 presents the nucleotide sequence of the H6/MAGE-1 expression cassette and flanking region contained within vCP235 (SEQ ID NO:109). The H6 promoter starts at position 74. The MAGE-1 start codon is at position 201, and the MAGE-1 stop codon is at position 1031. Positions 1 through 73 and positions 1032 through 1094 flank the H6/MAGE-1 expression cassette.

The NYVAC (vP866) insertion plasmid pMAW037 was generated by initially digesting pMAW034 with NruI/ BamHI. The resultant 879 bp fragment was isolated and inserted into NruI/BamHI digested pSPHAH6. The resultant plasmid was designated pMAW037.

Plasmid pSPHAH6 was generated in the following manner. Plasmid pSD544 (containing vaccinia sequences surrounding the site of the HA gene replaced with a polylinker region and translation termination codons in six reading frames) was digested with XhoI within the polylinker, filled in with the Klenow fragment of DNA polymerase I and treated with alkaline phosphatase. SP126 (containing the vaccinia H6 promoter) was digested with HindIII, treated with Klenow and the H6 promoter isolated by digestion with SmaI. Ligation of the H6 promoter fragment to pSD544 generated SPHA-H6 which contained the H6 promoter in the polylinker region (in the direction of HA transcription).

Plasmid pMAW037 was used in standard in vitro recombination experiments (Piccini et al., 1987) with NYVAC (vP866) as the rescue virus. FIG. 20 presents the nucleotide sequence of the H6/MAGE-1 expression cassette and flanking regions within pMAW037 (SEQ ID NO:110). The H6 promoter starts at position 52. The MAGE-1 start codon is at position 179, and the MAGE-1 stop codon is at position 1009. Positions 1 through 51 and positions 1010 through 1084 flank the H6/MAGE-1 expression cassette.

Example 17

Generation of an ALVAC- and NYVAC-Based CEA Recombinant Viruses

The CEA gene was provided in plasmid pGEM.CEA, which contains the CEA coding sequence (2,109 nucleotides) as well as 5' and 3' untranslated regions (Dr. J. Schlom, NCI-NIH). The 5' end of the CEA construct was modified to remove the 5' untranslated sequences and place the vaccinia H6 promotor before the ATG initiation codon of CEA. This was accomplished by PCR with the oligonucleotide pair CEA1 (SEQ ID NO:111) (5'-TATCGCGATATCCGTTAAGTTTGTATCGTAATGGA GTCTCCCTCG-3') and CEA2 (SEQ ID NO:112) (5'-TGCTAGATCTTTATCTCTCGACCACTGTATG-3') and plasmid PGEM.CEA as template. The resulting fragment links the 3' 30 nucleotides of the H6 promotor to the CEA initiation codon, extends 22 nucleotides past the ApaI site at position 278 of the CEA coding sequence, and terminates with a BglII site introduced by the PCR primer CEA2 (SEQ ID NO:114). Prior to cloning, this fragment was digested with EcoRV (site located within the 3' end of the H6 promotor) and BglII. The digested 5' PCR fragment was then included in a 3-way ligation with two fragments derived from plasmid pI4L.H6: an NcoI/BglII vector fragment and an NcoI/EcoRV fragment which contained the 5' portion of the H6 promotor. The resulting plasmid, designated pI4L.H6.CEA-5', contains the full length H6 promotor linked to a 5' CEA fragment extending from the ATG codon through the APaI site at position 278.

The 3' end of CEA was modified to remove the 3' untranslated region of CEA and place a vaccinia early transcription termination signal ($T_5NT$) followed by a series of restriction sites (XhoI, XbaI, SmaI, HindIII) after the TAG termination codon. This was accomplished by PCR with the oligonucleotide pair CEA3 (SEQ ID NO:113) (5'-CTATGAGTGTGGAATCCAGAACG-3') and CEA4 (SEQ ID NO:114) (5'-TCAGAAGCTT CCCGGGTCTA-GACTCGAGATAAAAACTATATCAGA GCAACC-3') and plasmid pGEM.CEA as template. The resulting fragment extends from a position 32 nucleotides 5' of the CEA HindII site located at position 1203 through the 3' end of the coding sequence. This fragment was cloned as a HindII/HindIII fragment into a HindII/HindIII-digested pGEM-.CEA vector fragment. The resulting plasmid, designated pGEM.CEA-3', contains the entire CEA gene as found in pGEM.CEA with a 3' end modified to remove the 3' untranslated region and replace it with a $T_5NT$ signal followed by XhoI, XbaI, SmaI, and HindIII restriction sites.

To generate an ALVAC C3 donor plasmid containing CEA, a BamHI/ApaI fragment containing the H6 promotor linked to the 5' end of CEA was obtained from pI4L.H6.CEA-5', an ApaI/XhoI fragment containing the remainder of the CEA coding sequence (plus $T_5NT$) was obtained from pGEM.CEA-3', and a BamHI/XhoI C3 vector fragment was derived from plasmid p126. C3. After subsequent 3-way ligation, the plasmid pH6.CEA.C3 was obtained. This plasmid contains the full length H6/CEA expression cassette inserted between left and right flanking arms of ALVAC DNA which direct insertion to the C3 sites on the ALVAC genome. Transcription of CEA is oriented from right to left.

Plasmid p126.C3, an ALVAC C3 donor plasmid, was derived as follows. This plasmid contains an insert consisting of cDNA derived from the *Plasmodium falciparum* SERA gene (Li et al., 1989; Bzik et al., 1989; Knapp et al., 1989; NOTE: SERA is also known as SERP I and p126) under the control of the entomopox virus 42K early promotor.

A. Methodology for Generating p126.C3

1. Construction of *P. falciparum* FCR3 Strain Blood Stage cDNA Library

Total RNA from human erythrocytes infected with *P. falciparum* FCR3 strain was provided by Dr. P. Delplace (INSERM-U42). Poly-A$^+$ RNA was isolated from this sample by use of oligo(dT) cellulose (Stratagene, La Jolla, Calif.) as described by Aviv and Leder (1972) and modified by Kingston (1987). Briefly, total RNA was mixed with oligo(dT) cellulose in Binding buffer (0.5M NaCl, 0.01M Tris-Cl, pH 7.5) and incubated for 30 minutes at room temperature. Poly-A$^+$ RNA/oligo(dT) cellulose complexes were pelleted by centrifugation and washed 3 times with Binding buffer. Purified poly-A$^+$ RNA was eluted from the oligo(dT) cellulose in Elution buffer (0.01M Tris-Cl, pH 7.5). A second elution with DEPC-treated $dH_2O$ was performed, the eluates were pooled, and the poly-A$^+$ RNA recovered by ethanol precipitation.

The purified poly-A$^+$ RNA was used as a template for the synthesis of first strand cDNA by reverse transcriptase in a reaction primed with oligo(dT) (Watson and Jackson, 1985; Klickstein and Neve, 1987). For this reaction, 12 ug poly-$^+$ RNA was incubated with 105 units AMV reverse transcriptase (Life Sciences, Inc., St. Petersburg, Fla.) in 100 mM Tris-Cl pH 8.3, 30 mM KCl, 6 mM $MgCl_2$, 25 mM DTT, 80 units RNasin, 1 mM each dNTP, and 24 ug/ml oligo(dT)$_{12-18}$ as primer for 2 hours at 42° C. After organic extractions, double stranded cDNA was obtained by use of DNA polymerase I and RNase H with first strand cDNA as template (Watson and Jackson, 1985: Klickstein and Neve, 1987). The first strand cDNA was incubated with 25 units DNA polymerase I and 1 unit RNase H in 20 mM Tris-Cl pH 6, 5 mM $MgCl_2$, 10 mM $(NH_4)_2SO_4$, 100 mM KCl, 500 ug/ml BSA, 25 mM DTT, and 0.1 mM each dNTP at 12° C. for one hour followed by one hour at room temperature to synthesize second strand cDNA. The double stranded cDNA was recovered by organic extractions and ethanol precipitation.

The double-stranded blood stage cDNA was then sequentially treated with T4 DNA polymerase to create blunt ends and EcoRI methylase to protect internal EcoRI sites. EcoRI linkers were then added followed by digestion with EcoRI and size selection on a 5–25% sucrose gradient. Fractions containing long cDNAs (1–10 Kb) were pooled and ligated into EcoRI cleaved Lambda ZAPII vector (Stratagene, La Jolla, Calif.). The resulting phage were packaged and used to infect the XL-1 Blue *E. coli* strain (Stratagene). The phage were then harvested from these cells and amplified by one additional cycle of infection of XL-1 Blue to produce a high titer FCR3 strain blood stage cDNA library.

2. Screen of cDNA Library for SERA cDNA Clones

The FCR3 strain cDNA library was screened by plaque hybridization with $^{32}$P end-labelled oligonucleotides derived from published sequences of SERA to detect cDNA. The cDNA library was plaqued on lawns of XL-1 Blue (Stratagene) in 150 mm dishes at a density of 100,000 plaques per dish. Plaques were transferred to nitrocellulose filters which were then soaked in 1.5M NaCl/0.5M NaOH for 2 minutes, 1.5M NaCl/0.5M Tris-Cl pH 8 for 5 minutes, 0.2M Tris-Cl pH 7.5/2×SSC for one minute, and baked for 2 hours in an 80° C. vacuum oven. Filters were prehybridized in 6×SSC, 5×Denhardts, 20 mM $NaH_2PO_4$, 500 ug/ml salmon sperm DNA for two hours at 42° C. Hybridizations were performed in 0.4% SDS, 6×SSC, 20 mM $NaH_2PO_4$, 500 ug/ml salmon sperm DNA for 18 hours at 42° C. after the addition $^{32}$P-labelled oligonucleotide. After hybridization, filters were rinsed 3 times with 6×SSC, 0.1% SDS, washed for 10 minutes at room temperature, and washed for 5 minutes at 58° C. Filters were then exposed to X-ray film at −70° C.

Plaques hybridizing with the oligonucleotide probe were cored from plates and resuspended in SM buffer (100 mM NaCl, 8 mM MgSO$_4$, 50 mM Tris-Cl pH 7.5, 0.01% gelatin) containing 4% chloroform. Dilutions of such phage stocks were used to infect XL-1 Blue, plaques were transferred to nitrocellulose, and the filters were hybridized with $^{32}$P-labelled oligonucleotides. Well isolated positive plaques were selected and subjected to two additional rounds of purification as just described.

3. Isolation of SERA cDNA-containing Plasmids from Positive Phage Clones

SERA cDNAs in the pBluescript plasmid vector (Stratagene) were obtained by an in vivo excision protocol developed for use with the lambda ZAPII vector (Stratagene). Briefly, purified recombinant lambda phage stocks were incubated with XL-1 Blue cells and R408 filamentous helper phage for 15 minutes at 37° C. After the addition of 2×YT media (1% NaCl, 1% yeast extract, 1.6% Bacto-tryptone), incubation was continued for 3 hours at 37° C. followed by 20 minutes at 70° C. After centrifugation, filamentous phage particles containing pBluescript phagemid (with cDNA insert) were recovered in the supernatant. Dilutions of the recovered filamentous phage stock were mixed with XL-1 Blue and plated to obtain colonies containing pBluescript plasmids with SERA cDNA inserts.

4. Generation of Malaria cDNA by PCR

By use of the polymerase chain reaction (PCR), the 5' portion of the coding sequence of SERA was amplified with specific oligonucleotide primers and first strand cDNA as template (Saiki et al. 1988, Frohman et al. 1988). SERA-specific first strand cDNA was synthesized by reverse transcriptase using the reaction conditions described above and specific oligonucleotides as primers. RNA was subsequently eliminated by treatment with RNase A prior to PCR. The GeneAmp DNA amplification kit (Perkin Elmer Cetus, Norwalk, Conn..) was used for PCR. Briefly, first strand cDNA in 50 mM KCl, 10 mM Tris-Cl pH 8.3, 1.5 mM MgCl$_2$, 0.01% gelatin was mixed with 200 uM each dNTP, 1 uM of each primer, and 2.5 units Taq polymerase. Reactions were processed in a Thermal Cycler (Perkin Elmer Cetus) with 1 cycle of denaturation, annealing, and extension at 94° C. for 2 minutes, 43° C. for 3 minutes, and 72° C. for 40 minutes; 40 cycles at 94° C. for 1 minute, 43° C. for 2 minutes, and 72° C. for 4 minutes followed by a final extension at 72° C. for 20 minutes.

The inclusion of restriction sites in primers used for PCR allowed the cloning of amplified SERA cDNA into plasmid vectors. Clones containing cDNAs derived from two independent PCRs were obtained for each SERA cDNA that was amplified in order to control for Taq polymerase errors.

B. Results

1. Isolation, Cloning and Characterization of SERA cDNA

We have isolated overlapping cDNA clones spanning the SERA coding sequence from the FCR3 strain of *P. falciparum*. The p126.6 cDNA, which extends from the EcoRI site at position 1892 (numbering based on SERP I gene of FCBR strain; Knapp et al., 1989) through the 3' end of the coding sequence, was isolated from the blood stage cDNA Lambda ZAPII cDNA library by hybridization to a SERA-specific oligonucleotide JAT2 (SEQ ID NO:115) (5'-GTCTCAGAACGTGTTCATGT-3'), which is derived from the 3' end of the SERA coding sequence (Bzik et al., 1989; Knapp et al., 1989). Clones derived from the 5' end of the SERA coding sequence were obtained by PCR with primers JAT15 (SEQ ID NO:116) (5'-CACGGATCCATGAAGTCATATATTTCCTT-3') and JAT16 (SEQ ID NO:117) (5'-GTGAAGCTTAATCCATAATCTTCAATAATT-3') and SERA first strand cDNA template (obtained with oligonucleotide primer JAT17 (SEQ ID NO:118) (5'-GTGAAGCTTTTATACATAACAGAAATAACA-3')) and were cloned into pUC19 (New England Biolabs, Beverly, Mass.). These 1923 bp cDNAs extend from the initiation codon to a point 31 bp 3' of the internal EcoRI site (position 1892). One such cDNA, p126.8, was found by DNA sequence analysis to contain a Taq polymerase error at nucleotide 1357. This error, an A to G substitution, resides within the 315 bp KpnI/NdeI restriction fragment. A second SERA 5' cDNA, p126.9, has no mutations within this KpnI/NdeI fragment. An unmutated 5' SERA cDNA was generated by replacing the 315 bp KpnI/NdeI fragment in p126.8 with the analogous fragment from p126.9 to generate p126.14. Full length SERA cDNA was generated by ligating the p126.14 5' cDNA as an XmaI/EcoRI fragment into a partial EcoRI/XmaI digested p126.6 vector fragment to generate p126.15.

Figure 21A:
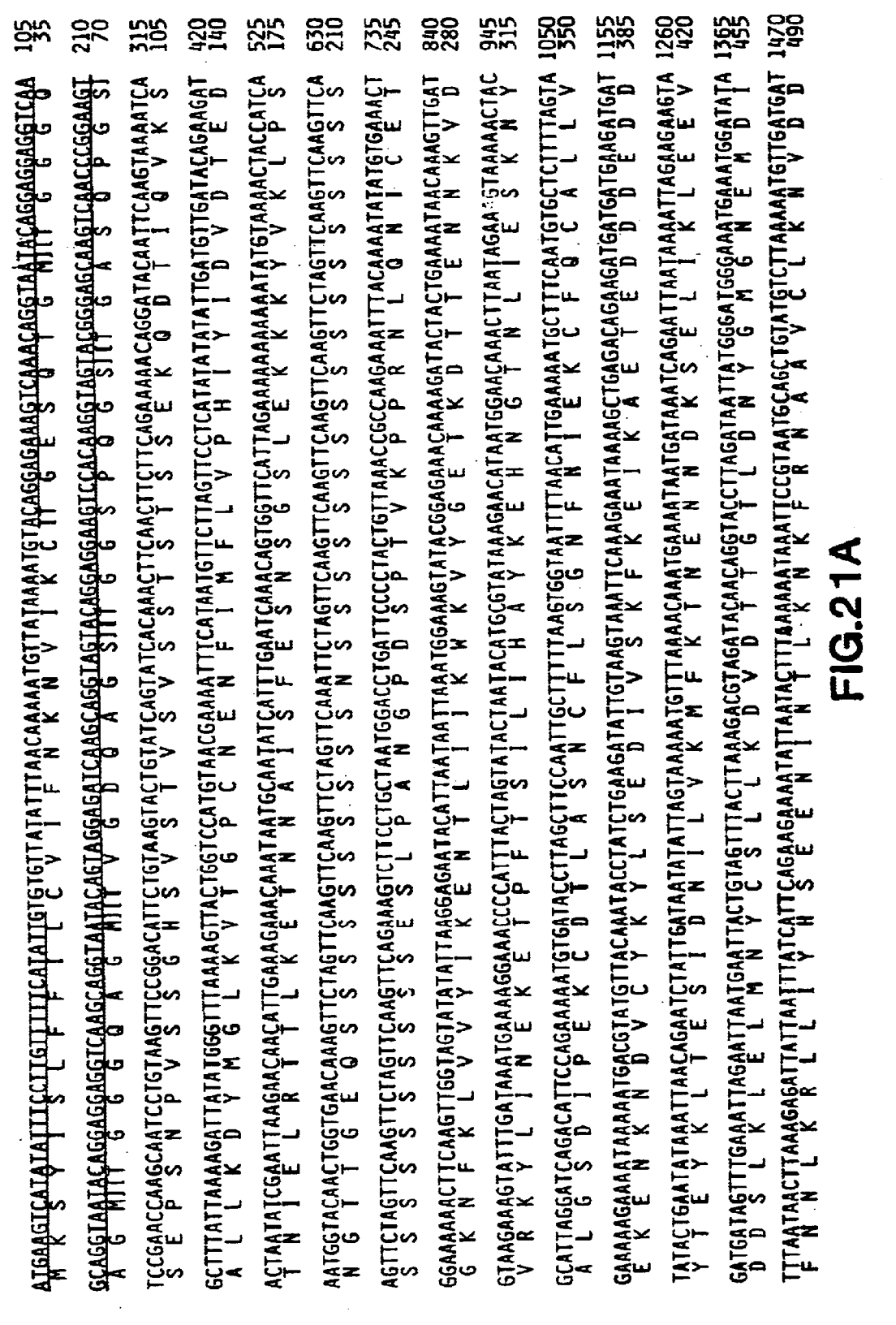
Figure 21B:
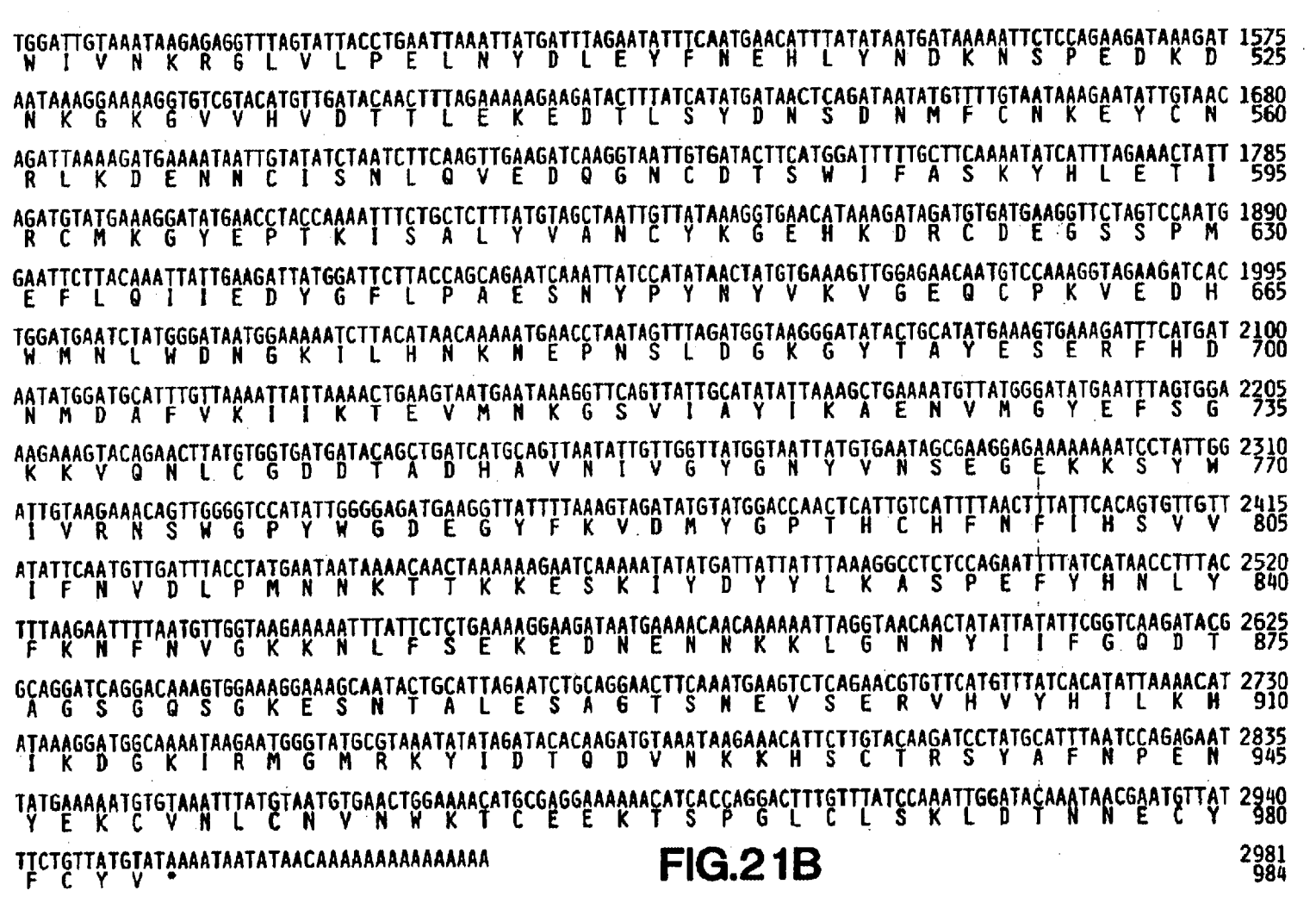

The complete nucleotide sequence of the p126.15 SERA cDNA insert was determined and is shown in FIGS. 21A and 21B (SEQ ID NO:119) along with the predicted amino acid sequence (SEQ ID NO:120). This cDNA contains a 2955 bp open reading frame encoding 984 amino acids that is identical to the SERA allele II gene in the FCR3 strain and the FCBR SERP I gene (Li et al., 1989, Knapp et al., 1989).

The SERA cDNA was isolated from p126.15 as a 3 Kb XmaI/EcoRV fragment and the XmaI end ligated into an XmaI/BglII digested pCOPCS-5H vector fragment. DNA polymerase I Klenow fragment was used to fill in the pCOPCS-5H BglII site which was subsequently ligated to the EcoRV end to generate p126.16. In this plasmid, SERA is under the control of the early/late vaccinia H6 promotor.

2. Modification of SERA cDNA

The 3' end of the SERA cDNA was modified to place a vaccinia early transcription termination signal (T$_5$NT; Yuen and Moss, 1987) and a series of restriction sites (XhoI, SmaI, SacI) immediately after the TAA termination codon. This was accomplished by PCR with oligonucleotides JAT51 (SEQ ID NO:121) (5'-TAGAATCTGCAGGAACTTCAA-3'), JAT52 (SEQ ID NO:122) (5'-CTACACGAGCTCCCGGGCTCGA GATAAAAATTATACATAACAGAAATAACATTC-3'), and plasmid p126.16 as template. The resulting ~300 bp amplified fragment was cloned as a PstI/SacI fragment into p126.16 digested with PstI and SacI to generate p126.17.

The 5' end of the SERA cDNA in p126.17 was modified to place several restriction sites (HindIII, SmaI, BamHI) and the 42K entomopox promotor before the ATG initiation codon. This was accomplished by PCR with oligonucleotides JAT53 (SEQ ID NO:123) (5'-CTAGAGAAGCTTCCCGGGATCCTCAAAATTG AAAATATATAATTACAATATAAAATGAAGTCATATA TTTCCTTGT-3'), JAT54 (SEQ ID NO:124) (5'-ACTTCCGGGTTGACTTGCT-3'), and plasmid p126.16 as template. The resulting 250 bp amplified fragment was cloned as a HindIII/HindII fragment into p126.17 digested with HindIII and HindII to generate p126.18. This plasmid contains a cassette consisting of the SERA cDNA controlled by the 42K entomopox promotor, with a vaccinia early transcription termination signal, and flanked by restriction sites at the 5' (HindIII, SmaI, BamHI) and 3' (XhoI, SmaI, SacI) ends.

The 42K promotor/SERA cassette was isolated from p126.18 as a BamHI/XhoI fragment and cloned into a BamHI/XhoI digested pSD553 vector fragment. The resulting plasmid is designated p126.ATI.

3. Generation of p126.C3

The 42K/SERA expression cassette was isolated from p126.ATI as a BamHI/XhoI fragment and cloned into a BamHI/XhoI-digested VQCP3L vector fragment. The resulting plasmid, designated p126.C3, is an ALVAC C3 donor plasmid.

4. Derivation of pSD553

The pSD553 vaccinia donor plasmid was used for the generation of p126.ATI. It contains the vaccinia K1L host range gene (Gillard et al., 1986) within flanking Copenhagen vaccinia arms, replacing the ATI region (orfs A25L, A26L; Goebel et al., 1990a,b). pSD553 was constructed as follows.

Left and right vaccinia flanking arms were constructed by PCR using pSD414, a pUC8-based clone of vaccinia SalI B (Goebel et al., 1990a,b) as template. The left arm was synthesized using synthetic deoxyoligonucleotides MPSYN267 (SEQ ID NO:85) (5'-GGGCTGAAGCTTGCTGGCCGCTCATTAGACAAGC GAATGAGGGAC-3') and MPSYN268 (SEQ ID NO:86) (5'-AGA TCT CCC GGG CTC GAG TAA TTA ATT AAT TTT TAT TAC ACC AGA AAA GAC GGC TTG AGA TC-3') as primers. The right arm was synthesized using synthetic deoxyoligonucleotides MPSYN269 (SEQ ID NO:87) (5'-TAA TTA CTC GAG CCC GGG AGA TCT AAT TTA ATT TAA TTT ATA TAA CTC ATT TTT TGA ATA TAC T-3') and MPSYN270 (SEQ ID NO:88) (5'-TAT CTC GAA TTC CCG CGG CTT TAA ATG GAC GGA ACT CTT TTC CCC-3') as primers. The two PCR-derived DNA fragments containing the left and right arms were combined in a further PCR reaction. The resulting product was cut with EcoRI/HindIII and a 0.9 kb fragment isolated. The 0.9 kb fragment was ligated with pUC8 cut with EcoRI/HindIII, resulting in plasmid pSD541. The polylinker region located at the vaccinia deletion locus was expanded as follows. pSD541 was cut with BglII/XhoI and ligated with annealed complementary synthetic deoxyoligonucleotides MPSYN333 (SEQ ID NO:125) (5'-GAT CTT TTG TTA ACA AAA ACT AAT CAG CTA TCG CGA ATC GAT TCC CGG GGG ATC CGG TAC CC-3')/MPSYN334 (SEQ ID NO:126) (5'-TCG AGG GTA CCG GAT CCC CCG GGA ATC GAT TCG CGA TAG CTG ATT AGT TTT TGT TAA CAA AA-3') generating plasmid pSD552. The K1L host range gene was isolated as a 1 kb BglII(partial)/HpaI fragment from plasmid pSD452 (Perkus et al., 1990). pSD552 was cut with BglII/HpaI and ligated with the K1L containing fragment, generating pSD553.

5. Derivation of VQCP3L

The VQCP3L ALVAC donor plasmid was used for the generation of p126.C3 and was constructed as follows. Insertion plasmid VQCP3L was derived as follows. An 8.5 kb canarypox BglII fragment was cloned in the BamHI site of pBS-SK plasmid vector to form pWW5. Nucleotide sequence analysis of a 7351 bp subgenomic fragment from ALVAC containing the C3 insertion site is presented in FIGS. 14A to 14C (SEQ ID NO:127). The C3 ORF is located between nucleotides 1458 to 2897. In order to construct a donor plasmid for insertion of foreign genes into the C3 locus with the complete excision of the C3 open reading frame, PCR primers were used to amplify the 5' and 3' sequences relative to C3. Primers for the 5' sequence were RG277 (SEQ ID NO:128) (5'-CAGTTGGTACCACTGGTATTTTATTTCAG-3') and RG278 (SEQ ID NO:129) (5'-TATCTGAATTCCTGCAGCCCGGGTTTTTATAGCTA ATTAGTCAAATGTGAGTTAATATTAG-3'). Primers for the 3' sequences were RG279 (SEQ ID NO:130) (5'TCGCTGAATTCGATATCAAGCTTATCGATTTTTAT GACTAGTTAATCAAATAAAAAGCATACAAGC-3') and RG280 (SEQ ID NO:131) (5'-TTATCGAGCTCTGTAACATCAGTATCTAAC-3'). The primers were designed to include a multiple cloning site flanked by vaccinia transcriptional and translational termination signals. Also included at the 5'-end and 3'-end of the left arm and right arm were appropriate restriction sites (ASP718 and EcoRI for left arm and EcoRI and SacI for right arm) which enabled the two arms to ligate into Asp718/SacI digested pBS-SK plasmid vector. The resultant plasmid was designated as pC3I. A 908 bp fragment of canarypox DNA, immediately upstream of the C3 locus was obtained by digestion of plasmid pWW5 with NsiI and SspI. A 604 bp fragment of canarypox and DNA was derived by PCR using plasmid pWW5 as template and oligonucleotides CP16 (SEQ ID NO:132) (5'-TCCGGTACCGCGGCCGCAGATA TTTGTTAGCTTCTGC-3') and CP17 (SEQ ID NO:133) (5'-TCGCTCGAGTAGGATACCTACCTACTACCTACG-3'). The 604 bp fragment was digested with Asp718 and XhoI (sites present at the 5' ends of oligonucleotides CP16 and CP17, respectively) and cloned into Asp718-XhoI digested and alkaline phosphatase treated IBI25 (International Biotechnologies, Inc., New Haven, Conn.) generating plasmid SPC3LA. SPC3LA was digested within IBI25 with EcoRV and within canarypox DNA with NsiI, and ligated to the 908 bp NsiI-SspI fragment generating SPCPLAX which contains 1444 bp of canarypox DNA upstream of the C3 locus. A 2178 bp BglII-StyI fragment of canarypox DNA was isolated from plasmids pXX4 (which contains a 6.5 kb NsiI fragment of canarypox DNA cloned into the PstI site of pBS-SK. A 279 bp fragment of canarypox DNA was isolated by PCR using plasmid pXX4 as template and oligonucleotides CP19 (SEQ ID NO:134) (5'-TCGCTCGAGCTTTCTTGACAATAACATAG-3') and CP20 (SEQ ID NO:135) (5'-TAGGAGCTCTTTATACTACTGGGTTACAAC-3'). The 279 bp fragment was digested with XhoI and SacI (sites present at the 5' ends of oligonucleotides CP19 and CP20, respectively) and cloned into SacI-XhoI digested and alkaline phosphatase treated IBI25 generating plasmid SPC3RA. To add additional unique sites to the polylinker, pC3I was digested within the polylinker region with EcoRI and ClaI, treated with alkaline phosphatase and ligated to kinased and annealed oligonucleotides CP12 (SEQ ID NO:136) (5'-AATTCCTCGAGGGATCC-3') and CP13 (SEQ ID NO:137) (5'-CGGGATCCCTCGAGG-3') (containing an EcoRI sticky end, XhoI site, BamHI site and a sticky end compatible with ClaI) generating plasmid SPCP3S. SPCP3S was digested within the canarypox sequences downstream of the C3 locus with StyI and SacI (pBS-SK) and ligated to a 261 bp BglII-SacI fragment from SPC3RA and the 2178 bp BglII-StyI fragment from pXX4 generating plasmid CPRAL containing 2572 bp of canarypox DNA downstream of the C3 locus. SPCP3S was digested within the canarypox sequences upstream of the C3 locus with Asp718 (in PBS-SK) and AccI and ligated to a 1436 bp Asp718-AccI fragment from SPCPLAX generating plasmid CPLAL containing 1457 bp of canarypox DNA upstream of the C3 locus. The derived plasmid was designated as SPCP3L. VQCP3L was derived from pSPCP3L by digestion with XmaI, phosphatase treating the linearized plasmid, and ligation to annealed, kinased oligonucleotides CP23 (SEQ ID NO:138) (5'-CCGGTTAATTAATTAGTTA TTAGA-CAAGG TGAAAACGAAACTATTTGTAGCTT AATTAATTAGGTCACC-3') and CP24 (SEQ ID NO:139) (5'-CCGGGGTCGACCTAATTAATTAAGCTAC AAAT-AGTTTCGTTTTCACCTTGTCTAATAACTAATT AATTAA-3').

DNA sequence analysis of pH6.CEA.C3 revealed a one nucleotide deletion (T) at position 1203 of the CEA coding sequence (eliminating a HindII site) which occurred during a previous cloning step. This deletion was corrected by replacing a 1047 nucleotide MscI fragment (extending from position 501 to 1548) from pH6.CEA.C3 with the analogous, unmutated MscI fragment from pGEM.CEA. The resulting plasmid was designated pH6.CEA.C3.2.

CEA has been inserted into ALVAC by recombination between NotI-linearized pH6.CEA.C3.2 donor plasmid and ALVAC rescuing virus. Recombinants containing CEA have been identified by plaque hybridization with a DNA probe derived from the CEA coding sequence (an NruI/XhoI fragment containing the full length CEA coding sequence).

A NruI/XhoI fragment containing the 3' end of the H6 promotor linked to the full length CEA coding sequence was isolated from pH6.CEA.C3.2. This fragment was ligated to an NruI/XhoI-digested pSPHA.H6 vector fragment, which was derived from the pSD544 HA donor plasmid by the insertion of a fragment containing the H6 promotor. The resulting plasmid was designated pH6.CEA.HA and contains the CEA coding sequence linked to the regenerated H6 promotor. The pH6.CEA.HA donor plasmid directs insertion of the H6/CEA expression cassette to the HA site of NYVAC. Transcription of CEA is oriented from left to right.

Plasmid pSD544 was derived as follows. pSD456 is a subclone of Copenhagen vaccinia DNA containing the HA gene (A56R; Goebel et al., 1990a,b) and surrounding regions. pSD456 was used as template in polymerase chain reactions for synthesis of left and right vaccinia arms flanking the A56R ORF. The left arm was synthesized using synthetic oligodeoxynucleotides MPSYN279 (SEQ ID NO:140) (5' CCCCCCGAATTCGTCGACGATTGTTCATGATGGCAAGAT 3') and MPSYN280 (SEQ ID NO:141) (5'-CCCGGGGGATCCCTCGAGGGTACCAAGCTT AATTAATTAAATATTAGTATAAAAAGTGATTTATTT TT-3') as primers. The right arm was synthesized using MPSYN281 (SEQ ID NO:142) (5'-AAGCTTGGTACCCTCGAGGGATCCCCGGGTAGC TAGCTAATTTTTCTTTTACGTATTATATATGTAAT AAACGTTC-3') and MPSYN312 (SEQ ID NO:143) (5'-TTTTTTCTGCAGGTAAGTATTTTTAAAACTTCTAA CACC-3') as primers. Gel-purified PCR fragments for the left and right arms were combined in a further PCR reaction. The resulting product was cut with EcoRI/HindIII. The resulting 0.9 kb fragment was gel-purified and ligated into pUC8 cut with EcoRI/HindIII, resulting in plasmid pSD544. FIGS. 22 and 23 present the nucleotide sequences of the H6/CEA expression cassettes and flanking regions in plasmids pH6.CEA.C3.2 and pH6.CEA.HA, respectively (SEQ ID NO:144/145, respectively). In FIG. 22, the H6 promoter begins at position 57. The CEA start codon begins at position 181 and the stop codon ends at position 2289. Positions 1 through 58 and 2290 through 2434 flank the H6/CEA expression cassette. In FIG. 23, the H6 promotor begins at position 60. The CEA start codon begins at position 184 and the stop codon ends at position 2292. Positions 1 through 59 and 2293 through 2349 flank the H6/CEA expression cassette.

Example 18

Murine IL-2 into ALVAC and NYVAC

Insertion of murine IL-2 into ALVAC. Plasmid pmut-1 (ATCC No. 37553) contains the murine IL-2 gene from American Type Culture Collection, Rockville, Md. The IL-2 gene was placed under the control of the vaccinia H6 promoter (Perkus et al., 1989) and the IL-2 3' noncoding end was removed in the following manner.

Template pRW825, containing the H6 promoter and a nonpertinent gene, was used in a polymerase chain reaction (PCR) with primers MM104 (SEQ ID NO:146) 5' ATCATCGGATCCCTGCAGCCCGGGT-TAATTAATTAGTGATAC 3' and MM105 (SEQ ID NO:147) 5' GAGCTGCATGCTGTACATTACGATA-CAAACTTAACGA 3'. The 5' end of MM104 contains BamHI, PstI and SmaI sites followed by a sequence which primes from the H6 promoter 5' end toward the 3'end. The 5' end of MM105 overlaps the IL-2 5' end and MM105 primes from the H6 promoter 3' end toward the 5' end. The resultant 228 base pair PCR derived fragment contains the H6 promoted 5' most base pairs of IL-2.

Template plasmid pmut-1 was used in a second PCR with primers MM106 (SEQ ID NO:148) 5' CGTTAAGTTTG-TATCGTAATGTACAGCATGCAGCTG 3' and MM107 (SEQ ID NO:149) 5' GAGGAGGAATTCCCCGGGTTAT-TGAGGGCTTGTTGAGA 3'. The 5' end of MM106 overlaps the 3' end of the H6 promoter and primes from the IL-2 5' end toward the 3' end. The 5' end of MM107 contains EcoRI and SmaI sites followed by a sequence which primes from the IL-2 3' end toward the 5' end. The resultant 546 base pair PCR derived fragment was pooled with the above 228 base pair PCR product and primed with MM104 and MM107. The resultant 739 base pair PCR derived fragment, containing the H6 promoted IL-2 gene, was digested with BamHI and EcoRI, generating a 725 base pair fragment, for insertion between the BamHI and EcoRI sites of pBS-SK (Stratagene, LaJolla, Calif.), yielding pMM151.

The 755 base pair pMM151 BamHI-XhoI fragment containing the H6 promoted IL-2 gene was inserted between the BamHI and XhoI sites of the C3 vector pCP3LSA-2. The resultant plasmid pMM153, contains the H6 promoted IL-2 gene in the C3 locus.

The nucleotide sequence of murine IL-2 from the translation initiation codon through the stop codon is given in FIG. 24 (SEQ ID NO:150).

C3 vector plasmid pCP3LSA-2 was derived in the following manner. Plasmid SPCP3L (Example 17) was digested with NsiI and NotI and a 6433 bp fragment isolated and ligated to annealed oligonucleotides CP34 (SEQ ID NO:151) 5' GGCCGCGTCGACATGCA 3' and CP35 (SEQ ID NO:152) 5' TGTCGACGC 3', generating plasmid pCP3LSA-2.

Recombination between donor plasmid pMM153 and ALVAC rescuing virus generated recombinant virus vCP275, which contains the vaccinia H6 promoted murine IL-2 gene in the C3 locus.

Insertion of murine IL-2 into NYVAC. Plasmid pMM151, defined above, was digested with BamHI/XhoI and a 755 base pair fragment containing the H6 promoted IL-2 gene was isolated. This BamHI/XhoI fragment was inserted between the BamHI and XhoI sites of the NYVAC TK vector pSD542. The resultant plasmid pMM154, contains the H6 promoted IL-2 gene in the TK locus.

Plasmid pSD542 was derived in the following manner. To modify the polylinker region, TK vector plasmid pSD513 (Example 7) was cut with PstI/BamHI and ligated with annealed synthetic oligonucleotides MPSYN288 (SEQ ID NO:153) 5' GGTCGACGGATCCT 3' and MPSYN289 (SEQ ID NO:154) 5' GATCAGGATCCGTCGACCTGCA 3', resulting in plasmid pSD542.

Recombination between donor plasmid pMM154 and NYVAC rescuing virus generated recombinant virus vP1239, which contains the H6 promoted murine IL-2 gene in the TK locus.

Expression of murine IL-2 in ALVAC and NYVAC based recombinants. ELISA assay. The level of expression of murine IL-2 produced by ALVAC and NYVAC based recombinants vCP275 and vP1239 was quantitated using an ELISA kit from Genzyme Corporation, Cambridge, Mass.

(InterTest-2X™ Mouse IL-2 ELISA Kit, Genzyme Corporation, Code # 2122-01). Duplicate dishes containing confluent monolayers of mouse L-929 cells (2×10$^6$ cells/dish) were infected with recombinant virus vCP275 or vP1239 expressing murine IL-2 or infected with ALVAC or NYVAC parental virus. Following overnight incubation at 37° C., supernatants were harvested and assayed for expression of murine IL-2 using the InterTest-2X™ Mouse IL-2 ELISA Kit as specified by the manufacturer (Genzyme Corporation, Cambridge, Mass.). The InterTest-2X™ Mouse IL-2 ELISA Kit is a solid-phase enzyme-immunoassay employing the multiple antibody sandwich principle. ELISA plates were read at 490 nm. Background from ALVAC or NYVAC samples was subtracted, and values from duplicate dishes were averaged. The quantity of murine IL-2 secreted is expressed as pg/ml, which is equivalent to pg/10$^6$ cells (Table 23).

TABLE 23

| Recombinant virus | Murine IL-2 secreted |
| --- | --- |
| vCP275 | 160 pg/ml |
| vP1239 | 371 pg/ml |

Example 19

Human IL-2 into ALVAC and NYVAC

Insertion of Human IL-2 into ALVAC. Plasmid pTCGF-11 (ATCC No. 39673) contains the human IL-2 gene from American Type Culture Collection, Rockville, Md. The IL-2 gene was placed under the control of the vaccinia H6 promoter (Perkus et al., 1989), two codons were corrected, and the IL-2 3' noncoding end was removed in the following manner.

Template plasmid pRW825, containing the H6 promoter and a nonpertinent gene, was used in a polymerase chain reaction (PCR) with primers MM104 (SEQ ID NO:146) 5' ATCATCGGATCCCTGCAGCCCGGGT-TAATTAATTAGTGATAC 3' and MM109 (SEQ ID NO:155) 5' GAGTTGCATCCTGTACATTACGATA-CAAACTTAACGGA 3'. The 5' end of MM104 contains BamHI, PstI and SmaI sites followed by a sequence which primes from the vaccinia H6 promoter 5' end toward the 3' end. The 5' end of MM109 overlaps the IL-2 5' end, and MM105 primes from the H6 promoter 3' end toward the 5' end. The resultant 230 base pair PCR derived fragment contains the H6 promoted 5' most base pairs of IL-2.

Template plasmid pTCGF-11 was used in a PCR with primers MM108 (SEQ ID NO:156) 5' CGTTAAGTTTG-TATCGTAATGTACAGGATGCAACTC 3' and MM112 (SEQ ID NO:157) 5' TTGTAGCTGTGTTTTCTTTGTA-GAACTTGAAGTAGGTGCACTGTTTGTGA-CAAGTGCAAGACTTAGTGCAATGCAAGAC 3'. The 5' end of MM108 overlaps the 3' end of the H6 promoter and primes from the IL-2 5' end toward the 3' end. MM112 primes from position 100, in the human IL-2 sequence (FIG. 25), toward the 5' end. The resultant 118 base pair fragment contains the 3' most base pairs of the H6 promoter and 5' 100 bp of the IL-2 gene.

Plasmid pTCGF-11 from American Type Culture Collection was sequenced, and the sequence was compared with the published sequence (Clark, et al., 1984). Two mutations resulting in amino acid changes were discovered. Oligonucleotide primers MM111 (SEQ ID NO:158) 5' TTCTA-CAAAGAAAACACAGCTACAACTGGAG-CATTTACTTCTGGATTTACAGATGATTTTGAATGG AATTAATAATTAC 3' and MM112 were used to correct these two base changes in pTCGF-11.

The corrected nucleotide sequence of human IL-2 from the translation initiation codon through the stop codon is given in FIG. 25 (SEQ ID NO:159).

Except for a silent G to T change in pTCGF-11 at position 114, the sequence in FIG. 25 is the same as the IL-2 sequence described in Clark, et al., 1984. The T at position 41 in the sequence in FIG. 25 is C in pTCGF-11, and the codon change is from leu to pro. The T at position 134 in the sequence in FIG. 25 is C in pTCGF-11, and the codon change is from leu to ser. The predicted amino acid sequences of other human, bovine, murine, ovine, and porcine IL-2 isolates were compared with the sequence in Clark, et al., 1984; the codons at positions 41 and 134 are both conserved as leu.

Template pTCGF-11 was used in a PCR with primers MM110 (SEQ ID NO:160) 5' GAGGAGGAATTC-CCCGGGTCAAGTCAGTGTTGAGATGA 3' and MM111. The 5' end of MM110 contains EcoRI and SmaI sites followed by a sequence which primes from the IL-2 3' end toward the 5' end. MM111 primes from position 75 toward the IL-2 3'end. The resultant 400 base pair PCR derived fragment was pooled with the above 230 and 118 base pair PCR products and primed with MM104 and MM110. The resultant 680 base pair PCR derived fragment, containing the vaccinia H6 promoted IL-2 gene, was digested with BamHI and EcoRI and inserted between the BamHI and EcoRI sites of pBS-SK (Stratagene, LaJolla, Calif.), yielding pRW956.

Plasmid pRW956 was digested with BamHI/XhoI and a 700 bp fragment containing the H6 promoted IL-2 gene was isolated. This fragment was inserted between the BamHI and XhoI sites of the C3 vector plasmid pCP3LSA-2 (Example 18). The resultant plasmid, pRW958, contains the H6 promoted IL-2 gene in the C3 locus.

Recombination between donor plasmid pRW958 and ALVAC rescuing virus generated recombinant virus vCP277, which contains the H6 promoted human IL-2 gene in the C3 locus.

Insertion of Human IL-2 into NYVAC. Plasmid pRW956, defined above, was digested with BamHI/XhoI and a 700 base pair fragment was isolated. This fragment, containing the vaccinia H6 promoted human IL-2 gene, was inserted between the BamHI and XhoI sites of the NYVAC TK vector plasmid pSD542 (Example 18). The resultant plasmid, pRW957, contains the H6 promoted human IL-2 gene in the TK locus.

Recombination between donor plasmid pRW957 and NYVAC rescuing virus generated recombinant virus vP1241, which contains the H6 promoted human IL-2 gene in the TK locus.

Expression of human IL-2 in ALVAC and NYVAC based recombinants. ELISA assay. The level of expression of human IL-2 produced by ALVAC and NYVAC based recombinants vCP277 and vP1241 was quantitated using a Human Interleukin-2 ELISA kit from Collaborative Biomedical Products, Inc., Becton Dickinson, Bedford, Mass. (IL-ISA 2™ Cat. No. 30020). Duplicate dishes containing confluent monolayers of human HeLa cells (2×10$^6$ cells/dish) were infected with recombinant virus vCP277 or vP1241 expressing human IL-2 or infected with ALVAC or NYVAC parental virus. Following overnight incubation at 37° C., supernatants were harvested and assayed for expression of human IL-2 using the IL-ISA 2™ Human Interleukin-2 ELISA kit as specified by the manufacturer (Collaborative Biomedical Products, Inc., Becton Dickinson, Bedford, Mass.). The IL-ISA 2™ Kit is a solid-phase enzyme-immunoassay employing the multiple antibody sandwich principle. ELISA plates were read at 490 nm. Background from ALVAC or NYVAC samples was subtracted, and values from duplicate dishes were averaged. The IL-ISA 2™ KitIL-2 quantitates human IL-2 in Biological Response Modifiers Program (BRMP) units (Gerrard et al., 1993). The quantity of human IL-2 secreted is expressed as BRMP u/ml, which is equivalent to BRMP u/$10^6$ cells (Table 24).

TABLE 24

| Recombinant virus | Human IL-2 secreted |
|---|---|
| vCP277 | 850 BRMP U/ml |
| vP1241 | 953 BRMP U/ml |

Example 20

Murine IFNγ into ALVAC and NYVAC

Insertion of Murine IFNγ into ALVAC. Plasmid pms10 was obtained from ATCC (#63170). Plasmid pms10 contains cDNA encompassing the entire mouse IFNγ coding sequence with flanking region cloned into the PstI site of pBR322.

Plasmid pMPI3H contains the vaccinia I3L promoter (Perkus et al., 1985; Schmitt and Stunnenberg, 1988) in pUC8. Plasmid pMPI3H is designed for cleavage at a HpaI site within the promoter and at a site in the downstream polylinker region to allow for downstream addition of the 3' end of the I3L promoter linked to a foreign gene.

Linkage of murine IFNγ gene with I3L promoter; Construction of pMPI3mIF. Murine IFNγ coding sequences with linkage to I3L promoter were synthesized by PCR using oligonucleotides MPSYN607 (SEQ ID NO:161) 5' TAAT-CATGAACGCTACACACTGC 3' and MPSYN608 (SEQ ID NO:162) 5' CCGGATCCCTGCAGTTATTGGGA-CAATCTCTT 3' as primers, and plasmid pms10 as template. The PCR product was cut with BamHI and a 510 bp fragment was isolated and ligated with vector plasmid pMPI3H cut with HpaI/BamHI. Following sequence verification, the resulting plasmid was designated pMPI3mIF.

Insertion of I3L/murine IFNγ cassette into the C3 locus; construction of pMPC3I3mIF. Plasmid pMPI3mIF was cut with HindIII and blunt ended with Klenow fragment of *E. coli* polymerase. The DNA was then cut with BamHI and a 0.6 kb fragment containing the I3L/murine IFNγ cassette was isolated. This fragment was ligated with vector plasmid pVQC3LSA-3 cut with SmaI/BamHI, resulting in insertion plasmid pMPC3I3mIF.

Nucleotide sequence of the I3L/murine IFNγ expression cassette is given in FIG. 26 (SEQ ID NO:163). The start codon for the murine IFNγ gene is at position 101, and the stop codon is at position 596.

Plasmid pVQC3LSA-3 was derived in the following manner. ALVAC C3 locus insertion plasmid VQCP3L (Example 17) was digested with NsiI and NotI and a 6503 bp fragment isolated and ligated to annealed oligonucleotides CP34 (SEQ ID NO:151) 5' GGCCGCGTCGACAT-GCA 3' and CP35 (SEQ ID NO:152) 5' TGTCGACGC 3', generating plasmid VQCP3LSA-3. (Note: Plasmid VQCP3LSA-3 is identical to plasmids VQCP3LSA-5 and VQCP3LSA, used in subsequent examples; see, e.g., Examples 24, 25, 26.)

Recombination between donor plasmid pMPC3I3mIF and ALVAC rescuing virus generated recombinant virus vCP271, which contains the I3L promoted murine IFNγ gene in the C3 locus.

Insertion of Murine IFNγ into NYVAC. Insertion of I3L/murine IFNã cassette into TK locus; construction of pMPTKI3mIF. Plasmid pMPI3mIF, defined above, was cut with HindIII and blunt ended with Klenow fragment of *E. coli* polymerase. The DNA was then cut with BamHI and a 0.6 kb fragment containing the I3L/murine IFNã cassette was isolated. This fragment was ligated with NYVAC TK vector plasmid pSD542 (Example 18) cut with SmaI/BamHI, resulting in insertion plasmid pMPTKI3mIF.

Recombination between donor plasmid pMPTKI3mIF and NYVAC rescuing virus generated recombinant virus vP1237, which contains the I3L promoted murine IFNγ gene in the TK locus.

Expression of murine IFNγ in ALVAC and NYVAC based recombinants. ELISA assay. The level of expression of murine IFNγ produced by ALVAC and NYVAC based recombinants vCP271 and vP1237 was quantitated using an ELISA kit from Genzyme Corporation, Cambridge, Mass. (InterTest-ã Kit, Genzyme Corporation, cat # 1557-00). Duplicate dishes containing confluent monolayers of mouse L-929 cells ($2\times10^6$ cells/dish) were infected with recombinant virus vCP271 or vP1237 expressing murine IFNγ or infected with ALVAC or NYVAC parental virus. Following overnight incubation at 37° C., supernatants were harvested and assayed for expression of murine IFNγ using the InterTest-ã Kit as specified by the manufacturer (Genzyme Corporation, Cambridge, Mass.). The InterTest-ã Kit is a solid-phase enzyme-immunoassay employing the multiple antibody sandwich principle. ELISA plates were read at 490 nm. Background from ALVAC or NYVAC samples was subtracted, and values from duplicate dishes were averaged. The quantity of murine IFNγ secreted is expressed as nanograms/ml, which is equivalent to ng/$10^6$ cells (Table 25).

TABLE 25

| Recombinant virus | Murine IFNγ secreted |
|---|---|
| vCP271 | 972 ng/ml |
| vP1237 | 3359 ng/ml |

Biological assay. The biological activity of murine IFNγ expressed by ALVAC and NYVAC based recombinants was quantitated using a standardized IFNγ bio-assay (Vogel et al., 1991). This assay quantitates IFN activity by titrating its ability to protect L-929 cells from VSV (vesicular stomatitis virus)-induced cytopathic effect (CPE).

Confluent monolayers of mouse L-929 cells ($2\times10^6$ cells/dish) were mock-infected or infected with NYVAC, vP1237, ALVAC, or vCP271 at an moi of 5. Dishes were inoculated in duplicate. Following the 1 hour adsorption period, 1 ml of fresh medium was added to each dish and they were incubated overnight at 37° C. The supernatants from both dishes were pooled, filtered through a 0.22 μm filter and tested for IFN activity as detailed below. Two-fold serial dilutions of supernatants were tested, beginning at undiluted for mock infected, NYVAC, and ALVAC infected dishes, or 1:100 and 1:1000 for vCP271 and vP1237 infected dishes.

In the IFN-γ bio-assay, 50 μl medium was added to all wells of a 96-well plate, followed by 50 μl of a serial dilution of a stock of commercial murine IFN-γ (Genzyme Corporation, MG-IFN, lot # B3649) or culture supernatant as described above. Next, 50 μl of L-929 cells ($3\times10^4$ cells) were added to each well, and plates were placed at 37° C. overnight. After 24 hours, cells were infected with 100 μl VSV (moi of 0.1). Plates were incubated at 37° C. overnight. After 24 hours, CPE was assessed. The well which gave the same CPE as VSV in the absence of interferon was defined as having 1 unit/ml interferon. This method coincided well with the interferon standard.

The interferon concentration in the supernatants is determined as the reciprocal of the dilution which gives similar CPE to the standard at 1 unit/ml interferon. For mock-infected, NYVAC and ALVAC infected cells, less than 20 units/ml interferon is produced. For vP1237, 14,000 units/ml IFN-γ is produced, and for vCP271, 3,600 units/ml IFN-γ is produced. vP1237 produced four-fold greater levels of IFN-γ than vCP271, confirming results seen above by the ELISA assay. The lack of protection conferred by supernatants from mock-infected and parental virus-infected cells shows that the protective activity in supernatants from vP1237- and vCP271-infected cells is IFN-γ. This was confirmed by a neutralization assay which showed that antisera to IFN-γ (Genzyme Corporation monoclonal hamster anti-murine IFN-γ, 1222-00, lot #B3847) but not antisera to murine IFN-α/β (Lee Biomolecular Research, INC., San Diego, Calif., No. 25301, lot. #89011) or murine IFN-β (Lee Biomolecular Research, Inc., No. 25101, lot. #87065) was capable of neutralizing the protective activity produced by these recombinants.

Example 21

Human IFNγ into ALVAC and NYVAC

Insertion of Human IFNγ into ALVAC. Plasmid p52 was obtained from ATCC (No. 65949). Plasmid p52 contains cDNA encoding the carboxy terminal 2/3 of the human IFN α coding sequence with untranslated 3' region cloned into the PstI site of pBR322.

Linkage of human IFNγ gene with I3L promoter; Construction of pMPI3hIF (A) The missing region of the human IFNγ gene was synthesized using long, overlapping PCR primers, MPSYN615 (SEQ ID NO:164) 5' TAATCATGAAATATA-CAAGTTATATCTTGGCTTTTCAGCTCTGCATCG TTTTGGGTTCTCTTGGCTGTTACTGCCAGG ACCCATATGTAAAAGAAGC 3' and MPSYN616 (SEQ ID NO:165) 5' TTCTTCAAAATGCCTAAGAAAAGAGT-TCCATTATCCGCTACATCTGAATGACCTGC ATTAAAATATTTCTTAAGGTTTT CTGCTTCTTTTA-CATATGGGTCCTGGC 3' with no extraneous template. The end of MPSYN615 is designed for cloning into the HpaI site of pMPI3H (Example 20). There are 25 bp of overlap between MPSYN615/MPSYN616. A 179 bp PCR product was isolated.

(B) The remainder of human IFNγ gene was synthesized using PCR primers MPSYN617 (SEQ ID NO:166) 5' TCTTTTCTTAGGCATTTGAAGAATTGGAAA GAG-GAGAGTGACAG 3' and MPSYN618 (SEQ ID NO:167) 5' CCCGGATCCCTGCAGTTACTGGGATGCTCTTCGA 3' with plasmid p52 as template. MPSYN617 has 25 bp overlap with missing region; MPSYN618 is designed for cloning into the downstream BamHI site of pMP13H. A ca. 350 bp PCR fragment was isolated.

(A+B) Combination PCR was performed using isolated fragments from (A) and (B), above, and external primers MPSYN615 and MPSYN618. The PCR product was digested with BamHI, and a ca. 510 bp fragment was isolated. This fragment was cloned into pMPI3H cut with HpaI/BamHI.

Following sequence confirmation, the resulting plasmid was designated pMPI3hIF. pMPI3hIF contains the human IFNγ gene under the control of the I3L promoter.

Insertion of I3L/human IFNγ cassette into C3 locus; construction of pMPC3I3hIF. Plasmid pMPI3hIF was cut with HindIII and blunt ended with Klenow fragment of E. coli polymerase. The DNA was then cut with BamHI and a 0.6 kb fragment containing the I3L/human IFNγ cassette was isolated. This fragment was ligated with ALVAC C3 vector plasmid pVQC3LSA-3 (Example 20) cut with SmaI/BamHI, resulting in ALVAC insertion plasmid pMPC3I3hIF.

Nucleotide sequence of the I3L/human IFNγ expression cassette is given in FIG. 27 (SEQ ID NO:168). The start codon for the human IFNγ gene is at position 101, and the stop codon is at position 599.

Recombination between donor plasmid pMPC3I3hIF and ALVAC rescuing virus generated recombinant virus vCP278, which contains the I3L promoted human IFNγ gene in the C3 locus.

Insertion of Human IFNγ into NYVAC. Insertion of I3L/human IFNγ cassette into TK locus; construction of pMPTKI3hIF. Plasmid pMPI3hIF, described above, was cut with HindIII and blunt ended with Klenow fragment of E. coli polymerase. The DNA was then cut with BamHI and a 0.6 kb fragment containing the I3L/human IFNγ cassette was isolated. This fragment was ligated with NYVAC TK vector plasmid pSD542 (Example 18) cut with SmaI/BamHI, resulting in NYVAC insertion plasmid pMPTKI3hIF.

Recombination between donor plasmid pMPTKI3hIF and NYVAC rescuing virus generated recombinant virus vP1244, which contains the vaccinia I3L promoted human IFNγ gene in the TK locus.

Expression of Human IFNγ in ALVAC and NYVAC Based Recombinants ELISA Assay

The level of expression of human IFNγ produced by ALVAC and NYVAC based recombinants vCP278 and vP1244 was quantitated using a human Interferon γ ELISA kit from Genzyme Corporation, Cambridge, Mass. (InterTest-γ™ Kit, Genzyme Corporation, cat # 1556-00). Duplicate dishes containing confluent monolayers of human HeLa cells ($2\times10^6$ cells/dish) were infected with recombinant virus vCP278 or vP1244 expressing human IFNγ or infected with ALVAC or NYVAC parental virus. Following overnight incubation at 37° C., supernatants were harvested and assayed for expression of human IFNγ using the InterTest-γ Kit as specified by the manufacturer (Genzyme Corporation, Cambridge, Mass.). The InterTest-γ Kit is a solid-phase enzyme-immunoassay employing the multiple antibody sandwich principle. ELISA plates were read at 490 nm. Background from ALVAC or NYVAC samples was subtracted, and values from duplicate dishes were averaged. The quantity of human IFNγ secreted is expressed as nanograms/ml, which is equivalent to ng/$10^6$ cells (Table 26).

TABLE 26

| Recombinant virus | Human IFNγ secreted |
|---|---|
| vCP278 | 9 ng/ml |
| vP1244 | 15 ng/ml |

Example 22

Murine IL-2 Plus IFNγ into ALVAC and NYVAC

Insertion of Murine IFNγ into C6 locus of ALVAC; addition to ALVAC-murine IL-2 recombinant virus. Derivation of C6 insertion vector. ALVAC C6 insertion vector pC6L was derived as follows. A 3.0 kb canarypox HindIII fragment containing the entire C6 ORF was cloned into the HindIII site of pBS-SK (Stratagene) to form plasmid pC6HIII3 kb. Nucleotide sequence of the canarypox insert in pC6HIII3 kb is presented in FIG. 28 (SEQ ID NO:169). In FIG. 28, the C6 ORF is located between nucleotides 377 to 2254.

Extension of canarypox sequence to the right of pC6HIII3 kb was obtained by sequence analysis of overlapping canarypox clones. In order to construct a donor plasmid for insertion of foreign genes into the C6 locus with the complete excision of the C6 open reading frame, flanking 5' and 3' arms were synthesized by using PCR primers and genomic canarypox DNA as template. The 380 bp 5' flanking arm was synthesized using primers C6A1 (SEQ ID NO:170) 5' ATCATCGAGCTCGCGGCCGCCTAT-CAAAAGTCTTAATGAGTT 3' and C6B1 (SEQ ID NO:171) 5' GAATTCCTCGAGCTGCAGCCCGGGTTTT-TATAGCTAATTAGTCATTTTTTCGTAAG-TAAGTATTTTTATTTAA 3'. The 1155 bp 3' flanking arm was synthesized using primers C6C1 (SEQ ID NO:172) 5' CCCGGGCTGCAGCTCGAGGAATTCTTTT-TATTGATTAACTAGTCAAATGAG-TATATATAATTGAAAAAGTAA 3' and C6D1 (SEQ ID NO:173) 5' GATGATGGTACCTTCATAAATA-CAAGTTTGATTAAACTTAAGTTG 3'. Left and right flanking arms synthesized above were combined by PCR reaction using primers C6A1 and C6D1, generating a full length product of 1613 bp. This PCR product was cut near the ends with SacI/KpnI and cloned into PBS-SK cut with SacI/KpnI, generating C6 insertion plasmid pC6L. pC6L contains, in the C6 deletion locus, a multicloning region flanked by translational stop codons and T5NT transcriptional terminators (Yuen and Moss, 1986). The sequence of pC6L is presented in FIG. 29 (SEQ ID NO:174). In FIG. 29, the multicloning region is located between nucleotide 407 and nucleotide 428.

Annealed synthetic oligonucleotides VQC (SEQ ID NO:175) 5' TTAATCAGGATCCTTAATTAATTAGT-TATTAGACAAGGTGAAACGAAAC-TATTTGTAGCTTAATTAATTAGCTGCAGCCCGGG 3' and VQN (SEQ ID NO:176) 5' CCCGGGCTGCAGCTAAT-TAATTAAGCTACAAAT-AGTTTCGTTTTCACCTTGTCTAATAAC-TAATTAATTAAGGATCCTGATTAA 3' were ligated into pBS-SK resulting in an intermediate plasmid. Plasmid pMM117 contains a SmaI/EcoRI polylinker fragment from this intermediate plasmid replacing the SmaI/EcoRI polylinker of pC6L.

Plasmid pMP42GPT contains the *Escherichia coli* xanthine-guanine phosphoribosyl transferase gene (Ecogpt gene) (Pratt and Subramani, 1983) under the control of an entomopox promoter (EPV 42 kDa). The 31 bp EPV 42 kDa promoter sequence (SEQ ID NO:177) used in pMP42GPT is 5' CAAAATTGAAAATATATAATTACAATATAAA 3'.

Insertion of 42 kDa/Ecogpt cassette into C6 locus; Construction of pMP117gpt-B. Plasmid pMP42GPT was cut with EcoRI and a 0.7 kb fragment containing the 42 kDa/ Ecogpt expression cassette was isolated. This fragment was inserted into vector plasmid pMM117 cut with EcoRI in both orientations, generating pMP117gpt-A and pMP117gpt-B.

Insertion of I3L/murine IFNγ cassette into C6 locus; construction of pMPC6mIFgpt. Plasmid pMPI3mIF (Example 20) was cut with HindIII and blunt ended with Klenow fragment of *E. coli* polymerase. The DNA was then cut with PstI (partial digest) and a 0.6 kb fragment containing the I3L/murine IFNγ cassette was isolated. Vector plasmid pMP117gpt-B was cut with SmaI (partial digest) and full length linear DNA was isolated. This was cut with PstI and the largest fragment was isolated. Vector and insert fragments were ligated, resulting in insertion plasmid pMPC6mIFgpt. In addition to the I3L/murine IFNγ expression cassette, plasmid pMPC6mIFgpt contains the 42 kDa/ Ecogpt expression cassette to allow for selection of recombinants through the use of mycophenolic acid (Boyle and Coupar, 1988; Falkner and Moss, 1988).

Recombination was accomplished between donor plasmid pMPC6mIFgpt and rescuing virus vCP275 (Example 18). Recombinant virus are plaque purified. The resultant ALVAC based recombinant virus contains the vaccinia I3L promoted murine IFNγ gene, as well as the EPV 42 kDa promoted Ecogpt gene, both in the C6 locus and the vaccinia H6 promoted murine IL-2 gene in the C3 locus.

Insertion of Murine IFNγ and Murine IL-2 into NYVAC. Insertion of I3L/murine IFNγ cassette into TK locus; construction of pMPTKm2IF. Plasmid pMPI3mIF (Example 20) was cut with HindIII and blunt ended with Klenow fragment of *E. coli* polymerase. The DNA was then cut with BamHI and a 0.6 kb fragment containing the I3L/murine IFNγ cassette was isolated. This fragment was ligated with vector plasmid pMM154 (Example 18) cut with SmaI/ BamHI, resulting in insertion plasmid pMPTKm2IF.

Recombination between donor plasmid pMPTKm2IF and NYVAC rescuing virus generated recombinant virus vP1243, which contains the vaccinia I3L promoted murine IFNγ gene and the vaccinia H6 promoted murine IL-2 gene, both in the TK locus.

Expression of Murine IL-2 in ALVAC and NYVAC Based Recombinants Comparison with Recombinants Coexpressing Murine IL-2 and Murine IFNγ ELISA Assay The level of expression of murine IL-2 produced by ALVAC based recombinants vCP275 and vCP288, and NYVAC based recombinants vP1239 and vP1243 was quantitated using a Murine Interleukin-2 ELISA kit from Collaborative Biomedical Products, Inc., Becton Dickinson, Bedford, Mass. (Mouse IL-2 ELISA kit Cat. No. 30032). Duplicate dishes containing confluent monolayers of murine L929 cells ($2 \times 10^6$ cells/dish) were infected with recombinant virus vCP275 or vP1239 expressing murine IL-2, recombinant virus vCP288 or vP1243 coexpressing murine IL-2 and murine IFNγ, or infected with ALVAC or NYVAC parental virus. Following overnight incubation at 37 C., supernatants were harvested and assayed for expression of murine IL-2 using the mouse Interleukin-2 ELISA kit as specified by the manufacturer (Collaborative Biomedical Products, Inc., Becton Dickinson, Bedford, Mass.). The mouse Interleukin-2 ELISA kit is a solid-phase enzyme-immunoassay employing the multiple antibody sandwich principle. ELISA plates were read at 490 nm. Background from ALVAC or NYVAC samples was subtracted, and values from duplicate dishes were averaged. The mouse Interleukin-2 ELISA kit quantitates murine IL-2 in Biological Response Modifiers Program (BRMP) units (Gerrard et al., 1993). The quantity of murine IL-2 secreted is expressed as BRMP u/ml, which is equivalent to BRMP u/$10^6$ cells (Table 27).

TABLE 27

| Recombinant virus | Cytokines expressed | Murine IL-2 secreted |
|---|---|---|
| vCP275 | mIL-2 | 1838 BRMP u/ml |
| vCP288 | mIL-2 + mIFNγ | 2124 BRMP u/ml |
| vP1239 | mIL-2 | 5030 BRMP u/ml |
| vP1243 | mIL-2 + mIFNγ | 4353 BRMP u/ml |

From the results reported in Table 27, it is evident that co-expression of murine IFNγ does not affect the level of murine IL-2 expression by ALVAC or NYVAC-based recombinants. Also, the level of murine IL-2 expression under the conditions of this assay is approximately twice as high for NYVAC based recombinants as it is for ALVAC based recombinants, in agreement with the results presented in Table 23, which were based on a different murine IL-2 ELISA assay (Intertest-2X™, Genzyme Corporation, Cambridge, Mass.).

Example 23

Human IL-2 Plus IFNγ into ALVAC and NYVAC

Insertion of Human IFNγ into C6 locus of ALVAC; addition to ALVAC-Human IL-2 recombinant virus. Insertion of I3L/human IFNγ cassette into C6 locus; construction of pMPC6I3hIF. Plasmid pMPI3hIF (Example 21) was cut with HindIII and blunt ended with Klenow fragment of *E. coli* polymerase. The DNA was then cut with BamHI and a 0.6 kb fragment containing the I3L/human IFNγ cassette was isolated. ALVAC C6 vector plasmid pMM117 (Example 22) was cut with BamHI (partial)/SmaI and the largest fragment was isolated. These fragments were ligated, resulting in insertion plasmid pMPC6I3hIF.

Recombination was accomplished between donor plasmid pMPC6I3hIF and rescuing virus vCP277 (Example 19). Recombinants are plaque purified. The resultant ALVAC based recombinant virus contains the vaccinia I3L promoted human IFNγ gene in the C6 locus and the vaccinia H6 promoted human IL-2 gene in the C3 locus (vCP277+IFNγ).

Insertion of Human IFNγ and IL-2 into NYVAC. Insertion of H6/human IL-2 cassette into the TK locus; construction of pMPTK2hIF. Plasmid pMPTKI3hIF (Example 21) was cut with PstI and phosphatased with Shrimp alkaline phosphatase. Plasmid pRW858 (Example 19) was cut with PstI and a 700 bp fragment isolated. Phosphatased vector and insertion fragment were ligated, resulting in plasmid pMPTK2hIF. In pMPTK2hIF, the two human cytokine gene cassettes are both contained within the NYVAC TK insertion site, oriented in a tail-to-tail orientation. The human IFNγ gene is under the control of the vaccinia I3L promoter, and the human IL-2 gene is under the control of the vaccinia H6 promoter.

Recombination was accomplished between donor plasmid pMPTKh2IF and NYVAC rescuing virus. Recombinants are plaque purified. The resultant NYVAC based recombinant virus contains the vaccinia I3L promoted human IFNγ gene and the vaccinia H6 promoted human IL-2 gene, both in the TK locus (NYVAC+IFNγ+IL-2).

Example 24

Murine IL-4 into ALVAC and NYVAC

Murine IL-4 into ALVAC. Plasmid p2A-E3, containing the murine IL-4 gene, (m IL-4) was obtained from the American Type Culture Collection (ATCC No. 37561). The murine IL-4 gene was placed under the control of the vaccinia E3L promoter by PCR as described below.

The vaccinia E3L promoter, a strong early promoter, is located immediately upstream from the vaccinia E3L open reading frame (Goebel et al., 1990).

Nucleotide sequence of the E3L/murine IL-4 expression cassette is presented in FIG. 30 (SEQ ID NO:178). In FIG. 30, the start codon of the murine IL-4 gene is at nucleotide position 68, and the stop codon is at nucleotide position 488.

The mIL-4 gene was amplified by PCR with oligonucleotide primers MIL45 (SEQ ID NO:179) 5' CTCACCCGGG-TACCGAATTCGAATAAAAAAATGATAAAGTA GGT-TCAGTTTTATTGCTGGTTGTGTTAGTTCTCTCT AAAAATGGGTCTCAACCCCCAG 3' and MIL43 (SEQ ID NO:180) 5' TTAGGGATCCAGATCTC-GAGATAAAAACTACGAGTAATCCATTTG-CATGATGCTC 3' and plasmid p2A-E3 (ATCC) as template. The resulting fragment contained the mIL-4 gene linked to the vaccinia E3L promotor and flanked by XmaI/KpnI/EcoRI and XhoI/BglII/BamHI sites at the 5' and 3' ends, respectively. The amplified E3L/mIL-4 fragment was digested with XmaI/BamHI and ligated to an XmaI/BamHI-digested pVQCP3LSA-5 vector fragment. Plasmid pVQCP3LSA-5 (same as VQCP3LSA-3, Example 20) is an ALVAC C3 locus insertion plasmid. The resulting C3 donor plasmid was designated pC3.MIL4.2. An expression cassette consisting of the *E. coli* gpt gene linked to the entomopox 42 kDa promoter was isolated as a SmaI fragment from plasmid pMP42GPT (Example 22), then cloned into a SmaI-digested pC3.MIL4.2 vector fragment. The resulting plasmid was designated pC3MIL4.gpt.

Recombination was accomplished between donor plasmid pC3MIL4.gpt and ALVAC rescuing virus using the mycophenolic acid selection system (Example 22). Recombinant virus are plaque purified. The resultant recombinant virus contains the murine IL-4 gene under the control of the vaccinia E3L promoter, as well as the Ecogpt gene under the control of the EPV 42 kDa promoter, both at the C3 locus of ALVAC.

Murine IL-4 into NYVAC. The mIL-4 gene was amplified by PCR with primers MIL45 (SEQ ID NO:179) and MIL43 (SEQ ID NO:180) and plasmid p2A-E3 (ATCC) as template. The resulting fragment contained the mIL-4 gene linked to the vaccinia E3L promotor and flanked by XmaI/KpnI/EcoRI and XhoI/BglII/BamHI sites at the 5' and 3' ends, respectively. The amplified E3L/mIL-4 fragment was digested with XmaI/BamHI. NYVAC TK insertion plasmid pSD542 (Example 18) was digested with XmaI/BamHI and ligated to the XmaI/BamHI-digested PCR fragment. The resulting TK donor plasmid was designated pTK-mIL4.

Recombination between donor plasmid pTK-mIL4 and NYVAC rescuing virus generated recombinant virus vP1248 which contains the vaccinia E3L promoted murine IL-4 gene in the TK locus.

Example 25

Human IL-4 into ALVAC and NYVAC

Human IL-4 into ALVAC. Plasmid pcD-hIL-4, containing the human IL-4 gene, was obtained from the American Type Culture Collection (ATCC No. 57593).

PCR fragment PCRhIL4-I was synthesized using plasmid pcD-hIL-4 as template DNA and synthetic oligonucleotides E3LIL4-C (SEQ ID NO:181) 5' GCTGGTTGTGTTAGTTCTCTCTAAAAATGGGTCTCACCTCCCAACTG 3' and E3LIL4-D (SEQ ID NO:182) 5' ATCATCTCTAGAATAAAAATCAGCTCGAACACTTTGAATATTTCTCTCTCATG 3' as primers.

Oligonucleotides E3LIL4-A (SEQ ID NO:183) 5' ATCATCAAGCTTGAATAAAAAAATGATAAAGTAGGTTCAGTTTTATTGCTGGTTGTGTTAGTTCTCTCTAAAA 3' and E3LIL4-B (SEQ ID NO:184) 5' TTTTAGAGAGAACTAACACAACCAGCAATAAAACTGAACCTACTTTATCATTTTTTTATTC 3' were annealed to generate Fragment II containing the vaccinia E3L promoter sequence (Example 24).

A second fusion PCR product (PCRhIL4-II) was obtained using PCR fragment PCRhIL4-I and Fragment II (annealed oligos) as DNA template and E3LIL4-D and E3LIL4-E (SEQ ID NO:185) 5' ATCATCAAGCTTGAATAAAAAAATGATAAAGTAGGTTCAG 3' as oligonucleotide primers. A complete HindIII/XbaI digest of PCRhIL4-II yielded an 536 bp fragment which was subsequently isolated. A complete HindIII/XbaI digest of pBS-SK+ (Stratagene) was performed and the 2.9 kb fragment isolated. The isolated fragments were ligated, resulting in plasmid pBShIL4.

FIG. 31 (SEQ ID NO:186) presents the nucleotide sequence of the expression cassette consisting of the E3L promoted human IL-4 gene. The start codon for the human IL-4 gene is at nucleotide position 62, and the stop codon is at nucleotide position 521.

A complete XbaI digest of plasmid pBShIL4 was performed. Ends were filled in using Klenow fragment of *E. coli* polymerase. This linearized plasmid was then digested with XhoI and the 536 bp fragment, containing the E3L promoter and human IL4 gene, was isolated. C3 insertion vector plasmid VQCP3LSA (same as pVQCP3LSA-3, Example 20) was completely digested with XhoI/SmaI and the 6.5 kb fragment isolated. The isolated fragments were ligated, resulting in insertion plasmid pC3hIL4.

Recombination between donor plasmid pC3hIL4 and ALVAC rescuing virus generated recombinant virus vCP290, which contains the vaccinia E3L promoted human IL-4 gene in the C3 locus.

Human IL-4 into NYVAC. Plasmid pBShIL4 (discussed above) contains the E3L/human IL-4 expression cassette in pBS-SK. A complete XbaI digest of plasmid pBShIL4 was performed. Ends were filled in using Klenow fragment of *E. coli* polymerase. This linearized plasmid was then digested with XhoI and the 536 bp fragment, containing the E3L promoter and human IL-4 gene, was isolated. NYVAC TK insertion vector plasmid pSD542 (Example 18) was completely digested with XhoI/SmaI and the 3.9 kb fragment isolated. The isolated fragments were ligated, resulting in insertion plasmid pTKhIL4.

Recombination between donor plasmid pTKhIL4 and NYVAC rescuing virus generated recombinant virus vP1250, which contains the vaccinia E3L promoted human IL-4 gene in the TK locus.

Example 26

Human GMCSF in ALVAC and NYVAC

Human GMCSF into ALVAC. Plasmid GMCSF, containing the gene encoding the human granulocyte-macrophage colony-stimulating factor (hGMCSF), was obtained from the American Type Culture Collection (ATCC No. 39754).

PCR fragment GMCSF-I was synthesized using plasmid GMCSF as template DNA and E3LGMC-A (SEQ ID NO:187) 5' GCTGGTTGTGTTAGTTCTCTCTAAAAATGTGGCTGCAGAGCCTGCTG 3' and E3LGMC-B (SEQ ID NO:188) 5' ATCATCCTCGAGATAAAAATCACTCCTGGACTGGCTCCCAGCAGTCAAAGGGG 3' as oligonucleotide primers.

Synthetic oligonucleotides E3LSMA-B (SEQ ID NO:189) 5' ATCATCCCCGGGGAATAAAAAAATGATAAAGTAGGTTCAGTTTTATTGCTGGTTGTGTTAGTTCTCTCTAAAA 3' and E3LIL4-B (SEQ ID NO:184; Example 25) were annealed to generate fragment GMCSF-P containing the vaccinia E3L promoter sequence.

A fusion PCR product (GMCSF-II) was obtained using fragments GMCSF-I and GMCSF-P as DNA templates and E3LSMA-A (SEQ ID NO:190) 5' ATCATCCCCGGGGAATAAAAAAATGATAAAGTAGGTTCAG3' and E3LGMC-B as oligonucleotide primers. A complete XhoI/SmaI digest of GMCSF-II yielded a 0.5 kb fragment which was subsequently isolated. A complete XhoI/SmaI digest of pBS-SK+ was performed and the 2.9 kb fragment isolated. The isolated fragments were ligated, resulting in plasmid pBSGMCSF, which contains the vaccinia E3L/hGMCSF expression cassette.

Nucleotide sequence of the vaccinia E3L/hGMCSF expression cassette is given in FIG. 32 (SEQ ID NO:191). In FIG. 32, the start codon for hGMCSF is at nucleotide position 62, the stop codon is at nucleotide position 494.

A complete XhoI/SmaI digest of pBSGMCSF (above) was performed and the 0.5 kb fragment, containing the vaccinia E3L promoter and hGMCSF gene, was isolated. ALVAC C3 insertion plasmid VQCP3LSA (Example 20) was completely digested with XhoI/SmaI and the 6.5 kb fragment isolated. The isolated fragments were ligated, resulting in plasmid pC3hGMCSF.

Recombination between donor plasmid pC3hGMCSF and ALVAC rescuing virus generated recombinant virus vCP285, which contains the vaccinia E3L promoted human GMCSF gene in the C3 locus.

Human GMCSF into NYVAC. A complete XhoI/SmaI digest of pBSGMCSF was performed and the 0.5 kb fragment, containing the vaccinia E3L promoter and hGMCSF gene, was isolated. pSD542 (Example 18) was completely digested with XhoI/SmaI and the 3.9 kb fragment isolated. The isolated fragments were ligated, resulting in plasmid pTKhGMCSF.

Recombination between donor plasmid pTKhGMCSF and NYVAC rescuing virus generated recombinant virus vP1246, which contains the vaccinia E3L promoted human GMCSF gene in the TK locus.

Expression of human GMCSF in ALVAC and NYVAC based recombinants. ELISA assay. The level of expression of human GMCSF produced by ALVAC and NYVAC based recombinants vCP285 and vP1246 was quantitated using an ELISA kit from Genzyme Corporation, Cambridge, Mass. (Factor-Test Human GM-CSF ELISA Kit, Genzyme Corporation, product code GM-TE.) Duplicate dishes containing confluent monolayers of human HeLa cells ($2\times10^6$ cells/dish) were infected with recombinant virus vCP285 or vP1246 expressing human GMCSF or infected with ALVAC or NYVAC parental virus. Following overnight incubation at 37° C., supernatants were harvested and assayed for expression of human GMCSF using the Factor-Test Human GM-CSF ELISA kit as specified by the manufacturer (Genzyme Corporation, Cambridge, Mass.). The Factor-Test Human GM-CSF ELISA Kit is a solid-phase enzyme-immunoassay employing the multiple antibody sandwich principle. ELISA plates were read at 490 nm. Background from ALVAC or NYVAC samples was subtracted, and values from duplicate dishes were averaged. The quantity of human GMCSF secreted is expressed as picograms(pg)/ml, which is equivalent to pg/$10^6$ cells (Table 28).

TABLE 28

| Recombinant virus | Human GMCSF secreted |
|---|---|
| vCP285 | 2413 pg/ml |
| vP1246 | 4216 pg/ml |

Example 27

Human IL-12 in ALVAC and NYVAC

Derivation of DNA encoding the two subunits of the human IL-12 gene. First strand cDNA synthesis was performed on total RNA isolated from human EBV transformed cell line GJBCL stimulated 24 hrs. with 100 nM Phorbol 12,13-Dibutyrate. Oligonucleotide primers used for PCR amplification of the genes encoding the p35 and p40 subunits (below) were based on the published human IL-12 sequence (Gubler et al., 1991).

The p40 subunit of the human IL-12 gene (hIL12p40) was obtained as PCR fragment PCR J60 using first strand cDNA from cell line GJBCL as template and oligonucleotides JP202 (SEQ ID NO:192) 5' CATCATATCGATGGTACCT-CAAAATTGAAAATATATAATTA-CAATATAAAATGTGTCACCAGCAGTTGG 3' and JP189 (SEQ ID NO:193) 5' TACTACGAGCTCTCAGATA-GAAATTATATCTTTTTGGG 3' as primers. PCR J60 was cut with SacI/ClaI and a 1.0 kb fragment was isolated and ligated with pBSSK+ (Stratagene), cut with SacI/ClaI, generating plasmid PBSHIL12p40II. In plasmid PBSHIL12p40II, hIL12p40 is under the control of the entomopox 42 kDa promoter (Example 22).

The sequence of the EPV 42 kDa/human IL-12 P40 expression cassette is presented in FIG. 33 (SEQ ID NO:194). In FIG. 33, the initiation codon for the human IL-12 P40 subunit is at nucleotide position 32, the stop codon is at nucleotide position 1017.

The p35 subunit of the human IL-12 gene (hIL12p35) was obtained as PCR fragment PCR J59 using first strand cDNA from cell line GJBCL as template as oligonucleotides JP186 (SEQ ID NO:195) 5' CATCATGGTACCTCAAAAT-TGAAAATATATAATTACAATATAAAAT-GTGTCCAGCGCGCAGCC 3' and JP201 (SEQ ID NO:196) 5' TACTACATCGATTTAGGAAGCATTCA-GATAG 3' as primers. PCR J59 was cut with Asp718/ClaI and a 0.7 kb fragment was isolated and ligated with pBSSK+ (Stratagene), generating plasmid PG2. The hIL12p35 gene was put under the control of the vaccinia E3L promoter (Example 24) by a PCR reaction using plasmid PG2 as template and oligonucleotides JP218 (SEQ ID NO:197) 5' CATCATGGTACCGAATAAAAAAT-GATAAAGTAGGTTCAGTTTTATTGCTG-GTTGTGTTAGTTCTCTAAAAATGT-GTCCAGCGCGCAGCC 3' and JP220 (SEQ ID NO:198) 5' CATCATATCGATTTAGGAAGCATTCA-GATAGCTCGTCAC 3' as primers. PCR J62 was cut with Asp718/ClaI and a 0.7 kb fragment was isolated and ligated with pBSSK+ (Stratagene), generating plasmid PBSHIL12p35II.

The sequence of the vaccinia E3L/human IL-12 P35 expression cassette is presented in FIG. 34 (SEQ ID NO:199). In FIG. 34, the initiation codon for the human IL-12 P35 subunit is at nucleotide position 62, the stop codon is at nucleotide position 719.

A cassette containing poxvirus-promoted genes for both subunits of human IL-12 was assembled in pBSSK+ by ligating a 0.7 kb Asp718/ClaI fragment from PBSHIL12p35II and a 1.0 kb Asp718/SacI fragment from PBSHIL12p40II into pBSSK+ cut with SacI/ClaI. The resulting plasmid was designated PBSHIL12. In PBSHIL12 the EPV 42 kDa/hIL12p40 cassette and the vaccinia E3L/hIL12p35 cassette are oriented in a head-to-head orientation relative to each other.

Human IL-12 into ALVAC. The combination cassette containing poxvirus-promoted genes for both subunits of human IL-12 was excised as a 1.7 kb SacI/ClaI fragment from plasmid PBSHIL12. The fragment was blunt-ended by treatment with the Klenow fragment of E. coli polymerase, and cloned into ALVAC C6 vector plasmid pC6L (Example 22) cut with SmaI. The resulting plasmid was designated pC6HIL12.

Recombination was performed between donor plasmid pC6HIL12 and ALVAC rescuing virus. Recombinant virus are plaque purified. The resultant recombinant virus (ALVAC+IL-12) contains both of the human IL-12 genes in the C6 locus of ALVAC.

Human IL-12 into NYVAC. The combination cassette containing poxvirus-promoted genes for both subunits of human IL-12 was excised as a 1.7 kb SacI/ClaI fragment from plasmid PBSHIL12. The fragment was blunt-ended by treatment with the Klenow fragment of E. coli polymerase, and cloned into NYVAC TK vector plasmid pSD542 (Example 18) cut with SmaI. The resulting plasmid was designated pTKHIL12.

Recombination was performed between donor plasmid pTKHIL12 and NYVAC rescuing virus. Recombinant virus are plaque purified. The resultant recombinant virus (NYVAC+IL-12) contains both of the human IL-12 genes in the TK locus of NYVAC.

Example 28

Murine B7 in ALVAC and NYVAC

Murine B7 into ALVAC. Preparation of cDNA for murine B7. Macrophages from a naive Balb/c mouse spleen were stimulated in vitro with Concanavalin A and LPS. Total RNA from these cells was used as a template for first-strand cDNA synthesis by reverse transcription using oligo dT as a primer. An aliquot of first strand cDNA preparation was used for the specific murine B7 cDNA amplification by PCR using the primers LF32 (SEQ ID NO:200) 5' TATCTG-GAATTCTATCGCGATATCCGT-TAAGTTTGTATCGTAATGGCTTGCAATTGTCAG 3' and LF33 (SEQ ID NO:201) 5' ATCGTAAGCTTAC-TAAAGGAAGACGGTCTG 3'. The specific primers LF32 and LF33 were derived from the published sequence of murine B7 (Freeman and al., 1991). Nucleotides 5' to the ATG in LF32 correspond to part of the vaccinia H6 promoter (Perkus et al., 1989). The amplified 951 nucleotide cDNA fragment containing the murine B7 gene was digested by EcoRI and HindIII and subsequently cloned into the corresponding sites of the plasmid pBSSK+ (Statagene). The resulting plasmid, pLF1, was digested with NruI and XhoI, and a 949 bp fragment containing part of the vaccinia H6 promoter and the entire murine B7 gene was isolated.

Plasmid pMPC616E6 contains a non relevant gene under the control of the vaccinia H6 promoter in the ALVAC C6 insertion locus. Plasmid pMPC616E6 was digested with NruI and XhoI, and the 4,403 bp NruI-XhoI fragment containing the bulk of the H6 promoter in the ALVAC C6 insertion locus was isolated. This vector fragment was ligated with the NruI/XhoI fragment from pLF1. The resulting plasmid was named pLF4.

Nucleotide sequence of the murine B7 gene is given in FIG. 35 (SEQ ID NO:202). In FIG. 35, the start codon for the murine B7 gene is at nucleotide 1 and the stop codon is at nucleotide 919.

Recombination between donor plasmid pLF4 and ALVAC rescuing virus generated recombinant virus vCP268, which contains the vaccinia H6 promoted murine B7 gene in the C6 locus.

Murine B7 into NYVAC. Plasmid pSIV12 contains a nonrelevant gene under the control of the vaccinia H6 promoter in the NYVAC I4L insertion locus. Plasmid pSIV12 was digested with NruI and XhoI, and the 3,557 bp NruI-XhoI fragment containing the bulk of the H6 promoter in the NYVAC I4L insertion locus was isolated. This fragment was ligated to annealed synthetic oligonucleotides LF57 (SEQ ID NO:203) 5' CGACATTTG-GATTTCAAGCTTCTACG 3' and LF58 (SEQ ID NO:204) 5' GATCCGTAGAAGCTTGAAATCCAAATGTCG 3' which contain an internal HindIII site. The resulting plasmid, pLF2, was digested with NruI and HindIII, and a 3,659 bp vector fragment was isolated. Plasmid pLF1 (above) was digested with NruI and HindIII, and a 951 bp NruI-HindIII fragment containing part of the vaccinia H6 promoter and the entire murine B7 gene was isolated. These two fragments were ligated, generating plasmid pLF3.

Plasmid pLF3 corresponds to an I4L NYVAC donor plasmid containing the entire murine B7 coding sequence under the control of the vaccinia H6 promoter.

Recombination between donor plasmid pLF3 and NYVAC rescuing virus generated recombinant virus vP1230, which contains the vaccinia H6 promoted murine B7 gene in the I4L locus.

Surface expression of B7 on murine tumor cells infected with ALVAC and NYVAC-based recombinants expressing murine B7. K1735 mouse melanoma cells and CC-36 mouse colon carcinoma cells were infected with 10 pfu per cell of NYVAC-B7 (vP1230), ALVAC-B7 (vCP268), or NYVAC or ALVAC parental virus for 1 hour, washed free of unadsorbed virus by centrifugation, and incubated at 37° C. B16 mouse melanoma cells were treated similarly except that the cells were infected with 5 pfu of virus per cell. After a 1 hr (K1735) or overnight (CC-36;B16) incubation, the cells were washed in PBS by centrifugation and resuspended in 1.0 ml of PBS. To each cell preparation, 0.005 ml of 1:5 diluted Fc Block (Pharmingen, San Diego, Calif. , cat. 01241A; purified anti-mouse Fcā II receptor) and 0.1 ml of 1:100 diluted FITC-rat anti-mouse B7 monoclonal antibody (Pharmingen, cat. 01944D) was added. The cells were incubated for 30 minutes at 4° C., washed twice in cold PBS by centrifugation and analyzed for cell-associated FITC fluorescence by flow cytometry (Becton-Dickinson FACScan).

Figure 36:
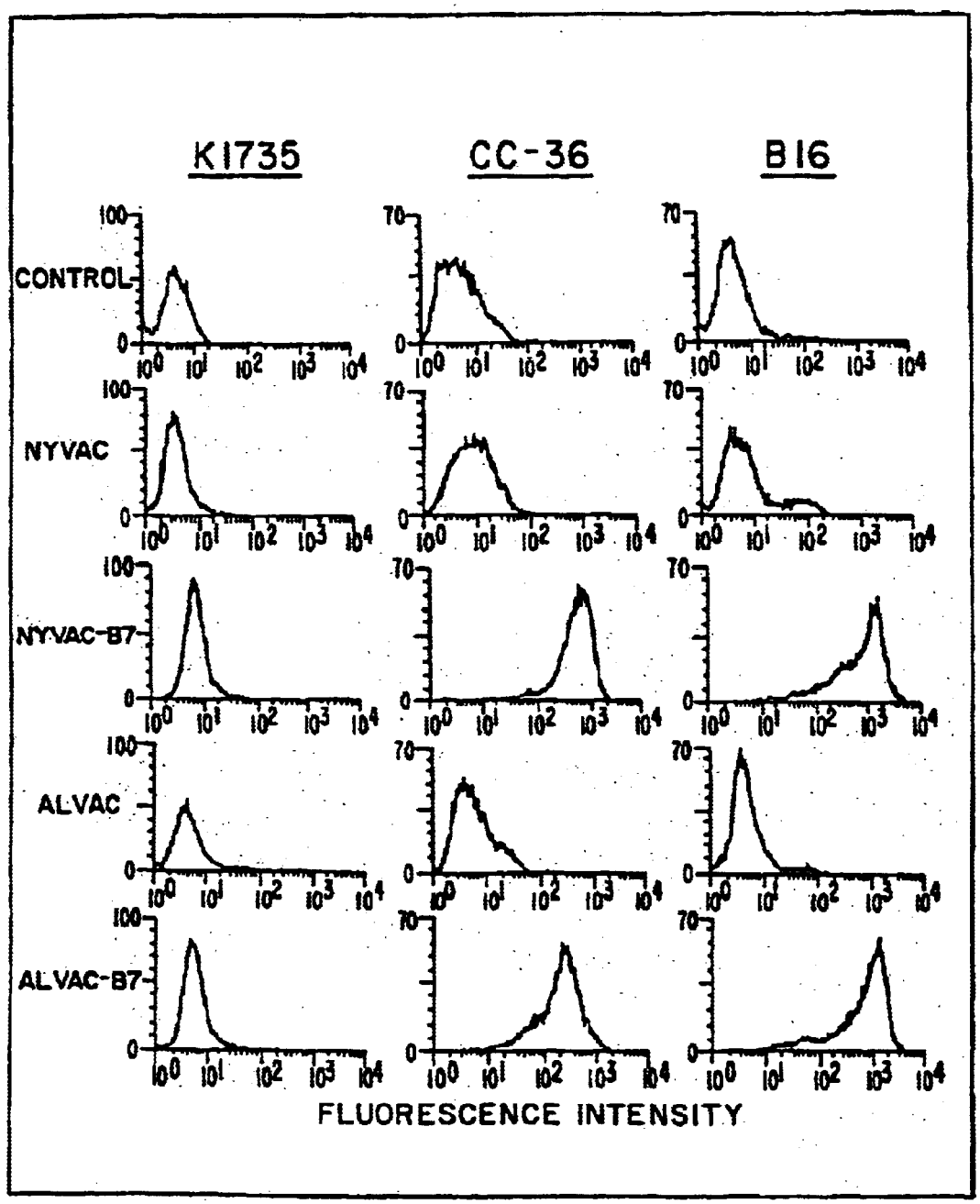
FIG. 36 shows flow cytometric analysis of murine B7 expression in NYVAC and ALVAC infected murine tumor cell lines.
Figure 41:
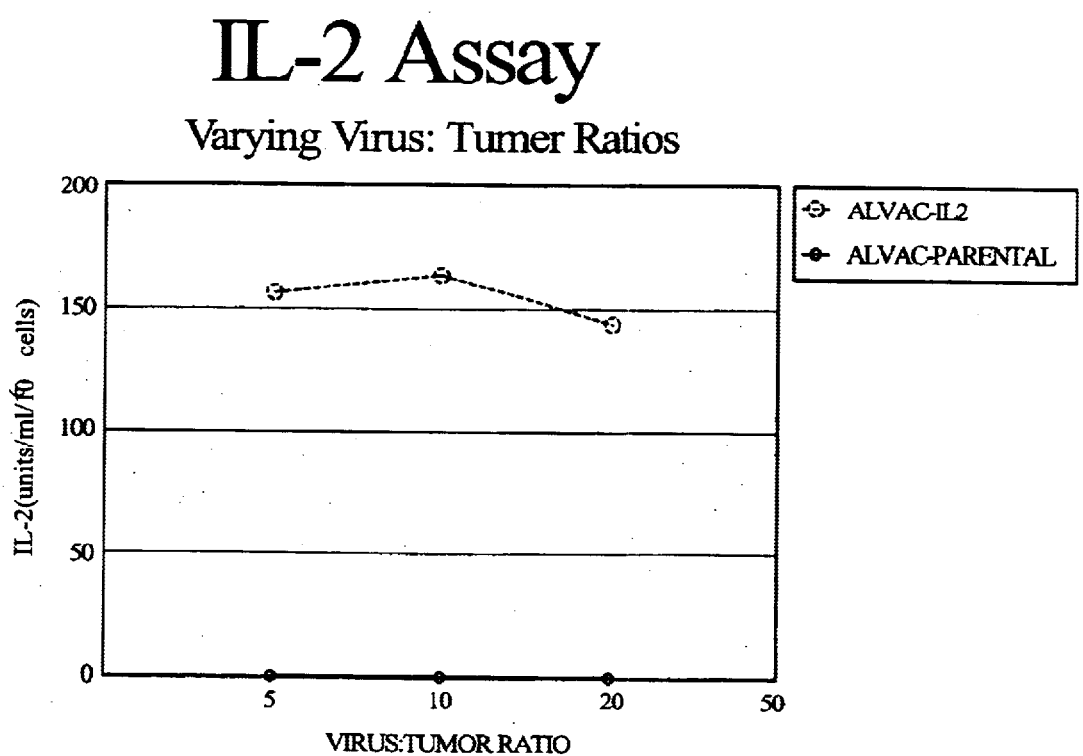
FIG. 41. IL2 Production by RM1 prostate tumor cells infected with ALVAC at the indicated virus; tumor ratios.

Although K1735 cells infected with NYVAC-B7 (vP1230) or ALVAC-B7 (vCP268) for 1 hour showed only slightly higher fluorescence than control uninfected or NYVAC or ALVAC infected cells, B7 expression in recombinant infected CC-36 and B16 cells was remarkable (FIG. 36). As demonstrated by the uninfected control cells, none of the three cell lines endogenously expresses murine B7. Clearly, infection of established murine tumor cell lines with NYVAC-B7 (vP1230) or ALVAC-B7 (vCP268), but not the vectors NYVAC or ALVAC, results in high levels of expression of the murine T-lymphocyte co-activator molecule, BB-1/B7.

Example 29

Human B7 in NYVAC

Preparation of cDNA for human B7. Macrophages from human peripheral blood were stimulated in vitro with Concanavalin A and LPS. Total RNA from these cells was used as a template for first-strand cDNA synthesis by reverse transcription using oligo dT as a primer. An aliquot of first strand DNA preparation was used for specific human B7 cDNA amplification by PCR using the primers LF62 (SEQ ID NO:205) 5' ATCGTAAGCTTATTATACAGGGCGTA-CACTTTC 3' and LF61bis (SEQ ID NO:206) 5' TATCTG-GAATTCTATCGCGATATCCGT-TAAGTTTGTATCGTAATGGGCCACACACGGAGG 3'.

The specific primers LF62 and LF61bis were derived from the published sequence of human B7 (Freeman and al., 1989). Nucleotides 5' to the ATG in LF61bis correspond to part of the vaccinia H6 promoter (Perkus et al., 1989). The amplified 997 nucleotide cDNA fragment containing the murine B7 gene was digested by EcoRI and HindIII and subsequently cloned into the corresponding sites of the plasmid pBSSK+ (Stratagene). This plasmid was designated pLF6.

The sequence for the human B7 gene is presented in FIG. 37 (SEQ ID NO:207). In FIG. 37, the start codon for the human B7 gene is at nucleotide position 1 and the stop codon is at nucleotide position 865.

Insertion of Human B7 into NYVAC. Plasmid pLF3 (Example 28) was digested with NruI and HindIII and a 3652 bp vector fragment containing the bulk of the H6 promoter in the NYVAC I4L insertion locus was isolated. Plasmid pLF6 (above) was digested with NruI and HindIII, and a 897 bp fragment containing part of the vaccinia H6 promoter and the entire human B7 gene was isolated. These two fragments were ligated, generating plasmid pLF7.

Plasmid pLF7 corresponds to an I4L NYVAC donor plasmid containing the entire human B7 coding sequence under the control of the vaccinia H6 promoter.

Recombination between donor plasmid pLF7 and NYVAC rescuing virus generated recombinant virus vP1245, which contains the vaccinia H6 promoted human B7 gene in the I4L locus.

Expression of human B7. FACScan. Human HeLa cells were infected with recombinant virus vP1245 expressing human B7 or with NYVAC parental virus. A monoclonal antibody specific for human B7 (Anti-BB1 (B7), Cat. No. 550024, Becton Dickinson Advanced Cellular Biology, San Jose, Calif.), was used to detect expression of human B7 on the surface of infected cells by flow cytometry (Becton-Dickinson FACScan) as described in Example 28. B7 was detected on the surface of cells infected with recombinant virus vP1245. B7 was not detected on the surface of uninfected cells or cells infected with NYVAC parental virus.

Immunoprecipitation. NYVAC based recombinant virus vP1245 was assayed for expression of the human B7 gene using immunoprecipitation. Recombinant or parental virus were inoculated onto preformed monolayers of tissue culture cells in the presence of radiolabelled $^{35}S$-methionine and treated as previously described (Taylor et al., 1990). Immunoprecipitation reactions were performed using a monoclonal antibody specific for human B7 (Anti-BB1(B7), Cat. No. 550024, Becton Dickinson Advanced Cellular Biology, San Jose, Calif.). A protein of between approximately 44 and 54 kDa was precipitated from cells infected with recombinant virus vP1245, in agreement with Freeman et al. (1989). The protein was not immunoprecipitated from uninfected cells or cells infected with NYVAC parental virus.

Example 30

Co-insertion of Murine IFNγ and Murine B7 into ALVAC and NYVAC

Co-Insertion of Murine IFNγ and Murine B7 into ALVAC. Recombination was accomplished between donor plasmid pLF4 (Example 28) and rescuing virus vCP271 (Example 20). Recombinant virus are plaque purified. The resultant ALVAC based recombinant virus (ALVAC+IFNγ+B7) contains the vaccinia I3L promoted murine IFNγ gene in the C3 locus and the vaccinia H6 promoted murine B7 gene in the C6 locus.

Co-Insertion of Murine IFNγ and Murine B7 into NYVAC. Recombination was accomplished between donor plasmid pMPTKmIF (Example 20) and rescuing virus vP1230 (Example 28). Recombinant virus are plaque purified. The resultant NYVAC based recombinant virus (NYVAC+IFNγ+B7) contains the vaccinia I3L promoted murine IFNγ gene in the TK locus and the vaccinia H6 promoted murine B7 gene in the I4L locus.

Example 31

Insertion of Wildtype and Mutant Forms of Murine P53 into ALVAC

The gene for the nuclear phosphoprotein p53 is the gene most frequently found to be mutated in a wide variety of human tumors (reviewed in Hollstein et al., 1991). NYVAC and ALVAC-based p53 recombinant virus are described in Example 15.

Insertion of wildtype Murine p53 into ALVAC. Plasmid p11-4 containing murine wild-type p53 was received from Arnold Levine (Princeton University, Princeton, N.J.). The p53 sequence is described in Pennica et al., (1984). The murine wild-type p53 gene was placed under the control of the vaccinia H6 promoter and the p53 3' non coding end was removed with PCR-derived fragments.

A fragment containing the H6 promoted 5' end of the p53 gene fused to the 3' end of the p53 gene was generated by several PCRs as described below.

PCR I: Plasmid pRW825, containing the H6 promoter and a nonpertinent gene, was used as template with oligonucleotides MM080 (SEQ ID NO:208) 5' ATTATTATTGGATCCTTAATTAATTAGTGATACGC 3' and MM081 (SEQ ID NO:209) 5' CTCCTCCATGGCAGTCATTACGATACAAACTTAAC 3' producing a 228 bp fragment containing the H6 promoter and the 5'-most base pairs of the murine p53 gene. MM080 anneals to the 5' end of the H6 promoter and primes toward the 3' end. MM081 anneals to the 3' end of the H6 promoter and primes toward the 5' end.

PCR II: Plasmid p11-4 was used as template with oligonucleotides MM082 (SEQ ID NO:210) 5' CGTTAAGTTTGTATCGTAATGACTGCCATGGAGGAGTC 3' and MM083 (SEQ ID NO:211) 5' TAGTAGTAGTAGTAGCTTCTGGAGGAAGTAGTTTCC 3' to generate a 129 bp fragment with the 3'-end of the H6 promoter, the 5' end of the p53 gene followed by 15 bp which overlaps PCR fragment PCRIII (described below). MM082 contains the 3' end of the H6 promoter and primes from the 5' end of the murine p53 gene. MM083 anneals to position 97 (FIG. 38) of the murine p53 gene and primes toward the 5' end.

PCRIII: Plasmid p11-4 was used as template with oligonucleotides MM084 (SEQ ID NO:212) 5' CAGAAGCTACTACTACTACTACCCACCTGCACAAGCGCC 3' and MM085 (SEQ ID NO:213) 5' AACTACTGTCCCGGGATAAAAATCAGTCTGAGTCAGGCCCCAC 3' to generate a 301 bp fragment. The 301 bp PCR-derived fragment contains the 3' end of the p53 gene, and the 5' end overlaps the 3' end of the PCRII product. MM084 (SEQ ID NO:212) primes from position 916 of the murine p53 gene toward the 3' end. MM085 (SEQ ID NO:213) primes from position 1173 toward gene 5' end. The three PCR products were pooled and primed with MM080 and MM085. The resultant 588 bp fragment contains a BamHI site followed by the H6 promoted 5' end of the p53 gene fused to the p53 gene 3' end followed by a SmaI site; the 5' end of the p53 gene ends at the XhoI site at position 37, and the 3' end starts at the SacII site at position 990 (FIG. 38). The 588 bp PCR-derived fragment was digested with BamHI and SmaI generating a 565 bp fragment which was inserted into BamHI/SmaI digested pNC5LSP5 (described below). The resultant plasmid, designated pMM136, was digested with KspI and XhoI to remove a 149 bp fragment, and the 953 bp KspI/XhoI fragment from p11-4 was inserted. The resultant plasmid, pMM148, contains the H6 promoted wild-type murine p53 in the ALVAC C5 insertion locus.

The construction of pNC5LSP5 is as follows. A C5 insertion vector plasmid pC5LSP (Example 14) was digested with EcoRI, treated with alkaline phosphatase and ligated to self-annealed oligonucleotide CP29 (SEQ ID NO:102) 5' AATTGCGGCCGC 3', then digested with NotI and linear purified followed by self-ligation. This procedure introduced a NotI site to pC5LSP, generating pNC5LSP5.

The nucleotide sequence of the wildtype murine p53 gene is presented in FIG. 38 (SEQ ID NO:214). The start codon is at position 1 and the stop codon is at position 1171.

Recombination between donor plasmid pMM148 and ALVAC rescuing virus generated recombinant virus vCP263. vCP263 contains the wild type murine p53 gene under the control of the vaccinia H6 promoter in the C5 locus.

Insertion of a mutant form of Murine p53 into ALVAC. Plasmid pSVK215 containing a mutant form of the murine p53 gene was received from Arnold Levine (Princeton University, Princeton, N.J.). The mutation in pSVKH215 changes the sequence GTAC of the murine p53 coding sequence (FIG. 38) nt positions 643 through 646 to CCAAGCTTGG. The insertion between nt positions 643 and 646 changes the predicted amino acid coding sequence from val-pro to pro-ser-leu-ala; and the insertion replaces a KpnI site with a HindIII site. The construction of pSVKH215 is described in Tan et al., (1986).

Plasmid pMM136 (described above) contains the vaccinia H6 promoted 5' end of the p53 gene fused to the 3' end of the p53 gene in an ALVAC C5 locus insertion plasmid. pMM136 was digested with KspI and XhoI to remove 149 bp, and the 960 bp KspI/XhoI fragment containing the mutation described above from pSVKH215 was inserted. The resultant plasmid, pMM149, contains the H6 promoted murine mutant p53 gene in the C5 locus.

Recombination between donor plasmid pMM149 and ALVAC rescuing virus generated recombinant virus vCP267. vCP267 contains the mutant form of the murine p53 gene under the control of the vaccinia H6 promoter in the C5 locus.

Example 32

Insertion of Mutant Forms of Human P53 into ALVAC and NYVAC

Mutant forms of Human p53 into ALVAC. FIG. 18 (Example 15) presented the sequence of the vaccinia H6 promoted human wild type p53 gene cassette in an ALVAC-based recombinant, vCP207. In this example, to facilitate description of the mutant forms of the human p53 gene being described, FIG. 39 (SEQ ID NO:215) presents only the coding sequence for the human wild type p53 gene. The start codon is at position 1 and the stop codon is at position 1180.

Plasmid Cx22A, containing a mutant form of the human p53 gene, was received from Arnold Levine (Princeton University, Princeton, N.J.). Relative to the wild type p53 sequence presented in FIG. 39, the G at nucleotide position 524 is substituted with an A, changing the arg amino acid at codon 175 of the wild type protein to a his amino acid in Cx22A.

Plasmid pMM110 (Example 15, FIG. 18) contains the vaccinia H6 promoted wildtype human p53 gene in the ALVAC C5 insertion site. The human p53 gene contains two PflmI sites. p53 coding sequences upstream from the first PflmI site and downstream from the second PflmI site are the same in pMM110 as in Cx22A. pMM110 was digested with PflmI to remove the 853 central base pairs of the p53 gene. The 853 bp PflmI fragment from Cx22A containing the base change at position 524 was inserted. The resultant plasmid, pMM143, contains the H6 promoted mutant p53 gene.

Recombination between donor plasmid pMM143 and ALVAC rescuing virus generated recombinant virus vCP270. vCP270 contains the mutant form of the human p53 gene under the control of the vaccinia H6 promoter in the C5 locus.

Plasmid pR4-2 containing a mutant form of the human p53 gene was received from Arnold Levine (Princeton University, Princeton, N.J.). Relative to the wild type p53 sequence presented in FIG. 39, the G at nucleotide position 818 is substituted by an A, changing the arg codon at amino acid position 273 to a his codon in pR4-2.

Plasmid pMM110 (Example 15, FIG. 18) contains the vaccinia H6 promoted human wildtype p53 gene in the ALVAC C5 insertion site. p53 coding sequences upstream from the first PflmI site and p53 coding sequences downstream from the second PflmI site are the same in pMM110 as in pR4-2. pMM110 was digested with PflmI to remove the 853 central base pairs of the p53 gene. The 853 bp PflmI fragment from pR4-2 containing the base change at nucleotide position 818 was inserted. The resultant plasmid, pMM144, contains the H6 promoted mutant form of the human p53 gene in the C5 insertion locus.

Recombination between donor plasmid pMM144 and ALVAC rescuing virus generated recombinant virus vCP269. vCP269 contains the mutant form of the human p53 gene under the control of the vaccinia H6 promoter in the C5 locus.

Mutant forms of Human p53 into NYVAC. Plasmid Cx22A, described above, contains a mutant form of the human p53 gene, in which the G at nucleotide position 524 (FIG. 39) is substituted by an A, changing the arg codon at amino acid position 175 to a his codon in Cx22A.

Plasmid pMM106 (Example 15) contains the vaccinia H6 promoted wild-type human p53 gene in the NYVAC I4L insertion locus. p53 coding sequences upstream from the first PflmI site and p53 coding sequences downstream from the second PflmI site are the same in pMM106 as in Cx22A. pMM106 was digested with PflmI to remove the 853 central base pairs of the p53 gene. The 853 bp PflmI fragment from Cx22A containing the base change at position 524 was inserted. The resultant plasmid, pMM140, contains the H6 promoted mutant p53 gene.

Recombination between donor plasmid pMM140 and NYVAC rescuing virus generated recombinant virus vP1234. vP1234 contains the mutant form of the human p53 gene under the control of the vaccinia H6 promoter in the I4L locus.

Plasmid pR4-2, described above, contains a mutant form of the human p53 gene, in which the G at nucleotide position 818 (FIG. 39) is substituted by an A, changing the arg codon at amino acid position 273 to a his codon in pR4-2.

pMM106 (Example 15) contains the H6 promoted wild-type human p53 gene in the I4L locus. p53 coding sequences upstream from the first PflmI site and p53 coding sequences downstream from the second PflmI site are the same in pMM106 as in pR4-2. pMM106 was digested with PflmI to remove the 853 central base pairs of the p53 gene. The 853 bp PflmI fragment from pR4-2 containing the base change at position 818 was inserted. The resultant plasmid, pMM141, contains the H6 promoted mutant p53 gene.

Recombination between donor plasmid pMM141 and NYVAC rescuing virus generated recombinant virus vP1233. vP1233 contains the mutant form of the human p53 gene under the control of the vaccinia H6 promoter in the I4L locus.

A listing of the wildtype and mutant forms of murine p53 and the mutant forms of human p53 present in ALVAC and NYVAC recombinants described in Examples 31 and 32 is provided in Table 29.

TABLE 29

| Recombinant Virus | Parent Virus | Species | Gene Insert |
| --- | --- | --- | --- |
| vCP263 | ALVAC | murine | w.t. p53 |
| vCP267 | ALVAC | murine | p53 (+3 aa) |
| vCP270 | ALVAC | human | p53 (aa 175; R to H) |
| vCP269 | ALVAC | human | p53 (aa 273; R to H) |
| vP1234 | NYVAC | human | p53 (aa 175; R to H) |
| vP1233 | NYVAC | human | p53 (aa 273; R to H) |

Immunoprecipitation. ALVAC and NYVAC based recombinants vP1101, vP1096, vP1098, vCP207, vCP193, vCP191 (all described in Example 15; Table 22, as well as ALVAC and NYVAC based recombinants vCP270, vCP269, vP1233, vP1234 described in this Example, Table 29), contain wild type or mutant forms of the human p53 gene. All of these recombinant virus were assayed for expression of the human p53 gene using immunoprecipitation.

Recombinant or parental virus were inoculated onto preformed monolayers of tissue culture cells in the presence of radiolabelled $^{35}$S-methionine and treated as previously described (Taylor et al., 1990). Immunoprecipitation reactions were performed using a human p53 specific monoclonal antibody 1801. A protein of between 47 and 53 kDa was precipitated from cells infected with any of the recombinant viruses, vP1101, vP1096, vP1098, vCP207, vCP193, vCP191, vCP270, vCP269, vP1233, or vP1234, but not from uninfected cells or cells infected with parental ALVAC or NYVAC virus.

Based upon the properties of the poxvirus vector systems, NYVAC, ALVAC and TROVAC cited above, such vectors expressing either wildtype or mutant forms of p53 provide valuable reagents to determine whether endogenous CTL activities can be detected in patient effector populations (TILs, PBMC, or lymph node cells); and, valuable vehicles for the stimulation or the augmenting of such activities; for instance, augmenting such activities by in vitro or ex vivo stimulation with these recombinant viruses. Further, the highly attenuated properties of both NYVAC and ALVAC allow the recombinants of the invention to be used for interventive immunotherapeutic modalities discussed above, e.g., in vivo interventive immunotherapy

Example 33

ERB-B-2 into COPAK

Plasmid ErbB2SphIstop was obtained from Jeffrey Marks (Duke University Center). ErbB2SphIstop contains a 3.8 kb human erb-B-2 cDNA insert cloned in pUC19. The insert extends from nt 150 through nt 3956 (Yamamoto et al., 1986) and contains the entire erb-B-2 coding sequence. In ErbB2SphIstop, the SphI site at nt 2038 was mutagenized by the addition of an XbaI linker, creating an in frame stop codon. The remaining, truncated, ORF thus specifies an extracellular, secretable form of the erb-B-2 gene product, mimicking the translation product of the 2.3 kb mRNA. Plasmid ErbB2SphIstop was digested with XhoI and the 3.8 kb erb-B-2 fragment was isolated. This isolated fragment was ligated with COPAK vector plasmid pSD555 cut with XhoI, resulting in plasmid pMM113.

Plasmid pSD555 was derived as follows. Plasmid pSD553 (Example 17) is a vaccinia deletion/insertion plasmid of the COPAK series. It contains the vaccinia K1L host range gene (Gillard et al., 1986) within flanking Copenhagen vaccinia arms, replacing the ATI region (orfs A25L, A26L; Goebel et al., 1990).

Plasmid pSD553 was cut with NruI and ligated with a SmaI/NruI fragment containing the synthetic vaccinia H6 promoter element (Perkus et al., 1989) upstream from the NruI site located at −26 relative to the translation initiation codon. The resulting plasmid, pMP553H6, contains the vaccinia H6 promoter element located downstream from the K1L gene within the A26L insertion locus.

To complete the vaccinia H6 promoter and add a multicloning region for the insertion of foreign DNA, plasmid pMP553H6 was cut with NruI/BamHI and ligated with annealed synthetic oligonucleotides MPSYN349 (SEQ ID NO:216) 5' CGATATCCGTTAAGTTTGTATCGTAATG-GAGCTCCTGCAGCCCGGGG 3' and MPSYN350 (SEQ ID NO:217) 5' GATCCCCCGGGCTGCAGGAGCTCCAT-TACGATACAAACTTAACGGATATCG 3'. The resulting plasmid, pSD555, contains the entire H6 promoter region followed by a multicloning region.

Recombination between donor plasmid pMM113 and NYVAC rescuing virus generated recombinant virus vP1100. vP1100 contains the erb-B-2 gene under the control of the vaccinia H6 promoter in the I4L locus, along with the vaccinia K1L host range gene.

Immunoprecipitation. Preformed monolayers of Vero cells were inoculated at 10 pfu per cell with parental NYVAC virus and recombinant virus vP1100 in the presence of radiolabelled $^{35}$S-methionine and treated as previously described (Taylor et al., 1990). Immunoprecipitation reactions were performed using a human erb-B-2 specific monoclonal antibody TA1-1C. A protein of approximately 97 kDa was precipitated from cells infected with vP1100, but not from uninfected cells or cells infected with parental NYVAC virus.

Example 34

Immunotherapy of Prostate Cancer Using Non-Replicative Canary—Pox (ALVAC) Virus Carrying Cytokine Genes and Bladder Tumor Studies The effect of local cytokine production on the growth and development of tumor immunity to the prostate tumor (RM-1; provided by Dr. Timothy C. Thompson, Baylor College of Medicine, Houston, Tex.) was tested. The cytokine genes (IL2, IFNγ, TNFα, GM-CSF, and IL12) and the co-stimulatory molecule, B7, were incorporated into the canary pox viral vector, ALVAC (Virogenetics, Inc, Troy, N.Y.). ALVAC is a canarypox virus that does not undergo productive replication in mammalian cells, although the protein production of extrinsic genes by treated cells is high. Parental ALVAC (cPpp) for five (5) hours. Preliminary studies using the ALVAC-IL2 vector (vCP275) measured IL2 production at varying virus: tumor ratios of 5:1, 10:1, and 20:1. IL2 concentrations were 156, 164 and 146 u/ml/ $10^6$ cells/24 hour, respectively. Because the 5:1 ratio gave equivalent IL2 levels, this infectivity ratio was used for all antitumor studies. Infected tumor cells were inoculated subcutaneoulsy in the back of C57BL/6 mice, and tumor growth and survival were followed. The initial studies tested the growth of RM-1 cells treated with ALVAC-IL2, ALCAC-IFNγ (vCP271), ALVAC-TNFα was observed to significantly (P<0.05) delay RM-1 outgrowth compared to parental virus control. ALVAC-TNFα treatment alone enhanced survival; however, all animals ultimately died of tumor. Studies were performed to determine the effect of ALVAC-TNFα combined with either ALVAC-IL2, ALVAC-B7 or ALVAC-IFNγ. Combination therapy with ALVAC-IL2 and ALVAC-TNFα significantly enhanced the ingibition of tumor growth (P<0.005). Furthermore, the combination of TNFα and IL2 induced RM-1 regression in 60% of treated mice. The regression resulted in complete cure since no tumor recurrence was observed during an observation period of 100 days. Histological analysis of the tumor regression site revealed mononuclear infiltration and tumor cell necrosis. No cytotoxic T lymphocyte (CTL) activity forward RM-1 cell was observed in mice rejecting RM-1 tumors, although allogeneic CTL were observed to kill RM-1 cells. Furthermore, no protection against subsequent tumor challenge was present in RM-1 cured mice. Finally, RM-1 cells were demonstrated to be resistant to the lytic effects of TNFα in vitro. These data suggest that the combination of ALVAC-TNFα and ALVAC-IL2 induced nonspecific immune mechanisms that resulted in tumor elimination.

Splenocytes from the same pool were incubated for 48 hours with 10 units per ml of Interleukin 2. Further, 51 chromium release assays performed on cells cultured in this manner demonstrate a specific lysis of RM1 target cells. EL4 control target cells were not lysed. Again, the lytic activity was restricted to TNFα plus IL2 and TNFα plus IL12. These immunological data suggest that cytotoxic T lymphocytes are generated when tumors are treated with TNFα plus IL12.

The data provided clearly show effective antitumor activity with selected cytokine vectors. The role of immune-effector cells is unclear. Vectors combined with TNFα all appear to be effective in inhibiting tumor outgrowth in immune-deficient mice (SCID mice). In normal mice, cytotoxic T Lymphocytes are activated by TNFα plus IL2 and TNFα plus IL12. These in vitro data suggest that an immune component may be functional and protection.

Prostrate Immunotherapy

Rationale. Prostate cancer is the most common visceral cancer and the second-leading cause of death from cancer in men in the United States. Definitive treatment of prostate cancer is limited to radical surgery for localized disease. Locally invasive and metastatic prostate cancer is treated in a palliative manner by oral estrogen or orchiectomy. The appearance of hormone independent cancer denoted tumor progression for which no treatment is available. In this study we activate an immune response to prostate tumor cells that eliminate both hormone sensitive and insensitive prostate cancer. An immune response to prostate associated antigens can be induced that will target immunoreactive cells to prostate cancer and result in tumor destruction. In these studies we activate the immune response by producing immuno-modulatory cytokines in tumor cells. This was accomplished by infecting tumor cells with recombinant viral constructs (ALVAC or NYVAC) expressing various cytokines. These vectors activate immunoreactive cells (both specific and nonspecific) that will destroy prostate tumor cells. The activation of such a response eliminate locals as well metastatic tumors.

Prostate Immunotherapy. The development of immunotherapy for prostate cancer is in its infancy. Sandra and associates demonstrated the effectiveness of immunizing with gene transfected prostate tumor cells in the Dunning rat prostate cancer model.

Studies in an animal model demonstrate that immunization against autologous prostate antigens can be induced and expressed specifically in the prostate.(Keetch, et al., 1994) Moreover, clinical studies show autoimmune reactivity to PSA in patients with symptomatic non-bacterial prostatitis. Thus, immune reactivity to prostate antigens such as PSA can be initiated with appropriated immunization protocols. These data suggest that immunoreactive immune cells capable of responding to prostate tumors can be developed.

Tumor Model. The RM1 (previously called MPR31-4) transplantable prostate tumor was obtained from Dr. Timothy Thompson (Baylor College of Medicine). The tumor is an oncogene transformed line developed as described. (Thompson, et al., 1989) Studies have established the RM1 model as an appropriate model for immunotherapy studies. The tumor is weakly immunogenic in that the pre immunization with irradiated tumor cells does not confer protection against subsequent tumor challenge. Tumors are maintained as cell lines in vitro.

Mice. Male mice (C57bl/6), syngeneic to the RM1 tumor, were purchased from Charles River, Inc. at 6–8 weeks of age. Upon arrival the mice are allowed to acclimate a minimum of 2 days prior to use. They are provided with food ad water ad libitum. Viral Vectors. The canary pos virus, ALVAC, which is non-replicative in primates, was used in the studies described below. The following constructs were tested:

ALVAC

Parental (CPpp)
Mu-IL2 (vCP275)
MU-IFNγ (cCP271)
HU-TNFα (vCP245)
Mu-B7 (vCP268)
Mu-IL-12 (vCP1303)
Mu-GMCSF (vP1277)

Virus is maintained at −70° C. until used.

Infection of tumor cells with virus. RM1 cells are removed from tissue culture flasks with 10 mM EDTA treatment for 10 minutes. The cells were washed three times with phosphate buffered saline (PBS; 0.1 M, pH 72.) The cells were resuspended to the desired concentration in DME (Washington University media Center) supplemented with 10 mM HEPES buffer, pH7.0. Viral vectors were thawed and diluted in the same medium added to the cells. The cultures were incubated at 37 C. for 5 hours, washed three times and injected in mice or were tested for cytokine production in vitro.

Tumor Inhibition Studies. Tumors treated as described above are injected subcutaneously at a concentration of $5 \times 10^5$ cells per mouse. Each group consisted of 5 mice. The outgrowth of the tumor is monitored twice a week for extended periods (see data for times). Twice a week tumors are measured at their widest and narrowest regions. Tumor volume was calculated and mean values for each treatment group is reported. Mice were sacrificed for humane reasons at varying times depending on the rate of tumor growth. Thus the data reported for some experimental groups has reduced time intervals.

Results

Evaluation of IL2 production by varying virus-to-cell ratios. MPR31-4 cells were infected with varying numbers of ALVAC-IL2. MPR31-4 ($10^6$) cells were exposed to virus as described above. Cells were incubated for 24 hours and supernatants were collected and measured for IL2. The results are shown in FIG. 60.

The data show equivalent production of IL2 by all infection ratios. Thus all subsequent experiments were performed using the 5:1 ratio.

Antitumor Effects of ALVAC Cytokine vectors. The effects of ALVAC-IL2, -IFNγ, -TNFα, and B7 were compared in an in vivo antitumor study. MPR31-4 tumor cells were infected with virus as described above and implanted in syngeneic mice. The results are shown below (FIG. 61).

The size of tumors for the parental and tumor only groups were not significantly different. In contrast, all ALVAC cytokine vectors were significantly smaller ($P<0.016$) when compared to the tumor only group. Only TNFα was significantly ($p<0.016$) smaller than the parental group.

Effect of Combination Therapy with ALVAC IL2 and TNFα. Studies were initiated to test the effects of ALVAC-IL2 in combination with ALVAC-TNFa. Both IL2 and TNFα significantly ($p<0.0001$) inhibited MPR31-4 outgrowth. The results are shown in FIG. 62.

The reason for the increased activity in this experiment is not known. As in previous experiments, TNFα showed significant ($P,0.0001$) inhibitory activity. Combination therapy with ALVAC-IL2 and ALVAC-TNFα showed enhanced antitumor activity. Of 5 mice treated with combination therapy, 3 developed tumor by day 7; however, all tumors regresse to undetectable levels by day 18. These animals were followed for 50 days without tumor regrowth. The remaining 2 mice developed tumors by day 21 that grew progressively but at a reduced rate throughout the remainder of the experiment. Preliminary tests for the presence or cytotoxic T lymphocyte activity were negative (data not shown). Flow cytometry studies demonstrated the expression of MHC Class on MPR31-4 cells.

Conclusions

ALVAC-IL2 and ALVAC-TNFα were observed to mediate antitumor activity against the MPR31-4 prostate tumor model. Combination therapy with ALVAC0-IL2 and ALVAC-TNFα provided optimal results with 3 mice experiencing tumor regression after initial tumor outgrowth. These mice did not develop subsequent tumors suggesting complete remission.

Example 35

Bladder Cancer Studies

Rationale. In 1993 there will be more than 50,000 new cases of transitional cell carcinoma of the urinary bladder cancer diagnosed in the United States. (Boring, et al. 1992) Approximately 80% of the new cases are superficial at initial diagnosis. After treatment by transuretheral surgical intervention, 40–80% of the new cases are superficial at initial diagnosis. After treatment by transurethral surgical intervention, 40–80% of the patients will suffer recurrent tumor within 3 years and 15–30% of these patients will develop invasive or metastatic disease (Althausen, et al. 1976; Fitzpatrick, et al., 1986; Gilbert, et al., 1978).

The current treatment for invasive bladder cancer is surgery with adjuvant radiation of chemotherapy. The response to this combined therapy approximate 50%. (Goffinet, et al.; van der Werf-Messing, 1978) Superficial bladder cancer is treated with adjuvant intavesical Mycobacterium bovis strain bacillus Calmette-Guerin (BCG) (Lamm, et al., 1991). While BCG is the most effective treatment for superficial bladder cancer, only approximately 70% of patients respond and treatment is not efficacious for muscle-invasive cancer. In addition, the instillation of viable bacteria into the bladder is not without risk. Systemic complications associated with the use of viable BCG are potentially serious.(Lamm, et al., 1989) Dissemination of bacteria in the form of pneumonitis, hepatitis, epididymitis/orchitis, renal abscess and granulomatous prostatitis have been observed. At least 7 deaths have been attributed to BCG sepsis after intravesical therapy. Recent unpublished studis suggest that efficacy can be increased by increasing the treatment number. The increase risk associated with the proposed enhanced treatment regimen and the lack of efficacy for muscle-invasive disease warrant the pursuit of alternative therapies.

These studies test the efficacy of ALVAC and NYVAC vectors carrying cytokine genes as a means of treating either or both superficial and invasive bladder cancer.

Tumor Model. The well characterized bladder tumor mode, MBT2, was used in these studies. Previous studies by us and others have shown this model to be predictive of the clinical response to the tested agent.

Mice. Female mice (C3H/He), syngeneic to the MBT2 tumor, were purchased from Charles River, In. at 6–8 weeks of age. Upon arrival the mice are allowed to acclimate a minimum of 2 days prior to use. They are provided with food and water ad libitum.

Viral Vectors. The canary pox virus, ALVAC, and the genetically modifie vaccinia virus, NYVAC, both of which are non-replicative in primates, were used in the studies described below. The following recombinants were tested:

| ALVAC | NYVAC |
|---|---|
| Parental (CPpp) | Parental (vP866) |
| Mu-IL2 (vCP275) | Mu-IL2 (vP1239) |
| MU-IFNγ (vCP271) | |
| Hu-TNFα (vCP245) | |
| Mu-B7 (vCP268) | |

Virus is maintained at −70 C. until used.

Infection of tumor cells with virus. MBT2 cells are removed from tissue culture flasks with 10 mM EDTA treatment for 10 minutes. The cells were washed three times with phosphate buffered saline (PBS; 0.1 M, PH 7.2). The cells were resuspended to the desired concentration in DME (Washington University Media Center) supplemented with 10 mM HEPES buffer, PH 7.0. Viral vectors were thawed and diluted in the same medium and added to the cells. The cultures were incubated at 37° C. for 5 hours, washed treet times and injected in mice or were tested for cytokine production in vitro.

Tumor Inhibition Studies. Tumor cells treated as described above are injected subcutaneously at a concentration of $10^5$ cells per mouse. Each group consisted of 5 mice. The outgrowth of the tumors was monitored twice a week for extended periods (see data for times). Once a week mice were examined for tumor growth. Mice were sacrificed for human reasons at varying times depending on the rate of tumor growth. The data reported show tumor incidence. In initial experiments, mice were followed for 81 days without change in the tumor incidence recorded at day 39. Initial studies were performed to determine the appropriate virus: tumor infectivity ratio and to compare the level and longevity of IL2 production by ALVAC and NYVAC (FIG. 63). ALVAC-IL2 and NYVAC-IL2 were used as representative test recombinants. The data showed that both ALVAC-IL2 and NYVAC-IL2 induced high and comparable levels of IL2 in infected MBT2 cells. ALVAC produced IL2 for longer time intervals and therefore, was selected for the initial studies. Additional preliminary studies were performed to assess the level of expression of the co-stimulatory molecule, B7, in MBT2 bladder tumor cells after infection with ALVAC-B7 (FIG. 64). The data show good expression of B7 at this infectivity ratio. Subsequent studies were performed with MBT2 infected as shown in FIG. 64.

Initial therapy studies were performed to assess the potential of ALVAC-IL2 as a therapeutic agent for bladder cancer. These studies were performed with ALVAC-IL2 treated with varying virus: tumor cell infectivity ratios as described in the materials and methods section above. Mice were injected with $10^5$ MBT2 cells treated previously with ALVAC IL2 (vCP275) or ALVAC-parental (CPpp). The data show that all infectivity ratios were effective in inhibiting MBT2 growth (FIG. 65). No tumor growth was observed with infectivity ratios of 5:1, 10:1 or 20:1.

Subsequent studies were performed with infectivity ratios of 5:1. The absence of tumor growth at these ALVAC-IL2:MBT2 ratios has been observed in multiple experiments.

Subsequent studies were performed to determine the effects of ALVAC-IL2 treatment on the growth of MBT2 after re-challenge. Mice were injected with ALVAC-IL2 treated MBT2 cells as shown in FIG. 65. Additional groups included mice immunized with irradiated MBT2 ($2\times10^6$ cells), IL2 transfected MBT2 cells ($2\times10^6$ cells, Obtained from Dr. W D W Heston, Memorial Sloan Kettering Cancer Institute, NY) (Conner, et al., 1993), ALVAC-B7 (vCP268) and parental ALVAC. Mice were injected subcutaneously and re-challenged 14 days later with $5\times10^5$ MBT2 cells by the same route (FIG. 66). The data show that neither irradiated MBT2 parental ALVAC, nor ALVAC-B7 provided protection. In contrast, ALVAC-IL2, ALVAC-IL2 plus ALVAC-B7, and IL2 transfected MBT2 were protected by prior treatment. Mice were followed for 81 days without tumor growth. In previous experiments both $10^4$ and $5\times10^4$ challenge doses for ALVAC-IL2 were used with the same results (data not shown).

Conclusions. The data show that ALVAC-IL2 is efficacious in inhibiting the outgrowth of tumors treated with ALVAC-IL2 recombinants. Also exposure to ALVAC-IL2 treated tumors is sufficient to induce protective immunity against subsequent challenge with untreated tumor cells. These data suggest that IL2 supplementation is sufficient to induce immunity to MBT2 tumors that otherwise would not be initiated as shown by the irradiated immunization controls (FIG. 66) and in transplantation resistance studies in which tumors were surgically removed prior to re-challenge (data not shown). Moreover, the protection observed with ALVAC-IL2 was equal to that observed with IL transfected MBT2 cells. Neither inhibition of MBT2 tumor growth nor inhibition of growth at re-challenge were observed with ALVAC-B7 infected MBT2 cells.

Having thus described in detail preferred embodiments of the present invention, it is to be understood that the invention defined by the appended claims is not to be limited to particular details set forth in the above description as many apparent variations thereof are possible without departing from the spirit or scope of the present invention.

REFERENCES

1. Almoguera, C., Shibata, D., Forrester, K., Martin, J., Arnheim, N., Peracho, M., Cell 53, 549–554 (1988).
2. Altenburger, W., C-P. Suter and J. Altenburger, Archives Virol. 105, 15–27 (1989).
3. Asher, A. L., Mulè, J. J., Reichert, C. M., et al., J. Immunol. 138, 963–974 (1987).
4. Avery, R. J., and Niven. J., Infect. and Immun. 26, 795–801 (1979).
5. Aviv, H., and Leder, P., Proc. Natl. Acad. Sci. USA 69, 1408–1412 (1972).
6. Behbehani, A. M., Microbiological Reviews 47, 455–509 (1983).
7. Bergoin, M., and Dales, S., In Comparative Virology, eds. K. Maramorosch and E. Kurstak, (Academic Press, NY) pp. 169–205 (1971).
8. Bernards, R., Destree, A., McKenzie, S., Gordon, E., Weinberg, R. A., and Panicali, D., PNAS USA 84, 6854–6858 (1987).
9. Bertholet, C., Drillien, R., and Wittek, R., Proc. Natl. Acad. Sci. USA 82, 2096–2100 (1985).
10. Boursnell, M. E. G., P. F. Green, J. I. A. Campbell, A. Deuter, R. W. Peters, F. M. Tomley, A. C. R. Samson, P. T. Emmerson, and Binns, M. M., Veterinary Microbiology 23, 305–316 (1990b).
11. Boursnell, M. E. G., P. F. Green, A. C. R. Samson, J. I. A. Campbell, A. Deuter, R. W. Peters, N. S. Millar, P. T. Emmerson, and Binns, M. M., Virology 178, 297–300. (1990c).
12. Boursnell, M. E. G., Green, P. F., Campbell, J. I. A., Deuter, A., Peters., R. W., Tomley, F. M., Samson, A. C. R., Chambers, P., Emmerson, P. T., and Binns, M. M., J. Gen. Virol. 71, 621–628 (1990a).
13. Boyle, D. B.; Coupar, B. E. H., Gene 65, 123–128 (1988).
14. Brunda, M. J., L. Luistro, R. R. Warrier, R. B. Wright, B. R. Hubbard, M. Murphy, S. F. Wolf and M. K. Gately, J. Exp. Med. 178, 1223–1230 (1993).
15. Buller, R. M. L., G. L. Smith, Cremer, K., Notkins, A. L., and Moss, B., Nature 317, 813–815 (1985).
16. Buller, R. M. L., Chakrabarti, S., Cooper, J. A., Twardzik, D. R., and Moss, B., J. Virol. 62, 866–874 (1988).
17. Bzik, D., Li, W., Horii, T., and Inselburg, J., Molec. Biochem. Parasitol. 30, 279–288 (1988).
18. Cadoz, M., A. Strady, B. Meignier, J. Taylor, J. Tartaglia, E. Paoletti and S. Plotkin, The Lancet, 339, 1429 (1992).
19. Cassel, W. A., D. R. Murray and H. S. Phillips Cancer 52, 856–860 (1983).
20. Chambers, P., N. S. Millar, and P. T. Emmerson, J. Gen. Virol. 67, 2685–2694 (1986).
21. Chen, L., S. Ashe, W. A. Brady, I. Hellstrom, K. E. Hellstrom, J. A. Ledbetter, P. McGowan and P. S. Linsley, Cell 71, 1093–1102 (1992).
22. Child, S. J., Palumbo, G. J., Buller, R. M. L., and Hruby, D. E. Virology 174, 625–629 (1990).
23. Clark, S. Arya, S., Wong-Staal, F., Matsumoto-Mobayashi, M., Kay, R., Kaufman, R., Brown, E., Shoemaker, C., Copeland, T., Oroszland, S., Smith, K., Sarngadharan, M, Lindner, S., and Gallo, R. PNAS 81, 2543–2547 (1984).
24. Clewell, D. B., J. Bacteriol 110, 667–676 (1972).
25. Clewell, D. B. and D. R. Helinski, Proc. Natl. Acad. Sci. USA 62, 1159–1166 (1969).
26. Colinas, R. J., R. C. Condit and E. Paoletti, Virus Research 18, 49–70 (1990).
27. Cooney E. L., Corrier A. C., Greenberg P. D., et al., Lancet 337, 567–572 (1991).
28. Coulie, P., Weynants, P., Muller, C., Lehmann, F., Herman, J., Baurain, J.-F., and Boon, T. In Specific Immunotherapy of Cancer with Vaccines, eds. Bystryn, J.-L., Ferrone, S., and Livingston, P. New York Academy of Science, New York. pp. 113–119 (1993).
29. Davidoff, A. M., Kerns, B. J. M., Iglehart, J. D., Marks, J. R., Cancer Res. 51, 2605–2610 (1991).
30. Davidoff, A. M., J. D. Iglehart, and J. R. Marks, PNAS USA 89, 3439–3442 (1992).
31. Dreyfuss, G., Adam, S. A., and Choi, Y. D., Mol. Cell. Biol. 4, 415–423 (1984).
32. Drillien, R., F. Koehren and A. Kirn, Virology 111, 488–499 (1981).
33. Edbauer, C., R. Weinberg, J. Taylor, A. Rey-Senelonge, J. F. Bouquet, P. Desmettre, and E. Paoletti, Virology 179, 901–904 (1990).
34. Engelke, D. R., Hoener, P. A., and Collins, F. S., Proc. Natl. Acad. Sci. USA 85, 544–548 (1988).
35. Espion, D., S. de Henau, C. Letellier, C.-D. Wemers, R. Brasseur, J. F. Young, M. Gross, M. Rosenberg, G. Meulemans and A. Burny, Arch. Virol. 95, 79–95 (1987).
36. Estin, C. D., Stevenson, U. S., Plowman, G. D., Hu, S.-L., Sridhar, P., Hellström, I., Brown, J. P., Hellström, K. E., PNAS USA 85, 1052–1056 (1988).
37. Etinger H. M., Altenburger W., Vaccine 9, 470–472 (1991).
38. Falkner, F. G.; Moss, B., J. Virol. 62, 1849–1854 (1988).
39. Fendly, B. M., Kotts, C., Vetterlein, D., Lewis, G. D., Winget, M., Carver, M. E., Watson, S. R., Sarup, J., Saks, S., Ullrich, A., Shepard, H. M., J. Biol. Resp. Mod. 9, 449–455 (1990).
40. Fenner, F., Virology 5, 502–529 (1958).
41. Fishbein, G. E., McClay, E., Berd, D., and M. J. Mastrangelo, Vaccine Res. 1, 123–128.
42. Flexner, C., Hugen, A., and Moss, B., Nature 330, 259–262 (1987).
43. Freeman, G. J., G. S. Gray, C. D. Gimmi, D. B. Lombard, L.-J. Zhou, M. White, J. D. Fingeroth, J. G. Gribben and L. M. Nadler, J. Exp. Med., 174, 625–631 (1991).
44. Freeman, G. J., A. S. Freedman, J. M. Segil, G. Lee, J. F. Whitman and L. M. Nadler, J. Immunol. 143, 2714–22 (1989).
45. Fries et al., 32nd Interscience Conference on Antimicrobial Agents and Chemotherapy, Anaheim, Calif. (October 1992).
46. Frohman, M., Dush, M., and Martin, G., Proc. Natl. Acad. Sci. USA 85, 8998–9002 (1988).
47. Fujiwara et al., Eur. J. Immunol. 14, 171–175 (1984).

48. Funahashi, S., T. Sato and H. Shida, J. Gen. Virol. 69, 35–47 (1988).
49. Garten, W., Kohama, T., and H-D. Klenk. J. Gen. Virol. 51, 207–211 (1980).
50. Gerrard, T. L., R. Thorpe, S. Jeffcoate and C. Reynolds, Biologicals 21, 77–79 (1993).
51. Ghendon, Y. Z., and Chernos, V. I., Acta Virol. 8, 359–368 (1964).
52. Gillard, S., Spehner, D., Drillien, R., and Kirn, A., Proc. Natl. Acad. Sci. USA 83, 5573–5577 (1986).
53. Goebel, S. J., Johnson, G. P., Perkus, M. E., Davis, S. W., Winslow, J. P., Paoletti, E., Virology 179, 247–266 (1990).
54. Goebel, S. J., G. P. Johnson, M. E. Perkus, S. W. Davis, J. P. Winslow and E. Paoletti, Virology 179, 517–563 (1990b).
55. Goldstein, D. J. and S. K. Weller, Virology 166, 41–51 (1988).
56. Greenberg, P. D., Adv. Immunol. 49, 281–355 (1991).
57. Gubler, U., A. O. Chua, D. S. Schoenhaut, C. D. Dwyer, W. McComas, R. Motyka, M. Nabavi, A. G. Wolitzky, P. M. Quinn, P. C. Familletti and M. K. Gately, Proc. Natl. Acad. Sci. USA 88, 4143–4147 (1991).
58. Guo, P., Goebel, S., Davis, S., Perkus, M. E., Languet, B., Desmettre, P., Allen, G., and Paoletti, E., J. Virol. 63, 4189–4198 (1989).
59. Hareuveni et al., Proc. Natl. Acad. Sci. USA 87, 9498–9502 (1990) .
60. Hareuveni et al., Vaccine 9(5), 618–626 (1991).
61. Hollstein, M., Sidransky, D., Vogelstein, B., Harris, C. C., Science 253, 49–53 (1991).
62. Hollstein, M., D. Sidransky, B. Vogelstein, C. C. Harris, Science 253, 49–53 (1991).
63. Homma, M., and M. Ohuchi, J. Virol. 12, 1457–1465 (1973).
64. Hruby, D. E. and L. A. Ball, J. Virol. 43, 403–409 (1982).
65. Hruby, D. E., R. A. Maki, D. B. Miller and L. A. Ball, Proc. Natl. Acad. Sci. USA 80, 3411–3415 (1983).
66. Hu, S.-L., Plowman, G. D., Sridhar, P., Stevenson, U. S., Brown, J. P., Estin, C. D., J. Virol. 62, 176–180 (1988).
67. Ichihashi, Y. and Dales, S., Virology 46, 533–543 (1971).
68. Itamura, S., H. Iinuma, H. Shida, Y. Morikawa, K. Nerome and A. Oya, J. Gen. Virol. 71, 2859–2865 (1990).
69. Jacobson, J. G., D. A. Leib, D. J. Goldstein, C. L. Bogard, P. A. Schaffer, S. K. Weller and D. M. Coen, Virology 173, 276–283 (1989).
70. Jamieson, A. T., G. A. Gentry and J. H. Subak-Sharpe, J. Gen. Virol. 24, 465–480 (1974).
71. Kantor, J., K. Irvine, S. Abrams, P. Snoy, R. Olsen, J. Greiner, H. Kaufman, D. Eggensperger, and J. Schlom. Cancer Res 52, 24 (1992).
72. Karupiah, G., R. V. Blanden, and I. A. Ramshaw, J. Exp. Med. 172, 1495–1503 (1990).
73. Karupiah, G., A. J. Ramshaw, I. A. Ramshaw, and R. V. Blanden, Scand. J. Immunol. 36, 99–105 (1992).
74. Kato, S., M. Takahashi, S. Kameyama and J. Kamahora, Biken's 2, 353–363 (1959).
75. Kaufman, H., Schlom, J., Kantor, J., Int. J. Cancer 48, 900–907 (1991).
76. Kieny, M. P., Lathe, R., Drillien, R., Spehner, D., Skory, S., Schmitt, D., Wiktor, T., Koprowski, H., and Lecocq, J. P., Nature (London) 312, 163–166 (1984).
77. Kingston, R., Preparation of poly (A)$^+$ RNA. Current Protocols in Molecular Biology. Ausubel, F., Brent, R., Kingston, R., Moore, D., Seidman, J., Smith, J., and Struhl, K., eds. p 4.5.1. John Wiley and Sons, N.Y. (1987).
78. Kleitmann W., Schottle A., Kleitmann B., et al., In Cell Culture Rabies Vaccines and Their Protective Effect in Man., ed. Kuwert/Wiktor/Koprowski, (International Green Cross—Geneva) pp. 330–337 (1981).
79. Klickstein, L., and Neve, R., Preparation of insert DNA from messenger RNA, Current Protocols in Molecular Biology. Ausubel, F., Brent, R., Kingston, R., Moore, D., Seidman, J., Smith, J., and Struhl, K., eds. pp 5.5.1–5.5.10. John Wiley and Sons, N.Y. (1987).
80. Knapp, B., Hundt, E., Nau, U., and Kupper, H., Molecular cloning, genomic structure, and localization in a blood stage antigen of *Plasmodium falciparum* characterized by a serine stretch. Molec. Biochem. Parasitol. 32, 73–84 (1989).
81. Knauf, V. C. and Nester, E. W., Plasmid 8, 45–54 (1982).
82. Kohonen-Corish, M. R. J., N. J. C. King, C. E. Woodhams and I. A. Ramshaw, Eur. J. Immunol. 20, 157–161 (1990).
83. Kotwal, G. J., A. W. Hugin and B. Moss, Virology 171, 579–587 (1989a).
84. Kotwal, G. J. and B. Moss, J. Virol. 63, 600–606 (1989b).
85. Kotwal, G. J., S. N. Isaacs, R. McKenzie, M. M. Frank and B. Moss, Science 250, 827–830 (1990).
86. Kotwal, G. J. and Moss, B., Nature (Lond.) 335, 176–178 (1988).
87. Kriegler, M., Perez, C., DeFay, K., et al., Cell 53, 45–53 (1988).
88. Kuwert E. K., Barsenbach C., Werner J., et al., In Cell Culture Rabies Vaccines and Their Protection Effect in Man, eds. Kuwert/Wiktor/Koprowski (International Green Cross—Geneva) pp. 160–167 (1981).
89. Lai, A. C.-K. and B. G.-T. Pogo, Virus Res. 12, 239–250 (1989).
90. Lamb, P. and Crawford, L., Mol. Cell. Biol. 6, 1379–1385 (1986).
91. Lathe, R. S., Kieny, M. P., Gerlinger, P., Clertant, P., Guizani, I., Cuzin, F. P. and Chambon. Nature 326, 878–880 (1987).
92. Le, L., R. Brasseur, C. Wemers, G. Meulemans, and A. Burny, Virus Genes 1, 333–350 (1988).
93. Li, W., Bzik, D., Horii, T., and Inselburg, J., Molec. Biochem. Parasitol. 33, 13–26 (1989).
94. Lindenmann, J. and P. A. Klein, J. Exp. Med. 126, 93–108 (1967).
95. Lindenmann J., Biochim. Biophys. Acta. 355, 49–75 (1974).
96. Lopez, A. F., M. J. Elliott, J. Woodcock and M. A. Vadas, Immunology Today 13, 495–500 (1992).
97. Mandecki, W., Proc. Natl. Acad. Sci. USA 83, 7177–7182 (1986).
98. Maniatis, T., Fritsch, E. F., and Sambrook, J. In Molecular cloning: a laboratory manual, (Cold Spring Harbor Laboratory, Cold Spring Harbor, N.Y.) (1982).
99. Matthews, R. E. F., Intervirology 17, 42–44 (1982b).
100. McGinnes, L. W., and T. G. Morrison, Virus Research 5, 343–356 (1986).
101. Merz, D. C., A. Scheid, and P. Choppin, J. Exper. Med. 151, 275–288 (1980).
102. Morgan, A. J., M. Mackett, S. Finerty, J. R. Arrand, F. T. Scullion and M. A. Epstein, J. Med. Virol. 25, 189–195 (1988).
103. Moss, B., E. Winters and J. A. Cooper, J. Virol. 40, 387–395 (1981).
104. Nagai, Y., H. D. Klenk, and R. Rott, Virology 72, 494–508 (1976).
105. Nagai, Y., T. Yoshida, M. Hamaguchi, H. Naruse, M. Iinuma, K. Maeno, and T. Matsumoto, Microbiol. Immunol. 24, 173–177 (1980).

106. Norrby, E., and Y. Gollmar, Infect. and Immun. 11, 231–239 (1975).
107. Ogawa, R., N. Yanagida, S. Saeki, S. Saito, S. Ohkawa, H. Gotoh, K. Kodama, K. Kamogawa, K. Sawaguchi and Y. Iritani, Vaccine 8, 486–490 (1990).
108. Paez, E., S. Dallo and M. Esteban, Proc. Natl. Acad. Sci. USA 82, 3365–3369 (1985).
109. Palumbo, G. J., Pickup, D. J., Fredrickson, T. N., Mcintyre, L. J., and Buller, R. M. L., Virology 172, 262–273 (1989).
110. Panicali, D. and E. Paoletti, Proc. Natl. Acad. Sci. USA 79, 4927–4931 (1982).
111. Panicali, D., Davis, S. W., Mercer, S. R., and Paoletti, E., J. Virol. 37, 1000–1010 (1981).
112. Pardoll, D., Current Opinion in Immunology 4, 619–623 (1992).
113. Patel, D. D. and Pickup, D. J., EMBO 6, 3787–3794 (1987). 114. Patel, D. D., Ray, C. A., Drucker, R. P., and Pickup, D. J., Proc. Natl. Acad. Sci. USA 85, 9431–9435 (1988).
115. Pennica, D., D. V. Goeddel, J. S. Hayflick, N. C. Reich, C. W. Anderson and A. J. Levine, Virology 134, 477–482 (1984).
116. Perkus, M. E., S. J. Goebel, S. W. Davis, G. P. Johnson, E. K. Norton and E. Paoletti, Virology 180, 406–410 (1991).
117. Perkus, M. E., Goebel, S. J., Davis, S. W., Johnson, G. P., Limbach, K., Norton, E. K., and Paoletti, E., Virology 179, 276–286 (1990).
118. Perkus, M. E., A. Piccini, B. R. Lipinskas and E. Paoletti, Science 229, 981–984 (1985).
119. Perkus, M. E., Limbach, K., and Paoletti, E., J. Virol. 63, 3829–3836 (1989).
120. Perkus, M. E., D. Panicali, S. Mercer and E. Paoletti, Virology 152, 285–297 (1986).
121. Perkus M. E., Piccini A., Lipinskas B. R., et al., Science 229, 981–984 (1985).
122. Piccini, A., M. E. Perkus, and E. Paoletti, Methods in Enzymology 153, 545–563 (1987).
123. Pickup, D. J., B. S. Ink, B. L. Parsons, W. Hu and W. K. Joklik, Proc. Natl. Acad. Sci. USA 81, 6817–6821 (1984).
124. Pickup, D. J., B. S. Ink, W. Hu, C. A. Ray and W. K. Joklik, Proc. Natl. Acad. Sci. USA 83, 7698–7702 (1986).
125. Pratt, D. and S. Subramani, *Nucleic Acids Research* 11, 8817–8823 (1983).
126. Ramshaw, I. A., J. Ruby and A. Ramsay, Tibtech 10, 424–426 (1992).
127. Reed, L. J. and Muench, H., Am. J. Hyg. 27, 493–497 (1938).
128. Riddell, S. R., Watanabe, K. S., Goodrich, J. M., Li, C. R., Agha, M. E., Greenberg, P. D., Science 257, 238–241 (1992).
129. Ronen, D., Teitz, Y., Goldfinger, N., Rotter, V. Nucleic Acids Research 20, 3435–3441 (1992).
130. Rosenberg, S. A., J. of Clinical Oncology 10, 180–199 (1992).
131. Ruby, J., A. Ramsey, G. Darupiah, & I. Ramshaw, Vaccine Res. 4, 347–356 (1992).
132. Saiki, R., Gelfand, D., Stoffel, S., Scharf, S., Higuchi, R., Horn, G., Mullis, K., and Erlich, H., Science 239, 487–491 (1988).
133. Sanger, F., Nickeln, S. Coulson, A. R., Proc. Natl. Acad. Sci. 74, 5463–5467 (1977).
134. Schmidtt, J. F. C. and H. G. Stunnenberg, J. Virol. 62, 1889–1897 (1988).
135. Schwartz, R. H., Cell 71, 1065–1068 (1992).
136. Seligmann, E. B., In Laboratory Techniques in Rabies, eds. M. M. Kaplan and H. Koprowski, (World Health Organization, Geneva) pp. 279–285 (1973).
137. Shapira, S. K., Chou, J., Richaud, F. V. and Casadaban, M. J., Gene 25, 71–82 (1983).
138. Shida, H., T. Tochikura, T. Sato, T. Konno, K. Hirayoshi, M. Seki, Y. Ito, M. Hatanaka, Y. Hinuma, M. Sugimoto, F. Takahashi-Nishimaki, T. Maruyama, K. Miki, K. Suzuki, M. Morita, H. Sashiyama and M. Hayami, EMBO 6, 3379–3384 (1987).
139. Shida, H., Hinuma, Y., Hatanaka, M., Morita, M., Kidokoro, M., Suzuki, K., Maruyzam, T., Takahashi-Nishimaki, F., Sugimoto, M., Kitamura, R., Miyazawa, T., and Hayami, M., J. Virol. 62, 4474–4480 (1988).
140. Shida, H., Virology 150, 451–462 (1986).
141. Shimizu, Y. H. Fujiwara, S. Ueda, N. Wakamiya, S. Kato, T. Hamaoka, Eur. J. Immunol. 14, 839–843 (1984).
142. Shimizu, Y., K. Hasumi, K. Masubuchi & Y. Okudaira, Cancer Immunol. Immunother. 27, 223–227 (1988).
143. Slabaugh, M., N. Roseman, R. Davis and C. Mathews, J. Virol. 62, 519–527 (1988).
144. Smith, J. S., P. A. Yager and G. M. Baer, In Laboratory Techniques in Rabies, eds. M. M. Kaplan and H. Koprowski (WHO Geneva) pp. 354–357 (1973).
145. Stanberry, L. R., S. Kit and M. G. Myers, J. Virol. 55, 322–328 (1985).
146. Tabor, S. and C. C. Richardson, Proc. Natl. Acad. Sci. USA 84, 4767–4771 (1987).
147. Tan, T., Wallis, J., Levine, A., Journal of Virology 59, 574–583 (1986).
148. Tartaglia, J., Pincus, S., Paoletti, E., Critical Reviews in Immunology 10, 13–30 (1990a).
149. Tartaglia, J., Perkus, M. E., Taylor, J., Norton, E. K., Audonnet, J.-C., Cox, W. I., Davis, S. W., Van Der Hoeven, J., Meignier, B., Riviere, M., Languet, B., Paoletti, E., Virology 188, 217–232 (1992).
150. Tartaglia, J., J. Taylor, W. I. Cox, J.-C. Audonnet, M. E. Perkus, A. Radaelli, C. de Giuli Morghen, B. Meignier, M. Riviere, K. Weinhold & Paoletti, E. In *AIDS Research Reviews*, W. Koff, F. Wong-Staal & R. C. Kenedy, Eds., Vol. 3, Marcel Dekker, NY (In press)(1993a).
151. Tartaglia, J. & Paoletti, E. In Immunochemistry of Viruses, II. The Basis for Serodiagnosis and Vaccines. M. H. V. van Regenmortel & A. R. Neurath, Eds. 125–151. Elsevier Science Publishers, Amsterdam (1990b).
152. Tartaglia, J., Jarrett, O., Desmettre, P., Paoletti, E. J. Virol. 67, 2370–2375 (1993b).
153. Tartaglia, J., R. Gettig & E. Paoletti. Encyclopedia of Virology (Vol. I), eds. Webster, R. G., and A. Granoff, Academic Press Limited, London, in press.
154. Taylor, J., C. Trimarchi, R. Weinberg, B. Languet, F. Guillemin, P. Desmettre and E. Paoletti, Vaccine 9, 190–193 (1991b).
155. Taylor, G., E. J. Stott, G. Wertz and A. Ball, J. Gen. Virol. 72, 125–130 (1991a).
156. Taylor, J., Edbauer, C., Rey-Senelonge, A., Bouquet, J.-F., Norton, E., Goebel, S., Desmettre, P., Paoletti, E., J. Virol. 64, 1441–1450 (1990).
157. Taylor, J., R. Weinberg, J. Tartaglia, C. Richardson, G. Alkhatib, D. Briedis, M. Appel, E. Norton & E. Paoletti, Virology 187, 321–328 (1992).
158. Taylor, J., Weinberg, R., Kawaoka, Y., Webster, R. G., and Paoletti, E., Vaccine 6, 504–508 (1988a).
159. Taylor, J., R. Weinberg, B. Lanquet, P. Desmettre, and E. Paoletti, Vaccine 6, 497–503 (1988b).
160. Taylor, J., C. Trimarchi, R. Weinberg, B. Languet, F. Guillemin, P. Desmettre & E. Paoletti, Vaccine 9, 190 (1991).

161. Toyoda, T., T. Sakaguchi, K. Imai, N. M. Inocencio, B. Gotoh, M. Hamaguchi, and Y. Nagai, Virology 158, 242–247 (1987).
162. Traversari, C., van der Bruggen, P., Luescher, I. F., Lurquin, C., Chomez, P., van Pel, A., De Plaen, E., Amar-Costesec, A., Boon, T., J. Exp. Med. 176, 1453–1457 (1992).
163. Trinchieri, G., Imm. Today 14, 335–338 (1993)
164. Ulrich, S. J., Anderson, C. W., Mercer, W. E., Appella, E., J. Biol. Chem. 267, 15259–15262 (1992).
165. van der Bruggen, P. and Van der Eynde, B., Curr. Topics in Immunology 4, 608–612 (1992).
166. van der Bruggen, P., Traversari, C., Chomez, P., Lurquin, C., De Plaen, E., Van de Eynde, B., Knuth, A., Boon, T., Science 254, 1643–1647 (1991).
167. Vogel, S. N., R. M. Friedman, and M. M. Hogan, Current Protocols in Immunology, 6.9.1–6.9.8 (1991).
168. Wallack, M. K., K. R. McNally, E. Leftheriotis, H. Seigler, C. Balch, H. Wanebo, A. Bartolucci & J. A. Bash, Cancer 57, 649–655 (1986).
169. Watson, C., and Jackson, J., In DNA Cloning, Volume I: a practical approach, Glover, D. M., ed. pp 79–88 (IRL Press, Oxford) (1985).
170. Weir, J. P. and B. Moss, J. Virol. 46, 530–537 (1983).
171. Yamamoto, T., S. Ikawa, T. Akiyama, K. Semba, N. Nomura, N. Miyajima, T. Saito and K. Toyoshima, Nature 319, 230–234 (1986).
172. Yuen, L. and B. Moss, J. Virol. 60, 320–323 (1986).
173. Yuen, L., and Moss, B., Proc. Natl. Acad. Sci. USA 84, 6417–6421 (1987).
174. Zhou, J., L. Crawford, L. McLean, X. Sun, M. Stanley, N. Almond and G. L. Smith, J. Gen. Virol. 71, 2185–2190 (1990).
175. Sanda M D, Ayagari S R, Jaffee E M, Epstein J I, Clift S L, Cohen L K, Dranoff G, Pardoll D M, Mulligan R C, Simons J W. Journal of Urology, 151:622.
176. Keetch D W, Humphrey P, Ratliff T L. Journal of Urology, 152:247–1994.
177. Thompson T C, Southgate J, Kitchener G, Land H. Cell, 56:917, 1989
178. Boring C C, Squires T S, Tong T: Cancer Statistics 1992. C. A. 1992;42:30.
179. Althausen A F, Trout G R, Daley J J: Non-invasive papillary carcinoma of the bladder associated with carcinoma in situ. J Urol 1976;116:575
180. Fitzpatrick J M, West A B, Butler M R, et al: Superficial bladder tumors: The importance of recurrence pattern following initial resection. J Urol 1986;135:920
181. Gilbert H A, Logan J L, Lagan A R, et al: The natural history of papillary transitional carcinoma of the bladder and its treatment in unselected population on the basis of histologic grading. J Urol 1978;119:486
182. Goffinet D R, Schneider M J, Glatstein E J, et al: Bladder cancer: Results of radiation therapy in 384 patients. Radiology 1875;117:149–152
183. van der Werf-Messing B: Cancer of the urinary bladder treated by interstitial radium implant. Int J Radiat Oncol Biol Phys 1978;4:373–378
184. Lamm D L, Blemenstein B A, Crawford E D, Montie J E, Scardino P, Grossman H B Stanisic T H, Smith J A, Sullivan J, Sarosdy M F, Crissman J D and Coltman C A: A randomized trial of intravesical Doxorubicin and immunotherapy with bacillus Calmette-Guerin for transitional-cell carcinoma of the bladder. N Engl J Med 1991;325:1205–1209.
185. Connor, J, Banneriji, R, Saito, S, Heston, W, Fair, W, Gilboa, E. Regression of bladder tumors in mice treated with interleukin 2 gene modified tumor cells. J. Exp. Med., 177(4):1127–1134, 1993.

What is claimed is:

1. A recombinant poxvirus containing therein exogenous DNA in a nonessential region of the poxvirus, wherein the poxvirus is an attenuated avipox Virus that expresses an exogenous DNA encoding carcinoembryonic antigen and an exogenous DNA encoding B7 protein.

2. The recombinant poxvirus according to claim 1, wherein the B7 protein is a murine B7.

3. The recombinant poxvirus according to claim 1, wherein the B7 protein is a human B7.

4. The recombinant poxvirus according to claim 1, wherein the B7 protein is encoded by SEQ. ID. No.: 202.

5. The recombinant poxvirus of claim 4 wherein the attenuated avipox virus is ALVAC.

6. The recombinant poxvirus according to claim 1, wherein the B7 protein is encoded by SEQ. ID. No.: 207.

7. The recombinant poxvirus of claim 6 wherein the attenuated avipox virus is ALVAC.

8. The recombinant poxvirus of claim 1 wherein the attenuated avipox virus is an attenuated canarypox virus.

9. The recombinant poxvirus of claim 1 wherein the attenuated avipox virus is an attenuated canarypox virus obtained by serial passage on chick embryo fibroblasts, subjection of a master viral seed to a plurality of successive plaque purifications under agar, and amplification of a plaque clone through a plurality of passages.

10. The recombinant poxvirus of claim 1 wherein the attenuated avipox virus is ALVAC.

11. A composition comprising a poxvirus as claimed in any one of claims 1–7 in admixture with a suitable carrier.

12. A method of expressing carcinoembryonic antigen and B7 protein in vivo, wherein the method comprises administering to a mammal a composition according to claim 11.

* * * * *